United States Patent
Yu et al.

(10) Patent No.: US 10,240,207 B2
(45) Date of Patent: Mar. 26, 2019

(54) CANCER TREATMENT WITH C-MET ANTAGONISTS AND CORRELATION OF THE LATTER WITH HGF EXPRESSION

(71) Applicant: Genentech, Inc., South San Francisco, CA (US)

(72) Inventors: Wei Yu, South San Francisco, CA (US); David Shames, South San Francisco, CA (US); Hartmut Koeppen, South San Francisco, CA (US); See Phan, South San Francisco, CA (US); Sandra Rost, South San Francisco, CA (US)

(73) Assignee: Genentech, Inc., South San Francisco, CA (US)

( * ) Notice: Subject to any disclaimer, the term of this patent is extended or adjusted under 35 U.S.C. 154(b) by 0 days.

(21) Appl. No.: 15/272,283

(22) Filed: Sep. 21, 2016

(65) Prior Publication Data

US 2017/0183740 A1      Jun. 29, 2017

Related U.S. Application Data

(63) Continuation of application No. PCT/US2015/022282, filed on Mar. 24, 2015.

(60) Provisional application No. 61/985,316, filed on Apr. 28, 2014, provisional application No. 61/969,706, filed on Mar. 24, 2014.

(51) Int. Cl.
    C12Q 1/6886    (2018.01)
    C07K 16/22     (2006.01)
    C07K 16/28     (2006.01)
    A61K 39/00     (2006.01)

(52) U.S. Cl.
    CPC ........... *C12Q 1/6886* (2013.01); *C07K 16/22* (2013.01); *C07K 16/2863* (2013.01); *A61K 2039/505* (2013.01); *C07K 2317/24* (2013.01); *C07K 2317/76* (2013.01); *C12Q 2600/158* (2013.01)

(58) Field of Classification Search
    None
    See application file for complete search history.

(56) References Cited

U.S. PATENT DOCUMENTS

| | | |
|---|---|---|
| 4,275,149 A | 6/1981 | Litman et al. |
| 4,318,980 A | 3/1982 | Boguslaski et al. |
| 4,342,566 A | 8/1982 | Theofilopoulos et al. |
| 4,676,980 A | 6/1987 | Segal et al. |
| 4,683,195 A | 7/1987 | Mullis et al. |
| 4,737,456 A | 4/1988 | Weng et al. |
| 4,816,567 A | 3/1989 | Cabilly et al. |
| 4,943,533 A | 7/1990 | Mendelsohn et al. |
| 5,169,939 A | 12/1992 | Gefter et al. |
| 5,183,884 A | 2/1993 | Kraus et al. |
| 5,208,020 A | 5/1993 | Chari et al. |
| 5,212,290 A | 5/1993 | Vogelstein et al. |
| 5,227,158 A | 7/1993 | Jardieu |
| 5,264,365 A | 11/1993 | Georgiou et al. |
| 5,316,921 A | 5/1994 | Godowski et al. |
| 5,328,837 A | 7/1994 | Godowski et al. |
| 5,362,716 A | 11/1994 | Kmiecki et al. |
| 5,416,064 A | 5/1995 | Chari et al. |
| 5,457,105 A | 10/1995 | Barker |
| 5,475,001 A | 12/1995 | Barker |
| 5,475,096 A | 12/1995 | Gold et al. |
| 5,480,968 A | 1/1996 | Kraus et al. |
| 5,500,362 A | 3/1996 | Robinson et al. |
| 5,550,362 A | 3/1996 | Robinson et al. |
| 5,508,192 A | 4/1996 | Georgiou et al. |
| 5,547,856 A | 8/1996 | Godowski et al. |
| 5,571,894 A | 11/1996 | Wels et al. |
| 5,587,458 A | 12/1996 | King et al. |
| 5,591,828 A | 1/1997 | Bosslet et al. |
| 5,602,095 A | 2/1997 | Pastan et al. |
| 5,616,582 A | 4/1997 | Barker |
| 5,624,821 A | 4/1997 | Winter et al. |
| 5,635,483 A | 6/1997 | Pettit et al. |
| 5,646,036 A | 7/1997 | Schwall et al. |
| 5,648,237 A | 7/1997 | Carter et al. |
| 5,648,260 A | 7/1997 | Winter et al. |
| 5,654,307 A | 8/1997 | Bridges et al. |
| 5,679,683 A | 10/1997 | Bridges et al. |
| 5,686,292 A | 11/1997 | Schwall et al. |
| 5,712,374 A | 1/1998 | Kuntsmann et al. |
| 5,714,586 A | 2/1998 | Kunstmann et al. |
| 5,731,168 A | 3/1998 | Carter et al. |
| 5,739,116 A | 4/1998 | Hamann et al. |
| 5,747,498 A | 5/1998 | Schnur et al. |

(Continued)

FOREIGN PATENT DOCUMENTS

| CN | 1154736 C | 6/2004 |
|---|---|---|
| CN | 101415730 A | 4/2009 |

(Continued)

OTHER PUBLICATIONS

Kunkel et al. Neuro Oncol. 2001. 3(2):82-88. (Year: 2001).*
Xie et al. PNAS. 2012. 109(2):570-575. (Year: 2012).*
Whitehead et al. Genome Biology. 2005. 6(2): Article R13. (Year: 2005).*
Evans et al. Nature. 2004. 429:464-468. (Year: 2004).*
Chan et al. G&P magazine. 2006. 6(3): 20-26. (Year: 2006).*
Kendrick. "A gene's mRNA level does not usually predict its protein level". Kendrick Labs, Inc. Sep. 25, 2014. (Year: 2014).*
Maier et al. FEBS Letters. 2009. 583:3966-3973. (Year: 2009).*
Pascal et al. BMC Genomics. 2008. 9:246. (Year: 2008).*

(Continued)

*Primary Examiner* — Joseph G. Dauner
(74) *Attorney, Agent, or Firm* — Morrison & Foerster LLP

(57) ABSTRACT

The present invention concerns cancer biomarkers. In particular, the invention concerns HGF as a biomarker for patient selection and patient prognosis in cancer, as well as methods of therapeutic treatment, articles of manufacture and methods for making them, diagnostic kits, methods of detection and methods of advertising related thereto.

25 Claims, 17 Drawing Sheets

Specification includes a Sequence Listing.

(56) References Cited

U.S. PATENT DOCUMENTS

| | | |
|---|---|---|
| 5,747,662 A | 5/1998 | Simmons et al. |
| 5,750,373 A | 5/1998 | Garrard et al. |
| 5,767,285 A | 5/1998 | Garrard et al. |
| 5,760,041 A | 6/1998 | Wissner et al. |
| 5,770,429 A | 6/1998 | Lonberg et al. |
| 5,770,599 A | 6/1998 | Gibson |
| 5,770,701 A | 6/1998 | McGahren et al. |
| 5,770,710 A | 6/1998 | McGahren et al. |
| 5,773,001 A | 6/1998 | Hamann et al. |
| 5,780,588 A | 7/1998 | Pettit et al. |
| 5,792,783 A | 8/1998 | Tang et al. |
| 5,807,706 A | 9/1998 | Carter et al. |
| 5,821,333 A | 10/1998 | Carter et al. |
| 5,821,337 A | 10/1998 | Carter et al. |
| 5,834,504 A | 11/1998 | Tang et al. |
| 5,840,523 A | 11/1998 | Simmons et al. |
| 5,869,049 A | 1/1999 | Noelle et al. |
| 5,866,572 A | 2/1999 | Barker |
| 5,871,959 A | 2/1999 | Rong et al. |
| 5,877,296 A | 3/1999 | Hamann et al. |
| 5,880,141 A | 3/1999 | Tang et al. |
| 5,891,996 A | 4/1999 | Mateo De Acosta Del Rio et al. |
| 5,968,509 A | 10/1999 | Gorman et al. |
| 6,002,008 A | 12/1999 | Wissner et al. |
| 6,027,888 A | 2/2000 | Georgiou et al. |
| 6,054,297 A | 4/2000 | Carter et al. |
| 6,075,181 A | 6/2000 | Kucherlapati et al. |
| 6,083,715 A | 7/2000 | Georgiou et al. |
| 6,084,095 A | 7/2000 | Bridges et al. |
| 6,099,841 A | 8/2000 | Hillan et al. |
| 6,121,022 A | 9/2000 | Presta et al. |
| 6,140,332 A | 10/2000 | Traxler et al. |
| 6,150,584 A | 11/2000 | Kucherlapati et al. |
| 6,194,551 B1 | 2/2001 | Idusogie et al. |
| 6,207,152 B1 | 3/2001 | Schwall et al. |
| 6,214,344 B1 | 4/2001 | Schwall et al. |
| 6,217,866 B1 | 4/2001 | Schlessinger et al. |
| 6,235,883 B1 | 5/2001 | Jakobovitis et al. |
| 6,248,516 B1 | 6/2001 | Winter et al. |
| 6,242,177 B1 | 7/2001 | Simmons et al. |
| 6,265,410 B1 | 7/2001 | Bridges et al. |
| 6,297,238 B1 | 10/2001 | Doyle et al. |
| 6,331,415 B1 | 12/2001 | Cabilly et al. |
| 6,344,455 B1 | 2/2002 | Bridges et al. |
| 6,344,459 B1 | 2/2002 | Bridges et al. |
| 6,391,874 B1 | 5/2002 | Cockerill et al. |
| 6,399,602 B1 | 6/2002 | Barker et al. |
| 6,455,534 B2 | 9/2002 | Bridges et al. |
| 6,468,529 B1 | 10/2002 | Schwall et al. |
| 6,521,620 B1 | 2/2003 | Bridges et al. |
| 6,524,832 B1 | 2/2003 | Kufe et al. |
| 6,548,640 B1 | 4/2003 | Winter |
| 6,582,959 B2 | 6/2003 | Kim |
| 6,596,726 B1 | 7/2003 | Bridges et al. |
| 6,599,902 B2 | 7/2003 | Cui et al. |
| 6,602,684 B1 | 8/2003 | Umana et al. |
| 6,602,863 B1 | 8/2003 | Bridges et al. |
| 6,630,579 B2 | 10/2003 | Chari et al. |
| 6,703,020 B1 | 3/2004 | Thorpe et al. |
| 6,713,484 B2 | 3/2004 | Bridges et al. |
| 6,737,056 B1 | 5/2004 | Presta |
| 6,790,852 B2 | 9/2004 | Brandt et al. |
| 6,884,879 B1 | 5/2005 | Baca et al. |
| 6,900,221 B1 | 5/2005 | Norris et al. |
| 6,979,556 B2 | 12/2005 | Simmons et al. |
| 6,982,321 B2 | 1/2006 | Winter |
| 7,041,870 B2 | 5/2006 | Tomizuka et al. |
| 7,060,269 B1 | 6/2006 | Baca et al. |
| 7,087,409 B2 | 8/2006 | Barbas, III et al. |
| 7,087,613 B2 | 8/2006 | Norris et al. |
| 7,189,826 B2 | 3/2007 | Rodman |
| 7,214,775 B2 | 5/2007 | Hanai et al. |
| 7,220,410 B2 | 5/2007 | Kim et al. |
| 7,332,580 B2 | 2/2008 | Adams et al. |
| 7,332,581 B2 | 2/2008 | Presta |
| 7,371,826 B2 | 5/2008 | Presta |
| 7,408,043 B2 | 8/2008 | Chang et al. |
| 7,476,724 B2 | 1/2009 | Dennis et al. |
| 7,481,993 B2 | 1/2009 | Cyr |
| 7,491,829 B2 | 2/2009 | Laird et al. |
| 7,498,298 B2 | 3/2009 | Doronina et al. |
| 7,504,256 B1 | 3/2009 | Ogawa |
| 7,521,541 B2 | 4/2009 | Eigenbrot et al. |
| 7,527,791 B2 | 5/2009 | Adams et al. |
| 7,615,529 B2 | 11/2009 | Kong-Beltran et al. |
| RE41,065 E | 12/2009 | Schnur et al. |
| 7,642,228 B2 | 1/2010 | Carter et al. |
| 7,695,936 B2 | 4/2010 | Carter et al. |
| 7,718,174 B2 | 5/2010 | Chung et al. |
| 7,723,330 B2 | 5/2010 | Blake et al. |
| 7,892,550 B2 | 2/2011 | Dennis et al. |
| 7,932,026 B2 | 4/2011 | Seshagiri |
| 8,003,662 B2 | 8/2011 | Blake et al. |
| 8,093,011 B2 | 1/2012 | Haley et al. |
| 8,124,085 B2 | 2/2012 | Nielsen et al. |
| 8,232,053 B2 | 7/2012 | Seshagiri |
| 8,232,062 B2 | 7/2012 | Seshagiri |
| 8,313,913 B2 | 11/2012 | Naksmura et al. |
| 8,361,744 B2 | 1/2013 | Marrichi et al. |
| 8,536,118 B2 | 9/2013 | Kong-Betran et al. |
| 8,735,098 B2 | 5/2014 | Marrichi et al. |
| 9,213,031 B2 | 12/2015 | Lee et al. |
| 9,213,032 B2 | 12/2015 | Lee et al. |
| 9,487,589 B2 | 11/2016 | Demeule et al. |
| 2002/0055537 A1 | 5/2002 | Gerlach et al. |
| 2002/0164328 A1 | 11/2002 | Sinkawa et al. |
| 2003/0115614 A1 | 6/2003 | Kanda et al. |
| 2003/0125370 A1 | 7/2003 | Cui et al. |
| 2003/0157104 A1 | 8/2003 | Waksal |
| 2003/0157108 A1 | 8/2003 | Presta |
| 2003/0190317 A1 | 10/2003 | Baca et al. |
| 2003/0203409 A1 | 10/2003 | Kim |
| 2003/0206899 A1 | 11/2003 | Ferrara et al. |
| 2004/0093621 A1 | 5/2004 | Shitara et al. |
| 2004/0109865 A1 | 6/2004 | Niwa et al. |
| 2004/0110282 A1 | 6/2004 | Kanda et al. |
| 2004/0110704 A1 | 6/2004 | Yamane et al. |
| 2004/0110758 A1 | 6/2004 | Player et al. |
| 2004/0132140 A1 | 7/2004 | Satoh et al. |
| 2004/0198750 A1 | 10/2004 | Green et al. |
| 2004/0242603 A1 | 12/2004 | Fujiwawa et al. |
| 2004/0259150 A1 | 12/2004 | Nakamura et al. |
| 2005/0009840 A1 | 1/2005 | Cui et al. |
| 2005/0009845 A1 | 1/2005 | Caferro et al. |
| 2005/0014934 A1 | 1/2005 | Hinton et al. |
| 2005/0019327 A1 | 1/2005 | Kim et al. |
| 2005/0031613 A1 | 2/2005 | Nakamura et al. |
| 2005/0037431 A1 | 2/2005 | Kirchhofer et al. |
| 2005/0054019 A1 | 3/2005 | Michaud et al. |
| 2005/0075340 A1 | 4/2005 | Zhang et al. |
| 2005/0079574 A1 | 4/2005 | Bond |
| 2005/0090500 A1 | 4/2005 | Norris et al. |
| 2005/0101650 A1 | 5/2005 | Aronov et al. |
| 2005/0112126 A1 | 5/2005 | Baca et al. |
| 2005/0119455 A1 | 6/2005 | Fuh et al. |
| 2005/0123546 A1 | 6/2005 | Umana et al. |
| 2005/0148574 A1 | 7/2005 | Aronov et al. |
| 2005/0186208 A1 | 8/2005 | Fyfe et al. |
| 2005/0227324 A1 | 10/2005 | Huang et al. |
| 2005/0245547 A1 | 11/2005 | Kim et al. |
| 2005/0266000 A1 | 12/2005 | Bond et al. |
| 2005/0272083 A1 | 12/2005 | Seshagiri |
| 2005/0276805 A1 | 12/2005 | Hanai et al. |
| 2006/0009453 A1 | 1/2006 | Geuns-Meyer et al. |
| 2006/0009493 A1 | 1/2006 | Koenig et al. |
| 2006/0025576 A1 | 2/2006 | Miller et al. |
| 2006/0035278 A9 | 2/2006 | Kirhhofer et al. |
| 2006/0134104 A1 | 6/2006 | Dennis et al. |
| 2006/0148748 A1 | 7/2006 | Rabin et al. |
| 2006/0211060 A1 | 9/2006 | Haley et al. |
| 2006/0216288 A1 | 9/2006 | Chang |
| 2006/0270594 A1 | 11/2006 | Kong-Beltran et al. |
| 2006/0293235 A1 | 12/2006 | Kirhhofer et al. |
| 2007/0015244 A1 | 1/2007 | Simmons et al. |

(56) References Cited

U.S. PATENT DOCUMENTS

| | | |
|---|---|---|
| 2007/0061900 A1 | 3/2007 | Murphy et al. |
| 2007/0092520 A1 | 4/2007 | Dennis et al. |
| 2007/0098707 A1 | 5/2007 | Kong-Beltran et al. |
| 2007/0117126 A1 | 5/2007 | Sidu et al. |
| 2007/0128111 A1 | 6/2007 | Reilly et al. |
| 2007/0129301 A1 | 6/2007 | Kirchhofer et al. |
| 2007/0134759 A1 | 6/2007 | Nishiya et al. |
| 2007/0160598 A1 | 7/2007 | Dennis et al. |
| 2007/0212738 A1 | 9/2007 | Haley et al. |
| 2007/0237764 A1 | 10/2007 | Birtalan et al. |
| 2007/0238726 A1 | 10/2007 | Blake et al. |
| 2007/0292936 A1 | 12/2007 | Barthelemy et al. |
| 2008/0008701 A1 | 1/2008 | Harding et al. |
| 2008/0063641 A1 | 3/2008 | Huang et al. |
| 2008/0069820 A1 | 3/2008 | Fuh et al. |
| 2008/0241884 A1 | 10/2008 | Shitara et al. |
| 2008/0286825 A1 | 11/2008 | Bottaro et al. |
| 2008/0299120 A1 | 12/2008 | Miller et al. |
| 2009/0002360 A1 | 1/2009 | Chen et al. |
| 2009/0042906 A1 | 2/2009 | Huang et al. |
| 2009/0053737 A1 | 2/2009 | Cao et al. |
| 2009/0155807 A1 | 6/2009 | Yauch |
| 2009/0182127 A1 | 7/2009 | Kjaergaard et al. |
| 2009/0226443 A1 | 9/2009 | Filvaroff et al. |
| 2009/0226455 A1 | 9/2009 | Filvaroff |
| 2009/0246206 A1 | 10/2009 | Nielsen et al. |
| 2010/0016241 A1 | 1/2010 | Kong-Beltran et al. |
| 2010/0028337 A1 | 2/2010 | Kong-Beltran et al. |
| 2010/0040634 A1 | 2/2010 | Kirhhofer et al. |
| 2010/0055099 A1 | 3/2010 | Filvaroff et al. |
| 2010/0062441 A1 | 3/2010 | Salgia |
| 2010/0196265 A1 | 8/2010 | Adams et al. |
| 2010/0254988 A1 | 10/2010 | Bossenmaier et al. |
| 2010/0254989 A1 | 10/2010 | Bossenmaier et al. |
| 2010/0255010 A1 | 10/2010 | Fuh et al. |
| 2010/0256356 A1 | 10/2010 | Blake et al. |
| 2010/0297615 A1 | 11/2010 | Seshagiri |
| 2011/0053931 A1 | 3/2011 | Gaudino et al. |
| 2011/0104176 A1 | 5/2011 | Cheong et al. |
| 2011/0111408 A1 | 5/2011 | Marrichi et al. |
| 2011/0129481 A1 | 6/2011 | Cheong et al. |
| 2011/0130406 A1 | 6/2011 | DeMeese et al. |
| 2011/0177058 A1 | 7/2011 | Kirhhofer et al. |
| 2011/0229890 A1 | 9/2011 | Seshagiri |
| 2011/0262436 A1 | 10/2011 | Bender et al. |
| 2011/0280870 A1 | 11/2011 | Schwall et al. |
| 2011/0287003 A1 | 11/2011 | Patel et al. |
| 2011/0300146 A1 | 12/2011 | Dennis et al. |
| 2012/0004191 A1 | 1/2012 | Abbadessa et al. |
| 2012/0082662 A1 | 4/2012 | Dennis et al. |
| 2012/0082663 A1 | 4/2012 | Dennis et al. |
| 2012/0089541 A1 | 4/2012 | Patel et al. |
| 2012/0121596 A1 | 5/2012 | Fuh et al. |
| 2012/0149031 A1 | 6/2012 | Goetsch et al. |
| 2012/0157480 A1 | 6/2012 | Haley et al. |
| 2012/0171210 A1 | 7/2012 | Kong-Beltran et al. |
| 2012/0225870 A1 | 9/2012 | Janne et al. |
| 2013/0004484 A1 | 1/2013 | Demeule et al. |
| 2013/0078252 A1 | 3/2013 | Wilson et al. |
| 2013/0096280 A1 | 4/2013 | Marrichi et al. |
| 2013/0129718 A1 | 5/2013 | Wong et al. |
| 2014/0030259 A1 | 1/2014 | French |
| 2014/0037625 A1 | 2/2014 | Patel et al. |
| 2014/0200156 A1 | 7/2014 | Kim et al. |
| 2015/0050275 A1 | 2/2015 | Wong et al. |
| 2015/0056207 A1 | 2/2015 | Filvaroff et al. |
| 2015/0064191 A1 | 3/2015 | Demeule et al. |
| 2015/0125452 A1 | 5/2015 | Wilson et al. |

FOREIGN PATENT DOCUMENTS

| | | |
|---|---|---|
| EP | 0 131 424 A2 | 1/1985 |
| EP | 0 404 097 A2 | 12/1990 |
| EP | 0 567 585 A1 | 11/1993 |
| EP | 0 599 274 A1 | 6/1994 |
| EP | 0 659 439 A2 | 6/1995 |
| EP | 0 425 235 B1 | 9/1996 |
| EP | 0 666 868 B1 | 4/2002 |
| EP | 1 718 677 A2 | 11/2006 |
| EP | 1 773 885 A2 | 4/2007 |
| EP | 1 356 052 A2 | 8/2008 |
| JP | 3375970 B2 | 2/2003 |
| JP | 2004530419 A | 10/2004 |
| WO | WO-89/06692 A1 | 7/1989 |
| WO | WO-90/13563 A1 | 11/1990 |
| WO | WO-92/05184 A1 | 4/1992 |
| WO | WO-92/13097 A1 | 8/1992 |
| WO | WO-92/20792 A1 | 11/1992 |
| WO | WO-93/01161 A1 | 1/1993 |
| WO | WO-93/11971 A1 | 6/1993 |
| WO | WO-1993/11791 A1 | 6/1993 |
| WO | WO-93/15754 A1 | 8/1993 |
| WO | WO-93/16185 A2 | 8/1993 |
| WO | WO-93/23541 A1 | 11/1993 |
| WO | WO-93/23550 A2 | 11/1993 |
| WO | WO-94/04679 A1 | 3/1994 |
| WO | WO-94/06909 A2 | 3/1994 |
| WO | WO-94/10202 A1 | 5/1994 |
| WO | WO-94/11026 A2 | 5/1994 |
| WO | WO-94/11026 A3 | 5/1994 |
| WO | WO-94/29348 A2 | 12/1994 |
| WO | WO-94/29351 A2 | 12/1994 |
| WO | WO-95/01376 A1 | 1/1995 |
| WO | WO-93/08829 A1 | 5/1995 |
| WO | WO-95/27062 A1 | 10/1995 |
| WO | WO-96/27011 A1 | 9/1996 |
| WO | WO-96/30046 A1 | 10/1996 |
| WO | WO-96/33980 A1 | 10/1996 |
| WO | WO-96/38557 A1 | 12/1996 |
| WO | WO-96/40210 A1 | 12/1996 |
| WO | WO-97/02266 A1 | 1/1997 |
| WO | WO-97/30087 A1 | 8/1997 |
| WO | WO-97/44453 A1 | 11/1997 |
| WO | WO-98/07695 A1 | 2/1998 |
| WO | WO-98/14451 A1 | 4/1998 |
| WO | WO-98/45331 A2 | 10/1998 |
| WO | WO-98/45332 A2 | 10/1998 |
| WO | WO-98/50038 A1 | 11/1998 |
| WO | WO-98/50433 A2 | 11/1998 |
| WO | WO-98/58964 A1 | 12/1998 |
| WO | WO-99/09016 A1 | 2/1999 |
| WO | WO-99/19488 A1 | 4/1999 |
| WO | WO-99/22764 A1 | 5/1999 |
| WO | WO-99/24037 A1 | 5/1999 |
| WO | WO-99/35146 A1 | 7/1999 |
| WO | WO-99/51642 A1 | 10/1999 |
| WO | WO-99/57142 A2 | 11/1999 |
| WO | WO-99/60023 A1 | 11/1999 |
| WO | WO-00/61739 A1 | 10/2000 |
| WO | WO-01/29246 A1 | 4/2001 |
| WO | WO-01/32651 A1 | 5/2001 |
| WO | WO-01/34574 A1 | 5/2001 |
| WO | WO-02/11677 A2 | 2/2002 |
| WO | WO-02/31140 A1 | 4/2002 |
| WO | WO-2003/011878 A1 | 2/2003 |
| WO | WO-2003/013541 A1 | 2/2003 |
| WO | WO-2003/018771 A2 | 3/2003 |
| WO | WO-03/087026 A1 | 10/2003 |
| WO | WO-2003/084570 A1 | 10/2003 |
| WO | WO-2003/085107 A1 | 10/2003 |
| WO | WO-2003/085119 A1 | 10/2003 |
| WO | WO-03/097641 A2 | 11/2003 |
| WO | WO-2004/016769 A2 | 2/2004 |
| WO | WO-2004/056312 A2 | 7/2004 |
| WO | WO-2004/058820 A2 | 7/2004 |
| WO | WO-2004/072117 A2 | 8/2004 |
| WO | WO-2004/076412 A2 | 9/2004 |
| WO | WO-2004/087207 A2 | 10/2004 |
| WO | WO-2004/108766 A2 | 12/2004 |
| WO | WO-2005/004808 A2 | 1/2005 |
| WO | WO-2005/012359 A2 | 2/2005 |
| WO | WO-2005/016382 A1 | 2/2005 |
| WO | WO-2005/017107 A2 | 2/2005 |
| WO | WO-2005/030140 A2 | 4/2005 |

(56) References Cited

FOREIGN PATENT DOCUMENTS

| | | |
|---|---|---|
| WO | WO-2005/035586 A1 | 4/2005 |
| WO | WO-2005/035778 A1 | 4/2005 |
| WO | WO-2005/044853 A2 | 5/2005 |
| WO | WO-2005/053742 A1 | 6/2005 |
| WO | WO-2005/063816 A2 | 7/2005 |
| WO | WO-2005/070891 A2 | 8/2005 |
| WO | WO-2005/080393 A1 | 9/2005 |
| WO | WO-2005/117973 A2 | 12/2005 |
| WO | WO-2005/121125 A1 | 12/2005 |
| WO | 2006/0009360 | 1/2006 |
| WO | WO-2006/014325 A2 | 2/2006 |
| WO | WO-2006/015371 A2 | 2/2006 |
| WO | WO-2006/021881 A2 | 3/2006 |
| WO | WO-2006/021886 A1 | 3/2006 |
| WO | WO-2006/091209 A2 | 8/2006 |
| WO | WO-2006/104911 A2 | 10/2006 |
| WO | WO-2006/104912 A2 | 10/2006 |
| WO | WO-2006/108048 A1 | 10/2006 |
| WO | WO-2006/113767 A2 | 10/2006 |
| WO | WO-2007/006665 A1 | 1/2007 |
| WO | WO-2007/042289 A2 | 4/2007 |
| WO | WO-2007/066185 A2 | 6/2007 |
| WO | WO-2007/103308 A2 | 9/2007 |
| WO | WO-2007/106503 A2 | 9/2007 |
| WO | WO-2007/115049 A2 | 10/2007 |
| WO | WO-2007/126788 A2 | 11/2007 |
| WO | WO-2007/126799 A2 | 11/2007 |
| WO | WO-2007/143090 A2 | 12/2007 |
| WO | WO-2007/143098 A2 | 12/2007 |
| WO | WO-2008/077546 A1 | 7/2008 |
| WO | WO-2008/127707 A1 | 10/2008 |
| WO | WO-2008/127710 A2 | 10/2008 |
| WO | WO-2008/140493 A2 | 11/2008 |
| WO | WO-2009/002521 A2 | 12/2008 |
| WO | WO-2009/007427 A2 | 1/2009 |
| WO | WO-2009/012140 A2 | 1/2009 |
| WO | WO-2009/054939 A1 | 4/2009 |
| WO | WO-2009/089004 A1 | 7/2009 |
| WO | WO-2009/106566 A2 | 9/2009 |
| WO | WO-2009/111691 A2 | 9/2009 |
| WO | WO-2009/111707 A1 | 9/2009 |
| WO | WO-2009/126834 A2 | 10/2009 |
| WO | WO-2009/134776 A2 | 4/2010 |
| WO | WO-2010/039248 A1 | 4/2010 |
| WO | WO-2010/045344 A1 | 4/2010 |
| WO | WO-2010/045345 A2 | 4/2010 |
| WO | WO-2010/053717 A1 | 5/2010 |
| WO | WO-2010/059654 A1 | 5/2010 |
| WO | WO-2010/093789 A2 | 8/2010 |
| WO | WO-2010/115552 A1 | 10/2010 |
| WO | WO-2011/008990 A1 | 1/2011 |
| WO | WO-2011/020925 A1 | 2/2011 |
| WO | WO-2011/057120 A1 | 5/2011 |
| WO | WO-01/45746 A2 | 6/2011 |
| WO | WO-2011/143665 A1 | 11/2011 |
| WO | WO-2012/030896 A2 | 3/2012 |
| WO | WO-2012/031027 A1 | 3/2012 |
| WO | WO-2012031027 A1 * | 3/2012 ....... G01N 33/57423 |
| WO | WO-2013/036872 A1 | 3/2013 |
| WO | WO-2013/043715 A1 | 3/2013 |
| WO | WO-2014/066860 A2 | 5/2014 |
| WO | WO-2015/161885 A1 | 10/2015 |

OTHER PUBLICATIONS

Cappuzzo, F. et al. (May 4, 2005). "Epidermal Growth Factor Receptor Gene and Protein and Gefitinib Sensitivity in Non-Small-Cell Lung Cancer," *J. Natl. Can. Inst.* 97(7):643-655.

Cappuzzo, F. et al. (Apr. 1, 2009). "Increased MET Gene Copy Number Negatively Affects Survival of Surgically Resected Non-Small-Cell Lung Cancer Patients," *J. Clin. Oncol.* 27(10):1667-1674.

Dieffenbach, C.W. et al. (1995). "General Concepts for PCR Primer Design" in *PCR Primer, A Laboratory Manual*, Cold Spring Harbor Laboratory Press, New York, pp. 133-143.

Innis, M.A et al. (1990). "Optimization of PCRs" Chapter 1 in *PCR Protocols, A Guide to Methods and Applications*, Academic Press, pp. 5-11.

Iressa. (Jul. 22, 2009)."Product Information, Annex 1. Summary of Product Characteristics," 30 pages.

Kabat et al. (1991). "Sequences of Proteins of Immunological Interest," *Fifth Edition. NIH :Publication 91-3242*, Bethesda MD vols. 1-3, Table of Contents, 21 pages.

Kallioniemi, A. et al. (Oct. 30, 1992). "Comparative Genomic Hybridization for Molecular Cytogenetic Analysis of Solid Tumors," *Science* 258:818-821.

O'Sullivan, M.J. et al. (1981). Methods for the Preparation of Enzyme-Antibody Conjugates for Use in Enzyme Immunoassay, Chapter 9 in *Methods in Enzymology*, J. Langone & H. Van Vunakis, eds., Academic Press, New York, 73:147-166.

Parkin, D.M. (Mar./Apr. 2005). "Global Cancer Statistics, 2002," *CA Cancer J. Clin.* 55(2):74-108.

Plasterer, T.N. (1997). "Primerselect: Primer and probe design," Chapter 25 in S.R. Swindell, Humana Press, N.J. Totowa, N.J., *Methods in Molecular Biology* 70:291-302.

Rosen, S. et al. (2000). "Primer3 on the WWW for General Users and for Biologist Programmers," Chapter 20 in *Bioinformatics Methods and Protocols: Methods in Molecular Biology*. S. Misener and Stephen A. Krawetz, eds., Humana Press, Totowa, N.J., pp. 365-385.

Sandler, A. et al. (Dec. 14, 2006). "Paclitaxel—Carboplatin Alone or With Bevacizumab for Non-Small-Cell Lung Cancer," *N. Engl. J. Med.* 355(24):2542-2550.

Scagliotti, G.V. et al. (Jul. 20, 2008). "Phase III Study Comparing Cisplatin Plus Gemcitabine With Cisplatin Plus Pemetrexed in Chemotherapy-Naïve Patients With Advanced-Stage Non-Small-Cell Lung Cancer," *J. Clin. Oncol.* 26(21):3543-3551.

Sharma et al. (Dec. 2007). "Oncogene Addiction: Setting the Stage for Molecularly Targeted Cancer Therapy," *Gene Dev.* 21(24):3214-3231.

Varella-Garcia, M. et al. (2009). "EGFR Fluorescence in Situ Hybridisation Assay: Guidelines for Application to Non-Small-Cell Lung Cancer," *J. Clin. Pathol.* 62:970-977.

Vergani, E. et al. (Dec. 2011). "Identification of MET and SRC Activation in Melanoma Cell Lines Showing Primary Resistance to PLX4032," *Neoplasia* 13(12):1132-1142.

Vitetta, E.S. et al. Nov. 20, 1987). "Redesigning Nature's Poisons to Create Anti-Tumor Reagents," *Science* 238:1098-1104.

Extended European Search Report and Search Opinion dated Sep. 28, 2017, for European Patent Application No. 17183227.2 filed on Jul. 26, 2017, 9 pages.

International Search Report for PCT Application No. PCT/US01/49143, dated Jun. 13, 2003, filed on Dec. 20, 2001, 4 pages.

International Preliminary Examination Report for PCT Application No. PCT/US01/49143, completed on Aug. 18, 2003, filed on Dec. 20, 2001, 2 pages.

European Examination Report dated Nov. 3, 2017, for European Application No. 15716253.8, filed on Jul. 19, 2016, 8 pages.

International Search Report dated Jul. 13, 2015, for PCT Application No. PCT/US2015/022282, filed on Mar. 24, 2015, 6 pages.

Written Opinion dated Jul. 13, 2015, for PCT Application No. PCT/US2015/022282, filed on Mar. 24, 2015, 8 pages.

Achen et al. "Vascular Endothelial Growth Factor D (VEGF-D) is a Ligand for the Tyrosine Kinases VEGF Receptor 2 (Flk1) and VEGF Receptor 3 (Flt4)," *PNAS USA* 95:548-553, (1998).

Afanasieva et al. "Single-chain antibody and its derivatives directed against vascular endothelial growth factor: application for antiangiogenic gene therapy," *Gene. Ther.* 10(21):1850-1859, (2003).

Almagro et al. "Humanization of Antibodies," *Front. Biosci.* 13:1619-1633, (Jan. 1, 2008).

American Cancer Society "Cancer Facts & Figures," *2012 Atlanta: American Cancer Society* pp. 1-65 (2012).

American Cancer Society http://www.cancer.org/cancer/kidneycancer/index, (2015).

American Cancer Society http://www.cancer.org/cancer/stomachcancer/index, (2014).

Amler et al. "Exploratory Biomark Analyses from a Placebo-Controlled Phase II Study of (OAM4558g) of MetMAb in Combi-

(56) References Cited

OTHER PUBLICATIONS nation with Erlotinib in Patients with Advanced Non-Small-Cell Lung Cancer (NSCLC)," *Slides World Conference on Lung Cancer—14th*, (Jul. 3, 2011).
Angeloni et al. "The Soluble Sema Domain of the RON Receptor Inhibits Macrophage-Stimulating Protein-Induced Receptor Activation" *J. Biol. Chem.* 279(5):3726-3732, (Jan. 2004).
Antipenko et al. "Structure of the Semaphorin-3A Receptor Binding Module," *Neuron* 39:589-598, (Aug. 14, 2003).
Antonoff et al. "Non-small Cell Lung Cancer: the Era of Targeted Therapy" *Lung Cancer Targets and Therapy* 3:31-41, ( 2012).
Arie et al. "Chaperone Function of FkpA, a Heat Shock Prolyl Isomerase, in the Periplasm of *Escherichia coli*" *Mol. Microbiol.* 39(1):199-210, ( 2001).
Arqule and Daiichi "Announce Discontinuation of Phase 3 MAR-QUEE Clinical Trial in Non-Small Cell Lung Cell Lung Cancer," *Press Release of ArQule and Daiichi* (Oct. 2, 2012).
Armstrong et al. "Validation of the M.D. Anderson Symptom Inventory Brain Tumor Module (MDASI-BT)," *J. Neuro-Oncology* 80(1):27-35, (Oct. 2006).
Arteaga et al. "HER3 and Mutant EGFR Meet MET," *Nat. Med.* 13(6):675-7, (Jun. 2007).
Asami et al. "Purification and Characterization of Hepatocyte Growth Factor from Injured Liver of Carbon Tetrachloride-Treated Rats," *J. Biol. Chem.* 109(1):8-13, (Jan. 1991).
Atwell et al. "Stable Heterodimers from Remodeling the Domain Interface of a Homodimer Using a Phage Display Library," *J. Mol. Biol.* 270(1):26-35, ( 1997).
Ausubel et al. "Short Protocols in Molecular Biology," *Current Protocols of Molecular Biology*, John Wiley and Sons (1995).
Avastin Prescribing Information (2004).
Baca et al. "Antibody Humanization Using Monovalent Phage Display," *J. Biol. Chem.* 272(16):10678-10684, (Feb. 7, 1997).
Bachleitmer-Hoffmann et al. "HER Kinase Activation Confers Resistance to MET Tyrosine Kinase Inhibition in MET Oncogene-Addicted Gastric Cancer Cells," *Mol. Cancer Ther.* 7(11):3499-3508, (Nov. 2008).
Bai et al., "Population Pharmacokinetic Analysis from Phase I and Phase II Studies of the Humanized Monovalent Antibody MetMAb in Patients with Advanced Solid Tumors," *Poster American Society of Clinical Oncology 47th Annual Meeting (ASCO 2011)*, (Jun. 3, 2011).
Barbas et al. "In Vitro Evolution of a Neutralizing Human Antibody to Human Immunodeficiency Virus Type 1 to Enhance Affinity and Broaden Strain Cross-Reactivity," *Proc. Natl. Acad. Sci. USA* 91:3809-3813, (Apr. 1994).
Bardelli et al. "Gab1 Coupling to the HGF/Met Receptor Multifunctional Docking Site Requires Binding of Grb2 and Correlates with the Transforming Potential," *Oncogene* 15:3103-3111, (1997).
Bean et al. "MET Amplification Occurs with or without T790M Mutations in EGFR Mutant Lung Tumors with Acquired Resistance to Gefitinib or Erlotinib," *Proc. Natl. Acad. Sci. USA* 104(52):20932-20937, (Dec. 2007).
Bellusci et al. *Oncogene* 9(4):1091-1099, (Apr. 1994).
Bendell et al. "A Randomized, Double-Blind, Phase II Study of First-Line FOLFOX Plus Bevacizumab with Onartuzumab Versus Placebo in Patients with Metastatic Colorectal Cancer (mCRC)," Poster 663/D5 Sep. 2011-Nov. 2012, *Gastrointestinal Cancer Symposium—2015 / ASCO-GI*, 1 page, (Jan. 15, 2015).
Bertotti et al. "Tyrosine Kinase Signal Specificity: Lessons from the HGF Receptor," *Trends Biochem. Sci.* 28(10):527-533, (Oct. 2003).
Bhargava et al. "Scatter Factor and Hepatocyte Growth Factor: Activities, Properties, and Mechanism," *Cell Growth Differ.* 3(1):11-20, (Jan. 1992).
Bianchi et al. "Malignant Mesothelioma: Global Incidence and Relationship with Asbestos," *Industrial Health* 45:379-387, (2007).
Birchmeier et al. "Met, Metastasis, Motility and More," *Nat. Rev. Mol. Cell Bio.* 4:915-925, (Dec. 2003).

Bladt et al. "Essential Role for the C-Met Receptor in the Migration of Myogenic Precursor Cell into the Limb Bud," *Nature* 376:768-771, (Aug. 31, 1995).
Blechman et al. "The Fourth Immunoglobulin Domain of the Stem Cell Factor Receptor Couples Ligand Binding to Signal Transduction," *Cell* 80:103-113, (Jan. 13, 1995).
Bloom et al. "Intrachain Disulfide Bond in the Core Hinge Region of Human IgG4," *Protein Sci.* 6L407-415, (1997).
Blumenschein et al. "Targeting the Hepatocyte Growth Factor—cMET Axis in Cancer Therapy,", *J Clin Oncol.* 30(26):3287-3296, (2012).
Boerner et al. "Production of Antigen-Specific Human Monoclonal Antibodies from in Vitro-Primed Human Splenocytes," *The Journal of Immunology* 147:86-95, (Jul. 1, 1991).
Boix et al. "C-Met mRNA Overexpression in Human Hepatocellular Carcinoma," *Hepatology* 19(1):88-91, (Jan. 1994).
Bolt et al. "The Generation of a Humanized, Non-Mitogenic CD3 Monoclonal Antibody Which Retains in Vitro Immunosuppressive Properties," *Eur. J. Immunol.* 23:403-411, (1993).
Bonine-Summers et al., "Epidermal Growth Factor Receptor Plays a Significant Role in Hepatocyte Growth Factor Mediated Biological Responses in Mammary Epithelial Cells," *Cancer Biology & Therapy* (e1-e10) 6(4):561-570, (Apr. 2007).
Bothmann and Pluckthun "The Periplasmic *Escherichia coli* Peptidylprolyl Cis, Trans-Isomerase FkpA," *J. Biol. Chem.* 275(22):17100-17105, (Jun. 2000).
Bottaro et al. "Identification of the Hepatocyte Growth Factor Receptor as the C-Met Proto-Oncogene Product," *Science* 251:802-804, (Feb. 15, 1991).
Brennan et al. "Preparation of Bispecific Antibodies by Chemical Recombination of Monoclonal $G_1$ Fragments," *Science* 229:81-83, (Jul. 5, 1985).
Brocks et al. "A TNF Receptor Antagonistic scFv, Which is Not Secreted in Mammalian Cells, is Expressed as a Soluble Mono- and Bivalent scFv Derivative in Insect Cells," *Immunotechnology* 3(3):173-184, (Oct. 1997).
Brodeur et al. "Monoclonal Antibody Production Techniques and Applications," *New York: Marcel Dekker, Inc.* pp. 51-63 (1987).
Bruggemann et al. "Designer Mice" The Production of Human Antibody Repertoires in Transgenic Animals, *Year Immunol.* 7:33-40, (1993).
Buck et al. "Inactivation of Akt by the Epidermal Growth Factor Receptor Inhibitor Erlotinib is Mediated by HER-3 in Pancreatic and Colorectal Tumor Cell Lines and Contributes to Erlotinib Sensitivity," *Mol. Cancer Ther.* 5(8):2051-2059, (Aug. 2006).
Bulgaru et al. "Erlotinib (Taraceva): a Promising Drug Targeting Epidermal Growth Factor Tyrosine Kinase," *Expert Rev Anticancer Ther.* 3(3):269-79, (Jun. 2003).
Bussolino et al. "Hepatocyte Growth Factor is a Potent Angiogenic Factor Which Stimulates Endothelial Cell Motility and Growth," *J. Cell Biol.* 119(3):629-641, (Nov. 1992).
Carter et al., "High level *Escherichia coli* Expression and Production of a Bivalent Humanized Antibody Fragment," *Bio-Technol* 10(2):163-167, (Feb. 1992).
Carter et al. "Humanization of an Anti-p185$^{HER2}$ Antibody for Human Cancer Therapy," *Proc. Natl. Acad Sci. USA* 89:4285-4289, (May 1992).
Catenacci et al. "Durable Complete Response of Metastatic Gastric Cancer with Anti-Met Therapy Followed by Resistance at Recurrence," *Cancer Discovery* 1(7):573-579, (2011).
CBTRUS http://cbtrus.org (2015).
Chamow et al. "A Humanized, Bispecific Immunoadhesin-Antibody That Retargets CD3:+ Effectors to Kill HIV-1-Infected Cells," *J. Immunol.* 153(9):4268-4280, (Nov. 1, 1994).
Chan et al. "Hepatocyte Growth Factor-Scatter Factor (HGF-SF) and the C-Met Receptor Isoforms of human HGF and their biological activities," *I.D. Goldberg and E.M. Rosen eds.*, Basel:Birkhauser Verlag pp. 67-79, (1993).
Chan et al. "Identification of a Competitive HGF Antagonist Encoded by an Alternative Transcript," *Science* 254(5036):1382-1385, (Nov. 29, 1991).

(56) References Cited

OTHER PUBLICATIONS

Chari et al. "Immunoconjugates Containing Novel Maytansinoids: Promising Anticancer Drugs," *Cancer Res.* 52:127-131, (Jan. 1, 1992).
Chen et al., "Chaperone Activity of DsbC*," *J. Biol. Chem.* 274(28):19601-19605, (Jul. 1999).
Chothia et al. "Canonical Structures for the Hypervariable Regions of Immunoglobulins," *J. Mol. Biol.* 196:901-917, (1987).
Chothia et al. "Domain Association in Immunoglobulin Molecules. The Packing of Variable Domains," *J. Mol. Biol.* 186(3):651-663, (Dec. 5, 1985).
Christensen et al. "Plasma Vascular Endothelial Growth Factor and Interleukin-8 as Biomarkers of Antitumor Efficacy of a Prototypical erbB Family Tyrosine Kinase Inhibitor," *Mol. Cancer Ther.* 4(6):938-947, (2005).
Christensen et al. "A Selective Small Molecule Inhibitor of C-Met Kinase Inhibits C-Met-Dependent Phenotypes in Vitro and Exhibits Cytoreductive Antitumor Activity in Vivo," *Cancer Research* 63(21):7345-7355, (Nov. 1, 2003).
Ciardiello et al. "Antitumor Effect and Potentiation of Cytotoxic Drugs Activity in Human Cancer Cells by ZD-1839 (IRESSA), an Epidermal Growth Factor Receptor-Selective Tyrosine Kinase Inhibitor" *Clin. Cancer Res.* 6(5):2053-63, (May 2000).
Ciardiello et al. "Interaction Between the Epidermal Growth Factor Receptor (EGFR) and the Vascular Endothelial Growth Factor (VEGF) Pathways: A Rational Approach for Multi-Target Anticancer Therapy," *Ann. Oncol.* 17(7s):vii 109-114, (2006).
Clackson et al. "Making Antibody Fragments Using Phage Display Libraries," *Nature* 352: 624-628, (Aug. 15, 1991).
Clark et al. "The Improved Lytic Function and in Vivo Efficacy of Monovalent Monoclonal CD3 Antibodies," *Eur. J. Immunol.* 19:381-388, (1989).
Cleeland et al. "Assessing Symptom Distress in Cancer Patients: The M.D. Anderson Symptom Inventory," *Cancer* 89(7):1634-1646, (Oct. 1, 2000).
Cloughesy et al. "Phase II Study of Onartuzumab Plus Bevacizumab Versus Placebo Plus Bevacizumab in Patients with Recurrent Glioblastoma," *Society for Neuro-Oncology—19th Annual Meeting / SNO*, 11 pages, (Nov. 13, 2014).
Clynes et al. "Fc Receptors are Required in Passive and Active Immunity to Melanoma," *P. Natl. Acad. Sci. USA* 95(2):652-656, (Jan. 1998).
Cobbold and Waldman "Therapeutic Potential of Monovalent Monoclonal Antibodies," *Nature* 308(Suppl. Mar. 29-Apr. 4):460-462, (1984).
Cole et al. "Monoclonal Antibodies and Cancer Therapy," *Alan R. Liss* p. 77-96, (1985).
Coligan et al. "Current Protocols in Immunology, vols. I and 2 Ed.," *John Wiley & Sons, Inc.* 1-3.12.14,(1991).
Coltella et al. "Role of the MET/HGF Receptor in Proliferation and Invasive Behavior of Osteosarcoma," *Faseb. J.* 17:1162-1164, (Jun. 2003).
Comoglio, P. "Hepatocyte Growth Factor-Scatter Factor (HGF-SF) and the C-Met Receptor Structure, Biosynthesis and Biochemical Properties of the HGF Receptor in Normal and Malignant Cells," *I.D. Goldberg and E.M. Rosen eds.*, Basel:Birkhauser Verlag. pp. 131-165, (1993).
Comoglio "The HGF Receptor and its Ligand: Structure, Signal Transduction and Biology," *Cell Biol. Int.* (Abstract S15-3), 18(5):375, (1994).
Cooper et al. "Amplification and Overexpression of the MET Gene in Spontaneously Transformed NIH3T3 Mouse Fibroblasts," *EMBO. J.* 5(10):2623-2628, (Oct. 1986).
Cooper et al. "Molecular Cloning of a New Transforming Gene from a Chemically Transformed Cell Line," *Nature* 311(5981):29-33, (Sep. 6, 1984).
Crawford et al. "A Novel B-RAF Inhibitor Blocks Interleukin-8 (IL-8) Synthesis in Human Melanoma Xenografts, Revealing IL-8 as a Potential Pharmacodynamic Biomarker," *Mol. Cancer Ther.* 7(3):492-499, (2008).

Crepaldi et al. "Targeting of the SF/HGF Receptor to the Basolateral Domain of Polarized Epithelial Cells," *J. Cell Biol.* 125(2):313-320, (Apr. 1994).
Cronin et al. "Measurement of Gene Expression in Archival Paraffin-Embedded Tissues," *Am. J. Pathol.* 164(1):35-42, (Jan. 2004).
Cunningham et al. MetGastric: A Randomized Phase III Study of Onartuzumab (MetMAb) in Combination with MFOLFOX6 in Patients with Metastatic (HER2−) Negative and (MET +) Positive Adenocarcinoma of the Stomach or Gastroesophageal Junction (GEC)* TPS4155 *American Society of Clinical Oncology—51st Annual Meeting / ASCO* (May 29, 2015).
Dall' Acqua et al. "Antibody Humanization by Framework Shuffling," *Methods* 36:43-60 (2005).
Dancey et al., "Issues and Progress with Protein Kinase Inhibitors for Cancer Treatment," *Nat Rev Drug Discov.* 2(4):296-313, (2003).
Danikovitch-Miagkova and Zbar "Dysregulation of Met Receptor Tyrosine Kinase Activity in Invasive Tumors," *J. Clin. Invest.* 109(7):863-867, (Apr. 2002).
David and Reisfeld "Protein Iodination with Solid State Lactoperoxidase," *Biochemistry—US* 13(5):1014-1021, (Feb. 26, 1974).
De Andres et al. "Improved Method for mRNA Extraction from Paraffin-Embedded Tissues," *Biotechniques* 18(1):42-44 (1995).
De Bono et al. "The ErbB Receptor Family: A Therapeutic Target for Cancer," *Trends Mol. Med.* 8:S19-26, (2002).
De Sauvage et al. "Stimulation of Megakaryocytopoiesis and Thrombopoiesis by the c-Mpl Ligand," *Nature* 369(6481):533-538, (Jun. 16, 1994).
De Vries et al. "The fms-Like Tyrosine Kinase, a Receptor for Vascular Endothelial Growth Factor," *Science* 255:989-991, (1992).
Defrances et al. "The Presence of Hepatocyte Growth Factor in the Developing Rat," *Development* 116(2):387-395, (Oct. 1992).
Dennis et al. "Albumin Binding as a General Strategy for Improving the Pharmacokinetics of Proteins," *J. Biol. Chem.* 277(38):35035-35043, (Sep. 20, 2002).
Di Renzo et al. "Overexpression and Amplification of the Met/HGF Receptor Gene During the Progression of Colorectal Cancer," *Clin. Cancer Res.* 1:147-154, (Feb. 1995).
Di Renzo et al. "Overexpression of the c-MET/HGF Receptor Gene in Human Thyroid Carcinomas," *Oncogene* 7(12):2549-2553, (Dec. 1992).
Di Renzo et al. "Selective Expression of the Met/HGF Receptor in Human Central Nervous System Microglia," *Oncogene* 8:219-222, (1993).
Dingemans et al., "First-line Erlotinib and Bevacizumab in Patients with Locally Advanced and/or Metastatic Non-Small-Cell Lung Cancer: Phase II Study Including Molecular Imaging," *Annals of Oncology* 22:559-66, ( 2011).
Dubowchik et al. "Doxorubicin Immunoconjugates Containing Bivalent, Lysosomally-Cleavable Dipeptide Linkages," *Bioorg. & Med. Chem. Letters* 12:1529-1532. (Feb. 15, 2002).
Duncan and Winter "The Binding Site for Clq on IgG," *Nature* 332:738-740, (Apr. 21, 1988).
Eder et al., "Novel Therapeutic inhibitors of the c-Met Signaling Pathway in Cancer" *Clinical Cancer Research*, 15:2207-2214, (2009).
Elliot et al. "The Role of Hepatocyte Growth Factor (Scatter Factor) in Epithelial-Mesenchymal Transition and Breast Cancer," *Can. J. Physiol. Pharmacol.* 80:91-102, (Feb. 2002).
Engelman et al. "MET Amplification Leads to Gefitinib Resistance in Lung Cancer by Activating ERBB3 Signaling," *Science* 316:1039-1043, (May 2007).
Exelixis Press Release, "Exelixis Initiates Phase ½ Trial of XL184 in Patients With Non-Small Cell Lung Cancer," (printed on Dec. 22, 2010) 2 pages, (Jan. 7, 2008).
Fan et al. "Blockade of Epidermal Growth Factor Receptor Function by Bivalent and Monovalent Fragments of 225 Anti-Epidermal Growth Factor Receptor Monoclonal Antibodies," *Cancer Res.* 53(18):4322-4328, (Sep. 15, 1993).
Fellouse et al. "Synthetic Antibodies from a Four-Amino-Acid Code: A Dominant Role for Tyrosine in Antigen Recognition," *Proc. Natl. Acad. Sci. USA* 101(34):12467-12472, (Aug. 24, 2004).

(56) References Cited

OTHER PUBLICATIONS

Fendly et al. "Characterization of Murine Monoclonal Antibodies Reactive to Either the Human Epidermal Growth Factor Receptor or HER2/neu Gene Product," *Cancer Res.* 50:1550-1558, (Mar. 1, 1990).

Feng et al. "Anti-MET Targeted Therapy Has Come of Age: The First Durable Complete Response with MetMAb in Metastatic Gastric Cancer," *Cancer Discovery* 1(7):550-4, (2011).

Ferguson et al. "EGF Activates its Receptor by Removing Interactions that Autoinhibit Ectodomain Dimerization," *Mol. Cell* 11:507-517, (Feb. 2003).

Ferrara and Davis-Smyth "The Biology of Vascular Endothelial Growth Factor," *Endocrine Reviews* 18(1):4-25, (Feb. 1987).

Ferrara "Vascular Endothelial Growth Factor," *Laboratory Investigation* 72(6):615-618, (1995).

Ferrara and Alitalo "Clinical Applications of Angiogenic Growth Factors and Their Inhibitors," *Nature Medicine* 5(12):1359-1364, (Dec. 1999).

Ferrone et al. "Handbook of Monoclonal Antibodies," *Park Ridge, NJ:Noyes Publications*, Chapter 22 and pp. 293-359, (1985).

Fischer et al., "Reactive Oxygen Species Mediate Met Receptor Transactivation by G Protein-Coupled Receptors and the Epidermal Growth Factor Receptor in Human Carcinoma Cells," *J. Biol. Chem.* 279(28):28970-28978, (Jul. 2004).

Fitzgerald et al. "Characterization of V3 Loop-Pseudomonas Exotoxin Chimeras. Candidate Vaccines for Human Immunodeficiency Virus-1," *J. Biol. Chem.* 273(16):9951-9958, (Apr. 1998).

Furge et al. "Met Receptor Tyrosine Kinase: Enhanced Signaling Through Adapter Proteins," *Oncogene* 19:5582-5589, (2000).

Gallop et al. "Applications of Combinatorial Technologies to Drug Discovery Background and Peptide Combinatorial Libraries," *J. Med. Chem.* 37(9):1233-1251, (Apr. 29, 1994).

Garrett et al. "Crystal Structure of a Truncated Epidermal Growth Factor Receptor Extracellular Domain Bound to Transforming Growth Factor Alpha," *Cell* 110:763-773, (Sep. 20, 2002).

Gazzano-Santoro et al. "A Non-Radioactive Complement-Dependent Cytotoxicity Assay for Anti-CD20 Monoclonal Antibody," *J. Immunol. Methods* 202(2):163-171, (Mar. 28, 1997).

Gherardi et al. "Functional Map and Domain Structure of MET, the Product of the C-Met Protooncogene and Receptor for Hepatocyte Growth Factor/Scatter Factor," *P. Natl. Acad. Sci. USA* 100(21):12039-12044, (Oct. 14, 2003).

Giaccone et al. "Gefitinib in Combination with Gemcitabine and Cisplatin in Advanced Non-Small-Cell Lung Cancer: A Phase III Trial-INTACT 1," *J. of Clinical Oncology* 22(5):777-784, (2004).

Giancotti et al. "Integrin Signaling," *Science* 285:1028-1032, (Aug. 13, 1999).

Giordano et al. "Biosynthesis of the Protein Encoded by the C-MET Proto-Oncogene," *Oncogene* 4:1383-1388, (1989).

Giordano et al. "Different Point Mutations in the MET Oncogene Elicit Distinct Biological Properties," *Faseb. J.* 14:339-406, (Feb. 2000).

Giordano et al. "The Semaphorin 4D Receptor Controls Invasive Growth by Coupling with MET," *Nat. Cell Biol.* 4:720-724, (Sep. 2002).

Giordano et al. "Transfer of Motogenic and Invasive Response to Scatter Factor/Hepatocyte Growth Factor by Transfection of Human met Protooncogene," *P. Natl. Acad. Sci. USA* 90(2):649-653, (Jan. 15, 1993).

Giordano et al. "Tyrosine Kinase Receptor Indistinguishable from the C-Met Protein," *Nature* 339(6220):155-156, (May 11, 1989).

Glennie and Stevenson "Univalent Antibodies Kill Tumour Cells in Vitro and in Vivo," *Nature* 295:712-714, (1982).

Godfrey et al. "Quantitative mRNA Expression Analysis from Formalin-Fixed, Paraffin-Embedded Tissues Using 5' Nuclease Quantitative Reverse Transcription-Polymerase Chain Reaction," *J. Mol. Diagnostics* 2(2):84-91, (2000).

Goding Monoclonal Antibodies: Principles and Practice "Production and Application of Monoclonal Antibodies in Cell Biology, Biochemistry, and Immunology," *Academic Press*. pp. 56-103, (1986).

Goetsch et al., "Selection Criteria for c-Met-Targeted Therapies: Emerging Evidence for Biomarkers," *Biomarkers Med.* 4(1):149-70, (2010).

Gohda et al. "Purification and Partial Characterization of Hepatocyte Growth Factor from Plasma of a Patient with Fulminant Hepatic Failure," *J. Clin. Invest.* 81(2):414-419, (Feb. 1988).

Gorman, C. "DNA Cloning: A Practical Approach High Efficiency Gene Transfer into Mammalian Cells," Glover, D.M., ed, Washington D.C.:*IRL Press* 2:143-190, (1985).

Griffiths et al. "Human Anti-Self Antibodies with High Specificity from Phage Display Libraries," *EMBO J*, 12(2):725-734 (1993).

Gruber et al. "Efficient Tumor Cell Lysis Mediated by a Bispecific Single Chain Antibody Expressed in *Escherichia coli*," *J. Immunol.*,152:5368-5374, (1994).

Grunwald et al. "Developing Inhibitors of the Epidermal Growth Factor Receptor for Cancer Treatment," *J Natl Cancer Inst.* 95(12):851-867, (Jun. 2003).

Guidance for Industry Clinical Trial Endpoints for the Approval of Non-Small Cell Lung Cancer Drugs and Biologics. U.S. Department of Health and Human Services; Food and Drug Administration; Center for Drug Evaluation and Research (CDER): Center for Biologics Evaluation and Research (CBER) (Jun. 2011).

Guix et al. "Acquired Resistance to EGFR Tyrosine Kinase Inhibitors in Cancer Cells is Mediated by Loss of IGF-Binding Proteins," *J. Clin. Invest.* 118(7):2609-2619, (Jul. 2008).

Guo et al. "Signaling Networks Assembled by Oncogenic EGFR and c-MET," *P. Natl. Acad. Sci. USA* 105(2):692-697, (Jan. 2008).

Guyer et al. "Immunoglobulin Binding by Mouse Intestinal Epithelial Cell Receptors," *J. Immunol.* 117:587-593, (1976).

Hahn et al. "Pilin-Based Anti-Pseudomonas Vaccines: Latest Developments and Perspectives," *Behring Ins. Mitt.* 98:315-325, (Feb. 1997).

Hainsworth et al. "A Phase III, Multicenter, Placebo-Controlled, Double-Blind, Randomized Clinical Trial to Evaluate the Efficacy of Bevacizumb (Avastin) in Combination with Erlotinib (Tarceva) Compared with Erlotinib Alone for Treatment of Advanced Non-Small-Cell Lung Cancer after Failure of Standard First-Line Chemotherapy (BETA)," *J. of Thoracic Oncology* 3(11 Suppl 4), (2008).

Hakimi et al. "Reduced Immunogenicity and Improved Pharmacokinetics of Humanized Anti-Tac in Cynomolgus Monkeys," *J. Immunol.* 147(4):1352-1359, (Aug. 15, 1991).

Hammanoue et al. "Neurotrophic Effect of Hepatocyte Growth Factor on Central Nervous System in Vitro," *J. Neurosci. Res.* 43:554-564, (1996).

Han et al. "Characterization of the DNF15S2 Locus on Human Chromosome 3: Identification of a Gene Coding for Four Kringle Domains with Homology to Hepatocyte Growth Factor," *Biochemistry—US* 30(40):9768-9780, (Oct. 8, 1991).

Hara et al. "Overproduction of Penicillin-Binding Protein 7 Suppresses Thermosensitive Growth Defect at Low Osmolarity Due to an spr Mutation of *Escherichia coli*," *Microb. Drug Resist.* 2(1):63-72, (1996).

Harris et al. "Therapeutic Antibodies—The Coming of Age," *Trends Biotechnol.* 11(2):42-44, (Feb. 1993).

Hartmann et al. "A Functional Domain in the Heavy Chain of Scatter Factor/Hepatocyte Growth Factor Binds the c-Met Receptor and Induces Cell Dissociation but Not Mitogenesis," *P. Natl. Acad. Sci. USA* 89(23):11574-11578, (Dec. 1, 1992).

Hartmann et al. "The Motility Signal of Scatter Factor/Hepatocyte Growth Factor Mediated Through the Receptor Tyrosine Kinase Met Requires Intracellular Action of Ras," *J. Biol. Chem.* 269(35):21936-21939, (Sep. 2, 1994).

Hawkins et al. "Selection of Phage Antibodies by Binding Affinity Mimicking Affinity Maturation," *J. Mol. Biol.* 226:889-896, (1992).

Heid et al. "Real Time Quantitative PCR," *Genome Research* 6:986-994. (1996).

(56) References Cited

OTHER PUBLICATIONS

Herbst et al. "IMC-C225, An Anti-Epidermal Growth Factor Receptor Monoclonal Antibody, for Treatment of Head and Neck Cancer," *Expert Opin. Biol. Ther.* 1(4):719-32, (Jul. 2001).

Herbst et al. "Gefitinib in Combination with Paclitaxel and Carboplatin in Advanced Non-Small-Cell Lung Cancer: A Phase III Trial-INTACT 2," *J. of Clinical Oncology* 22(5):785-794, (2004).

Hertle et al. "Dual-Function Vaccine for Pseudomonas Aeruginosa: Characterization of Chimeric Exotoxin A-Pilin Protein," *Infect. Immun.* 69(11):6962-6969, (Nov. 2001).

Hinman et al. "Preparation and Characterization of Monoclonal Antibody Conjugates of the Calicheamicins: A Novel and Potent Family of Antitumor Antibiotics," *Cancer Res.* 53:3336-3342 (Jul. 15, 1993).

Hirsch et al. "Epidermal Growth Factor Receptor Immunohistochemistry," *Cancer* 112:1114-1121, (2008).

Hirsch et al. "Efficacy and Safety Results from a Phase II, Placebo-Controlled Study of Onartuzumab Plus First-Line Platinum-Doublet Chemotherapy in Advanced Squamous-Cell Non-Small-Cell Lung Cancer (sq NSCLC)," *176 Chicago Multidisciplinary Symposium in Thoracic Oncology*, Chicago, USA, 30-Oct.-1, 1 page, (Nov. 2014).

Hod "A Simplified Ribonuclease Protection Assay," *Biotechniques* 13:852-854, (1992).

Hollinger et al. "'Diabodies': Small Bivalent and Bispecific Antibody Fragments," *Proc. Natl. Acad. Sci. USA* 90:6444-6448, (Jul. 1993).

Hoogenboom et al. "Overview of Antibody Phage-Display Technology and Its Applications," *Methods in Molecular Biology* (O'Brien et al., ed., Human Press, Totowa, NJ) 178:1-37, (2001).

Hoogenboom and Winter "By-Passing Immunisation: Human Antibodies from Synthetic Repertoires of Germline VH Gene Segments Rearranged in Vitro," *J. Mol. Biol.* 227:381-388, (Sep. 20, 1992).

Houck et al. "The Vascular Endothelial Growth Factor Family: Identification of a Fourth Molecular Species and Characterization of Alternative Splicing of RNA," *Mol. Endocrin.* 5(12):1806-1814, (1991).

Huang et al. "Quantitative Analysis of EGFR Viii Cellular Signaling Networks Reveals a Combinatorial Therapeutic Strategy for Glioblastoma," *Proc. Natl. Acad. Sci. USA* 104(31):12867-12872, (Jul. 2007).

Hudson et al. "Engineered Antibodies," *Nat. Med.* 9(1):129-134, (Jan. 2003).

Humphreys et al. "Formation of dimeric Fabs in *Escherichia coli*: Effect of Hinge Size and Isotype, Presence of Interchain Disulphide Bond, Fab' Expression Levels, Tail Piece Sequences and Growth Conditions," *J. Immunol. Methods* 209(2):193-202, (Dec. 1, 1997).

Hunter et al. "Preparation of Iodine-131 Labelled Human Growth Hormone of High Specific Activity," *Nature* 194(4827):495-496, (May 5, 1962).

Idusogie et al. "Mapping of the C1q Binding Site on Rituxan, a Chimeric Antibody with a Human IgG1 Fc," *J. Immunol.* 164:4178-4184, (2000).

Igawa et al. "Hepatocyte Growth Factor is a Potent Mitogen for Cultured Rabbit Renal Tubular Epithelial Cells," *Biochem. Biph. Res. Co.* 174(2):831-838, (Jan. 31, 1991).

Iyer et al. "Structure, Tissue-Specific Expression, and Transforming Activity of the Mouse Met Protooncogene," *Cell Growth Differ.* 1(2):87-95, (Feb. 1990).

Jackson et al. "In Vitro Antibody Maturation. Improvement of a High Affinity, Neutralizing Antibody Against IL-1 Beta," *J. Immunol.* 154(7):3310-3319, (Apr. 1, 1995).

Jaffers et al. "Monoclonal Antibody Therapy, Anti-Idiotypic and Non-Anti-Idiotypic Antibodies to OKT3 Arising Despite Intense Immunosuppression," *Transplantation* 41(5):572-578, (May 1986).

Jakobovits et al. "Analysis of Homozygous Mutant Chimeric Mice: Deletion of the Immunoglobulin Heavy-Chain Joining Region blocks B-Cell Development and Antibody Production," *Proc. Natl. Acad. Sci. USA* 90:2551-2555, (Mar. 1993).

Jakobovits et al. "Germ-Line Transmission and Expression of a Human-Derived Yeast Artificial Chromosome," *Nature* 362:255-258, (Mar. 18, 1993).

Jeffers et al. "Activating Mutations for the Met Tyrosine Kinase Receptor in Human Cancer,: *Proc. Natl. Acad. Sci. USA* 94:11445-11450, (Oct. 1997).

Jeffers et al. "Enhanced Tumorigencity and Invasion-Metastasis by Hepatocyte Growth Factor/Scatter Factor-met Signaling in Human Cells Concomitant with Induction of the Urokinase Proteolysis Network," *Mol. Cell Biol.* 16(3):1115-1125, (Mar. 1996).

Jeffrey et al. "Dipeptide-Based Highly Potent Doxorubicin Antibody Conjugates," *Bioorganic & Med. Chem. Letters* 16:358-362, (Nov. 3, 2006).

Jeltsch et al. "Hyperplasia of Lymphatic Vessels in VEGF-C Transgenic Mice," *Science* 276:1423-1425, (1997).

Jimeno et al. "Coordinated Epidermal Growth Factor Receptor Pathway Gene Overexpression Predicts Epidermal Growth Factor Receptor Inhibitor Sensitivity in Pancreatic Cancer," *Cancer Research* 68(8):2841-2849, (Apr. 2008).

Jin et al. "Expression of Scatter Factor and C-Met Receptor in Benign and Malignant Breast Tissue," *Cancer* 79(4):749-760, (Feb. 15, 1997).

Jin et al. "MetMab, the One-Armed 5D5 Anti-c-Met Antibody, Inhibits Orthotopic Pancreatic Growth and Improves Survival," *Cancer Res.* 68(11):4360, (Jun. 2008).

Johns et al. "Identification of the Epitope for the Epidermal Growth Factor Receptor-Specific Monoclonal Antibody 806 Reveals that it Preferentially Recognizes an Untethered Form of the Receptor," *J Biol. Chem.* 279(29):30375-303784, (Jul. 2004).

Jones et al. "A Phase 1B Study of Erlotinib Plus Capecitabine and Docetaxel in Metastatic Breast Cancer (MBC)," *Proc. Am. Soc. Clin. Oncol.* (Abstract 180) 22:45a, (2003).

Jones et al. "Replacing the Complementarity-Determining Regions in a Human Antibody With Those from a Mouse," *Nature* 321:522-525, (May 1986).

Jones et al. "Targeted Therapies for NSCLC," *U.S. Pharmacist* 32(10):5-13, (2007).

Joukov et al. "A Novel Vascular Endothelial Growth Factor, VEGF-C, is a Ligand for the Flt4 (VEGFR-3) and KDR (VEGFR-2) Receptor Tyrosine Kinases," *EMBO. J.* 15(7):1751 (1996).

Junghans et al. "Anti-Tac-H, a Humanized Antibody to the Interleukin 2 Receptor with New Features for Immunotherapy in Malignant and Immune Disorders," *Cancer Res.* 50(5):1495-1502, (Mar. 1, 1990).

Kabat et al. "Sequences of Proteins of Immunological Interest," *Fifth Edition. NIH :Publication 91-3242*, Bethesda MD vols. 1-3,pp. 688-696, (1991).

Kam et al. "Carbon Nanotubes as Multifunctional Biological Transporters and Near-Infrared Agents for Selective Cancer Cell Destruction," *Proc. Natl. Acad, Sci. USA* 102(33):11600-11605, (2005).

Kamiya "Human c-Met ELISA for the Quantitative Determination of c-Met in Human Serum, EDTA-Plasma or Cell Culture Media," No. KT-444, pp. 1-6 (Feb. 1, 2008).

Kanda et al. "Comparison of Cell Lines for Stable Production of Fucose-negative Antibodies with Enhanced ADCC," *Biotechnol. Bioeng.* 94(4):680-688, (2006).

Kashmiri et al. "SDR Grafting—A New Approach to Antibody Humanization," *Methods* 36(1):25-34, (2005).

Kent, W. "BLAT—The Blast-Like Alignment Tool," *Genome Res.* 12(4):656-664, (2002).

Khalil et al. "Targeting Epidermal Growth Factor Receptor: Novel Therapeutics in the Management of Cancer," *Expert Rev. Anticancer Ther.* 3(3):367-380, (Jun. 2003).

Khazaeli et al. "Phase I Trial of Multiple Large Doses of Murine Monoclonal Antibody CO17-1A II. Pharmacokinetics and Immune Response," *J. Natl. Cancer Inst.* 80(12):937-942, (Aug. 17, 1988).

Kim et al. "Localization of the Site of the Murine IgG1 Molecule that is Involved in Binding to the Murine Intestinal Fc Receptor," *J. Immunol.* 24:2429-2434, (1994).

Kim et al. et al., "Systemic Anti-Hepatocyte Growth Factor Monoclonal Antibody Therapy Induces the Regression of Intracranial Glioma Xenografts," *Clin. Cancer. Res.* 12(4):1292-1298, (Feb. 15, 2006).

(56) References Cited

OTHER PUBLICATIONS

King et al. "Monoclonal Antibody Conjugates of Doxorubicin Prepared with Branched Peptide Linkers: Inhibition of Aggregation by Methoxytriethyleneglycol Chains," *J. Med. Chem.* 45:4336-4343, (2002).
Klagsbrun and D'Amore "Regulators of Angiogenesis," *Annu. Rev. Physiol.* 53:217-239, (1991).
Klimka et al. "Human Anti-CD30 Recombinant Antibodies by Guided Phage Antibody Selection Using Cell Panning," *British J. Cancer* 83(2)252-260, (Mar. 10, 2000).
Knudsen and Vande Woude "Showering c-MET-Dependent Cancers with Drugs," *Curr. Opin. Genet. Dev.*18:87-96, ( 2008).
Kohler and Milstein "Continuous Cultures of Fused Cells Secreting Antibody of Predefined Specificity," *Nature* 256:495-497, (Aug. 7, 1975).
Kong et al. "Prognostic Significance of c-Met Expression in Glioblastomas," *Cancer* 115(1):140-148, (Jan. 1, 2009).
Kong-Beltran et al. "Somatic Mutations Lead to an Oncogenic Deletion of Met in Lung Cancer," *Cancer Res.* 66(1):283-289, (Jan. 1, 2006).
Kong-Beltran et al. "The Serna domain of Met is Necessary for Receptor Dimerization and Activation," *Cancer Cell* 6(1):75-84, (Jul. 2004).
Kontermann, R. "Recombinant Bispecific Antibodies for Cancer Therapy," *Acta Pharmacologica Sinica* 26(1):1-9, (2005).
Korn et al. "Overall Survival as the Outcome for Randomized Clinical Trials with Effective Subsequent Therapies," *J. of Clinical Oncology* 29:2439-2442, (2011).
Kostelny et al. "Formation of a Bispecific Antibody by the Use of Leucine Zippers," *J. Immunol.* 148(5):1547-1553, (Mar. 1, 1992).
Kozbor "A Human Hybrid Myeloma for Production of Human Monoclonal Antibodies," *J. Immunol.* 133(6):3001-3005, (Dec. 1984).
Kratz et al. "Prodrugs of Anthracyclines in Cancer Chemotherapy," *Current Med. Chem.* 13:477-523, (2006).
Kraus et al. "Isolation and Characterization of ERBB3, a Third Member of the ERBB/Epidermal Growth Factor Receptor Family: Evidence for Overexpression in a Subset of Human Mammary Tumors," *P. Natl. Acad. Sci. USA* 86:9193-9197, (Dec. 1989).
Krishnan et al. "Combination of Epidermal Growth Factor Receptor Targeted Therapy with Radiation Therapy for Malignant Gliomas," *Front Biosci.* 8:e1-13, (Jan. 2003).
Kuniyasu et al. "Aberrant Expression of C-met mRNA in Human Gastric Carcinomas," *Int. J. Cancer* 55:72-75, (1993).
Kwak et al. "Targeted Agents: The Rules of Combination," *Clin. Cancer Res.* 13(18 Pt 1):5232-5237, (Sep. 2007).
Lacouture "Mechanisms of Cutaneous Toxicities to EGFR Inhibitors," *Nat. Rev. Cancer* 6:803-812, (Oct. 2006).
Lal et al. "EGFRvIII and c-Met Pathway Inhibitors Synergized Against PTEN-Null/EGFRvIII+ Glioblastoma Xenografts," *Mol. Cancer Ther.* 8(7):1751-1760, (Jul. 2009).
Lawrence et al., "MET molecular mechanisms and therapies in lung cancer" *Cell Adhesion & Migration* 4(1):146-152, (2009).
Lee et al. "High-Affinity Human Antibodies from Phage-Displayed Synthetic Fab Libraries with a Single Framework Scaffold," *J. Mol. Biol.* 340(5):1073-1093, (Jul. 2004).
Lee et al. "Vascular Endothelial Growth Factor-Related Protein: A Ligand and Specific Activator of the Tyrosine Kinase Receptor Flt4," *PNAS USA* 93:1988-1992, (Mar. 1996).
Lee et al. "Bivalent Antibody Phage Display Mimics Natural Immunoglobulin,".*J. Immunol. Methods* 284(1-2):119-132, (2004).
Leong et al. "Epitope Retrieval with Microwaves," *Appl. Immunohistochem.* 4(3):201-207, (1996).
Leung et al. "Vascular Endothelial Growth Factor Is a Secreted Angiogenic Mitogen," *Science* 246:1306-1309, (1989).
Lev et al. "A Recombinant Ectodomain of the Receptor for the Stem Cell Factor (SCF) Retains Ligand-induced Receptor Dimerization and Antagonizes SCP-Stimulated Cellular Responses," *J. Biol. Chem.* 267(15):10866-10873, (May 25, 1992).
Li et al. "Human Antibodies for Immunotherapy Development Generated Via a Human B Cell Hybridomas Technology," *Proc. Natl. Acad. Sci. USA* 103(10):3557-3562, (Mar. 7, 2006).
Lindmark et al. "Binding of Immunoglobulins to Protein A and Immunoglobulin Levels in Mammalian Sera," *J. Immun Methods* 62:1-13, (1983).
Lindroos et al. "Hepatocyte Growth Factor (Hepatopoietin A) Rapidly Increases in Plasma before DNA Synthesis and Liver Regeneration Stimulated by Partial Hepatectomy and Carbon Tetrachloride Administration,"*Hepatology* 13(4):743-750, (Apr. 1991).
Liu et al. "A Novel Kinase Inhibitor, INCB28060, Blocks c-MET-Dependent Signaling, Neoplastic Activities, and Cross-Talk with EGFR and HER-3," *Clin. Cancer Res.* 17(22):7127-7138, (2011).
Liu et al. "Overexpression of C-met Proto-Oncogene but not Epidermal Growth Factor Receptor or C-erbB-2 in Primary Human Colorectal Carcinomas," *Oncogene* 7:181-185, (1992).
Liu et al. "Targeting the c-MET Signaling Pathway for Cancer Therapy," *Expert Opin. Inv. Drug* 17(7):997, (2008).
Lode et al. "Targeted Therapy with a Novel Enediyene Antibiotic Calicheamicin $\theta^1_1$ Effectively Suppresses Growth and Dissemination of Liver Metastases in a Syngeneic Model of Murine Neuroblastoma," *Cancer Res.* 58:2925-2928, (Jul. 15, 1998).
Lokker et al. "Generation and Characterization of a Competitive Antagonist of Human Hepatocyte Growth Factor, HGF/NK1," *J. Biol. Chem.* 268(23):17145-17150, (Aug. 15, 1993).
Lokker et al. "Structure-Function Analysis of Hepatocyte Growth Factor: Identification of Variants that Lack Mitogenic Activity Yet Retain High Affinity Receptor Binding," *EMBO. J.* 11(7):2503-2510, (1992).
Lonberg, N. "Human Antibodies from Transgenic Animals," *Nat. Biotech.* 23(9):1117-1125 (Sep. 2005).
Lonberg, N. "Fully Human Antibodies from Transgenic Mouse and Phage Display Platforms," *Curr. Opin. Immunol.* 20:450-459, (2008).
Longhi et al. "Primary Bone Osteosarcoma in the Pediatric Age: State of the Art," *Cancer Treat. Rev.* 32(6):423-436, (Jul. 24, 2006).
Lorenzato et al. "Novel Somatic Mutations of the MET Oncogene in Human Carcinoma Metastases Activating Cell Motility and Invasion," *Cancer Res.* 62:7025-7030, (Dec. 1, 2002).
Love et al. "The Ligand-Binding Face of the Semaphorins Revealed by the High-Resolution Crystal Structure of SEMA4S," *Nat. Struct. Biol.* 10(10):843-848. (Oct. 2003).
Lukac et al. "Toxoid of Pseudomonas Aeruginosa Exotoxin A Generated by Deletion of an Active-Site Residue," *Infect Immun.* 56(12):3095-8, (Dec. 1988).
Lynch et al. "Activating Mutations in the Epidermal Growth Factor Receptor Underlying Responsiveness of Non-Small-Cell Lung Cancer to Gefitinib," *New Engl. J. Med.* 350(21):2129-2139, (May 20, 2004).
Ma et al. "A Two-Gene Expression Ratio Predicts Clinical Outcome in Breast Cancer Patients Treated with Tamoxifen," *Cancer Cell* 5:607-616, (2004).
Ma et al. "Circulating Tumor Cells and Serum Tumor Biomarkers in Small Cell Lung Cancer," *Anticancer Res.* 23:49-62, (2003).
Ma et al. "A Selective Small Molecule c-MET Inhibitor, PHA665752, Cooperates with Rapamycin," *Clin. Cancer Res.* 11:2312-2319, (Mar. 15, 2005).
Maccallum et al. "Antibody-Antigen Interactions: Contact Analysis and Binding Site Topography," *J. Mol. Biol.* 262:732-745, (1996).
Maher et al. "Transcriptome Sequencing to Detect Gene Fusions in Cancer," *Nature* 458(7234):97-101, (Jan. 2009).
Mai et al. "Nonclinical Evaluation of the Serum Pharmacodynamic Biomarkers HGF and Shed MET Following Dosing with the Anti-MET Monovalent Monoclonal Antibody Onartuzumab," *Molec. Cancer Therp.* 13(2):540-552, (2013).
Maina et al. "Uncoupling of Grb2 from the Met Receptor in Vivo Reveals Complex Roles in Muscle Development," *Cell* 87:531-542, (Nov. 1, 1996).
Mark et al. "Expression and Characterization of Hepatocyte Growth Factor Receptor-IgG Fusion Proteins," *J. Biol. Chem.* 267(36):26166-26171, (Dec. 25, 1992).
Marks et al. "By-Passing Immunization: Human Antibodies from V-Gene Libraries Displayed on Phage," *J. Mol. Biol.* 222:581-597, (Dec. 5, 1991).

(56) References Cited

OTHER PUBLICATIONS

Marks and Bradbury "Antibody Engineering," *Methods in Molecular Biology* 248:161-175, (2003).
Marmor and Yarden "Role of Protein Ubiquitylation in Regulating Endocytosis of Receptor Tyrosine Kinases," *Oncogene* 23:2057-2070, (2004).
Martens et al., "A Novel One-Armed Anti-c-met Antibody Inhibits Glioblastoma Growth in Vivo," *Clin. Cancer Res.* 12(20):6144-6152, (Oct. 2006).
Marvin and Zhu "Recombinant Approaches to IgG-Like Bispecific Antibodies," *Acta Pharmacologica Sincia* 26(6):649-658, (Jun. 2005).
Matsumoto et al. "Roles of HGF as a Pleiotropic Factor in Organ Regeneration." *Exs.* 65:225-249, (1993).
Matsumoto et al. "Deletion of Kringle Domains or the N-Terminal Hairpin Structure in Hepatocyte Growth Factor Results in Marked Decreases in Related Biological Activities," *Biochem. Bioph. Res. Co.* 181(2):691-699, (Dec. 16, 1991).
Matsumoto et al. "Hepatocyte Growth Factor is a Potent Stimulator of Human Melanocyte DNA Synthesis and Growth," *Biochem. Bioph. Res. Co.*176(1):45-51, (Apr. 15, 1991).
Matthews et al. "A Receptor Tyrosine Kinase cDNA Isolated from a Population of Enriched Primitive Hematopoietic Cells and Exhibiting Close Genetic Linkage to c-kit," *PNAS USA* 88:9026-9030, (Oct. 1991).
Maulik et al. "Role of the Hepatocyte Growth Factor Receptor, c-MET, in Oncogenesis and Potential for Therapeutic Inhibition," *Cytokine Growth F. R.* 13(1):41-59, (Feb. 2002).
Medlineplus http://www.nlm.nih.gov/medlineplus/ency/article/000280.htm (2013).
McCafferty et al. "Phage Antibodies: Filamentous Phage Displaying Antibody Variable Domains," *Nature* 348:552-554, (Dec. 6, 1990).
Meiners et al. "Role of Morphogenetic Factor sin Metastasis of Mammary Carcinoma Cells," *Oncogene* 16:9-20, (1998).
Merchant et al. "Monovalent Antibody Design and Mechanism of Action of Onartuzumab, a MET Antagonist with Anti-Tumor Activity as a Therapeutic Agent," *PNAS* 110(32):E2987-E2996, (Jul. 23, 2013).
Merchant et al. "Combination Efficacy with MetMAb and Erlotinib in a NSCLC Tumor Model Highlight Therapeutic Opportunities for c-Met Inhibitors in Combination with EGFR Inhibitors" *Presented at 99th AACR Annual meeting* San Diego, CA (Abstract 1336), (Apr. 12-16, 2008).
Merchant et al. "Met and EGFR Family Members Cooperate to Drive NSCLC Tumor Growth," *Poster presented at 99th AACR Annual meeting* San Diego, CA (Abstract 1336) (Apr. 12-16, 2008).
Merchant et al. "MetMab Enhances Activity of Inhibitors of VEGF and EGFR in Multiple Pre-clinical Models of Cancer (Geneva, Switzerland)," *Presented at the 20th Annual AACR-NCI-EORTC International Conference: Molecular Targets and Cancer Therapeutics* (Abstract 556), (Oct. 21-24, 2008).
Merchant et al. "An Efficient Route to Human Bispecific IgG," *Nat. Biotechnol.* 16(7):677-681, (1998).
Merchant et al. "Overview of c-MET Signaling" *Presented at the 6th International Congress on Targeted Therapeutics in Oncology* Presentation, 24 pages (Aug. 24, 2007).
Meyer et al. "A Novel Vascular Endothelial Growth Factor Encoded by Orf Virus, VEGF-E, Mediates Angiogenesis Via Signalling Through VEGFR-2 (KDR) But Not VEGFR-1 (Flt-1) Receptor Tyrosine Kinases," *EMRO J.* 18(2):363-374, (1999).
Michalopoulos et al. "control of Hepatocyte Replication by Two Serum Factors," *Cancer Res.* 44(10):4414-4419, (Oct. 1984).
Michieli et al. "Targeting the Tumor and its Microenvironment by a Dual-Function Decoy Met Receptor," *Cancer Cell* 6(1):61-73, (Jul. 2004).
Miller et al. "Monoclonal Antibody Therapeutic Trials in Seven Patients with T-Cell Lymphoma," *Blood* 62:988-995, (1983).
Milstein and Cuello "Hybrid Hybridomas and Their use in Immunohistochemistry," *Nature* 305:537-540, (Oct. 6, 1983).
Miyazawa et al., "An Alternatively Processed mRNA Generated from Human Hepatocyte Growth Factor Gene," *Eur. Biochem.* 197(1):15-22, (Apr. 10, 1991).
Miyazawa et al. "Molecular Cloning and Sequence Analysis of cDNA for Human Hepatocyte Growth Factor," *Biochem. Bioph. Res. Co.* 163(2):967-973, (Sep. 15, 1989).
Mok et al. "Randomized Phase II Study of Ficlatuzumab (formerly AV-299), an Anti-Hepatocyte Growth Factor (HGF) Monoclonal Antibody (MAB) in Combination with Gefitinib (G) in Asian patients (pts) with NSCLC," *J. of Clinical Oncology* 29(SI5), (2011).
Montesano et al. "Identification of a Fibroblast-Derived Epithelial Morphogen as Hepatocyte Growth Factor," *Cell* 67:901-908, (Nov. 29, 1991).
Morello et al., "MET Receptor is Overexpressed but not Mutated in Oral Squamous Cell Carcinomas," *J. Cell Physiol.* 189:285-290, (2001).
Morin, Ryan et al. *BioTechniques* 45(1):81-94, (2008).
Morris, G. "Epitope Mapping Protocols," *Methods in Molecular Biology* vol. 66 (Humana Press, Totowa, NJ) (1996).
Morrison et al. "Chimeric Human Antibody Molecules: Mouse Antigen-Binding Domains With Human Constant Region Domains," *Proc. Natl. Acad. Sci. USA* 81:6851-6855, (Nov. 1984).
Morton et al. "In Vitro and in Vivo Activity of Fully-Human Monoclonal Antibodies for c-Met Protein Tyrosine Kinase," *Proceedings Annual Meeting Am. Association for Cancer Research* (XP-001194900)(Abstract # 5604) 44:1116 (Jul. 2003).
Moss et al. "Complete Results from Phase I Dose Escalation Study of METMB, a Monovalent Antagonist Antibody to the Receptor MET, Dosed as Single Agent and in combination with Bevacizumab in Patients with Advanced Solid Malignancies," *Annals of Oncology* 21(S8) (2010).
Moss et al. "Final Results from the Phase I Study of MetMAb, a Monovalent Antagonist Antibody to the Receptor MET, Dosed as Single Agent and in combination with Bevacizumab in Patients with Advanced Solid Malignancies," *Abstract AACR-NCI-EORTC Symposium on Molecular Targets and Cancer Therapeutics—23rd AACR* (Apr. 23, 2011).
Moyer et al. "Induction of Apoptosis and Cell Cycle Arrest by CP-358,774, An Inhibitor of Epidermal Growth Factor Receptor Tyrosine Kinase," *Cancer Research* 57(21):4838-4848, (Nov. 1997).
Muller et al. "VEGF and the Fab Fragment of a Humanized Neutralizing Antibody: Crystal Structure of the Complex at 2.4 Å Resolution and Mutational Analysis of the Interface," *Structure* 6(9):1153-1167, (Sep. 15, 1998).
Mullis et al. "Specific Enzymatic Amplification of DNA in Vitro: The Polymerase Chain Reaction," *Cold Spring Harbor Symp. Quant. Biol.* 51:263-273, (1987).
Munshi et al. "ARQ 197, a Novel and Selective Inhibitor of the Human c-Met Receptor Tyrosine Kinase with Antitumor Activity," *Mol. Cancer Ther.* 9(6):1544-1553, (2010).
Munson and Rodbard "Ligand: A Versatile Computerized Approach for Characterization of Ligand-Binding Systems," *Anal. Biochem.* 107(1):220-239, (Sep. 1, 1980).
Nagai et al. "Genetic Heterogeneity of the Epidermal Growth Factor Receptor in Non-Small Cell Lung Cancer Cell Lines Revealed by a Rapid and Sensitive Detection System, the Peptide Nucleic Acid-Locked Nucleic Acid PCR Clamp," *Cancer Research* 65(16):7276-82, (Aug. 2005).
Nagy et al. "Stability of Cytotoxic Luteinizing Hormone-Releasing Hormone Conjugate (AN-152) Containing Doxorubicin 14-O-Hemiglutarate in Mouse and Human serum in Vitro: Implications for the Design of Preclinical Studies," *Proc. Natl. Acad. Sci. USA* 97(2):829-834, (Jan. 18, 2000).
Naka et al. "Activation of Hepatocyte Growth Factor by Proteolytic Conversion of a Single Form to a Heterodimer," *J. Biol. Chem.* 267(28):20114-20119, (Oct. 5, 1992).
Nakamura et al. "Molecular Cloning and Expression of Human Hepatocyte Growth Factor," *Nature* 342:440-443, (Nov. 23, 1989).
Nakamura et al. "Partial Purification and Characterization of Hepatocyte Growth Factor from Serum of Hepatectomized Rats," *Biochem Bioph. Res.* 122:1450-1459, (Aug. 16, 1984).

(56) References Cited

OTHER PUBLICATIONS

Nakamura et al. "Purification and Characterization of a Growth Factor from Rat Platelets for Mature Parenchymal Hepatocytes in Primary Cultures," *Proc. Natl. Acad. Sci. USA* 83(17):6489-6493, (Sep. 1986).
Nakamura et al. "Purification and Subunit Structure of Hepatocyte Growth Factor from Rat Platelets," *Febs. Lett.* 224(2):311-316, (Nov. 1987).
Naldini et al. "Hepatocyte Growth Factor (HGF) Stimulates the Tyrosine Kinase Activity of the Receptor Encoded by the Proto-Oncogene c-MET," *Oncogene* 6(4):501-504, (Apr. 1991).
Naldini et al. "Scatter Factor and Hepatocyte Growth Factor are Indistinguishable Ligands for the MET Receptor," *EMBO. J.* 10(10):2867-2878, (Oct. 1991).
Namiki et al. "Preclinical Study of a 'Tailor-Made' Combination of Gene Therapy and Gefitinib (ZD 1839, IRESSA) for Disseminated Peritoneal Scirrhous Gastric Cancer," *Int. J. Cancer* 118:1545-1555, (2006).
Natali et al. "Overexpression of the Met/HGF Receptor in Renal Cell Carcinomas," *Int. J. Cancer* 69:212-217, (1996).
Navab et al., "Co-expression of Met and hepatocyte growth factor promotes systemic metastasis in NCI-H460 non-small cell lung carcinoma cells" *Neoplasia* 11(12):1292-1300, (2009).
Nguyen et al., "Association of the Multisubstrate Docking Protein Gab1 with the Hepatocyte Growth Factor Receptor Requires a Functional Grb2 Binding Site Involving Tyrosine 1356," *J. Biol. Chem.* 272(33):20811-20819, (Aug. 15, 1997).
Ni, Jian "Research Progress and Future Perspectives in Antibodomics and Antibodomic Drugs," *J. General Review* 26(4):265-268, (Oct. 23, 2006).
Nicolaou et al. "Calicheamicin $\theta^1_1$: a Rationally Designed Molecule with Extremely Potent and Selective DNA Cleaving Properties and Apoptosis Inducing Activity," *Angew. Chem. Int. Ed. Engl.* 33(2):183-186, (1994).
Nielsen and Routledge "Human T Cells Resistant to Complement Lysis by Bivalent Antibody Can be Efficiently Lysed by Dimers of Monovalent Antibody," *Blood* 100(12):4067-4073, (Dec. 1, 2002).
Novotny and Haber "Structural Invariants of Antigen Binding: Comparison of Immunoglobulin $V_L$-$V_H$ and $V_L$-$V_L$," *P. Natl. Acad. Sci. USA* 82(14):4592-4596, (Jul. 1985).
Nusrat et al. "Hepatocyte Growth Factor/Scatter Factor Effects on Epithelia. Regulation of Intercellular Junctions in Transformed and Natural Intestinal Epithelia and Induction of Rapid Wound Repair in a Transformed Model Epithelium," *J. Clin. Invest.* 93:2056-2065, (May 1994).
Nygren, H. "Conjugation of Horseradish Peroxidase to Fab Fragments with Different Homobifunctional and Heterobifunctional Cross-Linking Reagents," *J. Histochem. Cytochem.* 30(5):407-412, (May 1982).
Ogawa et al. "A Novel Type of Vascular Endothelial Growth Factor, VEGF-E (NZ-7 VEGF), Preferentially Utilizes KDR/Flk-1 Receptor and Carries a Potent Mitotic Activity Without Heparin-Binding Domain," *J. Biological Chem.* 273(47):31273-3128, (Nov. 1998).
Ogiso et al. "Crystal Structure of the Complex of Human Epidermal Growth Factor and Receptor Extracellular Domains," *Cell* 110:775-787, (Sep. 20, 2002).
Okajima et al. "Primary Structure of Rat Hepatocyte Growth Factor and Induction of Its mRNA During Liver Regeneration Following Hepatic Injury," *Eur. J. Biochem.* 193(2):375-381, (Oct. 24, 1990).
Okamoto et al. "TAK-701, a Humanized Monoclonal Antibody to Hepatocyte Growth Factor, Reverses Gefitinib Resistance Induced by Tumor-Derived HGF in Non-Small Cell Lung Cancer with and EGFR Mutation," *Mol. Cancer Ther.* 9(10):2785-92, (2010).
Okazaki et al. "Fucose Depletion from Human IgG1 Oligosaccharide Enhances Binding Enthalpy and Association Rate Between IgG1 and FcγRIIIa," *J. Mol. Biol.* 336:1239-1249, (2004).
Okuda et al. "Met Gene Copy Number Predicts the Prognosis for Completely Resected Non-Small Cell Lung Cancer," *Cancer Sci.* 99(11):2280-2285, (2008).

Olivero et al. "Novel Mutation in the ATP-Binding Site of the MET Oncogene Tyrosine Kinase in a HPRCC Family," *Int. J. Cancer* 82:640-643, (1999).
Olivero et al. "Overexpression and Activation of Hepatocyte Growth Factor/Scatter Factor in Human Non-Small-Cell Lung Carcinomas," *Brit. J. Cancer* 74:1862-1868, (1996).
ORIAN_ROUSSEAU et al., "CD44 is Required for Two Consecutive Steps in HGF/c-MET Signaling," *Gene. Dev.* 16:3074-3086, (2002).
Osbourn et al. "From Rodent Reagents to Human Therapeutics Using Antibody Guided Selection," *Methods* 36:61-68, (2005).
O'Sullivan et al. "Methods for the Preparation of Enzyme-Antibody Conjugates for use in Enzyme Immunoassay," *Methods in Enzym. Academic press*, New York 73:147-166, (1981).
Oza et al. "Phase II Study of Erlotinib (OSI-774) in Patients with Metastatic Colorectal Cancer," *Proc. Am. Soc. Clin. Oncol.* (Abstract 785) 22:196a, (2003).
Pacchiana et al. "Monovalency Unleashes the Full Therapeutic Potential of the DN-30 Anti-Met Antibody," *J. of Biological Chem.* 285(46):36149-36157, (2010).
Padlan E. "A Possible Procedure for Reducing the Immunogenicity of Antibody Variable Domains While Preserving Their Ligand-Binding Properties," *Mol. Immunol.* 28(4/5):489-498 (1991).
Paez et al. "EGFR Mutations in Lung Cancer: Correlation with Clinical Response to Gefitinib Therapy," *Science* 304:1497-1500, (Jun. 4, 2004).
Pain and Surolia "Preparation of Protein A-Peroxidase Monoconjugate Using a Heterobifunctional Reagent, and its Use in Enzyme Immunoassays," *J. Immunol. Methods* 40(2):219-230, (1981).
Palacios and Steinmetz "IL3-Dependent Mouse Clones That Express B-220 Surface Antigen, Contain Ig Genes in Germ-Line Configuration, and Generate B Lymphocytes in Vivo," *Cell* 41(3):727-734, (Jul. 1985).
Pao et al. "EGF Receptor Gene Mutations are Common in Lung Cancers from 'Never Smokers' and are Associated with Sensitivity of Tumors to Gefitinib and Erlotinib," *Proc. Natl. Acad. Sci. USA* 101(36):13306-13311, (Sep. 7, 2004).
Park et al. "Mechanism of Met Oncogene Activation," *Cell* 45:895-904, (Jun. 20, 1986).
Park et al. "Sequence of MET Protooncogene cDNA has Features Characteristic of the Tyrosine Kinase Family of Growth-Factor Receptors," *P. Natl. Acad. Sci. USA* 84(18):6379-6383, (Sep. 1987).
Parker and Barnes "mRNA: Detection by in Situ and Northern Hybridization," *Methods in Molecular Biology* {Abstract} 106:247-283 (1999).
Patel et al. "Epidermal Growth Factor Receptor Pathway Targeted Therapy in Patients with Aerodigestive Malignancies," *Curr. Opin. Oncol.* 18(6):609-614, (Nov. 2006).
Patel et al. "Results from FDG-PET Imaging in OAM4558g, a Randomized, Placebo-Controlled, Multi-center Phase II Trial of Erlotinib + MetMAb in Second-and-Third Line NSCLC," *Abstract World Conference on Lung Cancer—14th* (Jul. 3, 2011).
Peek et al. "Unusual Proteolytic Activation of Pro-hepatocyte Growth Factor by Plasma Kallikrein and Coagulation Factor XIa," *J. Biol. Chem.* 277(49):47804-47809, (Dec. 6, 2002).
Pelicci et al. "The Motogenic and Mitogenic Responses to HGF are Amplified by the Shc Adaptor Protein," *Oncogene* 10:1631-1638, (1995).
Perez-Soler et al. "A Phase II Trial of the Epidermal Growth Receptor (EGFR) Tyrosine Kinase Inhibitor OSI-774, Following Platinum-Based Chemotherapy, in Patients (pts) with Advanced EGFR-Expressing, Non-Small Cell Lung Cancer (NSCLC)," *Proc. Am. Soc. Clin. Oncol.* (Abstract 1235) 20:310a, (2001).
Peschard and Park "Escape from Cbl-Mediated Downregulation: A Recurrent Theme for Oncogenic Deregulation of Receptor Tyrosine Kinases," *Cancer Cell* 3:519-523, (Jun. 2003).
Peshcard et al. "A Conserved DpYR Motif in the Juxtamembrane Domain of the Met Receptor Family Forms an Atypical c-Cbl/Cbl-b Tyrosine Kinase Binding Domain Binding Site Required for Suppression of Oncogenic Activation," *J. Biol. Chem.* 279(28):29565-29571, (Jul. 9, 2004).

(56) References Cited

OTHER PUBLICATIONS

Peshcard et al. "Mutation of the c-Cbl TKB Domain Binding Site on the Met Receptor Tyrosine Kinase Converts It into a Transforming Protein," *Mol. Cell* 8:995-1004, (Nov. 2001).
Petrelli et al. "The Endophilin-CIN85-Cbl Complex Mediates Ligand-Dependent Downregulation of c-Met," *Nature* 416:187-190, (Mar. 14, 2002).
Plotnikov et al. "Structural Basis for FGF Receptor Dimerization and Activation," *Cell* 98:641-650, (Sep. 3, 1999).
Plowman et al. "Heregulin Induces Tyrosine Phosphorylation of HER4/p180erbB4," *Nature* 366:473-475, (Dec. 2, 1993).
Plowman et al. "Ligand-Specific Activation of HER4/p180erbB4, a Fourth Member of the Epidermal Growth Factor Receptor Family," *P. Natl. Acad. Sci. USA* 90:1746-1750, (Mar. 1993).
Pluckthun, A "Antibodies from *Escherichia coli*," *The Pharmacology of Monoclonal Antibodies* pp. 269-315 (1994).
Pollack et al. "Inhibition of Epidermal Growth Factor Receptor-Associated Tyrosine in Human Carcinomas with CP-358,774: Dynamics of Receptor Inhibition in Situ and Antitumor Effects in Athymic Mice," *J Pharmacol Exp Ther.* 291(2):739-48, (Nov. 1999).
Ponzetto et al. "Specific Uncoupling of GRB2 from the Met Receptor. Differential Effects on Transformation and Motility," *J. Biol. Chem.* 271(24):14119-14123, (Jun. 14, 1996).
Ponzetto et al. "A Multifunctional Docking Site Mediates Signaling and Transformation by the Hepatocyte Growth Factor/Scatter Receptor Family," *Cell* 77:261-271, (Apr. 22, 1994).
Ponzetto et al. "A Novel Recognition Motif for Phosphatidylinositol 3-Kinase Binding Mediates Its Association With the Hepatocyte Growth Factor/Scatter Factor Receptor," *Mol. Cell Biol.* 13(8):4600-4608, (Aug. 1993).
Ponzetto et al. "c-Met is Amplified but not Mutated in a Cell Line with a Activated Met Tyrosine Kinase," *Oncogene* 6(4):553-559, (Apr. 1991).
Popkov et al. "Human/Mouse Cross-Reactive Anti-VEGF Receptor 2 Recombinant Antibodies Selected from an Immune b9 Allotype Rabbit Antibody Library," *Journal of Immunological Methods* 288:149-164, (2004).
Prat et al. "Agonistic Monoclonal Antibodies Against the Met Receptor Dissect the Biological Response to HGF," *J. Cell Sci.* (111):237-247, (1998).
Prat et al. "C-Terminal Truncated Forms of Met, the Hepatocyte Growth Factor Receptor," *Mol. Cell Biol.* 11(12):5954-5962, (Dec. 1991).
Prat et al. "The HGF Receptor (Met): Transduction of Signals for Invasive Cell Growth," *Antibody Immunoconj.* 8(4):341-361, (1995).
Prat et al. "The Receptor Encoded by the Human c-Met Oncogene is Expressed in Hepatocytes, Epithelial Cells and Solid Tumors," *Int. J. Cancer* 49(3):323-328, (Sep. 30, 1991).
Presta et al. "Humanization of an Antibody Directed Against IgE," *J. Immunol.* 151(5):2623-2632, (Sep. 1, 1993).
Presta, L. "Antibody Engineering," *Curr. Op. Struct. Biol.* 2:593-596, (1992).
Presta et al. "Humanization of an Anti-Vascular Endothelial Growth Factor Monoclonal Antibody for the Therapy of Solid Tumors and Other Disorders," *Cancer Res.* 57:4593-4599, (Oct. 15, 1997).
Queen et al. "A Humanized Antibody That Binds to the Interleukin 2 Receptor," *Proc. Natl. Acad. Sci. USA* 86:10029-10033, (Dec. 1989).
Ramlau et al. "Efficacy and Safety in the Cross-Over Arm of OAM4558g; a Phase II Study Evaluating MetMAb in Combination with Erlotinib in Advanced NSCL," *Poster World Conference on Lung Cancer—14th* (Jul. 3, 2011).
Ramm and Pluckthun et al. "The Periplasmic *Escherichia coli* Peptidylprolyl cis, trans Isomerase FkpA," *J. Biol Chem* 275(22):17106-17113, (Jun. 2000).
Reznik et al. "Transcription-Dependent Epidermal Growth Factor Receptor Activation by Hepatocyte Growth Factor," *Mol. Cancer Res.* 6(1):139-50, (Jan. 2008).

Ridgway et al. "Knobs-Into-Holes' Engineering of Antibody CH3 Domains for Heavy Chain Heterodimerization," *Protein Eng.* 9(7):617-621, (1996).
Riechmann et al. "Reshaping Human Antibodies for Therapy," *Nature* 332:323-327, (Mar. 1988).
Ripka et al. "Two Chinese Hamster Ovary Glycosylation Mutants Affected in the Conversion of GDP-Mannose to GDP-Fucose," *Arch. Biochem. Biophys.* 249(2):533-545 (Sep. 1986).
Robertson et al. "RTK Mutations and Human Syndromes when Good Receptors Turn Bad," *Trends Genet.* 16(8):265-271, (Aug. 16, 2000).
Rodig et al. "Abstract 1729: An Exploratory Biomarker Analysis Evaluating the Effect of the c-MET Inhibitor Tivantinib (ARQ 197) and Erlotinib in NSCLC Patients in a Randomized, Double-Blinded Phase 2 Study," *Cancer Research* 72(8 Suppl 1), (2012).
Rodriques et al. "Alternative Splicing Generates Isoforms of the met Receptor Tyrosine Kinase Which Undergo Differential Processing," *Mol. Cell Biol.* 11(6):2962-2970, (Jun. 1991).
Rodriques et al. "Development of a Humanized Disulfide-Stabilized Anti-p185$^{HER2}$ Fv-β-Lactamase Fusion Protein for Activation of a Cephalosporin Doxorubicin Prodrug," *Cancer Res.* 55(1):63-70, (Jan. 1, 1995).
Rong et al. "Tumorigenicity of the met Porto-Oncogene and the Gene for Hepatocyte Growth Factor," *Mol Cell Biol.* 12(11):5152-5158, (Nov. 1992).
Rosen et al. "AMG102, an HGF/SF Antagonist, in Combination with Anti-Angiogenesis Targeted Therapies in Adult Patients with Advanced Solid Tumors," *J. Clin. Oncol.* 26(15s):3570, (May 2008).
Rosok et al. "A Combinatorial Library Strategy for the Rapid Humanization of Anticarcinoma BR96 Fab," *J. Biol. Chem.* 271(37):22611-22618, (Sep. 13, 1996).
Routledge et al. "A Humanized Monovalent CD3 Antibody Which Can Activate Homologous Complement," *Eur. J. Immunol.* 21:2717-2725, (1991).
Routledge et al. "The Effect of Aglycosylation on the Immunogenicity of a Humanized Therapeutic CD3 Monoclonal Antibody," *Transplantation* 60(8):847-853, (Oct. 27, 1995).
Royal and Park et al. "Hepatocyte Growth Factor-Induced Scatter of Madin-Darby Canine Kidney Cells Requires Phosphatidylinositol 3-Kinase," *J. Biol. Chem.* 270(46):27780-27787, (Nov. 17, 1995).
Rubin et al. "A Broad-Spectrum Human Lung Fibroblast-Derived Mitogen is a Variant of Hepatocyte Growth Factor," *P. Natl. Acad. Sci. USA* 88(2):415-419, (Jan. 15, 1991).
Rupp and Locker "Annual Meeting Abstracts," *Lab Invest.* 56(1):67A (1987).
Russell et al. "Partial Characterization of a Hepatocyte Growth Factor From Rat Platelets," *J. Cell Physiol.* 119(2):183-192, (May 1984).
Salgia et al. "Complete Results from a Phase Ia Dose-Escalation and Dose-Expansion Study of Single-Agent MetMab, a Monovalent Antagonist Antibody to the Receptor MET, Administered Intravenously in Patients with Locally Advanced or Metastatic Solid Tumors," *Abstract AACR 101st Annual Meeting*, Washington, D.C. p. 2774, (2010).
Sano et al. "Abstract 2728: Onartuzumab (MetMAb) Restores Sensitivity to Erlotinib in EGFR NSCLC Cells Expressing HGF," *Cancer Research* 72(8 Suppl 1), (Apr. 15, 2012).
Sato, Y. "Molecular Diagnosis of Tumor Angiogenesis and Anti-Angiogenic Cancer Therapy," *Int. J. Clin. Oncol.* 8:200-206, (2003).
Sattler et al. "The Role of the c-Met Pathway in Lung Cancer and the Potential for Targeted Therapy," *Ther. Adv. Med. Oncol.* 3(4):171-84, (2011).
Schena et al. "Parallel Human Genome Analysis: Microarray-Based Expression Monitoring of 1000 Genes," *Proc. Natl. Arnd. Sci. USA* 93(2):106-149, (1996).
Scheving et al. "Integral Role of the EGF Receptor in HGF-Mediated Hepatocyte Proliferation," *Biochem. Bioph. Res. Co.* 290(1):197-203, (Jan. 2002).
Schier et al. "Identification of Functional and Structural Amino-Acid Residues by Parsimonious Mutagenesis," *Gene.* 16:147-155, (1996).

(56) References Cited

OTHER PUBLICATIONS

Schlessinger et al. "Growth Factor Signaling by Receptor Tyrosine Kinases," *Neuron* 9:383-391, (1992).

Schlom J. "Monoclonal Antibodies: They're More and Less Than You Think," *Molecular Foundations of Oncology "6" Broder*, S. ed. Baltimore, MD; Williams & Wilkins pp. 95-134, (1991).

Schmidt et al. "Germline and Somatic Mutations in the Tyrosine Kinase Domain of the MET Proto-Oncogene in Papillary Renal Carcinomas," *Nat. Genet.* 16:68-73, (May 1997).

Schmidt et al. "Novel Mutation of the MET Proto-Oncogene in Papillary Renal Carcinomas," *Oncogene* 18:2343-2350, (1999).

Schmidt et al. "Scatter Factor/Hepatocyte Growth Factor is Essential for Liver Development," *Nature* 373:699-702, (Feb. 23, 1995).

Schwall et al. "Heparin Induces Dimerization and Confers Proliferative Activity Onto the Hepatocyte Growth Factor Antagonists NK1 and NK2," *J. Cell Biol.* 133:709-718, (May 1996).

Sears et al. "Effects of Monoclonal Antibody Immunotherapy on Patients with Gastrointestinal Adenocarcinoma," *J. Biol. Response Mod.* 3(2):138-150, (1984).

Seidel et al. "Role of hepatocyte Growth Factor and its Receptor c-Met in Multiple Myeloma," *Medical Oncology* 15:145-153, (Sep. 1998).

Seiwert et al. "The MET Receptor Tyrosine Kinase is a Potential Novel Therapeutic Target for Head and Neck Squamous Cell Carcinoma," *Cancer Res.* 69(7):3021-31, (Apr. 2009).

Seki et al. "Isolation and Expression of cDNA for Different Forms of Hepatocyte Growth Factor from Human Leukocyte," *Bipchem. Bioph. Res. Co.* 172(1):321-327, (Oct. 15, 1990).

Semba et al. "A v-erbB-Related Protooncogene, c-erbB-2, is Distinct from the c-erbB-1/Epidermal Growth Factor-Receptor Gene and is Amplified in a Human Salivary Gland Adenocarcinoma," *Proc. Natl. Acad. Sci. USA* 82:6497-6501, (Oct. 1985).

Sequist et al. "Randomized Phase II Study of Erlotinib Plus Tivantinib Versus Erlotinib Plus Placebo in Previously Treated Non-Small-Cell Lung Cancer," *J. Clin. Oncol.* 29:3307-15, (2011).

Sequist et al. "Final Results from ARQ 197-209: a Global Randomized Placebo-Controlled Phase 2 Clinical Trial of Erlotinib Plus ARQ 197 Versus Erlotinib Plus Placebo in Previously Treated EGFR-Inhibitor Naïve Patients with Advanced Non-Small Cell Lung Cancer (NSCLC),". Presented at *ESMO Congress, Milan*, (Oct. 9, 2010).

Seymour et al. "Epidermal Growth Factor Receptor Inhibitors: An Update on Their Development as Cancer Therapeutics," *Curr. Opin. Investig. Drugs* 4(6):658-666, (Jun. 2003).

Shah et al. "Randomized Phase II Study of FOLFOX with or without the MET Inhibitor, Onartuzumab, in Advanced Gastroespohageal Adenocarcinoma (GEC)," *Gastrointestinal Cancers Symposium*, 1 page, (2015).

Shames et al., "The High Incidence of Overlap Between Actionable Biomarkers in NSCLC: Potential Impact on Future Clinical Trial Design," *ESMO* 1 page, (2014).

Sharma et al. "In the Clinic: Ongoing Clinical Trials Evaluating c-MET-Inhibiting Drugs," *Ther. Adv. Med. Oncol.* 3(S1):S37-S50, (2011).

Sharma et al. "Oncogene Addiction: Setting the Stage for Molecularly Targeted Cancer Therapy," *Genes Dev.* 21:3214-3231, (2007).

Shawler et al. "Human Immune Response to Multiple Injections of Murine Monoclonal IgF," *J. Immunol.* 135(2):1530-1535, (1985).

Shepherd et al. "A Randomized Placebo-Controlled Trial of Erlotinib in Patients with Advance Non-Small Cell Lung Cancer (NSCLC) Following Failure of 1st Line or 2nd Line Chemotherapy," *Abstract ASCO Annual Meetings*, p. 7022, (2004).

Shi et al. "Antigen Retrieval Immunohistochemistry: Past, Present, and Future," *J. Histochem. Cytochem* 45(3):327-343, (1997).

Shibuya et al. "Nucleotide Sequence and Expression of a Novel Human Receptor-Type Tyrosine Kinase Gent (flt) Closely Related to the fms Family," *Oncogene* 8:519-527, (1990).

Shields et al."High Resolution Mapping of the Binding Site on Human IgG1 for FcγRI, FcγRII, FcγIII, and FcRn and Design of IgF1 Variants with Improved Binding to the FcγR*," *J. Biol. Chem.* 276(9):6591-6604, (Mar. 2, 2001).

Shtiegmann and Yarden "The Role of Ubiquitylation in Signaling by Growth Factor for Non-Small Cell Lung Cancer," *Semin. Cancer Biol.* 13:29-40, (2003).

Sidhu et al. "Phage-Displayed Antibody Libraries of Synthetic Heavy Chain Complementarity Determining Regions," *J. Mol. Biol.* 338(2):299-310, (2004).

Siegfried et al. "The Clinical Significance of Hepatocyte Growth Factor for Non-Small Cell Lung Cancer," *Ann. Thorac. Surg.* 66:1915-1918, (1988).

Simmons and Yansura "Translational Level is a Critical Factor for the Secretion of Heterologous Proteins in *Escherichia coli*," *Nat. Biotechnol.* 14:629-634, (May 1996).

Simmons et al. "Expression of Full-Length Immunoglobulins in *Escherichia coli*: Rapid and Efficient Production of Aglycosylated Antibodies," *J. Immunol. Methods* 263:133-147, (2002).

Sims et al. "A Humanized CD18 Antibody Can Block Function Without Cell Destruction," *J. Immunol.* 151(4):2296-2308, (Aug. 15, 1993).

Smith et al. "Cardiac Glycoside-Specific Antibodies in the Treatment of Digitalis Intoxication," *Antibodies Human Diagnosis Therapy* 365-389, (1977).

Smolen et al. "Amplification of MET May Identify a Subset of Cancers with Extreme Sensitivity to the Selective Tyrosine Kinase Inhibitor PHA-665752," *PNAS* 103(7):2316-2321, (2006).

Soker et al. "Neuropilin-1 is Expressed by Endothelial and Tumor Cells as an Isoform-Specific Receptor for Vascular Endothelial Growth Factor," *Cell* 92:735-45 (Mar. 1998).

Soloman et al. "EGFR Blockade with ZD1839 ("IRESSA") Potentiates the Antitumor Effects of Single and Multiple Fractions of Ionizing Radiation in Human A431 Squamous Cell Carcinoma. Epidermal Growth Factor Receptor," *Int. J. Radiat. Oncol. Biol Phys.* 55(3):713-723, (Mar. 2003).

Soulieres et al. "Multicenter Phase II Study of Erlotinib, An Oral Epidermal Growth Factor Tyrosine Kinase Inhibitor, in Patients with Recurrent or Metastatic Squamous Cell Cancer of the Head and Neck," *J. Clin. Oncol.* 22(1):77-85, (Jan. 2004).

Specht et al. "Quantitative Gene Expression Analysis in Microdissected Archival Formalin-Fixed and Paraffin-Embedded Tumor Tissue," *Am. J. Pathol.* 158(2):419-429, (Feb. 2001).

Spigel et al. "ESMO 2010 Late Breaking Abstract No. LBA15," *Annals Oncol.* 21( Suppl 8):viii7, (2010).

Spigel et al. "Final Efficacy Results from a Randomized Phase II Study (OAM4558g) Evaluating MetMAb or Placebo in Combination with Erlotinib in Advanced NSCLC," *Abstract World Conference on Lung Cancer—14th* (Jul. 3, 2011).

Spigel et al. "Final Efficacy Results from OAM4558g, a Randomized Phase II Study Evaluating MetMAb or Placebo in Combination with Erlotinib in Advanced NSCLC," *J. of Clinical Oncology* 28(15S):7505, (2011).

Spigel et al. "Treatment Rationale Study Design for the MetLung Trial: A randomized Double-Blind Phase III Study of Onartuzumab (MetMAb) in Combination with Erlotinib Versus Erlotinib Alone in Patients Who have Received Standard Chemotherapy for Stage IIIB or IV Met-Positive Non-Small-Cell Lung Cancer," *Clinical Lung Cancer* 13(6):500-504, (2012).

Spigel et al. "Onartuzumab Plus Erlotinib Versus Erlotinib in Previously Treated Stage IIIb or IV NSCLC: Results from the Pivotal Phase 3 Randomized, Multicenter, Placebo-Controlled MET Lung (OAM4971g) Global Trial," Abstract ID: 8000, *American Society of Clinical Oncology—50th Annual Meeting / ASCO*, 17 pages, (May 30, 2014).

Staerz et al. "Hybrid antibodies can target sites for attack by T cells," *Nature* 314(6012 Suppl Apr. 18-24):628-631, (Apr. 18-24, 1985).

Stevenson et al. "A Chimeric Antibody With Dual Fc Regions (bisFabFc) Prepared by Manipulations at the IgG Hinge," *Anti-Cancer Drug Des.* 3(4):219-230, (1989).

Stoker et al. "Scatter Factor is a Fibroblast-Derived Modulator of Epithelial Cell Mobility," *Nature* 327(6119):239-242, (May 21, 1987).

(56) References Cited

OTHER PUBLICATIONS

Stragliotto et al. "Multiple Infusion of Anti-Epidermal Growth Factor Receptor (EGFR) Monoclonal Antibody (EMD 55,900) in Patient with Recurrent Malignant Gliomas," *Eur. J. Cancer* 32A(4):636-640, (Apr. 1996).
Streit and Detmar "Angiogenesis, Lymphangiogenesis, and Melanoma Metastasis," *Oncogene* 22:3172-3179, (2003).
Sunitha et al. "Hepatocyte Growth Factor Stimulates Invasion Across Reconstituted Basement Membranes by a New Human Small Intestinal Cell Line," *Clin. Exp. Metastasis* 12(2):143-154, (Mar. 1994).
Surati et al. "Role of MetMAb (OA-5D5) in c-MET Active Lung Malignancies," *Expert Opin. Biol. Ther.* 11(12):1655-1662, (2011).
Suzuki et al. "Expression of the C-Met Protooncogene in Human Hepatocellular Carcinoma," *Hepatology* 20:1231-1236, (Nov. 1994).
Tamagnone et al. "Plexins are a Large Family of Receptors for Transmembrane, Secreted, and GPI-Anchored Semaphorins in Vertebrates," *Cell* 99:71-80, (Oct. 1, 1999).
Tang et al. "Dual MET-EGFR Combinatorial Inhibition Against T790M-EGFR-Mediated Erlotinib-Resistant Lung Cancer," *Brit. J. Cancer* 99(6):911-922, (Sep. 2008).
Tanizaki et al. "MET Tyrosine Kinase Inhibitor Crizotinib (PF-02341066) Shows Differential Antitumor Effects in Non-Small Cell Lung Cancer According to MET Alterations," *Journal of Thoracic Oncology* 6(10):1624-1631, (2011).
Taraceva Prescribing Information 24 pages (2004).
Tashiro et al. "Deduced Primary Structure of Rat Hepatocyte Growth Facto rand Expression of the MRNA in Rat Tissues," *P. Natl. Acad. Sci. USA* 87(8):3200-3204, (Apr. 1990).
Tempest et al. "Structure of the Met Protein and Variation of Met Protein Kinase Activity Among Human Tumour Cell Lines," *Brit. J. Cancer* 58(1):3-7, (Jul. 1998).
Terman et al. "Identification of the KDR Tyrosine Kinase as a Receptor for Vascular Endothelial Cell Growth Factor," *Biochem. Biophys. Res. Commun.* 187(3):1579-1586, (Sep. 30, 1992).
Terman et al. "Identification of a New Endothelial Cell Growth Factor Receptor Tyrosine Kinase," *Oncogene* 6(9):1677-1683, (1991).
Tonini et al. "Molecular Basis of Angiogenesis and Cancer," *Oncogene* 22:6549-6556, (2003).
Torgov et al., "Generation of an Intensely Potent Anthracycline by a Monoclonal Antibody—β-Galactosidase Conjugate," *Bioconj. Chem.* 16:717-721, (2005).
Traunecker et al. "Bispecific Single Chain Molecules (Janusins) Target Cytotoxic Lymphocytes on HIV Infected Cells," *EMBO J.* 10(12):3655-3659, (1991).
Trusolino and Comoglio "Scatter-Factor and Semaphorin Receptors: Cell Signaling for Invasive Growth," *Nature Rev. Cancer* 2(4):289-300, (Apr. 2002).
Trusolino et al. "A Signaling Adapter Function for Alpha6beta4 Integrin in the Control of HGF-Dependent Invasive Growth," *Cell* 107:643-654, (Nov. 30, 2001).
Turke et al., "Preexistence and clonal selection of MET amplification in EGFR mutant NSCLC," *Cancer Cell* 17(1):77-88, (Jan. 2010).
Tutt et al. "Trispecific F(ab')$_3$ Derivatives That Use Cooperalve Signaling Via the TCR/CD3 Complex and CD2 to Activate and Redirect Resting Cytotoxic T Cells," *J. Immunol.* 147(1):60-69, (Jul. 1, 1991).
Uehara et al. "Placental Defect and Embryonic Lethality in Mice Lacking Hepatocyte Growth Factor/Scatter Factor," *Nature* 373:702-705, (Feb. 23, 1995).
Ullrich et al. "Human Epidermal Growth Factor Receptor cDNA Sequence and Aberrant Expression of the Amplified Gene in A431 Epidermoid Carcinoma Cells," *Nature* 309:418-425, (May 1984).
Ullrich and Schlessinger "Signal Transduction by Receptors with Tyrosine Kinase Activity," *Cell* 61:203-212, (Apr. 20, 1990).
Van Dijk and Van De Winkel "Human Antibodies as Next Generation Therapeutics," *Curr. Opin. Pharmacol* 5:368-374, (2001).
Van Vactor and Lorenz, "Neural Development: The Semantics of Axon Guidance," *Curr. Biol.* 9(6):R201-204, (1999).

Vanhove et al. "Selective Blockade of CD28 and not CTLA-4 with a Single-Chain Fv-Alpha I-Antitrypsin Fusion Antibody," *Blood* 102(2):564-570, (Jul. 15, 2003).
Vashishtha et al. "Adverse Events and Patterns of Tumor Progression in Met Diagnostic Subgroups in OAM4558g: a Phase II Study Evaluating MetMAb or Placebo in Combination with Erlotinib in Advanced NSCLC," *Poster World Conference on Lung Cancer—14$^{th}$* (Jul. 3, 2011).
Vashishtha et al. "Safety Data and Patterns of Progression in MET Diagnostic Subgroups in OAM4558g: a Phase II Study Evaluating MetMAb in Combination with Erlotinib in Advanced NSCLC," *Abstract American Society of Clinical Oncology 47$^{th}$ Annual Meeting (ASCO 2011)*, (Jun. 3, 2011).
Velculescu et al. "Serial Analysis of Gene Expression," *Science* 270(5235):484-487, (Oct. 20, 1995).
Velculescu et al. "Characterization of the Yeast Transcriptome," *Cell* 88(2):243-251 (1997).
VENTANA® Reference No. 790-4430, CONFIRM anti-Total c-MET (SP44) Rabbit Monoclonal Primary Antibody product package, available Aug. 18, 2009.
Verhoeyen et al. "Reshaping Human Antibodies: Grafting an Antilysozyme Activity," *Science* 239:1534-1536, (Feb. 8, 1988).
Vollmers and Brändlein "The 'Early Birds': Natural IgM Antibodies and Immune Surveillance," *Histology and Histopathology*, 20(3):927-937, (2005).
Vollmers and Brändlein "Death by Stress: Natural IgM-Induced Apoptosis," *Methods and Findings in Experimental and Clinical Pharmacology*, 27(3):185-191, (2005).
Wakelee et al., "Efficacy and Safety of Onartuzumab in Combination with First-Line Bevacizumab- or Pemetrexed-Based Chemotherapy Regimens in Advanced Non-Squamous Non-Small-Cell Lung Cancer (nsNSCLC): Results from a Phase II, Placebo-Controlled Study (GO27821)," *177 Chicago Multidisciplinary Symposium in Thoracic Oncology*, Chicago, USA 2 pages, (Oct. 30-Nov. 1, 2014).
Wall et al. "Type IV Pili and Cell Motility," *Mol. Microbiol.* 32(1):1-10, (Apr. 1999).
Wang et al. "Activation of the Met Receptor by Cell Attachment Induces and Sustains Hepatocellular Carcinomas in Transgenic Mice," *J. Cell Biol.* 153(5):1023-1033, (May 28, 2001).
Wang et al. "RNA-Seq: a revolutionary tool for transcriptomics" *Nature Reviews Genetics* 10(1):57-63, (Jan. 2009).
Weidner et al. "Interaction Between Gab1 and the C-Met Receptor Tyrosine Kinase is Responsible for Epithelial Morphogenesis," *Nature* 384:173-176, (Nov. 14, 1996).
Weidner et al. "Scatter Factor: Molecular Characteristics and Effect on the Invasiveness of Epithelial Cells," *J. Cell Biol.* 111(5 Pt 1):2097-2108, (Nov. 1990).
Weis et al. "Detection of Rare mRNAs Via Quantitative RT-PCR," *Trends in Genetics* 8(8):263-264, (1992).
Wen et al. "Updated Response Assessment Criteria for High-Grade Gliomas: Response Assessment in Neuro-Oncology Working Group," *J. Clin. Oncol.* 28:1963-1972, (Apr. 10, 2010).
Wiesmann et al. "Crystal Structure at 1.7 A Resolution of VEGF in Complex with Domain 2 of the Flt-1 Receptor," *Cell* 91:695-704, (Nov. 28, 1997).
Wiesmann et al. "Crystal Structure of Nerve Growth Factor in Complex with the Ligand-Binding Domain of the TrkA Receptor," *Nature* 401:184-188, (Sep. 9, 1999).
Winter el al. "Making Antibodies by Phage Display Technology," *Ann. Rev. Inununol.* 12:433-455, (1994).
Wright et al. "Effect of Glycosylation on Antibody Function: Implications for Genetic Engineering," *TIBTECH* 15:26-32, (Jan. 1997).
Yamada et al. "Immunohistochemistry with Antibodies to Hepatocyte Growth Factor and its Receptor Protein (c-MET) in Human Brain Tissues," *Brain Res.* 637(1-2):308-312, (Feb. 21, 1994).
Yamamoto et al. "Similarity of Protein Encoded by the Human c-erb-B-2 Gene to Epidermal Growth Factor Receptor," *Nature* 319:230-234, (Jan. 16, 1986).
Yamane-Ohnuki et al. "Establishment of FUT8 Knockout Chinese Hamster Ovary Cells: An Ideal Host Cell Line for Producing

(56) References Cited

OTHER PUBLICATIONS

Completely Defucosylated Antibodies with Enhances Antibody-Dependent Cellular Cytotoxicity," *Biotech. Bioeng.* 87(5):614-622, (Sep. 5, 2004).

Yansura and Simmons "Nucleotide Sequence Selection for Increased Expression of Heterologous Genes in *Escherichia coli,*" *Methods* 4(2):151-158, (1992).

Yarden and Ullrich "Growth Factor Receptor Tyrosine Kinases," *Ann. Rev. Biochem.* 57:433-478, (1988).

Yelton et al. "Affinity Maturation of the BR96 Anti-Carcinoma Antibody by Codon-Based Mutagenesis," *The Journal of Immunology* 155:1994-2004, (1995).

Yu et al. "Exploratory Biomarker Analysis from a Placebo-Controlled Phase II Study (OAM4558g) of MetMAb in Combination with Erlotinib in Patients with Advanced Non-Small-Cell Lung Cancer (NSCLC)," *World Conference on Lung Cancer—14th* (Jul. 3, 2011).

Yu et al. "Exploratory Biomarker Analyses from OAM4558g: a Placebo-Controlled Phase II Study of Erlotinib + MetMAb in Patients with Advanced Non-Small-Cell Lung Cancer (NSCLC)," *Poster American Society of Clinical Oncology 47th Annual Meeting (ASCO 2011)*, (Jun. 3, 2011).

Zaczek et al. "The Diverse Signaling Network of EGFR, HER2, HER3 and HER4 Tyrosine Receptors and the Consequences for Therapeutic Approaches," *Histol Histopathol* 20:1005-1015, (2005).

Zhang et al. "Enhanced Growth of Human Met-Expressing Xenografts in a New Strain of Immunocompromised Mice Transgenic for Human Hepatocyte Growth Factor/Scatter Factor," *Oncogene* 24(1):101-106 ,(Jan. 2005).

Zola H. Monoclonal Antibodies: A Manual of Techniques "6"*CRC Press* 147-158, (1987).

Zucali et al. "Role of cMET Expression in Non-Small-Cell Lung Cancer Patients Treated with EGFR Tyrosine Kinase Inhibitors," *Ann Oncol.* 19(9):1605-12, (Sep. 2008).

Ausubel et al. (1987). *Current Protocols of Molecular Biology*, John Wiley & Sons, TOC, 7 pages.

\* cited by examiner

|  | PBO+BEV (N=16) | ONA+BEV (N=14) |
|---|---|---|
| Responders | 0 | 5 |
| Non-responders | 16 | 9 |
|  |  |  |
| Response Rate (95% CI) | 0 (0, 20.6%) | 35.7% (12.8%, 64.9%) |
|  |  |  |
| Difference in Response Rate (95% CI) | 35.7% (0.6%, 65.7%) | |
| P-value (Fisher Exact Test) | 0.014 | |
|  |  |  |
| Complete Responders (CR) | 0 | 1 |
| Partial Responders (PR) | 0 | 4 |

FIG. 21

CANCER TREATMENT WITH C-MET ANTAGONISTS AND CORRELATION OF THE LATTER WITH HGF EXPRESSION

CROSS-REFERENCE TO RELATED APPLICATIONS

This is a continuation of PCT application No.: PCT/US2015/022282, filed Mar. 24, 2015, which claims priority benefit to provisional application No. 61/985,316 filed on Apr. 28, 2014 and provisional application No. 61/969,706 filed on Mar. 24, 2014, the contents of which are incorporated herein by reference in their entirety.

SUBMISSION OF SEQUENCE LISTING ON ASCII TEXT FILE

The content of the following submission on ASCII text file is incorporated herein by reference in its entirety: a computer readable form (CRF) of the Sequence Listing (file name: 146392030501Seqlist.txt, date recorded: Dec. 5, 2016, size: 30 KB).

FIELD OF THE INVENTION

The present invention concerns methods of therapeutic treatment. In particular, the invention concerns the treatment of human cancer patients using c-met antagonist. In addition, the invention concerns biomarkers, such as hepatocyte growth factor.

BACKGROUND

Cancer remains to be one of the most deadly threats to human health. In the U.S., cancer affects nearly 1.3 million new patients each year, and is the second leading cause of death after heart disease, accounting for approximately 1 in 4 deaths. It is also predicted that cancer may surpass cardiovascular diseases as the number one cause of death within 5 years. Solid tumors are responsible for most of those deaths. Although there have been significant advances in the medical treatment of certain cancers, the overall 5-year survival rate for all cancers has improved only by about 10% in the past 20 years. Cancers, or malignant tumors, metastasize and grow rapidly in an uncontrolled manner, making timely detection and treatment extremely difficult.

Gliomas account for 81% of all malignant brain and CNS tumors. Glioblastoma—World Health Organization (WHO) grade IV astrocytoma—accounts for 60% to 70% of malignant gliomas and remains the most aggressive sub-type of glioma. It occurs mostly in adults (median age at diagnosis: 64 years) and its incidence is estimated to be 3.05/100,000 in the United States and less than 2/100,000 in Europe. With 1- and 5-year overall survival of 29% and 3%, respectively, the prognosis of glioblastoma remains particularly poor (Central Brain Tumor Registry of the United States (2005), (CBTRUS; available on the world wide web at cbtrus.org).

Although some progress has been made in the treatment of glioblastoma, this disease faces a highly unmet medical need with limited treatment options.

Mesothelioma is a form of cancer that develops from cells of the mesothelium, the protective lining that covers many of the internal organs. The incidence of malignant mesothelioma shows marked variations from one country to another. In the countries with the highest incidence rates, Australia, Belgium, and Great Britain, the incidence rate is estimated to be around 3/100,000. Evidence indicates a relationship between exposure to asbestos and development of mesothelioma. The latency period between first exposure to asbestos and diagnosis of mesothelioma varies widely, likely as a result of variation in the intensity of exposure to asbestos. Malignant mesothelioma remains a serious health problem because of the poor results of current therapies. Bianchi, C. and Bianchi, T., *Industrial Health*, 45: 379-387 (2007).

Hepatocellular carcinoma (HCC, also called malignant hepatoma) is the most common type of liver cancer. Most cases of HCC are secondary to either viral hepatitis infection (hepatitis B or C) or cirrhosis. HCC is one of the most common tumors worldwide. It occurs more often in men than women and is usually seen in people age 50 or older. If the cancer cannot be completely removed by surgery, HCC usually results in death within 3 to 6 months (MedlinePlus (2013); available on the world wide web at nlm-.nih.gov/medlineplus/ency/article/000280.htm).

Gastric cancer, or stomach cancer, is most commonly caused by infection by the bacteria *Helicobacter pylori*. About 90 to 95% of cancers of the stomach are adenocarcinomas. Gastic cancer occurs mostly in adults (average age at diagnosis: 69 years). The incidence of gastric cancer is about 1 in 111. The overall 5-year relative survival rate of all people with gastric cancer in the United States is about 29% (American Cancer Society (2014); available on the world wide web at www.cancer.org/cancer/stomachcancer/index).

Renal cell carcinoma is the most common type of kidney cancer, accounting for about 90% of kidney cancers. Renal cell carcinoma occurs mostly in adults (average age at diagnosis: 64). The lifetime risk of developing kidney cancer is about 1 in 63. The 5-year survival rate of people diagnosed with kidney cancer varies with the stage of the cancer, from those having stage I kidney cancer having a 5-year survival rate of 81% to those with stage IV kidney cancer having a 5-year survival rate of 8% (American Cancer Society (2015); available on the world wide web at cancer.org/cancer/kidneycancer/index).

Sarcomas are cancers that arise from transformed cells of mesenchymal origin. Sarcomas can result from a number of tissues including bone, cartilage, fat, muscle, vascular, and hematopoietic tissue. There are about 15,000 new cases of sarcoma in the United States each year. The 5-year survival rate for osteosarcoma is about 70% (Longi, A., et al., Cancer Treat. Rev., 32(6); 423-36 (2006).

All references cited herein, including patent applications and publications, are incorporated by reference in their entirety.

SUMMARY OF THE INVENTION

Uses of a c-met antagonist for effectively treating cancer patients are provided. This application also provides better methods for diagnosing disease and for treating disease optionally with c-met antagonist. The c-met antagonist is optionally used in combination with a VEGF antagonist for effectively treating cancer.

In particular, hepatocyte growth factor (interchangeably termed "HGF") biomarker is used to identify a patient population in which anti-c-met antagonist, optionally plus VEGF antagonist, treatment provides clinically meaningful benefit. In particular, the invention provides data from a randomized phase II clinical trial of anti-c-met antibody MetMAb (onartuzumab) in combination with anti-VEGF antibody (bevacizumab) in subjects with recurrent glioblastoma. HGF biomarker was used to identify a patient population in which MetMAb plus bevacizumab treatment provided clinically meaningful benefit, evaluated by progression-free survival and overall survival. In the clinical trial, treatment with MetMAb and bevacizumab provided a clinically meaningful benefit to patients with recurrent glioblastoma that expressed high levels of HGF biomarker. The results showed that the efficacy, as evaluated by progression free survival (PFS) and overall survival (OS), was positive especially when compared to PFS and OS data for bevacizumab treatment alone. The difference was statistically significant, and the addition of MetMab to bevacizumab increased both progression free and overall survival in patients with recurrent glioblastoma that expressed high levels of HGF biomarker. The clinical trial data also showed that treatment with MetMAb in combination with bevacizumab increased the risk of progression and death in patients with recurrent glioblastoma that expressed low levels of HGF biomarker, relative to risk of progression and death in such patients treated with bevacizumab alone. The results showed that the efficacy, as evaluated by PFS and OS, was worse in the MetMAb and bevacizumab treated patients when compared with PFS and OS data for bevacizumab treatment alone in patients with glioblastoma that expressed low levels of HGF biomarker. The difference was statistically significant.

In one aspect, provided are methods for treating a patient with cancer comprising administering an effective amount of a c-met antagonist to the patient if the patient's cancer has been found to have a high amount of an HGF biomarker.

In some embodiments the patient's cancer overexpresses c-met. In some embodiments, the patient's cancer displays c-met amplification. In some embodiments, the patient's cancer does not display c-met amplification.

In some embodiments, the patient's cancer expresses both c-met and HGF. In some embodiments, HGF secreted from a cell binds c-met on the surface of the cell from which it was secreted in an autocrine manner. In some embodiments, the patient's cancer expresses both c-met and HGF and signals in an autocrine manner. In some embodiments. HGF expression in a patient's cancer is determined using IHC or ISH or other methods known in the art.

In some embodiments, the c-met antagonist is an antagonist anti-c-met antibody. In some embodiments, the anti-c-met antibody comprises a (a) HVR1 comprising sequence GYTFTSYWLH (SEQ ID NO: 1); (b) HVR2 comprising sequence GMIDPSNSDTRFNPNFKD (SEQ ID NO: 2); (c) HVR3-HC comprising sequence ATYRSYVTPLDY (SEQ ID NO: 3); (d) HVR1-LC comprising sequence KSSQSLLYTSSQKNYLA (SEQ ID NO: 4); (e) HVR2-LC comprising sequence WASTRES (SEQ ID NO: 5); and (f) HVR3-LC comprising sequence QQYYAYPWT (SEQ ID NO: 6). In some embodiments, the anti-c-met antibody binds an onartuzumab epitope. In some embodiments, the anti-c-met antibody is onartuzumab. In some embodiments, an effective amount of the anti-c-met antibody is 15 mg/kg every three weeks. In some embodiments, an effective amount of the anti-c-met antibody is 10 mg/kg every two weeks. In some embodiments, the c-met antagonist is one or more of crizotinib, tivantinib, carbozantinib, MGCD-265, ficlatuzumab, humanized TAK-701, rilotumumab, foretinib, h224G11, DN-30, MK-2461, E7050, MK-8033, PF-4217903, AMG208, JNJ-38877605, EMD1204831, INC-280, LY-2801653, SGX-126, RP1040, LY2801653, BAY-853474, and/or LA480.

In some embodiments, treatment is with an effective amount of a combination of a c-met antagonist and VEGF antagonist. In some embodiments, the VEGF antagonist is an anti-VEGF antibody. In some embodiments, the anti-VEGF antibody binds the A4.6.1 epitope. In some embodiments, the anti-VEGF antibody is bevacizumab. In some embodiments, the anti-VEGF antibody comprises a variable heavy chain (VH) and a variable light chain (VL), wherein the VH has an amino acid sequence of EVQLVESGGG LVQPGGSLRL SCAASGYTFT NYGMNWVRQA PGKGLEWVGW INTYTGEPTY AADFKRRFIT SLDTSKSTAY LQMNSLRAED TAVYYCAKYP HYYGSSIHWYF DVWGQGILVT VSS (SEQ ID NO: 14) and the VL has an amino acid sequence of DIQMTQSPSS LSASVGDRVT ITCSASQDIS NYLNWYQQKP GKAPKVLIYF TSSLIHSGVPS RFSGSGSGTD FLTIISSLQP EDFATYYCQQ YSTVPWTFGQ GTIKVEIKR. (SEQ ID NO: 15). In some embodiments, the effective amount of said anti-VEGF antibody is 10 mg/kg intravenously every two weeks. In some embodiments, the effective amount of said anti-VEGF antibody, wherein said effective amount of said anti-VEGF antibody is 15 mg/kg intravenously every three weeks. In some embodiments, the effective amount of the anti-VEGF antibody is administered initially intravenously over 90 minutes, with subsequent infusions over 60 minutes and then 30 minutes. In some embodiments, the anti-VEGF antibody is administered second to said patient at the first cycle. In some embodiments, subsequent administrations of the anti-VEGF antibody are either prior to or after the c-met antagonist. In some embodiments, the VEGF antagonist is administered concurrently with said c-met antagonist.

In some embodiments, the patient is less than 50 years old. In some embodiments, the patient is equal to or greater than 50 years old. In some embodiments, the patient has a Karnofsky performance status of 70% to 80%. In some embodiments, the patient has a Karnofsky performance status of 90% to 100%.

In some embodiments, the patient has greater PFS and/or OS relative to a patient who does not have high HGF biomarker. In some embodiments, the patient has greater PFS and/or OS relative to a patient who is treated with VEGF antagonist alone.

In some embodiments, the HGF biomarker is HGF mRNA, and HGF biomarker mRNA expression is determined in a sample from the patient using in situ hybridization (ISH). In some embodiments, high HGF biomarker is an ISH score of 2+ and/or 3+. In some embodiments, high HGF biomarker is an ISH score of 2+ and 3+. In some embodiments, high HGF mRNA biomarker is presence of about 12 or more HGF ISH signal positive cells in the sample. In some embodiments, high HGF mRNA biomarker is presence of about 15 or more HGF ISH signal positive cells in the sample. In some embodiments, high HGF mRNA biomarker is presence of about 20 or more HGF ISH signal positive cells in the sample. In some embodiments, high HGF mRNA biomarker is presence of about 25 or more HGF ISH signal positive cells in the sample. In some embodiments, high HGF mRNA biomarker is presence of about 30 or more HGF ISH signal positive cells in the sample. In some embodiments, high HGF mRNA biomarker is presence of about 35 or more HGF ISH signal positive cells in the sample. In some embodiments, high HGF mRNA biomarker is 1% or more HGF ISH signal positive cells in the sample. In some embodiments, high HGF mRNA biomarker is 2% or more of HGF ISH signal positive cells in the sample. In some embodiments, high HGF mRNA biomarker is 3% or more of HGF ISH signal positive cells in the sample. In some embodiments, high HGF mRNA biomarker is 4% or more of HGF ISH signal positive cells in the sample. In some embodiments, high HGF mRNA biomarker is 5% or more of HGF ISH signal positive cells in the sample. In some embodiments, high HGF mRNA biomarker is 10% or more of HGF ISH signal positive cells in the sample.

In some embodiments, the HGF biomarker expression is nucleic acid expression and is determined in a sample from the patient using an amplification based assay, RNA-seq, microarray analysis, SAGE, MassARRAY technique, or FISH. In some embodiments, the amplification based assay is a polymerase chain reaction (PCR) based assay (e.g., quantitative PCR, real-time PCR, quantitative real-time PCR (qRT-PCR), reverse transcriptase PCR (rt-PCR), and reverse transcription quantitative PCR (rt-qPCR)).

In some embodiments, the HGF biomarker is HGF mRNA, and HGF biomarker mRNA expression is determined in a sample from the patient using an amplification based assay, RNA-seq, microarray analysis, SAGE, MassARRAY technique, or FISH. In some embodiments, the amplification based assay is a PCR based assay (e.g., quantitative PCR, real-time PCR, quantitative real-time PCR (qRT-PCR), reverse transcriptase PCR (rt-PCR) and reverse transcription quantitative PCR (rt-qPCR)). In some embodiments, the PCR based assay is rt-qPCR. In some embodiments, high HGF biomarker is an HGF expression level in the upper 50% of a reference patient population. In some embodiments, high HGF biomarker is an HGF expression level in the upper 40% of a reference patient population. In some embodiments, high HGF biomarker is an HGF expression level in the upper 35% of a reference patient population. In some embodiments, high HGF biomarker is an HGF expression level in the upper 30% of a reference patient population. In some embodiments, high HGF biomarker is an HGF expression level in the upper 25% of a reference patient population. In some embodiments, high HGF biomarker is an HGF expression level in the upper 20% of a reference patient population.

In some embodiments, the sample is of the patient's cancer. A sample of the patient's cancer may include cancer cells, lymphocytes, leukocytes, stroma, blood vessels, connective tissue, basal lamina, and any other cell type in association with the cancer. In some embodiments, the sample comprises cancer cells and benign stromal cells. In some embodiments the cancer is glioblastoma, mesothelioma hepatocellular carcinoma, renal cell carcinoma, gastric cancer, sarcoma (e.g., osteosarcoma), non-small cell lung cancer, small cell lung cancer, breast cancer, gall bladder cancer, or pancreatic cancer. In some embodiments, the cancer is glioblastoma, mesothelioma, renal cell carcinoma, gastric cancer, hepatocellular carcinoma or sarcoma. In some embodiments, the cancer is glioblastoma. In some embodiments, the cancer is previously treated glioblastoma. In some embodiments, the sample comprises glioblastoma cells and benign stromal cells. In some embodiments, the benign stromal cells are one or more of reactive astrocytes, glial cells, pericytes and endothelial cells. In some embodiments, the cancer is mesothelioma. In some embodiments, the cancer is a previously treated mesothelioma. In some embodiments, the sample comprises mesothelioma cells and benign stromal cells. In some embodiments, the cancer is gastric cancer. In some embodiments, the cancer is a previously treated gastric cancer. In some embodiments, the cancer comprises gastric cancer cells and benign stromal cells. In some embodiments, the benign stromal cells are one or more of fibroblasts, macrophages, and endothelial cells. In some embodiments, the cancer is renal cell carcinoma. In some embodiments, the cancer is a previously treated renal cell carcinoma. In some embodiments, the sample comprises renal cell carcinoma cells and benign stromal cells. In some embodiments, the cancer is hepatocellular carcinoma. In some embodiments, the cancer is a previously treated hepatocellular carcinoma. In some embodiments, the sample comprises hepatocellular carcinoma cells and benign stromal cells. In some embodiments, the cancer is sarcoma (e.g., osteosarcoma). In some embodiments, the cancer is a previously treated sarcoma (e.g., previously treated osteosarcoma). In some embodiments, the sample comprises sarcoma cells and benign stromal cells. In some embodiments, the sample is of a patient's tumor. A tumor sample may include cancer cells, lymphocytes, leukocytes, stroma, blood vessels, connective tissue, basal lamina, and any other cell type in association with the tumor.

In some embodiments, the sample is obtained prior to treatment with c-met antagonist. In some embodiments, the sample is obtained prior to treatment with VEGF antagonist. In some embodiments, the sample is obtained prior to treatment with a cancer medicament.

In some embodiments, the sample is formalin fixed and paraffin embedded. In some embodiments, the ISH is detected using hybridization-based signal amplification.

In some embodiments, RNA is isolated from the sample. In some embodiments, RNA is isolated from the formalin fixed and paraffin embedded sample. In some embodiments, the isolated RNA is purified. In some embodiments, the purified RNA is used as the RNA source for an amplification-based assay. In some embodiments, the amplification-based assay is a PCR based assay. In some embodiments, the PCR based assay is rt-qPCR.

In some embodiments the cancer is glioblastoma, mesothelioma, hepatocellular carcinoma, renal cell carcinoma, gastric cancer, sarcoma (e.g., osteosarcoma), non-small cell lung cancer, small cell lung cancer, breast cancer, gall bladder cancer, or pancreatic cancer. In some embodiments, the cancer is glioblastoma, mesothelioma, renal cell carcinoma, gastric cancer, hepatocellular carcinoma or sarcoma. In some embodiments, the cancer is previously treated glioblastoma. In some embodiments, the cancer is a previously treated mesothelioma. In some embodiments, the cancer is a previously treated renal cell carcinoma. In some embodiments, the cancer is previously treated gastric cancer. In some embodiments, the cancer is a previously treated hepatocellular carcinoma. In some embodiments, the cancer is a previously treated sarcoma.

In one aspect, provided are methods for treating a patient with cancer comprising administering a therapeutically effective amount of a medicament other than a c-met antagonist to the patient if the patient's cancer has been found to have a low amount of an HGF biomarker.

In one aspect, the invention provides methods for identifying a cancer patient who is likely to respond to treatment with a c-met antagonist comprising the step of determining whether the patient's cancer has a high amount of an HGF biomarker, wherein the HGF biomarker expression indicates that the patient is likely to respond to treatment with the c-met antagonist.

In some embodiments, the HGF biomarker is HGF mRNA, and HGF biomarker mRNA expression is determined in a sample from the patient using in situ hybridization (ISH). In some embodiments, high HGF biomarker is an ISH score of 2+ and/or 3+. In some embodiments, high HGF biomarker is an ISH score of 2+ and 3+. In some embodiments, high HGF mRNA biomarker is presence of about 12 or more HGF ISH signal positive cells in the sample. In some embodiments, high HGF mRNA biomarker is presence of about 15 or more HGF ISH signal positive cells in the sample. In some embodiments, high HGF mRNA biomarker is presence of about 20 or more HGF ISH signal positive cells in the sample. In some embodiments, high HGF mRNA biomarker is presence of about 25 or more HGF ISH signal positive cells in the sample. In some embodiments, high HGF mRNA biomarker is presence of about 30 or more HGF ISH signal positive cells in the sample. In some embodiments, high HGF mRNA biomarker is presence of about 35 or more HGF ISH signal positive cells in the sample. In some embodiments, high HGF mRNA biomarker is 1% or more HGF ISH signal positive cells in the sample. In some embodiments, high HGF mRNA biomarker is 2% or more of HGF ISH signal positive cells in the sample. In some embodiments, high HGF mRNA biomarker is 3% or more of HGF ISH signal positive cells in the sample. In some embodiments, high HGF mRNA biomarker is 4% or more of HGF ISH signal positive cells in the sample. In some embodiments, high HGF mRNA biomarker is 5% or more of HGF ISH signal positive cells in the sample. In some embodiments, high HGF mRNA biomarker is 10% or more of HGF ISH signal positive cells in the sample.

In some embodiments, the HGF biomarker expression is nucleic acid expression and is determined in a sample from the patient using an amplification based assay, RNA-seq, microarray analysis, SAGE, MassARRAY technique, or FISH. In some embodiments, the amplification based assay is a polymerase chain reaction (PCR) based assay (e.g., quantitative PCR, real-time PCR, quantitative real-time PCR (qRT-PCR), reverse transcriptase PCR (rt-PCR), and reverse transcription quantitative PCR (rt-qPCR)).

In some embodiments, the HGF biomarker is HGF mRNA, and HGF biomarker mRNA expression is determined in a sample from the patient using an amplification based assay, RNA-seq, microarray analysis, SAGE, MassARRAY technique, or FISH. In some embodiments, the amplification based assay is a polymerase chain reaction (PCR) based assay (e.g., quantitative PCR, real-time PCR, quantitative real-time PCR (qRT-PCR), reverse transcriptase PCR (rt-PCR) and reverse transcription quantitative PCR (rt-qPCR)). In some embodiments, high HGF biomarker is an HGF expression level in the upper 50% of a reference patient population. In some embodiments, high HGF biomarker is an HGF expression level in the upper 40% of a reference patient population. In some embodiments, high HGF biomarker is an HGF expression level in the upper 35% of a reference patient population. In some embodiments, high HGF biomarker is an HGF expression level in the upper 30% of a reference patient population. In some embodiments, high HGF biomarker is an HGF expression level in the upper 25% of a reference patient population. In some embodiments, high HGF biomarker is an HGF expression level in the upper 20% of a reference patient population.

In one aspect, provided are methods for identifying a cancer patient who is less likely to respond to treatment with a c-met antagonist comprising the step of determining whether the patient's cancer has a low amount of an HGF biomarker, wherein the HGF biomarker expression indicates that the patient is less likely to respond to treatment with the c-met antagonist. In some embodiments, HGF biomarker nucleic acid expression is determined in a sample from the patient using in situ hybridization (ISH). In some embodiments, low HGF mRNA biomarker is an ISH score of less than 2+. In some embodiments, low HGF mRNA biomarker is an ISH score of less than 1+. In some embodiments, low HGF mRNA biomarker is an ISH score of 0 or 1+. In some embodiments, low HGF mRNA biomarker is an ISH score of 0. In some embodiments, low HGF biomarker is presence of HGF ISH positive signal in 10 or fewer cells. In some embodiments, low HGF biomarker is presence of HGF ISH positive signal in 5 or fewer cells. In some embodiments, low HGF biomarker is presence of HGF ISH positive signal in no cells.

In one aspect, provided are methods for identifying a cancer patient who is less likely to respond to treatment with a c-met antagonist comprising the step of determining whether the patient's cancer has a low amount of an HGF biomarker, wherein the HGF biomarker expression indicates that the patient is less likely to respond to treatment with the c-met antagonist. In some embodiments, HGF biomarker nucleic acid expression is determined in a sample from the patient using an amplification based assay, RNA-seq, microarray analysis, SAGE, MassARRAY technique, or FISH. In some embodiments, the amplification based assay is a polymerase chain reaction (PCR) based assay (e.g., quantitative PCR, real-time PCR, quantitative real-time PCR (qRT-PCR), reverse transcriptase PCR (rt-PCR), and reverse transcription quantitative PCR (rt-qPCR)). In some embodiments, low HGF mRNA biomarker is an HGF expression level in the lower 50% of a reference patient population. In some embodiments, low HGF mRNA biomarker is an HGF expression level in the lower 60% of a reference patient population. In some embodiments, low HGF mRNA biomarker is an HGF expression level in the lower 65% of a reference patient population. In some embodiments, low HGF mRNA biomarker is an HGF expression level in the lower 70% of a reference patient population. In some embodiments, low HGF mRNA biomarker is an HGF expression level in the lower 75% of a reference patient population. In some embodiments, low HGF mRNA biomarker is an HGF expression level in the lower 80% of a reference patient population.

In some embodiments, a patient is a human patient. The patient may be a cancer patient, i.e. one who is suffering or at risk for suffering from one or more symptoms of cancer. Moreover, the patient may be a previously treated cancer patient. The patient may be a glioblastoma patient, i.e. one who is suffering or at risk for suffering from one or more symptoms of glioblastoma. Moreover, the patient may be a previously treated glioblastoma patient. In some embodiments, the patient has been treated with no more than one prior line of chemotherapy. In some embodiments, the patient was previously treated with temozolomide. In some embodiments, the patient was previously treated with temozolomide in combination with radiation. In some embodiments, the patient was previously treated with temozolomide in combination with another agent. In some embodiments, the glioblastoma is 2nd line glioblastoma. The patient may be a mesothelioma patient, i.e. one who is suffering or at risk for suffering from one or more symptoms of mesothelioma. Moreover, the patient may be a previously treated mesothelioma patient. In some embodiments, the patient has been treated with no more than one prior line of chemotherapy. In some embodiments, the patient was previously treated with chemotherapy in combination with radiation. In some embodiments, the patient was previously treated with chemotherapy in combination with another agent. In some embodiments, the mesothelioma is 2nd line mesothelioma. The patient may be a gastric cancer patient, i.e. one who is suffering or at risk for suffering from one or more symptoms of gastric cancer. Moreover, the patient may be a previously treated gastric cancer patient. In some embodiments, the patient has been treated with no more than one prior line of chemotherapy. In some embodiments, the patient was previously treated with chemotherapy in combination with radiation. In some embodiments, the patient was previously treated with chemotherapy in combination with another agent. In some embodiments, the gastric cancer is 2nd line gastric cancer. The patient may be a renal cell carcinoma patient, i.e. one who is suffering or at risk for suffering from one or more symptoms of renal cell carcinoma. Moreover, the patient may be a previously treated renal cell carcinoma patient. In some embodiments, the patient has been treated with no more than one prior line of chemotherapy. In some embodiments, the patient was previously treated with chemotherapy. In some embodiments, the patient was previously treated with chemotherapy in combination with radiation. In some embodiments, the patient was previously treated with chemotherapy in combination with another agent. In some embodiments, the renal cell carcinoma is 2nd line renal cell carcinoma. The patient may be a hepatocellular carcinoma patient, i.e. one who is suffering or at risk for suffering from one or more symptoms of hepatocellular carcinoma. Moreover, the patient may be a previously treated hepatocellular carcinoma patient. In some embodiments, the patient has been treated with no more than one prior line of chemotherapy. In some embodiments, the patient was previously treated with chemotherapy. In some embodiments, the patient was previously treated with chemotherapy in combination with radiation. In some embodiments, the patient was previously treated with chemotherapy in combination with another agent. In some embodiments, the hepatocellular carcinoma is 2nd line hepatocellular carcinoma.

In some embodiments, the sample is a collection of cells or fluids obtained from a cancer patient. The source of the tissue or cell sample may be solid tissue as from a fresh, frozen and/or preserved organ or tissue sample or biopsy or aspirate; blood or any blood constituents; bodily fluids such as cerebrospinal fluid, amniotic fluid, peritoneal fluid, or interstitial fluid; cells from any time in gestation or development of the subject. The tissue sample may contain compounds which are not naturally intermixed with the tissue in nature such as preservatives, anticoagulants, buffers, fixatives, nutrients, antibiotics, or the like. Examples of tumor samples herein include, but are not limited to, tumor biopsy, fine needle aspirate, bronchiolar lavage, pleural fluid, sputum, urine, a surgical specimen, circulating tumor cells, serum, plasma, circulating plasma proteins, ascitic fluid, primary cell cultures or cell lines derived from tumors or exhibiting tumor-like properties, as well as preserved tumor samples, such as formalin-fixed, paraffin-embedded tumor samples or frozen tumor samples. A tumor sample may include cancer cells, lymphocytes, leukocytes, stroma, blood vessels, connective tissue, basal lamina, and any other cell type in association with the tumor. In one embodiment the sample comprises glioblastoma tumor sample (e.g., glioblastoma tumor sample comprising benign stroma, e.g., reactive astrocytes, glial cells, pericytes and/or endothelial cells). In some embodiments, the sample comprises a macro-dissected glioblastoma tumor sample (e.g., where morphologically normal brain tissue has been removed from the tumor sample). In some embodiments, the macro-dissected glioblastoma tumor sample comprises benign stroma (e.g., reactive astrocytes, glial cells, pericytes and/or endothelial cells). In some embodiment, the sample is of glioblastoma biopsy. In some embodiments, the sample is of glioblastoma cancer resection. In some embodiments, the sample was obtained after the patient's glioblastoma recurred. In some embodiments, the sample was obtained before the patient's glioblastoma recurred. In one embodiment the sample comprises mesothelioma tumor sample (e.g., mesothelioma tumor sample comprising benign stroma). In some embodiments, the sample comprises a macro-dissected mesothelioma tumor sample (e.g., where morphologically normal mesothelium tissue has been removed from the tumor sample). In some embodiments, the macro-dissected mesothelioma tumor sample comprises benign stroma. In some embodiment, the sample is of mesothelioma biopsy. In some embodiments, the sample is of mesothelioma cancer resection. In some embodiments, the sample was obtained after the patient's mesothelioma recurred. In some embodiments, the sample was obtained before the patient's mesothelioma recurred. In one embodiment the sample comprises gastric cancer tumor sample (e.g., gastric cancer tumor sample comprising benign stroma, e.g., fibroblasts, macrophages and/or endothelial cells). In some embodiments, the sample comprises a macro-dissected gastric cancer tumor sample (e.g., where morphologically normal gastric tissue has been removed from the tumor sample). In some embodiments, the macro-dissected gastric cancer tumor sample comprises benign stroma (e.g., fibroblasts, macrophages and/or endothelial cells). In some embodiment, the sample is of gastric cancer biopsy. In some embodiments, the sample is of gastric cancer resection. In some embodiments, the sample was obtained after the patient's gastric cancer recurred. In some embodiments, the sample was obtained before the patient's gastric cancer recurred. In one embodiment the sample comprises renal cell carcinoma tumor sample (e.g., renal cell carcinoma tumor sample comprising benign stroma). In some embodiments, the sample comprises a macro-dissected renal cell carcinoma tumor sample (e.g., where morphologically normal renal tissue has been removed from the tumor sample). In some embodiments, the macro-dissected renal cell carcinoma tumor sample comprises benign stroma. In some embodiment, the sample is of renal cell carcinoma biopsy. In some embodiments, the sample is of renal cell carcinoma cancer resection. In some embodiments, the sample was obtained after the patient's renal cell carcinoma recurred. In some embodiments, the sample was obtained before the patient's renal cell carcinoma recurred. In one embodiment the sample comprises hepatocellular carcinoma tumor sample (e.g., hepatocellular carcinoma tumor sample comprising benign stroma). In some embodiments, the sample comprises a macro-dissected hepatocellular carcinoma tumor sample (e.g., where morphologically normal liver tissue has been removed from the tumor sample). In some embodiments, the macro-dissected hepatocellular carcinoma tumor sample comprises benign stroma. In some embodiment, the sample is of hepatocellular carcinoma biopsy. In some embodiments, the sample is of hepatocellular carcinoma cancer resection. In some embodiments, the sample was obtained after the patient's hepatocellular carcinoma recurred. In some embodiments, the sample was obtained before the patient's hepatocellular carcinoma recurred.

In some embodiments, the sample is of the patient's cancer. In some embodiments, the sample is of the patient's glioblastoma. In some embodiments, the glioblastoma is previously treated. In some embodiments, the sample comprises glioblastoma cells and benign stromal cells. In some embodiments, the benign stromal cells are one or more of reactive astrocytes, glial cells, pericytes and endothelial cells. In some embodiments, the sample is of the patient's mesothelioma. In some embodiments, the mesothelioma is previously treated. In some embodiments, the sample comprises mesothelioma cells and benign stromal cells. In some embodiments, the sample is of the patient's gastric cancer. In some embodiments, the gastric cancer is previously treated.

In some embodiments the sample comprises gastric cancer cells and benign stromal cells. In some embodiments, the benign stromal cells are one or more of fibroblasts, macrophages, and endothelial cells. In some embodiments, the cancer is renal cell carcinoma. In some embodiments, the cancer is a previously treated renal cell carcinoma. In some embodiments, the sample comprises renal cell carcinoma cells and benign stromal cells. In some embodiments, the cancer is hepatocellular carcinoma. In some embodiments, the cancer is a previously treated hepatocellular carcinoma. In some embodiments, the sample comprises hepatocellular carcinoma cells and benign stromal cells. In some embodiments, the cancer is sarcoma (e.g., osteosarcoma). In some embodiments, the cancer is a previously treated sarcoma (e.g., previously treated osteosarcoma). In some embodiments, the sample comprises sarcoma cells and benign stromal cells.

In some embodiments, a patient who is previously treated for glioblastoma has received prior cancer therapy for glioblastoma. In some embodiments, the patient has been treated with no more than one prior line of chemotherapy. In some embodiments, the patient was previously treated with temozolomide. In some embodiments, the patient was previously treated with temozolomide in combination with radiation. In some embodiments, the patient was previously treated with temozolomide in combination with another agent. In some embodiments, the glioblastoma is second-line glioblastoma.

In some embodiments, a patient who is previously treated for mesothelioma has received prior cancer therapy for mesothelioma. In some embodiments, the patient has been treated with no more than one prior line of chemotherapy. In some embodiments, the patient was previously treated with chemotherapy in combination with radiation. In some embodiments, the patient was previously treated with chemotherapy in combination with another agent. In some embodiments, the mesothelioma is second-line mesothelioma.

In some embodiments, a patient who is previously treated for gastric cancer has received prior cancer therapy for gastric cancer. In some embodiments, the patient has been treated with no more than one prior line of chemotherapy. In some embodiments, the patient was previously treated with chemotherapy in combination with radiation. In some embodiments, the patient was previously treated with chemotherapy in combination with another agent. In some embodiments, the gastric cancer is second-line gastric cancer.

In some embodiments, a patient who is previously treated for renal cell carcinoma has received prior cancer therapy for renal cell carcinoma. In some embodiments, the patient has been treated with no more than one prior line of chemotherapy. In some embodiments, the patient was previously treated with chemotherapy in combination with radiation. In some embodiments, the patient was previously treated with chemotherapy in combination with another agent. In some embodiments, the renal cell carcinoma is second-line renal cell carcinoma.

In some embodiments, a patient who is previously treated for hepatocellular carcinoma has received prior cancer therapy for hepatocellular carcinoma. In some embodiments, the patient has been treated with no more than one prior line of chemotherapy. In some embodiments, the patient was previously treated with chemotherapy in combination with radiation. In some embodiments, the patient was previously treated with chemotherapy in combination with another agent. In some embodiments, the hepatocellular carcinoma is second-line hepatocellular carcinoma.

In some embodiments, the sample is obtained prior to treatment with c-met antagonist. In some embodiments, the sample is obtained prior to treatment with VEGF antagonist. In some embodiments, the sample is obtained prior to treatment with c-met antagonist and a VEGF antagonist. In some embodiments, the sample is obtained prior to treatment with a cancer medicament. In some embodiments, the sample is formalin fixed and paraffin embedded. In some embodiments, the ISH is detected using hybridization-based signal amplification. In some embodiments, RNA is isolated from the sample. In some embodiments, RNA is isolated from the formalin fixed and paraffin embedded sample. In some embodiments, the isolated RNA is purified. In some embodiments, the purified RNA is used as the RNA source for an amplification-based assay. In some embodiments, the amplification-based assay is a PCR based assay. In some embodiments, the PCR based assay is rt-qPCR.

In some embodiments the cancer is glioblastoma, mesothelioma, hepatocellular carcinoma, renal cell carcinoma, gastric cancer, sarcoma (e.g., osteosarcoma), non-small cell lung cancer, small cell lung cancer, breast cancer, gall bladder cancer, or pancreatic cancer. In some embodiments, the cancer is glioblastoma, mesothelioma, renal cell carcinoma, gastric cancer, hepatocellular carcinoma or sarcoma. In some embodiments, the cancer is previously treated glioblastoma. In some embodiments, the cancer is previously treated mesothelioma. In some embodiments, the cancer is previously treated renal cell carcinoma. In some embodiments, the cancer is previously treated gastric cancer. In some embodiments, the cancer is previously treated hepatocellular carcinoma. In some embodiments, the cancer is previously treated sarcoma.

In some embodiments, the c-met antagonist is an antagonist anti-c-met antibody. In some embodiments, the anti-c-met antibody comprises a (a) HVR1 comprising sequence GYTFTSYWLH (SEQ ID NO: 1); (b) HVR2 comprising sequence GMIDPSNSDTRFNPNFKD (SEQ ID NO: 2); (c) HVR3-HC comprising sequence ATYRSYVTPLDY (SEQ ID NO: 3); (d) HVR1-LC comprising sequence KSSQSLLYTSSQKNYLA (SEQ ID NO: 4); (e) HVR2-LC comprising sequence WASTRES (SEQ ID NO: 5); and (f) HVR3-LC comprising sequence QQYYAYPWT (SEQ ID NO: 6). In some embodiments, the anti-c-met antibody binds an onartuzumab epitope. In some embodiments, the anti-c-met antibody is onartuzumab. In some embodiments, an effective amount of the anti-c-met antibody is 15 mg/kg every three weeks. In some embodiments, an effective amount of the anti-c-met antibody is 10 mg/kg every two weeks. In some embodiments, the c-met antagonist is one or more of crizotinib, tivantinib, carbozantinib, MGCD-265, ficlatuzumab, humanized TAK-701, rilotumumab, foretinib, h224G11, DN-30, MK-2461, E7050, MK-8033, PF-4217903, AMG208, JNJ-38877605, EMD1204831, INC-280, LY-2801653, SGX-126, RP1040, LY2801653, BAY-853474, and/or LA480.

In some embodiments, the VEGF antagonist is an anti-VEGF antibody. In some embodiments, the anti-VEGF antibody binds the A4.6.1 epitope. In some embodiments, the anti-VEGF antibody is bevacizumab. In some embodiments, the anti-VEGF antibody comprises a variable heavy chain (VH) and a variable light chain (VL), wherein the VII has an amino acid sequence of EVQLVESCGGG LVQPGG-SLRL SCAASGYTFT NYGMNWVRQA PGK-GLEWVGW INTYTGEPTY AADFKRRFTF SLDTSK-STAY LQMNSLRAED TAVYYCAKYP HYYGSSHWYF DVWGQGILVT VSS (SEQ ID NO: 14) and the VL has an amino acid sequence of DIQMTQSPSS LSASVGDRVT ITCSASQDIS NYLNWYQQKP GKAPKVLYF TSSLHS-GVPS RFSGSGSGTD FTLTISSLQP EDFATYYCQQ YSTVPWTFGQ GTKVEIKR. (SEQ ID NO: 15). In some embodiments, the effective amount of said anti-VEGF antibody is 10 mg/kg intravenously every two weeks. In some embodiments, the effective amount of said anti-VEGF antibody, wherein said effective amount of said anti-VEGF antibody is 15 mg/kg intravenously every three weeks. In some embodiments, the effective amount of said anti-VEGF antibody is administered initially intravenously over 90 minutes, with subsequent infusions over 60 minutes and then 30 minutes. In some embodiments, the anti-VEGF antibody is administered second to said patient at the first cycle. In some embodiments, the anti-VEGF antibody is administered to the patient either prior to or after said c-met antagonist. In some embodiments, the VEGF antagonist is administered concurrently with said c-met antagonist.

In some embodiments, the patient is less than 50 years old. In some embodiments, the patient is equal to or greater than 50 years old. In some embodiments, the patient has a Karnofsky performance status of 70% to 80%. In some embodiments, the patient has a Karnofsky performance status of 90% to 100%.

In some embodiments, the patient has greater PFS and/or OS relative to a patient who does not have high HGF biomarker. In some embodiments, the patient has greater PFS and/or OS relative to a patient who is treated with VEGF antagonist alone.

In one aspect, provided are methods of identifying a patient having glioblastoma (e.g., previously treated glioblastoma) as likely to respond to a therapy comprising (a) anti-c-met antibody (e.g., onartuzumab) and (b) anti-VEGF antibody (e.g., bevacizumab) the methods comprising: (i) measuring HGF biomarker in a sample from the patient, wherein the HGF biomarker is HGF nucleic acid (e.g., mRNA) and measuring is by ISH; and (ii) identifying the patient as more likely to respond to the therapy comprising (a) c-met antagonist antibody (e.g., onartuzumab) and (b) anti-VEGF antibody (e.g., bevacizumab) when the sample has high HGF biomarker. In some embodiments, the methods further comprise (iii) selecting the therapy comprising (a) c-met antagonist antibody (e.g., onartuzumab) and (b) anti-VEGF antibody (e.g., bevacizumab) or recommending a therapy comprising (a) c-met antagonist antibody (e.g., onartuzumab) and (b) anti-VEGF antibody (e.g., bevacizumab) for the patient. In some embodiments, the methods further comprise (iv) treating the patient with therapy comprising (a) c-met antagonist antibody (e.g., onartuzumab) and (b) anti-VEGF antibody (e.g., bevacizumab).

In one aspect, provided are methods of identifying a patient having glioblastoma (e.g., previously treated glioblastoma) as likely to respond to a therapy comprising anti-c-met antibody (e.g., onartuzumab) the methods comprising: (i) measuring HGF biomarker in a sample from the patient, wherein the HGF biomarker is HGF nucleic acid (e.g., mRNA) and measuring is by ISH; and (ii) identifying the patient as more likely to respond to the therapy comprising c-met antagonist antibody (e.g., onartuzumab) when the sample has high HGF biomarker. In some embodiments, the methods further comprise (iii) selecting the therapy comprising c-met antagonist antibody (e.g., onartuzumab) or recommending a therapy comprising c-met antagonist antibody (e.g., onartuzumab) for the patient. In some embodiments, the therapy further comprises a second cancer medicament. In some embodiments, the methods further comprise (iv) treating the patient with therapy comprising c-met antagonist antibody (e.g., onartuzumab).

In one aspect, provided are methods of identifying a patient having mesothelioma (e.g., previously treated mesothelioma) as likely to respond to a therapy comprising (a) anti-c-met antibody (e.g., onartuzumab) and (b) anti-VEGF antibody (e.g., bevacizumab) the methods comprising: (i) measuring HGF biomarker in a sample from the patient, wherein the HGF biomarker is HGF nucleic acid (e.g., mRNA) and measuring is by ISH; and (ii) identifying the patient as more likely to respond to the therapy comprising (a) c-met antagonist antibody (e.g., onartuzumab) and (b) anti-VEGF antibody (e.g., bevacizumab) when the sample has high HGF biomarker. In some embodiments, the methods further comprise (iii) selecting the therapy comprising (a) c-met antagonist antibody (e.g., onartuzumab) and (b) anti-VEGF antibody (e.g., bevacizumab) or recommending a therapy comprising (a) c-met antagonist antibody (e.g., onartuzumab) and (b) anti-VEGF antibody (e.g., bevacizumab) for the patient. In some embodiments, the methods further comprise (iv) treating the patient with therapy comprising (a) c-met antagonist antibody (e.g., onartuzumab) and (b) anti-VEGF antibody (e.g., bevacizumab).

In one aspect, provided are methods of identifying a patient having mesothelioma (e.g., previously treated mesothelioma) as likely to respond to a therapy comprising anti-c-met antibody (e.g., onartuzumab) the methods comprising: (i) measuring HGF biomarker in a sample from the patient, wherein the HGF biomarker is HGF nucleic acid (e.g., mRNA) and measuring is by ISH; and (ii) identifying the patient as more likely to respond to the therapy comprising c-met antagonist antibody (e.g., onartuzumab) when the sample has high HGF biomarker. In some embodiments, the methods further comprise (iii) selecting the therapy comprising c-met antagonist antibody (e.g., onartuzumab) or recommending a therapy comprising c-met antagonist antibody (e.g., onartuzumab) for the patient. In some embodiments, the therapy further comprises a second cancer medicament. In some embodiments, the methods further comprise (iv) treating the patient with therapy comprising c-met antagonist antibody (e.g., onartuzumab).

In one aspect, provided are methods of identifying a patient having gastric cancer (e.g., previously treated gastric cancer) as likely to respond to a therapy comprising (a) anti-c-met antibody (e.g., onartuzumab) and (b) anti-VEGF antibody (e.g., bevacizumab) the methods comprising: (i) measuring HGF biomarker in a sample from the patient, wherein the HGF biomarker is HGF nucleic acid (e.g., mRNA) and measuring is by ISH; and (ii) identifying the patient as more likely to respond to the therapy comprising (a) c-met antagonist antibody (e.g., onartuzumab) and (b) anti-VEGF antibody (e.g., bevacizumab) when the sample has high HGF biomarker. In some embodiments, the methods further comprise (iii) selecting the therapy comprising (a) c-met antagonist antibody (e.g., onartuzumab) and (b) anti-VEGF antibody (e.g., bevacizumab) or recommending a therapy comprising (a) c-met antagonist antibody (e.g., onartuzumab) and (b) anti-VEGF antibody (e.g., bevacizumab) for the patient. In some embodiments, the methods further comprise (iv) treating the patient with therapy comprising (a) c-met antagonist antibody (e.g., onartuzumab) and (b) anti-VEGF antibody (e.g., bevacizumab).

In one aspect, provided are methods of identifying a patient having gastric cancer (e.g., previously treated gastric cancer) as likely to respond to a therapy comprising anti-c-met antibody (e.g., onartuzumab) the methods comprising: (i) measuring HGF biomarker in a sample from the patient, wherein the HGF biomarker is HGF nucleic acid (e.g., mRNA) and measuring is by ISH; and (ii) identifying the patient as more likely to respond to the therapy comprising c-met antagonist antibody (e.g., onartuzumab) when the sample has high HGF biomarker. In some embodiments, the methods further comprise (iii) selecting the therapy comprising c-met antagonist antibody (e.g., onartuzumab) or recommending a therapy comprising c-met antagonist antibody (e.g., onartuzumab) for the patient. In some embodiments, the therapy further comprises a second cancer medicament. In some embodiments, the methods further comprise (iv) treating the patient with therapy comprising c-met antagonist antibody (e.g., onartuzumab).

In one aspect, provided are methods of identifying a patient having renal cell carcinoma (e.g., previously treated renal cell carcinoma) as likely to respond to a therapy comprising (a) anti-c-met antibody (e.g., onartuzumab) and (b) anti-VEGF antibody (e.g., bevacizumab) the methods comprising: (i) measuring HGF biomarker in a sample from the patient, wherein the HGF biomarker is HGF nucleic acid (e.g., mRNA) and measuring is by ISH; and (ii) identifying the patient as more likely to respond to the therapy comprising (a) c-met antagonist antibody (e.g., onartuzumab) and (b) anti-VEGF antibody (e.g., bevacizumab) when the sample has high HGF biomarker. In some embodiments, the methods further comprise (iii) selecting the therapy comprising (a) c-met antagonist antibody (e.g., onartuzumab) and (b) anti-VEGF antibody (e.g., bevacizumab) or recommending a therapy comprising (a) c-met antagonist antibody (e.g., onartuzumab) and (b) anti-VEGF antibody (e.g., bevacizumab) for the patient. In some embodiments, the methods further comprise (iv) treating the patient with therapy comprising (a) c-met antagonist antibody (e.g., onartuzumab) and (b) anti-VEGF antibody (e.g., bevacizumab).

In one aspect, provided are methods of identifying a patient having renal cell carcinoma (e.g., previously treated renal cell carcinoma) as likely to respond to a therapy comprising anti-c-met antibody (e.g., onartuzumab) the methods comprising: (i) measuring HGF biomarker in a sample from the patient, wherein the HGF biomarker is HGF nucleic acid (e.g., mRNA) and measuring is by ISH; and (ii) identifying the patient as more likely to respond to the therapy comprising c-met antagonist antibody (e.g., onartuzumab) when the sample has high HGF biomarker. In some embodiments, the methods further comprise (iii) selecting the therapy comprising c-met antagonist antibody (e.g., onartuzumab) or recommending a therapy comprising c-met antagonist antibody (e.g., onartuzumab) for the patient. In some embodiments, the therapy further comprises a second cancer medicament. In some embodiments, the methods further comprise (iv) treating the patient with therapy comprising c-met antagonist antibody (e.g., onartuzumab).

In one aspect, provided are methods of identifying a patient having hepatocellular carcinoma (previously treated hepatocellular carcinoma) as likely to respond to a therapy comprising (a) anti-c-met antibody (e.g., onartuzumab) and (b) anti-VEGF antibody (e.g., bevacizumab) the methods comprising: (i) measuring HGF biomarker in a sample from the patient, wherein the HGF biomarker is HGF nucleic acid (e.g., mRNA) and measuring is by ISH; and (ii) identifying the patient as more likely to respond to the therapy comprising (a) c-met antagonist antibody (e.g., onartuzumab) and (b) anti-VEGF antibody (e.g., bevacizumab) when the sample has high HGF biomarker. In some embodiments, the methods further comprise (iii) selecting the therapy comprising (a) c-met antagonist antibody (e.g., onartuzumab) and (b) anti-VEGF antibody (e.g., bevacizumab) or recommending a therapy comprising (a) c-met antagonist antibody (e.g., onartuzumab) and (b) anti-VEGF antibody (e.g., bevacizumab) for the patient. In some embodiments, the methods further comprise (iv) treating the patient with therapy comprising (a) c-met antagonist antibody (e.g., onartuzumab) and (b) anti-VEGF antibody (e.g., bevacizumab).

In one aspect, provided are methods of identifying a patient having hepatocellular carcinoma (e.g., previously treated hepatocellular carcinoma) as likely to respond to a therapy comprising anti-c-met antibody (e.g., onartuzumab) the methods comprising: (i) measuring HGF biomarker in a sample from the patient, wherein the HGF biomarker is HGF nucleic acid (e.g., mRNA) and measuring is by ISH; and (ii) identifying the patient as more likely to respond to the therapy comprising c-met antagonist antibody (e.g., onartuzumab) when the sample has high HGF biomarker. In some embodiments, the methods further comprise (iii) selecting the therapy comprising c-met antagonist antibody (e.g., onartuzumab) or recommending a therapy comprising c-met antagonist antibody (e.g., onartuzumab) for the patient. In some embodiments, the therapy further comprises a second cancer medicament. In some embodiments, the methods further comprise (iv) treating the patient with therapy comprising c-met antagonist antibody (e.g., onartuzumab).

In one aspect, provided are methods of identifying a patient having sarcoma (e.g., previously treated sarcoma) as likely to respond to a therapy comprising (a) anti-c-met antibody (e.g., onartuzumab) and (b) anti-VEGF antibody (e.g., bevacizumab) the methods comprising: (i) measuring HGF biomarker in a sample from the patient, wherein the HGF biomarker is HGF nucleic acid (e.g., mRNA) and measuring is by ISH; and (ii) identifying the patient as more likely to respond to the therapy comprising (a) c-met antagonist antibody (e.g., onartuzumab) and (b) anti-VEGF antibody (e.g., bevacizumab) when the sample has high HGF biomarker. In some embodiments, the methods further comprise (iii) selecting the therapy comprising (a) c-met antagonist antibody (e.g., onartuzumab) and (b) anti-VEGF antibody (e.g., bevacizumab) or recommending a therapy comprising (a) c-met antagonist antibody (e.g., onartuzumab) and (b) anti-VEGF antibody (e.g., bevacizumab) for the patient. In some embodiments, the methods further comprise (iv) treating the patient with therapy comprising (a) c-met antagonist antibody (e.g., onartuzumab) and (b) anti-VEGF antibody (e.g., bevacizumab).

In one aspect, provided are methods of identifying a patient having sarcoma (e.g., previously treated sarcoma) as likely to respond to a therapy comprising anti-c-met antibody (e.g., onartuzumab) the methods comprising: (i) measuring HGF biomarker in a sample from the patient, wherein the HGF biomarker is HGF nucleic acid (e.g., mRNA) and measuring is by ISH; and (ii) identifying the patient as more likely to respond to the therapy comprising c-met antagonist antibody (e.g., onartuzumab) when the sample has high HGF biomarker. In some embodiments, the methods further comprise (iii) selecting the therapy comprising c-met antagonist antibody (e.g., onartuzumab) or recommending a therapy comprising c-met antagonist antibody (e.g., onartuzumab) for the patient. In some embodiments, the therapy further comprises a second cancer medicament. In some embodiments, the methods further comprise (iv) treating the patient with therapy comprising c-met antagonist antibody (e.g., onartuzumab).

In one aspect, provided are methods of identifying a patient having glioblastoma (e.g., previously treated glioblastoma) as likely to respond to a therapy comprising (a) anti-c-met antibody (e.g., onartuzumab) and (b) anti-VEGF antibody (e.g., bevacizumab) the methods comprising: (i) measuring HGF biomarker in a sample from the patient, wherein the HGF biomarker is HGF nucleic acid (e.g., mRNA) and measuring is by a PCR based assay (e.g., rt-qPCR); and (ii) identifying the patient as more likely to respond to the therapy comprising (a) c-met antagonist antibody (e.g., onartuzumab) and (b) anti-VEGF antibody (e.g., bevacizumab) when the sample has high HGF biomarker. In some embodiments, the methods further comprise (iii) selecting the therapy comprising (a) c-met antagonist antibody (e.g., onartuzumab) and (b) anti-VEGF antibody (e.g., bevacizumab) or recommending a therapy comprising (a) c-met antagonist antibody (e.g., onartuzumab) and (b) anti-VEGF antibody (e.g., bevacizumab) for the patient. In some embodiments, the methods further comprise (iv) treating the patient with therapy comprising (a) c-met antagonist antibody (e.g., onartuzumab) and (b) anti-VEGF antibody (e.g., bevacizumab).

In one aspect, provided are methods of identifying a patient having glioblastoma (e.g., previously treated glioblastoma) as likely to respond to a therapy comprising anti-c-met antibody (e.g., onartuzumab) the methods comprising: (i) measuring HGF biomarker in a sample from the patient, wherein the HGF biomarker is HGF nucleic acid (e.g., mRNA) and measuring is by a PCR based assay (e.g., rt-qPCR); and (ii) identifying the patient as more likely to respond to the therapy comprising c-met antagonist antibody (e.g., onartuzumab) when the sample has high HGF biomarker. In some embodiments, the methods further comprise (iii) selecting the therapy comprising c-met antagonist antibody (e.g., onartuzumab) or recommending a therapy comprising c-met antagonist antibody (e.g., onartuzumab) for the patient. In some embodiments, the therapy further comprises a second cancer medicament. In some embodiments, the methods further comprise (iv) treating the patient with therapy comprising c-met antagonist antibody (e.g., onartuzumab).

In one aspect, provided are methods of identifying a patient having mesothelioma (e.g., previously treated mesothelioma) as likely to respond to a therapy comprising (a) anti-c-met antibody (e.g., onartuzumab) and (b) anti-VEGF antibody (e.g., bevacizumab) the methods comprising: (i) measuring HGF biomarker in a sample from the patient, wherein the HGF biomarker is HGF nucleic acid (e.g., mRNA) and measuring is by a PCR based assay (e.g., rt-qPCR); and (ii) identifying the patient as more likely to respond to the therapy comprising (a) c-met antagonist antibody (e.g., onartuzumab) and (b) anti-VEGF antibody (e.g., bevacizumab) when the sample has high HGF biomarker. In some embodiments, the methods further comprise (iii) selecting the therapy comprising (a) c-met antagonist antibody (e.g., onartuzumab) and (b) anti-VEGF antibody (e.g., bevacizumab) or recommending a therapy comprising (a) c-met antagonist antibody (e.g., onartuzumab) and (b) anti-VEGF antibody (e.g., bevacizumab) for the patient. In some embodiments, the methods further comprise (iv) treating the patient with therapy comprising (a) c-met antagonist antibody (e.g., onartuzumab) and (b) anti-VEGF antibody (e.g., bevacizumab).

In one aspect, provided are methods of identifying a patient having mesothelioma (e.g., previously treated mesothelioma) as likely to respond to a therapy comprising anti-c-met antibody (e.g., onartuzumab) the methods comprising: (i) measuring HGF biomarker in a sample from the patient, wherein the HGF biomarker is HGF nucleic acid (e.g., mRNA) and measuring is by a PCR based assay (e.g., rt-qPCR); and (ii) identifying the patient as more likely to respond to the therapy comprising c-met antagonist antibody (e.g., onartuzumab) when the sample has high HGF biomarker. In some embodiments, the methods further comprise (iii) selecting the therapy comprising c-met antagonist antibody (e.g., onartuzumab) or recommending a therapy comprising c-met antagonist antibody (e.g., onartuzumab) for the patient. In some embodiments, the therapy further comprises a second cancer medicament. In some embodiments, the methods further comprise (iv) treating the patient with therapy comprising c-met antagonist antibody (e.g., onartuzumab).

In one aspect, provided are methods of identifying a patient having gastric cancer (e.g., previously treated gastric cancer) as likely to respond to a therapy comprising (a) anti-c-met antibody (e.g., onartuzumab) and (b) anti-VEGF antibody (e.g., bevacizumab) the methods comprising: (i) measuring HGF biomarker in a sample from the patient, wherein the HGF biomarker is HGF nucleic acid (e.g., mRNA) and measuring is by a PCR based assay (e.g., rt-qPCR); and (ii) identifying the patient as more likely to respond to the therapy comprising (a) c-met antagonist antibody (e.g., onartuzumab) and (b) anti-VEGF antibody (e.g., bevacizumab) when the sample has high HGF biomarker. In some embodiments, the methods further comprise (iii) selecting the therapy comprising (a) c-met antagonist antibody (e.g., onartuzumab) and (b) anti-VEGF antibody (e.g., bevacizumab) or recommending a therapy comprising (a) c-met antagonist antibody (e.g., onartuzumab) and (b) anti-VEGF antibody (e.g., bevacizumab) for the patient. In some embodiments, the methods further comprise (iv) treating the patient with therapy comprising (a) c-met antagonist antibody (e.g., onartuzumab) and (b) anti-VEGF antibody (e.g., bevacizumab).

In one aspect, provided are methods of identifying a patient having gastric cancer (e.g., previously treated gastric cancer) as likely to respond to a therapy comprising anti-c-met antibody (e.g., onartuzumab) the methods comprising: (i) measuring HGF biomarker in a sample from the patient, wherein the HGF biomarker is HGF nucleic acid (e.g., mRNA) and measuring is by a PCR based assay (e.g., rt-qPCR); and (ii) identifying the patient as more likely to respond to the therapy comprising c-met antagonist antibody (e.g., onartuzumab) when the sample has high HGF biomarker. In some embodiments, the methods further comprise (iii) selecting the therapy comprising c-met antagonist antibody (e.g., onartuzumab) or recommending a therapy comprising c-met antagonist antibody (e.g., onartuzumab) for the patient. In some embodiments, the therapy further comprises a second cancer medicament. In some embodiments, the methods further comprise (iv) treating the patient with therapy comprising c-met antagonist antibody (e.g., onartuzumab).

In one aspect, provided are methods of identifying a patient having renal cell carcinoma (e.g., previously treated renal cell carcinoma) as likely to respond to a therapy comprising (a) anti-c-met antibody (e.g., onartuzumab) and (b) anti-VEGF antibody (e.g., bevacizumab) the methods comprising: (i) measuring HGF biomarker in a sample from the patient, wherein the HGF biomarker is HGF nucleic acid (e.g., mRNA) and measuring is by a PCR based assay (e.g., rt-qPCR); and (ii) identifying the patient as more likely to respond to the therapy comprising (a) c-met antagonist antibody (e.g., onartuzumab) and (b) anti-VEGF antibody (e.g., bevacizumab) when the sample has high HGF biomarker. In some embodiments, the methods further comprise (iii) selecting the therapy comprising (a) c-met antagonist antibody (e.g., onartuzumab) and (b) anti-VEGF antibody (e.g., bevacizumab) or recommending a therapy comprising (a) c-met antagonist antibody (e.g., onartuzumab) and (b)

anti-VEGF antibody (e.g., bevacizumab) for the patient. In some embodiments, the methods further comprise (iv) treating the patient with therapy comprising (a) c-met antagonist antibody (e.g., onartuzumab) and (b) anti-VEGF antibody (e.g., bevacizumab).

In one aspect, provided are methods of identifying a patient having renal cell carcinoma (e.g., previously treated renal cell carcinoma) as likely to respond to a therapy comprising anti-c-met antibody (e.g., onartuzumab) the methods comprising: (i) measuring HGF biomarker in a sample from the patient, wherein the HGF biomarker is HGF nucleic acid (e.g., mRNA) and measuring is by a PCR based assay (e.g., rt-qPCR); and (ii) identifying the patient as more likely to respond to the therapy comprising c-met antagonist antibody (e.g., onartuzumab) when the sample has high HGF biomarker. In some embodiments, the methods further comprise (iii) selecting the therapy comprising c-met antagonist antibody (e.g., onartuzumab) or recommending a therapy comprising c-met antagonist antibody (e.g., onartuzumab) for the patient. In some embodiments, the therapy further comprises a second cancer medicament. In some embodiments, the methods further comprise (iv) treating the patient with therapy comprising c-met antagonist antibody (e.g., onartuzumab).

In one aspect, provided are methods of identifying a patient having hepatocellular carcinoma (e.g. previously treated hepatocellular carcinoma) as likely to respond to a therapy comprising (a) anti-c-met antibody (e.g., onartuzumab) and (b) anti-VEGF antibody (e.g., bevacizumab) the methods comprising: (i) measuring HGF biomarker in a sample from the patient, wherein the HGF biomarker is HGF nucleic acid (e.g., mRNA) and measuring is by a PCR based assay (e.g., rt-qPCR); and (ii) identifying the patient as more likely to respond to the therapy comprising (a) c-met antagonist antibody (e.g., onartuzumab) and (b) anti-VEGF antibody (e.g., bevacizumab) when the sample has high HGF biomarker. In some embodiments, the methods further comprise (iii) selecting the therapy comprising (a) c-met antagonist antibody (e.g., onartuzumab) and (b) anti-VEGF antibody (e.g., bevacizumab) or recommending a therapy comprising (a) c-met antagonist antibody (e.g., onartuzumab) and (b) anti-VEGF antibody (e.g., bevacizumab) for the patient. In some embodiments, the methods further comprise (iv) treating the patient with therapy comprising (a) c-met antagonist antibody (e.g., onartuzumab) and (b) anti-VEGF antibody (e.g., bevacizumab).

In one aspect, provided are methods of identifying a patient having hepatocellular carcinoma (e.g., previously treated hepatocellular carcinoma) as likely to respond to a therapy comprising anti-c-met antibody (e.g., onartuzumab) the methods comprising: (i) measuring HGF biomarker in a sample from the patient, wherein the HGF biomarker is HGF nucleic acid (e.g., mRNA) and measuring is by a PCR based assay (e.g., rt-qPCR); and (ii) identifying the patient as more likely to respond to the therapy comprising c-met antagonist antibody (e.g., onartuzumab) when the sample has high HGF biomarker. In some embodiments, the methods further comprise (iii) selecting the therapy comprising c-met antagonist antibody (e.g., onartuzumab) or recommending a therapy comprising c-met antagonist antibody (e.g., onartuzumab) for the patient. In some embodiments, the therapy further comprises a second cancer medicament. In some embodiments, the methods further comprise (iv) treating the patient with therapy comprising c-met antagonist antibody (e.g., onartuzumab).

In one aspect, provided are methods of identifying a patient having sarcoma (e.g., previously treated sarcoma) as likely to respond to a therapy comprising (a) anti-c-met antibody (e.g., onartuzumab) and (b) anti-VEGF antibody (e.g., bevacizumab) the methods comprising: (i) measuring HGF biomarker in a sample from the patient, wherein the HGF biomarker is HGF nucleic acid (e.g., mRNA) and measuring is by a PCR based assay (e.g., rt-qPCR); and (ii) identifying the patient as more likely to respond to the therapy comprising (a) c-met antagonist antibody (e.g., onartuzumab) and (b) anti-VEGF antibody (e.g., bevacizumab) when the sample has high HGF biomarker. In some embodiments, the methods further comprise (iii) selecting the therapy comprising (a) c-met antagonist antibody (e.g., onartuzumab) and (b) anti-VEGF antibody (e.g., bevacizumab) or recommending a therapy comprising (a) c-met antagonist antibody (e.g., onartuzumab) and (b) anti-VEGF antibody (e.g., bevacizumab) for the patient. In some embodiments, the methods further comprise (iv) treating the patient with therapy comprising (a) c-met antagonist antibody (e.g., onartuzumab) and (b) anti-VEGF antibody (e.g., bevacizumab).

In one aspect, provided are methods of identifying a patient having sarcoma (e.g., previously treated sarcoma) as likely to respond to a therapy comprising anti-c-met antibody (e.g., onartuzumab) the methods comprising: (i) measuring HGF biomarker in a sample from the patient, wherein the HGF biomarker is HGF nucleic acid (e.g., mRNA) and measuring is by a PCR based assay (e.g., rt-qPCR); and (ii) identifying the patient as more likely to respond to the therapy comprising c-met antagonist antibody (e.g., onartuzumab) when the sample has high HGF biomarker. In some embodiments, the methods further comprise (iii) selecting the therapy comprising c-met antagonist antibody (e.g., onartuzumab) or recommending a therapy comprising c-met antagonist antibody (e.g., onartuzumab) for the patient. In some embodiments, the therapy further comprises a second cancer medicament. In some embodiments, the methods further comprise (iv) treating the patient with therapy comprising c-met antagonist antibody (e.g., onartuzumab).

In one aspect, provided are methods for determining HGF biomarker expression, comprising the step of determining whether a patient's cancer has a high level of HGF biomarker, wherein the HGF biomarker expression is mRNA expression and is determined in a sample from the patient using ISH, wherein high HGF biomarker expression is an ISH score greater than 2+, wherein the high HGF biomarker expression indicates that the patient is likely to have increased OS and/or PFS when the patient is treated with an anti-c-met antibody (e.g., onartuzumab) in combination with an anti-VEGF antibody (e.g., bevacizumab).

In one aspect, provided are methods for determining HGF biomarker expression, comprising the step of determining whether a patient's cancer has a high level of HGF biomarker, wherein the HGF biomarker expression is mRNA expression and is determined in a sample from the patient using ISH, wherein high HGF biomarker expression is an ISH score greater than 2+, wherein the high HGF biomarker expression indicates that the patient is likely to have increased OS and/or PFS when the patient is treated with an anti-c-met antibody (e.g., onartuzumab). In some embodiments, the patient is treated with an anti-c-met antibody (e.g., onartuzumab) optionally in combination with a second cancer medicament.

In one aspect, provided are methods for determining HGF biomarker expression, comprising the step of determining whether a patient's cancer has a high level of HGF biomarker, wherein the HGF biomarker expression is mRNA expression and is determined in a sample from the patient using a PCR based assay (e.g., rt-qPCR), wherein high HGF biomarker expression is an HGF expression level in the upper 25% of a reference patient population, wherein the high HGF biomarker expression indicates that the patient is likely to have increased OS and/or PFS when the patient is treated with an anti-c-met antibody (e.g., onartuzumab) in combination with an anti-VEGF antibody (e.g., bevacizumab).

In one aspect, provided are methods for determining HGF biomarker expression, comprising the step of determining whether a patient's cancer has a high level of HGF biomarker, wherein the HGF biomarker expression is mRNA expression and is determined in a sample from the patient using a PCR based assay (e.g., rt-qPCR), wherein high HGF biomarker expression is an HGF expression level in the upper 25% of a reference patient population, wherein the high HGF biomarker expression indicates that the patient is likely to have increased OS and/or PFS when the patient is treated with an anti-c-met antibody (e.g., onartuzumab). In some embodiments, the patient is treated with an anti-c-met antibody (e.g., onartuzumab) optionally in combination with a second cancer medicament.

In some embodiments, recommending a treatment refers to using the information or data generated relating to the level or presence of c-met in a sample of a patient to identify the patient as suitably treated or not suitably treated with a therapy. In some embodiments the therapy may comprise c-met antibody (e.g., onartuzumab). In some embodiments, the therapy may comprise VEGF antagonist (e.g., bevacizumab). In some embodiments, the therapy may comprise anti-c-met antibody (e.g., onartuzumab) in combination with VEGF antagonist (e.g., bevacizumab). The information or data may be in any form, written, oral or electronic. In some embodiments, using the information or data generated includes communicating, presenting, reporting, storing, sending, transferring, supplying, transmitting, delivering, dispensing, or combinations thereof. In some embodiments, communicating, presenting, reporting, storing, sending, transferring, supplying, transmitting, delivering, dispensing, or combinations thereof are performed by a computing device, analyzer unit or combination thereof. In some further embodiments, communicating, presenting, reporting, storing, sending, transferring, supplying, transmitting, dispensing, or combinations thereof are performed by an individual (e.g., a laboratory or medical professional). In some embodiments, the information or data includes a comparison of the level of HGF to a reference level. In some embodiments, the information or data includes an indication that HGF is present or absent in the sample. In some embodiments, the information or data includes an indication that HGF ISH signal intensity is present at a particular level (e.g., 0, 1+, 2+, 3+). In some embodiments, the information or data includes an indication that HGF ISH signal intensity is present in a particular percentage of cells (e.g., glioblastoma tumor cells and benign stromal cells, mesothelioma tumor cells and benign stromal cells, gastric cancer tumor cells and benign stromal cells, hepatocellular carcinoma tumor cells and benign stromal cells, renal cell carcinoma tumor cells and benign stromal cells, or sarcoma tumor cells and benign stromal cells). In some embodiments, the information or data includes an indication that HGF mRNA expression levels are in a particular percentile compared to the HGF mRNA expression levels in tumors obtained from a reference population of patients comprising a representative number of patients comprising patients with a particular cancer (e.g., upper 50%, upper 40, upper 35%, upper 30%, upper 25%, upper 20%, lower 50%, lower 60%, lower 65%, lower 70%, lower 75%, lower 80%). In some embodiments, the information or data includes an indication that the patient is suitably treated or not suitably treated with a therapy comprising c-met antagonist antibody (e.g., onartuzumab). In some embodiments, the information or data includes an indication that the patient is suitably treated or not suitably treated with a therapy comprising c-met antagonist antibody (e.g., onartuzumab) in combination with a second cancer medicament. In some embodiments, the information or data includes an indication that the patient is suitably treated or not suitably treated with a therapy comprising c-met antagonist antibody (e.g., onartuzumab) in combination with VEGF antagonist (e.g., bevacizumab).

In one aspect, provided are methods for advertising a c-met antibody comprising promoting, to a target audience, the use of the c-met antibody for treating a patient with cancer based on expression of an HGF biomarker. In some embodiments, the promotion is by a package insert accompanying a commercial formulation of the anti-c-met antibody. In some embodiments, the promotion is by a package insert accompanying a commercial formulation of a second medicament. In some embodiments, the second medicament is a chemotherapeutic agent. In some embodiments, the second medicament is a VEGF antagonist. In some embodiments, the anti-c-met antibody is onartuzumab and the VEGF antagonist is bevacizumab. In some embodiments, the patient is selected for treatment with a c-met antagonist if the cancer sample expresses the biomarker at a high level. In some embodiments, the promotion is by a package insert where the package insert provides instructions to receive therapy with anti-c-met antibody in combination with a VEGF antagonist. In some embodiments, the promotion is followed by the treatment of the patient with the anti-c-met antibody with or without the second medicament.

In some embodiments, promoting includes the promotion of therapeutic agent(s), such as an anti-c-met antagonist (e.g., onartuzumab) and/or VEGF antagonist (e.g., bevacizumab), for an indication, such as glioblastoma (e.g., recurrent glioblastoma), mesothelioma (e.g., recurrent mesothelioma), gastric cancer (e.g., recurrent gastric cancer), renal cell carcinoma (e.g., recurrent renal cell carcinoma), hepatocellular carcinoma (e.g., recurrent hepatocellular carcinoma), or sarcoma (e.g., recurrent sarcoma) treatment, where such promoting is authorized by the Food and Drug Administration (FDA) as having been demonstrated to be associated with statistically significant therapeutic efficacy and acceptable safety in a population of subjects.

In one aspect, provided are diagnostic kits comprising one or more reagent for determining expression of an HGF biomarker in a sample from a cancer patient, wherein detection of a high amount of the HGF biomarker means extended survival (e.g., PFS and/or OS) when the patient is treated with an effective amount of a c-met antagonist. In son embodiments, the cancer is glioblastoma, mesothelioma, hepatocellular carcinoma, renal cell carcinoma, gastric cancer, sarcoma (e.g., osteosarcoma), non-small cell lung cancer, small cell lung cancer, breast cancer, gall bladder cancer, or pancreatic cancer. In some embodiments, the cancer is previously treated glioblastoma, mesothelioma, renal cell carcinoma, gastric cancer, hepatocellular carcinoma, or sarcoma (e.g., osteosarcoma). In some embodiments, detection of a high amount of the HGF biomarker means extended survival (e.g., PFS and/or OS) when the patient is treated with an effective amount of a combination of c-met antagonist and a second cancer medicament. In some embodiments, detection of a high amount of the HGF biomarker means extended survival (e.g., PFS and/or OS) when the patient is treated with an effective amount of a combination of c-met antagonist and the standard of care anti-tumor agent. In some embodiments, detection of a high amount of the HGF biomarker means extended survival (e.g., PFS and/or OS) when the patient is treated with an effective amount of a combination of a c-met antagonist and a VEGF antagonist. In some embodiments, the kits further comprise instructions to use the kit to select a c-met antagonist to treat the previously treated cancer patient if a high amount of the HGF biomarker is determined.

In one aspect, provided are methods of making any of the diagnostic kits provided herein comprising combining in a package a pharmaceutical composition comprising a cancer medicament and a package insert indicating that the pharmaceutical composition is for treating a patient with cancer based on expression of an HGF biomarker.

In some embodiments of any of the methods of the invention, the methods further comprise testing the sample of the patient's cancer for a biomarker. In some embodiments, the biomarker is c-met biomarker. In some embodiments, high c-met biomarker is determined using any of the methods provided herein. In some embodiments, the biomarker is an HGF biomarker. In some embodiments, high HGF biomarker is determined using any of the methods provided herein.

BRIEF DESCRIPTION OF THE FIGURES

FIG. 21: shows overall response rate (ORR) in HGF-PCR high (upper 25%) patients in bevacizumab+onartuzumab arm compared to patients in bevacizumab+placebo arm.

DETAILED DESCRIPTION OF EMBODIMENTS OF THE INVENTION

I. Definitions

Figure 1:
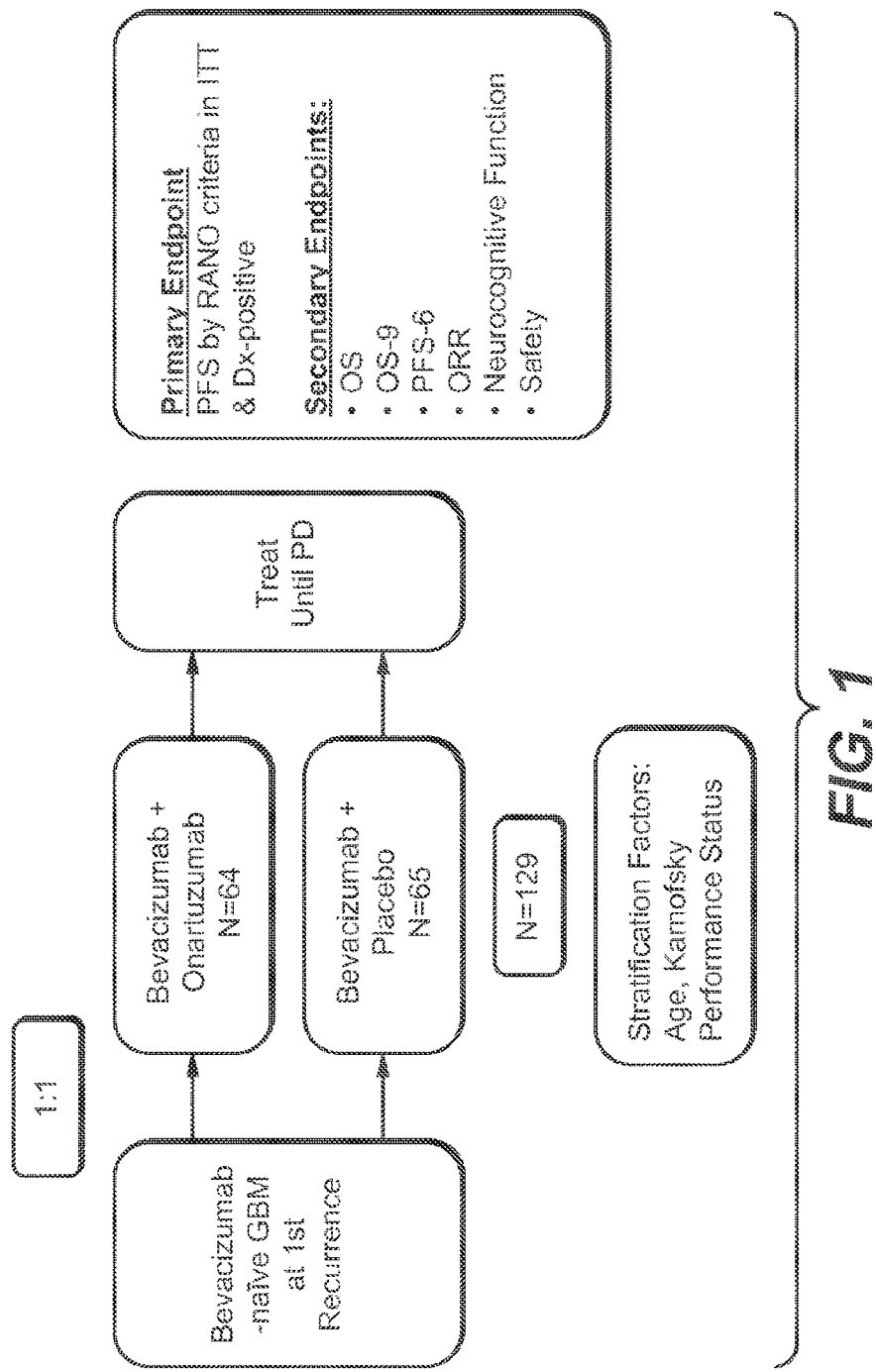
FIG. 1: shows an overview of the study design

An "anti-angiogenesis agent" or "angiogenesis inhibitor" refers to a small molecular weight substance, a polynucleotide, a polypeptide, an isolated protein, a recombinant protein, an antibody, or conjugates or fusion proteins thereof, that inhibits angiogenesis, vasculogenesis, or undesirable vascular permeability, either directly or indirectly. It should be understood that the anti-angiogenesis agent includes those agents that bind and block the angiogenic activity of the angiogenic factor or its receptor. For example, an anti-angiogenesis agent is an antibody or other antagonist to an angiogenic agent as defined throughout the specification or known in the art, e.g., but are not limited to, antibodies to VEGF-A or to the VEGF-A receptor (e.g., KDR receptor or Flt-1 receptor), VEGF-trap, anti-PDGFR inhibitors such as GLEEVEC™ (Imatinib Mesylate). Anti-angiogensis agents also include native angiogenesis inhibitors, e.g., angiostatin, endostatin, etc. See, e.g., Klagsbrun and D'Amore, Annu. Rev. Physiol., 53:217-39 (1991); Streit and Detmar, Oncogene, 22:3172-3179 (2003) (e.g., Table 3 listing anti-angiogenic therapy in malignant melanoma); Ferrara & Alitalo, Nature Medicine 5:1359-1364 (1999); Tonini et al., Oncogene, 22:6549-6556 (2003) (e.g., Table 2 listing known antiangiogenic factors); and Sato. Int. J. Clin. Oncol., 8:200-206 (2003) (e.g., Table 1 lists anti-angiogenic agents used in clinical trials).

The term "bevacizumab" refers to a recombinant humanized anti-VEGF monoclonal antibody generated according to Presta et al. (1997) Cancer Res. 57:4593-4599, also known as "rhuMAb VEGF" or "AVASTIN®". It comprises mutated human IgG1 framework regions and antigen-binding complementarity-determining regions from the murine anti-human VEGF monoclonal antibody A.4.6.1 that blocks binding of human VEGF to its receptors. Approximately 93% of the amino acid sequence of bevacizumab, including most of the framework regions, is derived from human IgG1, and about 7% of the sequence is derived from the murine antibody A4.6.1. Bevacizumab binds to the same epitope as the monoclonal anti-VEGF antibody A4.6.1 produced by hybridoma ATCC HB 10709.

The "epitope A4.6.1" refers to the epitope recognized by the anti-VEGF antibody bevacizumab (AVASTIN®) (see Muller Y et al., Structure 15 Sep. 1998, 6:1153-1167). In certain embodiments of the invention, the anti-VEGF antibodies include, but are not limited to, a monoclonal antibody that binds to the same epitope as the monoclonal anti-VEGF antibody A4.6.1 produced by hybridoma ATCC HB 10709; a recombinant humanized anti-VEGF monoclonal antibody generated according to Presta et al. (1997) Cancer Res. 57:4593-4599.

The term "intravenous infusion" refers to introduction of a drug into the vein of an animal or human subject over a period of time greater than approximately 5 minutes, preferably between approximately 30 to 90 minutes, although, according to the invention, intravenous infusion is alternatively administered for 10 hours or less.

A "maintenance" dose herein refers to one or more doses of a therapeutic agent administered to the subject over or after a treatment period. Usually, the maintenance doses are administered at spaced treatment intervals, such as approximately every week, approximately every 2 weeks, approximately every 3 weeks, or approximately every 4 weeks. By "maintenance therapy" is meant a therapeutic regimen that is given to reduce the likelihood of disease recurrence or progression. Maintenance therapy can be provided for any length of time, including extended time periods up to the life-span of the subject. Maintenance therapy can be provided after initial therapy or in conjunction with initial or additional therapies. Dosages used for maintenance therapy can vary and can include diminished dosages as compared to dosages used for other types of therapy. See also "maintenance" herein.

Herein, a "patient" is a human patient. The patient may be a "cancer patient," i.e. one who is suffering or at risk for suffering from one or more symptoms of cancer. Moreover, the patient may be a previously treated cancer patient. The patient may be a "glioblastoma patient," i.e. one who is suffering or at risk for suffering from one or more symptoms of glioblastoma. Moreover, the patient may be a previously treated glioblastoma patient. In some embodiments, the patient has been treated with no more than one prior line of chemotherapy. In some embodiments, the patient was previously treated with temozolomide. In some embodiments, the patient was previously treated with temozolomide in combination with radiation. In some embodiments, the patient was previously treated with temozolomide in combination with another agent. In some embodiments, the glioblastoma is 2nd line glioblastoma.

The term "c-met" or "Met", as used herein, refers, unless indicated otherwise, to any native or variant (whether native or synthetic) c-met polypeptide. The term "wild type c-met" generally refers to a polypeptide comprising the amino acid sequence of a naturally occurring c-met protein. The term "wild type c-met sequence" generally refers to an amino acid sequence found in a naturally occurring c-met.

The term "hepatocyte growth factor" or "HGF" as used herein, refers, unless indicated otherwise, to any native or variant (whether native or synthetic) HGF polypeptide. The term "wild type HGF" generally refers to a polypeptide comprising the amino acid sequence of a naturally occurring HGF protein. The term "wild type HGF sequence" generally refers to an amino acid sequence found in a naturally occurring HGF.

The terms "anti-c-met antibody" and "an antibody that binds to c-met refer to an antibody that is capable of binding c-met with sufficient affinity such that the antibody is useful as a diagnostic and/or therapeutic agent in targeting c-met In one embodiment, the extent of binding of an anti-c-met antibody to an unrelated, non-c-met protein is less than about 10% of the binding of the antibody to c-met as measured, e.g., by a radioimmunoassay (RIA). In certain embodiments, an antibody that binds to c-met has a dissociation constant (Kd) of ≤1 µM, ≤100 nM, ≤10 nM, ≤1 nM, ≤0.1 nM, ≤0.01 nM, or ≤0.001 nM (e.g. $10^{-8}$ M or less, e.g. from $10^{-8}$ M to $10^{-13}$ M, e.g., front $10^{-9}$ M to $10^{-13}$ M). In certain embodiments, an anti-c-met antibody binds to an epitope of c-met that is conserved among c-met from different species.

The terms "anti-HGF antibody" and "an antibody that binds to HGF refer to an antibody that is capable of binding c-met with sufficient affinity such that the antibody is useful as a diagnostic and/or therapeutic agent in targeting HGF. In one embodiment, the extent of binding of an anti-HGF antibody to an unrelated, non-HGF protein is less than about 10% of the binding of the antibody to c-met as measured, e.g., by a radioimmunoassay (RIA). In certain embodiments, an antibody that binds to HGF has a dissociation constant (Kd) of ≤1 µM, ≤100 nM, ≤10 nM, ≤1 nM, ≤0.1 nM, ≤0.01 nM, or ≤0.001 nM (e.g. $10^{-7}$ M or less, e.g. from $10^{-8}$ M to $10^{-13}$ M, e.g., from $10^{-9}$ M to $10^{-13}$ M). In certain embodiments, an anti-HGF antibody binds to an epitope of c-met that is conserved among HGF from different species.

"C-met activation" refers to activation, or phosphorylation, of the c-met receptor. Generally, c-met activation results in signal transduction (e.g. that caused by an intracellular kinase domain of a c-met receptor phosphorylating tyrosine residues in c-met or a substrate polypeptide). C-met activation may be mediated by c-met ligand (HGF) binding to a c-met receptor of interest. HGF binding to c-met may activate a kinase domain of c-met and thereby result in phosphorylation of tyrosine residues in the c-met and/or phosphorylation of tyrosine residues in additional substrate polypeptides(s).

A "population" of subjects refers to a group of subjects with cancer, such as in a clinical trial, or as seen by oncologists following FDA approval for a particular indication, such as glioblastoma therapy.

For the methods of the invention, the term "instructing" a patient means providing directions for applicable therapy, medication, treatment, treatment regimens, and the like, by any means, but preferably in writing, such as in the form of package inserts or other written promotional material.

For the methods of the invention, the term "promoting" means offering, advertising, selling, or describing a particular drug, combination of drugs, or treatment modality, by any means, including writing, such as in the form of package inserts. Promoting herein refers to promotion of therapeutic agent(s), such as an anti-c-met antagonist (e.g., onartuzumab) and/or VEGF antagonist (e.g., bevacizumab), for an indication, such as glioblastoma (e.g., recurrent glioblastoma) treatment, where such promoting is authorized by the Food and Drug Administration (FDA) as having been demonstrated to be associated with statistically significant therapeutic efficacy and acceptable safety in a population of subjects.

The term "marketing" is used herein to describe the promotion, selling or distribution of a product (e.g., drug). Marketing specifically includes packaging, advertising, and any business activity with the purpose of commercializing a product.

For the purposes herein, a patient who is "previously treated" for glioblastoma has received prior cancer therapy for glioblastoma. In some embodiments, the patient has been treated with no more than one prior line of chemotherapy. In some embodiments, the patient was previously treated with temozolomide. In some embodiments, the patient was previously treated with temozolomide in combination with radiation. In some embodiments, the patient was previously treated with temozolomide in combination with another agent. In some embodiments, the glioblastoma is second-line glioblastoma.

A "cancer medicament" is a drug effective for treating cancer. Examples of cancer medicaments include the chemotherapeutic agents and chemotherapy regimens noted below; c-met antagonists, including anti-c-met antibodies, such as onartuzumab; and VEGF antagonist, include anti-VEGF antibodies, such as bevacizumab.

The term "biomarker" or "marker" as used herein refers generally to a molecule, including a gene, mRNA, protein, carbohydrate structure, or glycolipid, the expression of which in or on a tissue or cell or secreted can be detected by known methods (or methods disclosed herein) and is predictive or can be used to predict (or aid prediction) for a cell, tissue, or patient's responsiveness to treatment regimes. The biomarker of particular interest herein is HGF.

As used herein, "negative c-met staining intensity" or "negative staining intensity" means c-met staining intensity of TOV-112D, H522, H1155, LXFL529 and/or H23. In some embodiments, negative c-met staining intensity means c-met staining intensity of control cell line TOV-12D. In some embodiments, negative c-met staining intensity means c-met staining intensity of control cell line H522. In some embodiments, negative c-met staining intensity means c-met staining intensity of control cell line H1155. In some embodiments, negative c-met staining intensity refers to c-met staining intensity of control cell line LXFL529. In some embodiments, negative c-met staining intensity means c-met staining intensity of control cell line H23. Methods for c-met IHC are known in the art. In some embodiments, c-met staining intensity is determined using c-met antibody (e.g., SP44) staining of formalin-fixed paraffin embedded cell control cell pellets (e.g., prepared in a tissue microarray).

As used herein, "weak c-met staining intensity" or "weak staining intensity" means c-met IHC staining intensity of control cell line H1703, HEK-293, and/or H460. In some embodiments, weak c-met staining intensity means c-met staining intensity of control cell line H1703. In some embodiments, weak c-met staining intensity means c-met staining intensity of control cell line HEK-293. In some embodiments, weak c-met staining intensity means c-met staining intensity of control cell line H460. Methods for c-met IHC are known in the art. In some embodiments, c-met staining intensity is determined using c-met antibody (e.g., SP44) staining of formalin-fixed paraffin embedded cell control cell pellets (e.g., prepared in a tissue microarray).

As used herein, "moderate c-met staining intensity" or "moderate staining intensity" means c-met IHC staining intensity of control cell line A549 and/or SKMES1. In some embodiments, moderate c-met staining intensity means c-met staining intensity of control cell line A549. In some embodiments, moderate c-met staining intensity means c-met staining intensity of control cell line SKMES1. Methods for c-met IHC are known in the art. In some embodiments, c-met staining intensity is determined using c-met antibody (e.g., SP44) staining of formalin-fixed paraffin embedded cell control cell pellets (e.g., prepared in a tissue microarray).

As used herein, "strong c-met staining intensity" or "strong staining intensity" means c-met IHC, staining intensity of control cell line EBC-1 and/or H441. In some embodiments, strong c-met staining intensity means c-met staining intensity of control cell line EBC-1. In some embodiments, strong c-met staining intensity means c-met staining intensity of control cell line H441. Methods for c-met IHC are known in the art. In some embodiments, c-met staining intensity is determined using c-met antibody (e.g., SP44) staining of formalin-fixed paraffin embedded cell control cell pellets (e.g., prepared in a tissue microarray).

By "patient sample" is meant a collection of cells or fluids obtained from a cancer patient. The source of the tissue or cell sample may be solid tissue as from a fresh, frozen and/or preserved organ or tissue sample or biopsy or aspirate; blood or any blood constituents; bodily fluids such as cerebrospinal fluid, amniotic fluid, peritoneal fluid, or interstitial fluid; cells from any time in gestation or development of the subject. The tissue sample may contain compounds which are not naturally intermixed with the tissue in nature such as preservatives, anticoagulants, buffers, fixatives, nutrients, antibiotics, or the like. Examples of tumor samples herein include, but are not limited to, tumor biopsy, fine needle aspirate, bronchiolar lavage, pleural fluid, sputum, urine, a surgical specimen, circulating tumor cells, serum, plasma, circulating plasma proteins, ascitic fluid, primary cell cultures or cell lines derived from tumors or exhibiting tumor-like properties, as well as preserved tumor samples, such as formalin-fixed, paraffin-embedded tumor samples or frozen tumor samples. In one embodiment the sample comprises glioblastoma tumor sample (e.g., glioblastoma tumor sample comprising benign stroma, e.g., reactive astrocytes, glial cells, pericytes and/or endothelial cells). In some embodiments, the sample comprises a macro-dissected glioblastoma tumor sample (e.g., where morphologically normal brain tissue has been removed from the tumor sample). In some embodiments, the macro-dissected glioblastoma tumor sample comprises benign stroma (e.g., reactive astrocytes, glial cells, pericytes and/or endothelial cells). In some embodiment, the sample is of glioblastoma biopsy. In some embodiments, the sample is of glioblastoma cancer resection. In some embodiments, the sample was obtained after the patient's glioblastoma recurred. In some embodiments, the sample was obtained before the patient's glioblastoma recurred.

An "effective response" of a patient or a patient's "responsiveness" to treatment with a medicament and similar wording refers to the clinical or therapeutic benefit imparted to a patient at risk for, or suffering from, cancer (e.g., glioblastoma) upon administration of the cancer medicament. Such benefit includes any one or more of: extending survival (e.g., increasing overall and/or progression-free survival); resulting in an objective response (including a complete response or a partial response); or improving signs or symptoms of cancer, etc., including extending time to deterioration of clinically relevant disease-related symptoms experienced by patients with glioblastoma (e.g., previously treated glioblastoma). In some embodiments, the symptom is any one or more (in any combination) of seizure, neurocognitive functions (including but not limited to: orientation to person, time and/or place), reading, writing, and comprehension. In one embodiment, the biomarker(s) (e.g., HGF mRNA expression, for example, as determined using ISH and/or qPCR) is used to identify the patient who is expected to have extended survival (e.g., increased overall and/or progression-free survival) when treated with c-met antagonist and VEGF antagonist, relative to a patient who is treated with VEGF antagonist alone. The incidence of biomarker(s) herein (e.g. as determined by HGF mRNA ISH and/or rtPCR analysis) effectively predicts, or predicts with high sensitivity, such effective response.

By "extending survival" is meant increasing overall or progression free survival in a patient treated in accordance with the present invention relative to an untreated patient and/or relative to a patient treated with one or more approved anti-tumor agents, but not receiving treatment in accordance with the present invention. In a particular example, "extending survival" means extending progression-free survival (PFS) and/or overall survival (OS) of cancer patients receiving the combination therapy of the present invention (e.g. treatment with a combination of c-met antagonist (e.g., onartuzumab) and VEGF antagonist (e.g., bevacizumab) relative to patients treated with bevacizumab only. In another particular example, "extending survival" means extending progression-free survival (PFS) and/or overall survival (OS) of cancer patients (e.g., a population of cancer patients) receiving the combination therapy of the present invention (e.g. treatment with a combination of onartuzumab and bevacizumab) relative to patients (e.g. a population of cancer patients) treated with bevacizumab only.

"Survival" refers to the patient remaining alive, and includes overall survival as well as progression free survival. In the studies underlying the present invention the event used for survival analysis was death from any cause.

"Overall survival" refers to the patient remaining alive for a defined period of time, such as 1 months, 2 months, 3 months, 4 months, 5 months, 6 months, 7 months, 8 months, 9 months, 10 months, 1 year, 2 year, 3 year, etc, from the time of diagnosis or treatment. Survival can be estimated by the Kaplan-Meier method.

"Progression free survival" refers to the patient remaining alive, without the cancer progressing or getting worse. In some embodiments, the patient remains alive for one month, two months, three months, four months, five months, six months, seven months, eight months, nine-months, ten months, or more, without the cancer progressing or getting worse. In one aspect of the invention, PFS for glioblastoma can be assessed by the Response Assessment in Neuro-Oncology (RANO) criteria. Wen et al. J Clin Oncol 2010; 28:1963-72. In some embodiments, PFS is assessed using the RESIST criteria.

By "extending survival" is meant increasing overall or progression free survival in a treated patient relative to an untreated patient (i.e, relative to a patient not treated with the medicament), or relative to a patient who does not express a biomarker at the designated level, and/or relative to a patient treated with an approved anti-tumor agent. In some embodiments, the overall or progression free survival is increased one month, two months, three months, four months, five months, six months, seven months, eight months, nine-months, ten months, or more.

An "objective response" refers to a measurable response, including complete response (CR) or partial response (PR).

By "complete response" or "CR" is intended the disappearance of all signs of cancer in response to treatment. This does not always mean the cancer has been cured.

"Partial response" or "PR" refers to a decrease in the size of one or more tumors or lesions, or in the extent of cancer in the body, in response to treatment.

"Overall response rate" or "Objective response rate" means the percentage of people who experience a decrease in the size (or amount for blood cancers) of the cancer for a minimum amount of time.

Hazard ratio (HR) is a statistical definition for rates of events. For the purpose of the invention, hazard ratio is defined as representing the probability of an event in the experimental arm divided by the probability of an event in the control arm at any specific point in time. "Hazard ratio" in progression free survival analysis is a summary of the difference between two progression free survival curves, representing the reduction in the risk of death on treatment compared to control, over a period of follow-up.

The term "VEGF" or "VEGF-A" is used to refer to the 165-amino acid human vascular endothelial cell growth factor and related 121-, 145-, 189-, and 206-amino acid human vascular endothelial cell growth factors, as described by, e.g., Leung et al. Science, 246:1306 (1989), and Houck et al. Mol. Endocrin., 5:1806 (1991), together with the naturally occurring allelic and processed forms thereof. VEGF-A is part of a gene family including VEGF-B, VEGF-C, VEGF-D, VEGF-E, VEGF-F, and PlGF. VEGF-A primarily binds to two high affinity receptor tyrosine kinases, VEGFR-1 (Flt-1) and VEGFR-2 (Flk-1/KDR), the latter being the major transmitter of vascular endothelial cell mitogenic signals of VEGF-A. Additionally, neuropilin-1 has been identified as a receptor for heparin-binding VEGF-A isoforms, and may play a role in vascular development. The term "VEGF" or "VEGF-A" also refers to VEGFs from non-human species such as mouse, rat, or primate. Sometimes the VEGF from a specific species is indicated by terms such as hVEGF for human VEGF or mVEGF for murine VEGF. Typically, VEGF refers to human VEGF. The term "VEGF" is also used to refer to truncated forms or fragments of the polypeptide comprising amino acids 8 to 109 or 1 to 109 of the 165-amino acid human vascular endothelial cell growth factor. Reference to any such forms of VEGF may be identified in the application, e.g., by "VEGF (8-109)," "VEGF (1-109)" or "VEGF165." The amino acid positions for a "truncated" native VEGF are numbered as indicated in the native VEGF sequence. For example, amino acid position 17 (methionine) in truncated native VEGF is also position 17 (methionine) in native VEGF. The truncated native VEGF has binding affinity for the KDR and Flt-1 receptors comparable to native VEGF.

An "anti-VEGF antibody" is an antibody that binds to VEGF with sufficient affinity and specificity. The antibody selected will normally have a binding affinity for VEGF, for example, the antibody may bind hVEGF with a Kd value of between 100 nM-1 pM. Antibody affinities may be determined by a surface plasmon resonance based assay (such as the BIAcore assay as described in PCT Application Publication No. WO2005/012359); enzyme-linked immunoabsorbent assay (ELISA); and competition assays (e.g. RIA's), for example. In certain embodiments, the anti-VEGF antibody of the invention can be used as a therapeutic agent in targeting and interfering with diseases or conditions wherein the VEGF activity is involved. Also, the antibody may be subjected to other biological activity assays, e.g., in order to evaluate its effectiveness as a therapeutic. Such assays are known in the art and depend on the target antigen and intended use for the antibody. Examples include the HUVEC inhibition assay; tumor cell growth inhibition assays (as described in WO 89/06692, for example); antibody-dependent cellular cytotoxicity (ADCC) and complement-mediated cytotoxicity (CDC) assays (U.S. Pat. No. 5,500,362); and agonistic activity or hematopoiesis assays (see WO 95/27062). An anti-VEGF antibody will usually not bind to other VEGF homologues such as VEGF-B or VEGF-C, nor other growth factors such as PlGF, PDGF or bFGF.

A "VEGF antagonist" refers to a molecule capable of neutralizing, blocking, inhibiting, abrogating, reducing or interfering with VEGF activities including its binding to one or more VEGF receptors. VEGF antagonists include anti-VEGF antibodies and antigen-binding fragments thereof, receptor molecules and derivatives which bind specifically to VEGF thereby sequestering its binding to one or more receptors, anti-VEGF receptor antibodies and VEGF receptor antagonists such as small molecule inhibitors of the VEGFR tyrosine kinases.

A "chimeric VEGF receptor protein" is a VEGF receptor molecule having amino acid sequences derived from at least two different proteins, at least one of which is a VEGF receptor protein. In certain embodiments, the chimeric VEGF receptor protein is capable of binding to and inhibiting the biological activity of VEGF.

The term "gene amplification" refers to a process by which multiple copies of a gene or gene fragment are formed in a particular cell or cell line.

The terms "level of expression" or "expression level" in general are used interchangeably and generally refer to the amount of a polynucleotide, mRNA, or an amino acid product or protein in a biological sample. "Expression" generally refers to the process by which gene-encoded information is converted into the structures present and operating in the cell. Therefore, according to the invention "expression" of a gene may refer to transcription into a polynucleotide, translation into a protein, or even posttranslational modification of the protein. Fragments of the transcribed polynucleotide, the translated protein, or the post-translationally modified protein shall also be regarded as expressed whether they originate from a transcript generated by alternative splicing or a degraded transcript, or from a post-translational processing of the protein, e.g., by proteolysis. In some embodiments, "level of expression" refers to presence or absence of or amount or prevalence (e.g., percentage of cells expressing HGF mRNA) of HGF mRNA, e.g., as assessed by ISH and/or rtPCR.

The phrase "based on expression of" when used herein means that information about expression level or presence or absence of expression (e.g., presence or absence or prevalence of (e.g., percentage of cells displaying) HGF ISH signal, e.g. in glioblastoma tumor cells and associated benign stroma) of the one or more biomarkers herein is used to inform a treatment decision, information provided on a package insert, or marketing/promotional guidance etc.

The phrase "does not possess substantial biomarker expression" or "substantially no biomarker expression" with respect to a biomarker, as used herein, means the biomarker does not exhibit an expression level that is above background level (in some embodiments, that is above background level that is statistically significant). The phrase "little to no biomarker expression" with respect to a biomarker, as used herein, means the biomarker does not display a biologically meaningful amount of expression. As would be understood in the art, amount of expression may be determined quantitatively or qualitatively, so long as a comparison between a biomarker sample and a reference counterpart can be done. The expression can be measured or detected according to any assay or technique known in the art, including, e.g., those described herein (such as ISH).

The "amount" or "level" of a biomarker associated with an increased clinical benefit to a cancer (e.g., glioblastoma) patient refers to a detectable level in a biological sample wherein the level of biomarker is associated with increased patient clinical benefit. These can be measured by methods known to the expert skilled in the art and also disclosed by this invention. The expression level or amount of biomarker assessed can be used to determine the response to the treatment. In some embodiments, the amount or level of biomarker is determined using ISH (e.g., of a patient cancer sample, e.g., glioblastoma sample that comprises tumor cells and benign stroma cells). In some embodiments, high HGF mRNA is associated with an increased clinical benefit. In some embodiments, high HGF mRNA is determined using ISH. In some embodiments, high HGF mRNA is an HGF ISH signal intensity of at least +2. In some embodiments, high HGF mRNA is an HGF ISH signal intensity of at least +3. In some embodiments, high HGF mRNA is an HGF ISH signal intensity of +2 or +3. In some embodiments, high HGF mRNA is determined using PCR (e.g., rtPCR).

The "amount" or "level" of a biomarker associated with a decreased clinical benefit to a cancer (e.g., NSCLC) patient refers to lack of detectable biomarker or a low detectable level in a biological sample, wherein the level of biomarker is associated with decreased clinical benefit to the patient. These can be measured by methods known to the expert skilled in the art and also disclosed by this invention. The expression level or amount of biomarker assessed can be used to determine the response to the treatment. In some embodiments, the amount or level of biomarker is determined using ISH (e.g., of patient cancer sample, e.g. that comprises tumor cells and benign stroma cells). In some embodiments, low HGF mRNA is associated with a decreased clinical benefit. In some embodiments, low HGF mRNA is determined using ISH. In some embodiments, low HGF mRNA is an HFG ISH signal intensity of 0. In some embodiments, low HGF mRNA is an HGF ISH signal intensity of +1. In some embodiments, low HGF mRNA is an HGF ISH signal intensity of 0 or +1. In some embodiments, low HGF mRNA is determined using PCR (e.g., rtPCR).

A cancer or biological sample which "displays HGF mRNA expression" is one which, in a diagnostic test, expresses (including overexpresses) HGF mRNA. A glioblastoma sample which "displays HGF mRNA expression" is one which, in a diagnostic test, expresses (including overexpresses) HGF mRNA. In some embodiments, a glioblastoma sample includes tumor cells and benign stromal cells.

A cancer or biological sample which "displays c-met amplification" is one which, in a diagnostic test, has amplified c-met gene. In some embodiments, amplified c-met gene is an average (in a population of cell) of greater than or equal to 5 or more copies of the c-met gene, or an average of eight or more copies of a c-met gene, or more, such as 10 or more, 15 or more or 20 or more copies of a c-met gene.

A cancer or biological sample which "does not display c-met amplification" is one which, in a diagnostic test, does not have amplified c-met gene.

The term "mutation", as used herein, means a difference in the amino acid or nucleic acid sequence of a particular protein or nucleic acid (e.g., DNA, RNA) relative to the wild-type protein or nucleic acid, respectively. A mutated protein or nucleic acid can be expressed from or found on one allele (heterozygous) or both alleles (homozygous) of a gene. In the present invention, mutations are generally somatic. Mutations include sequence rearrangements such as insertions, deletions, and point mutations (including single nucleotide/amino acid polymorphisms).

The term "primer" refers to a single stranded polynucleotide that is capable of hybridizing to a nucleic acid and allowing the polymerization of a complementary nucleic acid, generally by providing a free 3' —OH group.

The term "array" or "microarray" refers to an ordered arrangement of hybridizable array elements, preferably polynucleotide probes (e.g., oligonucleotides), on a substrate. The substrate can be a solid substrate, such as a glass slide, or a semi-solid substrate, such as nitrocellulose membrane.

The term "amplification" refers to the process of producing one or more copies of a reference nucleic acid sequence or its complement. Amplification may be linear or exponential (e.g., PCR). A "copy" does not necessarily mean perfect sequence complementarity or identity relative to the template sequence. For example, copies can include nucleotide analogs such as deoxyinosine, intentional sequence alterations (such as sequence alterations introduced through a primer comprising a sequence that is hybridizable, but not fully complementary, to the template), and/or sequence errors that occur during amplification.

The term "housekeeping biomarker" refers to a biomarker or group of biomarkers (e.g., polynucleotides and/or polypeptides) which are typically similarly present in all cell types. In some embodiments, the housekeeping biomarker is a "housekeeping gene." A "housekeeping gene" refers herein to a gene or group of genes which encode proteins whose activities are essential for the maintenance of cell function and which are typically similarly present in all cell types.

"Amplification," as used herein generally refers to the process of producing multiple copies of a desired sequence. "Multiple copies" mean at least two copies. A "copy" does not necessarily mean perfect sequence complementarity or identity to the template sequence. For example, copies can include nucleotide analogs such as deoxyinosine, intentional sequence alterations (such as sequence alterations introduced through a primer comprising a sequence that is hybridizable, but not complementary, to the template), and/or sequence errors that occur during amplification.

The term "multiplex-PCR" refers to a single PCR reaction carried out on nucleic acid (e.g., DNA or RNA) obtained from a single source (e.g., an individual) using more than one primer set for the purpose of amplifying two or more DNA sequences in a single reaction.

"ISH" or "in situ hybridization" refers to a type of hybridization that uses a complementary DNA or RNA strand (e.g. primer or probe) to localize a specific DNA or RNA sequence in a portion or section of tissue or cells (in situ). In some embodiments, a complementary DNA strand is used to localize a specific RNA sequence in a portion or section of tissue or cells in situ. In some embodiments, ISH further comprises hybridization-bused amplification.

"Stringency" of hybridization reactions is readily determinable by one of ordinary skill in the art, and generally is an empirical calculation dependent upon probe length, washing temperature, and salt concentration. In general, longer probes require higher temperatures for proper annealing, while shorter probes need lower temperatures. Hybridization generally depends on the ability of denatured DNA or RNA to reanneal when complementary strands are present in an environment below their melting temperature. The higher the degree of desired homology between the probe and hybridizable sequence, the higher the relative temperature which can be used. As a result, it follows that higher relative temperatures would tend to make the reaction conditions more stringent, while lower temperatures less so. For additional details and explanation of stringency of hybridization reactions, see Ausubel et al., Current Protocols in Molecular Biology. Wiley Interscience Publishers, (1995).

A "section" of a tissue sample is meant a single part or piece of a tissue sample, e.g. a thin slice of tissue or cells cut from a tissue sample. It is understood that multiple sections of tissue samples may be taken and subjected to analysis. In some embodiments, the same section of tissue sample may be analyzed at both morphological and molecular levels. In some embodiments, the same section of tissue sample may be analyzed with respect to both polypeptides and polynucleotides.

By "correlate" or "correlating" is meant comparing, in any way, the performance and/or results of a first analysis or protocol with the performance and/or results of a second analysis or protocol. For example, one may use the results of a first analysis or protocol in carrying out a second protocols and/or one may use the results of a first analysis or protocol to determine whether a second analysis or protocol should be performed. With respect to the embodiment of polynucleotide analysis or protocol, one may use the results of the polynucleotide expression analysis or protocol to determine whether a specific therapeutic regimen should be performed.

The term "substantially the same," as used herein, denotes a sufficiently high degree of similarity between two numeric values, such that one of skill in the art would consider the difference between the two values to be of little or no biological and/or statistical significance within the context of the biological characteristic measured by said values (e.g., Kd values or expression). The difference between said two values is, for example, less than about 50%, less than about 40%, less than about 30%, less than about 20%, and/or less than about 10% as a function of the reference/comparator value.

The phrase "substantially different," as used herein, denotes a sufficiently high degree of difference between two numeric values such that one of skill in the art would consider the difference between the two values to be of statistical significance within the context of the biological characteristic measured by said values (e.g., Kd values). The difference between said two values is, for example, greater than about 10%, greater than about 20%, greater than about 30%, greater than about 40%, and/or greater than about 50% as a function of the value for the reference/comparator molecule.

The word "label" when used herein refers to a detectable compound or composition. The label is typically conjugated or fused directly or indirectly to a reagent, such as a polynucleotide probe or an antibody, and facilitates detection of the reagent to which it is conjugated or fused. The label may itself be detectable (e.g., radioisotope labels or fluorescent labels) or, in the case of an enzymatic label, may catalyze chemical alteration of a substrate compound or composition which results in a detectable product.

The technique of "polymerase chain reaction" or "PCR" as used herein generally refers to a procedure wherein minute amounts of a specific piece of nucleic acid, RNA and/or DNA, are amplified. Generally, sequence information from the ends of the region of interest or beyond needs to be available, such that oligonucleotide primers can be designed; these primers will be identical or similar in sequence to opposite strands of the template to be amplified. The 5' terminal nucleotides of the two primers may coincide with the ends of the amplified material. PCR can be used to amplify specific RNA sequences, specific DNA sequences from total genomic DNA, and cDNA transcribed from total cellular RNA, bacteriophage or plasmid sequences, etc. See generally Mullis et al., *Cold Spring Harbor Symp. Quant. Biol.,* 51: 263 (1987); Erlich, ed., PCR Technology, (Stockton Press, NY, 1989). As used herein, PCR is considered to be one, but not the only, example of a nucleic acid polymerase reaction method for amplifying a nucleic acid test sample, comprising the use of a known nucleic acid (DNA or RNA) as a primer and utilizes a nucleic acid polymerase to amplify or generate a specific piece of nucleic acid or to amplify or generate a specific piece of nucleic acid which is complementary to a particular nucleic acid.

"Treatment" refers to both therapeutic treatment and prophylactic or preventative measures. Those in need of treatment include those already having a benign, pre-cancerous, or non-metastatic tumor as well as those in which the occurrence or recurrence of cancer is to be prevented.

The term "therapeutically effective amount" refers to an amount of a therapeutic agent (medicament) to treat or prevent a disease or disorder in a mammal. In the case of cancers (e.g., glioblastoma, e.g., previously treated glioblastoma), the therapeutically effective amount of the therapeutic agent may reduce the number of cancer cells; reduce the primary tumor size; inhibit (i.e., slow to some extent and preferably stop) cancer cell infiltration into peripheral organs; inhibit (i.e., slow to some extent and preferably stop) tumor metastasis; inhibit, to some extent, tumor growth; and/or relieve to some extent one or more of the symptoms associated with the disorder. To the extent the drug may prevent growth and/or kill existing cancer cells, it may be cytostatic and/or cytotoxic. For cancer therapy, efficacy in vivo can, for example, be measured by assessing the duration of survival, time to disease progression (TTP), the response rates (RR), duration of response, and/or quality of life and/or TDD.

The terms "cancer" and "cancerous" refer to or describe the physiological condition in mammals that is typically characterized by unregulated cell growth. Included in this definition are benign and malignant cancers. By "early stage cancer" or "early stage tumor" is meant a cancer that is not invasive or metastatic or is classified as a Stage 0, I, or II cancer. Examples of cancer include, but are not limited to, carcinoma, lymphoma, blastoma (including medulloblastoma and retinoblastoma), sarcoma (including liposarcoma and synovial cell sarcoma), neuroendocrine tumors (including carcinoid tumors, gastrinoma, and islet cell cancer), mesothelioma, schwannoma (including acoustic neuroma), meningioma, adenocarcinoma, melanoma, and leukemia or lymphoid malignancies. Additional examples of cancer include, but are not limited to, glioblastoma (e.g., recurrent glioblastoma, 2nd line glioblastoma). In some embodiments, the cancer is lung cancer (e.g., NSCLC), renal cell carcinoma, gastric cancer, melanoma, breast cancer (e.g., triple negative breast cancer), colorectal cancer, sarcoma (e.g., osteosarcoma), cancer, bladder cancer, hepatocellular carcinoma, prostate cancer.

The term "concurrently" is used herein to refer to administration of two or more therapeutic agents, where at least part of the administration overlaps in time. Accordingly, concurrent administration includes a dosing regimen when the administration of one or more agent(s) continues after discontinuing the administration of one or more other agent(s).

The term "polynucleotide," when used in singular or plural, generally refers to any polyribonucleotide or polydeoxyribonucleotide, which may be unmodified RNA or DNA or modified RNA or DNA. Thus, for instance, polynucleotides as defined herein include, without limitation, single- and double-stranded DNA, DNA including single- and double-stranded regions, single- and double-stranded RNA, and RNA including single- and double-stranded regions, hybrid molecules comprising DNA and RNA that may be single-stranded or, more typically, double-stranded or include single- and double-stranded regions. In addition, the term "polynucleotide" as used herein refers to triple-stranded regions comprising RNA or DNA or both RNA and DNA. The strands in such regions may be from the same molecule or from different molecules. The regions may include all of one or more of the molecules, but more typically involve only a region of some of the molecules. One of the molecules of a triple-helical region often is an oligonucleotide. The term "polynucleotide" specifically includes cDNAs. The term includes DNAs (including cDNAs) and RNAs that contain one or more modified bases. Thus. DNAs or RNAs with backbones modified for stability or for other reasons are "polynucleotides" as that term is intended herein. Moreover, DNAs or RNAs comprising unusual bases, such as inosine, or modified bases, such as tritiated bases, are included within the term "polynucleotides" as defined herein. In general, the term "polynucleotide" embraces all chemically, enzymatically and/or metabolically modified forms of unmodified polynucleotides, as well as the chemical forms of DNA and RNA characteristic of viruses and cells, including simple and complex cells.

The term "oligonucleotide" refers to a relatively short polynucleotide, including, without limitation, single-stranded deoxyribonucleotides, single- or double-stranded ribonucleotides, RNA:DNA hybrids and double-stranded DNAs. Oligonucleotides, such as single-stranded DNA probe oligonucleotides, are often synthesized by chemical methods, for example using automated oligonucleotide synthesizers that are commercially available. However, oligonucleotides can be made by a variety of other methods, including in vitro recombinant DNA-mediated techniques and by expression of DNAs in cells and organisms.

An antibody having a "biological characteristic" of a designated antibody is one which possesses one or more of the biological characteristics of that antibody which distinguish it from other antibodies that bind to the same antigen.

An "antibody that binds to the same epitope" as a reference antibody refers to an antibody that blocks binding of the reference antibody to its antigen in a competition assay by 50% or more, and conversely, the reference antibody blocks binding of the antibody to its antigen in a competition assay by 50% or more. An exemplary competition assay is provided herein.

The phrase "providing a diagnosis" as used herein refers to using the information or data generated relating to the level or presence of HGF (e.g., level or presence or prevalence (e.g., percentage of cells expressing) of HGF mRNA) in a sample of a patient to diagnose glioblastoma in the patient. The information or data may be in any form, written, oral or electronic. In some embodiments, using the information or data generated includes communicating, presenting, reporting, storing, sending, transferring, supplying, transmitting, delivering, dispensing, or combinations thereof. In some embodiments, communicating, presenting, reporting, storing, sending, transferring, supplying, transmitting, dispensing, or combinations thereof are performed by a computing device, analyzer unit or combination thereof. In some further embodiments, communicating, presenting, reporting, storing, sending, transferring, supplying, transmitting, dispensing, or combinations thereof are performed by an individual (e.g., a laboratory or medical professional). In some embodiments, the information or data includes a comparison of the level of HGF (e.g., level of HGF mRNA, e.g., measured using ISH or PCR) to a reference level. In some embodiments, the information or data includes a prevalence of HGF ISH signal (e.g., prevalence of positive HGF ISH signal in cells in a glioblastoma tumor sample). In some embodiments, the information or data includes an indication that HGF (e.g., HGF mRNA) is present or absent in the sample. In some embodiments, the information or data includes an indication that the patient is diagnosed with glioblastoma (in some embodiments. HGF-positive glioblastoma).

The phrase "recommending a treatment" as used herein refers to using the information or data generated relating to the level or presence of c-met in a sample of a patient to identify the patient as suitably treated or not suitably treated with a therapy. In some embodiments the therapy may comprise c-met antibody (e.g., onartuzumab). In some embodiments, the therapy may comprise VEGF antagonist (e.g., bevacizumab). In some embodiments, the therapy may comprise anti-c-met antibody (e.g., onartuzumab) in combination with VEGF antagonist (e.g., bevacizumab). The information or data may be in any form, written, oral or electronic. In some embodiments, using the information or data generated includes communicating, presenting, reporting, storing, sending, transferring, supplying, transmitting, delivering, dispensing, or combinations thereof. In some embodiments, communicating, presenting, reporting, storing, sending, transferring, supplying, transmitting, delivering, dispensing, or combinations thereof are performed by a computing device, analyzer unit or combination thereof. In some further embodiments, communicating, presenting, reporting, storing, sending, transferring, supplying, transmitting, dispensing, or combinations thereof are performed by an individual (e.g., a laboratory or medical professional). In some embodiments, the information or data includes a comparison of the level of HGF to a reference level. In some embodiments, the information or data includes an indication that HGF is present or absent in the sample. In some embodiments, the information or data includes an indication that HGF ISH signal intensity is present at a particular level (e.g., 0, +1, +2, +3). In some embodiments, the information or data includes an indication that HGF ISH signal intensity is present in a particular percentage of cells (e.g., glioblastoma tumor cells and benign stromal cells). In some embodiments, the information or data includes an indication that the patient is suitably treated or not suitably treated with a therapy comprising c-met antagonist antibody (e.g., onartuzumab). In some embodiments, the information or data includes an indication that the patient is suitably treated or not suitably treated with a therapy comprising c-met antagonist antibody (e.g., onartuzumab) in combination with VEGF antagonist (e.g., bevacizumab).

A "target audience" is a group of people or an institution to whom or to which a particular medicament is being promoted or intended to be promoted, as by marketing or advertising, especially for particular uses, treatments, or indications, such as individual patients, patient populations, readers of newspapers, medical literature, and magazines, television or internet viewers, radio or internet listeners, physicians, drug companies, etc.

A "package insert" is used to refer to instructions customarily included in commercial packages of therapeutic products, that contain information about the indications, usage, dosage, administration, contraindications, other therapeutic products to be combined with the packaged product, and/or warnings concerning the use of such therapeutic products, etc.

The term "antibody" herein is used in the broadest sense and encompasses various antibody structures, including hut not limited to monoclonal antibodies, polyclonal antibodies, multispecific antibodies (e.g., bispecific antibodies), and antibody fragments so long as they exhibit the desired antigen-binding activity.

An "antibody fragment" refers to a molecule other than an intact antibody that comprises a portion of an intact antibody that binds the antigen to which the intact antibody binds. Examples of antibody fragments include but are not limited to Fv, Fab, Fab', Fab'-SH, F(ab')$_2$; diabodies; linear antibodies; single-chain antibody molecules (e.g. scFv); and multispecific antibodies formed from antibody fragments.

The term "chimeric" antibody refers to an antibody in which a portion of the heavy and/or light chain is derived from a particular source or species, while the remainder of the heavy and/or light chain is derived from a different source or species.

The "class" of an antibody refers to the type of constant domain or constant region possessed by its heavy chain. There are five major classes of antibodies: IgA, IgD, IgE, IgG, and IgM, and several of these may be further divided into subclasses (isotypes), e.g., IgG$_1$, IgG$_2$, IgG$_3$, IgG$_4$, IgA$_1$, and IgA$_2$. The heavy chain constant domains that correspond to the different classes of immunoglobulins are called α, δ, ε, γ, and μ, respectively.

The term "Fc region" herein is used to define a C-terminal region of an immunoglobulin heavy chain that contains at least a portion of the constant region. The term includes native sequence Fc regions and variant Fc regions. In one embodiment, a human IgG heavy chain Fc region extends from Cys226, or front Pro230, to the carboxyl-terminus of the heavy chain. However, the C-terminal lysine (Lys447) of the Fc region may or may not be present. Unless otherwise specified herein, numbering of amino acid residues in the Fc region or constant region is according to the EU numbering system, also called the EU index, as described in Kabat et al., *Sequences of Proteins of Immunological Interest,* 5th Ed. Public Health Service. National Institutes of Health. Bethesda, Md. 1991.

"Framework" or "FR" refers to variable domain residues other than hypervariable region (HVR) residues. The FR of a variable domain generally consists of four FR domains:

FR1, FR2, FR3, and FR4. Accordingly, the HVR and FR sequences generally appear in the following sequence in VH (or VL): FR1-H1(L1)-FR2-H2(L2)-FR3-H3(L3)-FR4.

The terms "full length antibody," "intact antibody," and "whole antibody" are used herein interchangeably to refer to an antibody having a structure substantially similar to a native antibody structure or having heavy chains that contain an Fc region as defined herein.

A "human antibody" is one which possesses an amino acid sequence which corresponds to that of an antibody produced by a human or a human cell or derived from a non-human source that utilizes human antibody repertoires or other human antibody-encoding sequences. This definition of a human antibody specifically excludes a humanized antibody comprising non-human antigen-binding residues.

A "human consensus framework" is a framework which represents the most commonly occurring amino acid residues in a selection of human immunoglobulin VL, or VH framework sequences. Generally, the selection of human immunoglobulin VL or VH sequences is from a subgroup of variable domain sequences. Generally, the subgroup of sequences is a subgroup as in Kabat et al., *Sequences of Proteins of Immunological Interest*, Fifth Edition, NIH Publication 91-3242, Bethesda Md. (1991), vols. 1-3. In one embodiment, for the VL, the subgroup is subgroup kappa I as in Kabat et al., supra. In one embodiment, for the VH, the subgroup is subgroup III as in Kabat et al., supra.

A "humanized" antibody refers to a chimeric antibody comprising amino acid residues from non-human HVRs and amino acid residues from human FRs. In certain embodiments, a humanized antibody will comprise substantially all of at least one, and typically two, variable domains, in which all or substantially all of the HVRs (e.g., CDRs) correspond to those of a non-human antibody, and all or substantially all of the FRs correspond to those of a human antibody. A humanized antibody optionally may comprise at least a portion of an antibody constant region derived from a human antibody. A "humanized form" of an antibody, e.g., a non-human antibody, refers to an antibody that has undergone humanization.

The term "hypervariable region" or "HVR" as used herein refers to each of the regions of an antibody variable domain which are hypervariable in sequence ("complementarity determining regions" or "CDRs") and/or form structurally defined loops ("hypervariable loops") and/or contain the antigen-contacting residues ("antigen contacts"). Generally, antibodies comprise six HVRs: three in the VH (H1, H2, H3), and three in the VL (L1, L2, L3). Exemplary HVRs herein include:
(a) hypervariable loops occurring at amino acid residues 26-32 (L1), 50-52 (L2), 91-96 (L3), 26-32 (H1), 53-55 (H2), and 96-101 (H3) (Chothia and Lesk, J. Mol. Biol. 196:901-917 (1987));
(b) CDRs occurring at amino acid residues 24-34 (L1), 50-56 (L2), 89-97 (L3), 31-35b (H1), 50-65 (H2), and 95-102 (H3) (Kabat et al., *Sequences of Proteins of Immunological Interest*, 5th Ed. Public Health Service, National Institutes of Health, Bethesda, Md. (1991));
(c) antigen contacts occurring at amino acid residues 27c-36 (L1), 46-55 (L2), 89-96 (L3), 30-35b (H1), 47-58 (H2), and 93-101 (H3) (MacCallum et al. *J. Mol. Biol.* 262: 732-745 (1996)); and
(d) combinations of (a), (b), and/or (c), including HVR amino acid residues 46-56 (L2), 47-56 (L2), 48-56 (L2), 49-56 (L2), 26-35 (H1), 26-35b (H1), 49-65 (H2), 93-102 (H3), and 94-102 (H3). In one embodiment, HVR residues comprise those identified elsewhere in the specification.

Unless otherwise indicated, HVR residues and other residues in the variable domain (e.g., FR residues) are numbered herein according to Kabat et al., supra.

The term "cytotoxic agent" as used herein refers to a substance that inhibits or prevents a cellular function and/or causes cell death or destruction. Cytotoxic agents include, but are not limited to, radioactive isotopes (e.g., $At^{211}$, $I^{131}$, $I^{125}$, $Y^{90}$, $Re^{186}$, $Re^{188}$, $Sm^{153}$, $Bi^{212}$, $P^{32}$, $Pb^{212}$ and radioactive isotopes of Lu); chemotherapeutic agents or drugs (e.g., methotrexate, adriamicin, vinca alkaloids (vincristine, vinblastine, etoposide), doxorubicin, melphalan, mitomycin C, chlorambucil, daunorubicin or other intercalating agents); growth inhibitory agents; enzymes and fragments thereof such as nucleolytic enzymes; antibiotics; toxins such as small molecule toxins or enzymatically active toxins of bacterial, fungal, plant or animal origin, including fragments and/or variants thereof; and the various antitumor or anti-cancer agents disclosed below.

"Effector functions" refer to those biological activities attributable to the Fc region of an antibody, which vary with the antibody isotype. Examples of antibody effector functions include: C1q binding and complement dependent cytotoxicity (CDC); Fc receptor binding; antibody-dependent cell-mediated cytotoxicity (ADCC); phagocytosis; down regulation of cell surface receptors (e.g. B cell receptor); and B cell activation.

An "immunoconjugate" is an antibody conjugated to one or more heterologous molecule(s), including but not limited to a cytotoxic agent.

The term "monoclonal antibody" as used herein refers to an antibody obtained from a population of substantially homogeneous antibodies, i.e., the individual antibodies comprising the population are identical and/or bind the same epitope, except for possible variant antibodies, e.g., containing naturally occurring mutations or arising during production of a monoclonal antibody preparation, such variants generally being present in minor amounts. In contrast to polyclonal antibody preparations, which typically include different antibodies directed against different determinants (epitopes), each monoclonal antibody of a monoclonal antibody preparation is directed against a single determinant on an antigen. Thus, the modifier "monoclonal" indicates the character of the antibody as being obtained from a substantially homogeneous population of antibodies, and is not to be construed as requiring production of the antibody by any particular method. For example, the monoclonal antibodies to be used in accordance with the present invention may be made by a variety of techniques, including but not limited to the hybridoma method, recombinant DNA methods, phage-display methods, and methods utilizing transgenic animals containing all or part of the human immunoglobulin loci, such methods and other exemplary methods for making monoclonal antibodies being described herein.

A "naked antibody" refers to an antibody that is not conjugated to a heterologous moiety (e.g., a cytotoxic moiety) or radiolabel. The naked antibody may be present in a pharmaceutical formulation.

"Native antibodies" refer to naturally occurring immunoglobulin molecules with varying structures. For example, native IgG antibodies are heterotetrameric glycoproteins of about 150,000 daltons, composed of two identical light chains and two identical heavy chains that are disulfide-bonded. From N- to C-terminus, each heavy chain has a variable region (VH), also called a variable heavy domain or a heavy chain variable domain, followed by three constant domains (CH1, CH2, and CH3). Similarly, from N- to C-terminus, each light chain has a variable region (VL), also called a variable light domain or a light chain variable domain, followed by a constant light (CL) domain. The light chain of an antibody may be assigned to one of two types, called kappa (κ) and lambda (λ), based on the amino acid sequence of its constant domain.

For the purposes herein, "Onartuzumab" and "MetMAb", which are used interchangeably, refer to an antibody comprising the variable light and variable heavy amino acid sequences in SEQ ID NOs: 8 and 7, respectively, and Fc sequence of SEQ ID NO:13. In some embodiments, it comprises the light chain amino acid sequence in SEQ ID NO: 12, and heavy chain amino acid sequence in SEQ ID NO: 11 and Fc sequence of SEQ ID NO: 13. The antibody is optionally produced by E. coli cells. The terms "Onartuzumab" and "MetMAb" herein cover biosimilar versions of the drug with the United States Adopted Name (USAN) or International Nonproprietary Name (INN): Onartuzumab.

The "Onartuzumab epitope" refers to the epitope recognized by the anti-c-met antibody onartuzumab (see Merchant, M. et al. PNAS (2013) 110(32): E2987-E2996).

The term "pharmaceutical formulation" refers to a sterile preparation that is in such form as to permit the biological activity of the medicament to be effective, and which contains no additional components that are unacceptably toxic to a subject to which the formulation would be administered.

A "sterile" formulation is aseptic or free from all living microorganisms and their spores.

A "kit" is any manufacture (e.g. a package or container) comprising at least one reagent, e.g., a medicament for treatment of cancer (e.g., glioblastoma), or a reagent (e.g., antibody) for specifically detecting a biomarker gene or protein of the invention. The manufacture is preferably promoted, distributed, or sold as a unit for performing the methods of the present invention.

A "pharmaceutically acceptable carrier" refers to an ingredient in a pharmaceutical formulation, other than an active ingredient, which is nontoxic to a subject. A pharmaceutically acceptable carrier includes, but is not limited to, a buffer, excipient, stabilizer, or preservative.

"Percent (%) amino acid sequence identity" with respect to a reference polypeptide sequence is defined as the percentage of amino acid residues in a candidate sequence that are identical with the amino acid residues in the reference polypeptide sequence, after aligning the sequences and introducing gaps, if necessary, to achieve the maximum percent sequence identity, and not considering any conservative substitutions as part of the sequence identity. Alignment for purposes of determining percent amino acid sequence identity can be achieved in various ways that are within the skill in the art, for instance, using publicly available computer software such as BLAST, BLAST-2, ALIGN or Megalign (DNASTAR) software. Those skilled in the art can determine appropriate parameters for aligning sequences, including any algorithms needed to achieve maximal alignment over the full length of the sequences being compared. For purposes herein, however, % amino acid sequence identity values are generated using the sequence comparison computer program ALIGN-2. The ALIGN-2 sequence comparison computer program was authored by Genentech, Inc., and the source code has been filed with user documentation in the U.S. Copyright Office, Washington D.C., 20559, where it is registered under U.S. Copyright Registration No. TXU510087. The ALIGN-2 program is publicly available from Genentech, Inc., South San Francisco, Calif., or may be compiled from the source code. The ALIGN-2 program should be compiled for use on a UNIX operating system, including digital UNIX V4.0D. All sequence comparison parameters are set by the ALIGN-2 program and do not vary.

In situations where ALIGN-2 is employed for amino acid sequence comparisons, the % amino acid sequence identity of a given amino acid sequence A to, with, or against a given amino acid sequence B (which can alternatively be phrased as a given amino acid sequence A that has or comprises a certain % amino acid sequence identity to, with, or against a given amino acid sequence B) is calculated as follows:

$$100 \text{ times the fraction } X/Y$$

where X is the number of amino acid residues scored as identical matches by the sequence alignment program ALIGN-2 in that program's alignment of A and B, and where Y is the total number of amino acid residues in B. It will be appreciated that where the length of amino acid sequence A is not equal to the length of amino acid sequence B, the % amino acid sequence identity of A to B will not equal the % amino acid sequence identity of B to A. Unless specifically stated otherwise, all % amino acid sequence identity values used herein are obtained as described in the immediately preceding paragraph using the ALIGN-2 computer program.

A "chemotherapeutic agent" is a chemical compound useful in the treatment of cancer. Examples of chemotherapeutic agents include alkylating agents, such as, for example, temozolomide, the imidazotetrazine derivative of the alkylating agent dacarbazine. Additional examples of chemotherapeutics agents include, e.g., paclitaxel or topotecan or pegylated liposomal doxorubicin (PLD). Other examples of chemotherapeutic agents include alkylating agents such as thiotepa and CYTOXAN® (cyclosphosphamide); alkyl sulfonates such as busulfan, improsulfan and piposulfan; aziridines such as benzodopa, carboquone, meturedopa, and uredopa; ethylenimines and methylamelamines including altretamine, triethylenemelamine, trietylenephosphoramide, triethiylenethiophosphoramide and trimethylolomelamine; acetogenins (especially bullatacin and bullatacinone); a camptothecin; bryostatin; callystatin; CC-1065 (including its adozelesin, carzelesin and bizelesin synthetic analogues); cryptophycins (particularly cryptophycin 1 and cryptophycin 8); dolastatin; duocarmycin (including the synthetic analogues, KW-2189 and CB1-TM1); eleutherobin; pancratistatin; a sarcodictyin; spongistatin; nitrogen mustards such as chlorambucil, chlornaphazine, cholophosphamide, estramustine, ifosfamide, mechlorethamine, mechlorethamine oxide hydrochloride, melphalan, novembichin, phenesterine, prednimustine, trofosfamide, uracil mustard; nitrosureas such as carmustine, chlorozotocin, fotemustine, lomustine, nimustine, and ranimnustine; antibiotics such as the enediyne antibiotics (e.g., calicheamicin, especially calicheamicin gammaII and calicheamicin omegaII (see, e.g., Agnew, Chem. Intl. Ed. Engl., 33: 183-186 (1994)); dynemicin, including dynemicin A; bisphosphonates, such as clodronate; an esperamicin; as well as neocarzinostatin chromophore and related chromoprotein enediyne antiobiotic chromophores), aclacinomysins, actinomycin, authramycin, azaserine, bleomycins, cactinomycin, carabicin, caminomycin, carzinophilin, chromomycinis, dactinomycin, daunorubicin, detorubicin, 6-diazo-5-oxo-L-norleucine, ADRIAMYCIN® doxorubicin (including morpholino-doxorubicin, cyanomorpholino-doxorubicin, 2-pyrrolino-doxorubicin and deoxydoxorubicin), epirubicin, esorubicin, idarubicin, marcellomycin, mitomycins such as mitomycin C, mycophenolic acid, nogalamycin, olivomycins, peplomycin, potfiromycin, puromycin, quelamycin, rodorubicin, streptonigrin, streptozocin, tubercidin, ubenimex, zinostatin, zorubicin; anti-metabolites such as methotrexate and 5-fluorouracil (5-FU); folic acid analogues such as denopterin, methotrexate, pteropterin, trimetrexate; purine analogs such as fludarabine, 6-mercaptopurine, thiamiprine, thioguanine; pyrimidine analogs such as ancitabine, azacitidine, 6-azauridine, carmofur, cytarabine, dideoxyuridine, doxifluridine, enocitabine, floxuridine; androgens such as calusterone, dromostanolone propionate, epitiostanol, mepitiostane, testolactone; anti-adrenals such as aminoglutethimide, mitotane, trilostane; folic acid replenisher such as frolinic acid; aceglatone; aldophosphamide glycoside; aminolevulinic acid; eniluracil; amsacrine; bestrabucil; bisantrene; edatraxate; defofamine; demecolcine; diaziquone; elformithine; elliptinium acetate; an epothilone; etoglucid; gallium nitrate; hydroxyurea; lentinan; lonidainine; maytansinoids such as maytansine and ansamitocins; mitoguazone; mitoxantrone; mopidanmol; nitraerine; pentostatin; phenamet; pirarubicin; losoxantrone; podophyllinic acid; 2-ethylhydrazide; procarbazine; PSK® polysaccharide complex (JHS Natural Products, Eugene, Oreg.); razoxane; rhizoxin; sizofuran; spirogermanium; tenuazonic acid; triaziquone; 2,2',2"-trichlorotriethylamine; trichothecenes (especially T-2 toxin, verracurin A, roridin A and anguidine); urethan; vindesine; dacarbazine; mannomustine; mitobronitol; mitolactol; pipobroman; gacytosine; arabinoside ("Ara-C"); cyclophosphamide; thiotepa; taxoids, e.g., TAXOL® paclitaxel (Bristol-Myers Squibb Oncology, Princeton, N.J.), ABRAXANE® Cremophor-free, albumin-engineered nanoparticle formulation of paclitaxel (American Pharmaceutical Partners, Schaumberg, Ill.), and TAXOTERE® docetaxel (Rhone-Poulenc Rorer, Antony, France); chloranbucil; GEMZAR® gemcitabine; 6-thioguanine; mercaptopurine; methotrexate; platinum analogs such as cisplatin, oxaliplatin and carboplatin; vinblastine; platinum; etoposide (VP-16); ifosfamide; mitoxantrone; vincristine; NAVELBINE® vinorelbine; novantrone; teniposide; edatrexate; daunomycin; aminopterin; xeloda; ibandronate; irinotecan (Camptosar, CPT-11) (including the treatment regimen of irinotecan with 5-FU and leucovorin); topoisomerase inhibitor RFS 2000; difluoromethylornithine (DMFO); retinoids such as retinoic acid; capecitabine; combretastatin; leucovorin (LV); lapatinib (TYKERB®) that reduce cell proliferation and pharmaceutically acceptable salts, acids or derivatives of any of the above. In some embodiments, the chemotherapeutic agent is temozolomide; procarbazine; lomustine; vincristine (PCV); carmustine, carmustine infused wafers, cisplatin; and pharmaceutically acceptable salts, acids or derivatives of any of the above.

II. Cancer Medicaments

In one aspect, provided are methods of treatment for cancer, comprising administering a c-met antagonist. In some embodiments, the methods of treatment for cancer comprise administering a c-met antagonist optionally in combination with a second cancer medicament. In some embodiments, the methods of treatment for cancer comprise administering a combination of a c-met antagonist and a VEGF antagonist. In one aspect, provided are methods for selecting patients who can be treated with cancer medicaments based on expression of one or more of the biomarkers disclosed herein. Examples of cancer medicaments include, but are not limited to:
  c-met antagonists, including anti-c-met antibodies.
  VEGF antagonists, including anti-VEGF antibodies.
  Chemotherapeutic agents and chemotherapy regimens.
  Other medicaments or combinations thereof in development, or approved, for treating cancer, e.g., glioblastoma, mesothelioma, gastric cancer, hepatocellular carcinoma, renal cell carcinoma, and sarcoma.

c-Met Antagonists

In one embodiment, the medicament is an antibody, including but not limited to an antibody which binds to human c-met. In some embodiments, the antibody interferes with (e.g., blocks) c-met binding to hepatocyte growth factor (HGF). In some embodiments, the antibody binds to c-met. In some embodiments, the antibody binds to HGF. In one embodiment, the extent of binding of an anti-c-met antibody to an unrelated, non-c-met protein is less than about 10% of the binding of the antibody to c-met as measured, e.g., by a radioimmunoassay (RIA). In one embodiment, the extent of binding of an anti-HGF antibody to an unrelated, non-c-met protein is less than about 10% of the binding of the antibody to HGF as measured, e.g., by a radioimmunoassay (RIA). The antibody herein includes: monoclonal antibodies, including a chimeric, humanized or human antibodies. In one embodiment, the antibody is an antibody fragment, e.g., a Fv, Fab, Fab', one-armed antibody, scFv, diabody, or F(ab')$_2$ fragment. In another embodiment, the antibody is a full length antibody, e.g., an intact IgG1 antibody or other antibody class or isotype as defined herein. In one embodiment, the antibody is monovalent. In another embodiment, the antibody is a one-armed antibody (i.e., the heavy chain variable domain and the light chain variable domain form a single antigen binding arm) comprising an Fc region, wherein the Fc region comprises a first and a second Fc polypeptide, wherein the first and second Fc polypeptides are present in a complex and form a Fc region that increases stability of said antibody fragment compared to a Fab molecule comprising said antigen binding arm. The one-armed antibody may be monovalent.

In one embodiment, the anti-c-met antibody is onartuzumab. In another embodiment, the anti-c-met antibody comprises a heavy chain variable domain comprising one or more of (a) HVR1 comprising sequence GYTFTSYWLH (SEQ ID NO:1); (b) HVR2 comprising sequence GMIDPSNSDTRFNPNFKD (SEQ ID NO: 2); and/or (c) HVR3-HC comprising sequence ATYRSYVTPLDY (SEQ ID NO: 3). In some embodiments, the antibody comprises a light chain variable domain comprising one or more of (a) HVR1-LC comprising sequence KSSQSLLYTSSQKNYLA (SEQ ID NO: 4); HVR2-LC comprising sequence WASTRES (SEQ ID NO: 5); and/or (c) HVR3-LC comprising sequence QQYYAYPWT (SEQ ID NO: 6). In some embodiments the anti-c-met antibody comprises a heavy chain variable domain comprising (a) HVR1 comprising sequence GYTFTSYWLH (SEQ ID NO: 1); (b) HVR2 comprising sequence GMIDPSNSDTRFNPNFKD (SEQ ID NO: 2); and (c) HVR3-HC comprising sequence ATYRSYVTPLDY (SEQ ID NO: 3) and a light chain variable domain comprising (a) HVR1-LC comprising sequence KSSQSLLYTSSQKNYLA (SEQ ID NO: 4); HVR2-LC comprising sequence WASTRES (SEQ ID NO: 5); and (c) HVR3-LC comprising sequence QQYYAYPWT (SEQ ID NO: 6).

In any of the above embodiments, for example, an anti-c-met antibody can be humanized. In one embodiment, an anti-c-met antibody comprises HVRs as in any of the above embodiments, and further comprises an acceptor human framework, e.g. a human immunoglobulin framework or a human consensus framework.

In another aspect, an anti-c-met antibody comprises a heavy chain variable domain (VH) sequence having at least 90%, 91%, 92%, 93%, 94%, 95%, 96%, 97%, 98%, 99%, or 100% sequence identity to the amino acid sequence of SEQ ID NO:7. In certain embodiments, a VH sequence having at least 90%, 91%, 92%, 93%, 94%, 95%, 96%, 97%, 98%, or 99% identity contains substitutions (e.g., conservative substitutions), insertions, or deletions relative to the reference sequence, but an anti-c-met antibody comprising that sequence retains the ability to bind to human c-met. In certain embodiments, a total of 1 to 10 amino acids have been substituted, altered inserted and/or deleted in SEQ ID NO:7. In certain embodiments, substitutions, insertions, or deletions occur in regions outside the HVRs (i.e., in the FRs). Optionally, the anti-c-met antibody comprises the VH sequence in SEQ ID NO:7, including post-translational modifications of that sequence.

In another aspect, an anti-c-met antibody is provided, wherein the antibody comprises a light chain variable domain (VL) having at least 90%, 91%, 92%, 93%, 94%, 95%, 96% 97%, 98%, 99%, or 100% sequence identity to the amino acid sequence of SEQ ID NO:8. In certain embodiments, a VL sequence having at least 90%, 91%, 92%, 93%, 94%, 95%, 95%, 97%, 98%, or 99% identity contains substitutions (e.g., conservative substitutions), insertions, or deletions relative to the reference sequence, but an anti-c-met antibody comprising that sequence retains the ability to hind to c-met. In certain embodiments, a total of 1 to 10 amino acids have been substituted, inserted and/or deleted in SEQ ID NO:8. In certain embodiments, the substitutions, insertions, or deletions occur in regions outside the HVRs (i.e., in the FRs). Optionally, the anti-c-met antibody comprises the VL sequence in SEQ ID NO: 8, including post-translational modifications of that sequence.

In yet another embodiment, the anti-c-met antibody comprises a VL region having at least 90%, 91%, 92%, 93%, 94%, 95%, 96%, 97%, 98%, 99%, or 100%, sequence identity to the amino acid sequence of SEQ ID NO:8 and a VII region having at least 90%, 91%, 92%, 93%, 94%, 95%, 96%, 97%, 98%, 99%, or 100% sequence identity to the amino acid sequence of SEQ ID NO:7. In yet a further embodiment, the anti-c-met antibody comprises a HVR-L1 comprising amino acid sequence SEQ ID NO: 1; an HVR-L2 comprising amino acid sequence SEQ ID NO: 2; an HVR-L3 comprising amino acid sequence SEQ ID NO: 3; an HVR-H1 comprising amino acid sequence SEQ ID NO: 4; an HVR-H2 comprising amino acid sequence SEQ ID NO: 5; and an HVR-H3 comprising amino acid sequence SEQ ID NO: 6.

In another aspect, the anti-c-met antibody comprises a VH as in any of the embodiments provided above, and a VL as in any of the embodiments provided above. In some embodiments, the anti-c-met antibody is monovalent and further comprises a Fc polypeptide.

In another aspect, the c-met antagonist binds to an onartuzumab epitope. In some embodiments, the c-met antagonist (e.g., anti-c-met antibody) binds to human c-met at a binding site that comprises at least one amino acid residue from 1) A319-A347; 2) S360-V427; 3) L439-T457; or 4) R461-L480, wherein the position of the amino acid residues is based on (or according to) the position in SEQ ID NO: 16. In some embodiments, the binding site comprises at least one amino acid residue selected from the group consisting of: A327, Q328, R331, Q332, I333, G334, A335, S336, L337, N338, D339, K368, Y369, R426, I446, G448, D449, or R469 of c-met wherein the position of the amino acid residues is based on the position in SEQ ID NO: 16. In some embodiments, the binding site comprises at least one amino acid residue from A319-A347. In some embodiments, the binding site comprises at least one of amino acid residues A327, Q328, R331, Q332, I333, G334, A335, S336, L337, N338, or D339. In some embodiments, the binding site comprises at least one of amino acid residues Q328, R331, L337, and N338. In some embodiments according to any one of the embodiments in this paragraph, the binding site further comprises at least one amino acid residue from 1) S360-V427; 2) L439-T457; or 3) R461-L480. In some embodiments according to any one of the embodiments in this paragraph, the binding site comprises at least one amino acid residue selected from the group consisting of K368, Y369, R426, I446, G448, D449, and R469. In some embodiments according to any one of the embodiments described above, the binding site comprises amino acid residues Q328, R331, L337, and N338. In some embodiments, the binding site further comprises amino acid residues R331, Q332, I333, G334, A335, S336, D339, K368, Y369, R426, I446, G448, D449, and R469.

In a further aspect, the invention provides an antibody that binds to the same epitope as an anti-c-met antibody provided herein. For example, in certain embodiments, an antibody is provided that binds to the same epitope as an anti-c-met antibody comprising a VH sequence of SEQ ID NO:7 and a VL sequence of SEQ ID NO:8.

In another aspect, the invention provides an anti-c-met antibody with the same biological characteristics as onartuzumab.

In a further aspect of the invention, an anti-c-met antibody according to any of the embodiments herein can be a monoclonal antibody, including a monovalent, chimeric, humanized or human antibody. In one embodiment, an anti-c-met antibody is an antibody fragment, e.g., a one-armed, Fv, Fab, Fab', scFv, diabody, or F(ab')2 fragment. In another embodiment, the antibody is a full length antibody, e.g., an intact IgG1 or IgG4 antibody or other antibody class or isotype as defined herein. According to another embodiment, the antibody is a bispecific antibody. In one embodiment, the bispecific antibody comprises the HVRs or comprises the VH and VL regions described above.

In some embodiments, the anti-c-met antibody is monovalent, and comprises (a) a first polypeptide comprising a heavy chain variable domain having the sequence: EVQLVESGGGLVQPGGSLRLSCAASGYTFTSYWLH-WVRQAPGKGLEWVGMIDPSNSDTRFNPN FKDRFTI-SADTSKNTAYLQMNSLRAEDTAVYYCATYRSYVT-PLDYWGQGTLVTVSS (SEQ 11) NO):7), CH1 sequence, and a first Fc polypeptide; (b) a second polypeptide comprising a light chain variable domain having the sequence: DIQMTQSPSSLSASVGDRVTITCKSSQSLLYTSSQK-NYLAWYQQKPGKAPKLLIYWASTR ESGVPSRF-SGSGSGTDFTLTISSLQPEDFATYYCQQYYAYPWTF-GQGTKVEIKR (SEQ ID NO: 8), and CL1 sequence; and (c) a third polypeptide comprising a second Fc polypeptide. In some embodiments, the first polypeptide comprises Fc sequence CPPCPAPELLGGPSVFLFPPKPKDTLMISRT-PEVTCVVVDVSHEDPEVKFNWYVDGVEVHNAKT KPREEQYNSTYRVVSVLTVLHQDWLNGKEYKCK-VSNKALPAPIEKTISKAKGQPREPQVYTLPPW SREEMTKNQVSLSCAVKGFYPSDIAVEWESNGQPEN-NYKTTPPVLDSDGSFFLVSKLTVDKSRW QQGNVF-SCSVMHEALHNHYTQKSLSLSPGK (SEQ ID NO: 9) and the second polypeptide comprises the Fc sequence CPPCPAPELLGGPSVFLFPPKPKDTLMISRTPEVTCV-VVDVSHEDPEVKFNWYVDGVEVHNAKT KPRE-EQYNSTYRVVSVLTVLHQDWLNGKEYKCKVSNKA- LPAPIEKTISKAKGQPREPQVYTLPPW
SREEMTKNQVSLSCAVKGFYPSDIAVEWESNGQPEN-
NYKTTPPVLDSDGSFFLVSKLTVDKSR WQQGNVF-
SCSVMHEALHNHYTQKSLSLSPGK (SEQ ID NO: 10).

In another embodiments, the anti-c-met antibody is monovalent and comprises (a) a first polypeptide comprising a heavy chain, said polypeptide comprising the sequence: EVQLVESGGGLVQPGGSLRLSCAASGYTFTSYWLH-WVRQAPGKGLEWVGMIDPSNSDTRFNPN FKDRFTI-SADTSKNTAYLQMNSLRAEDTAVYYCATYRSYVT-PLDYWGQGTLVTVSSASTKGPS
VFPLAPSSKSTSGGTAALGCLVKDYFPEPVTVSWNS-GALTSGVHTFPAVLQSSGLYSLSSVVTVP SSSLFTQ-TYINCVNIIKPSNTKVDKKVEPKSCDKTIITCPPCPA-PELLGGPSVFLFPPKPKDTLMISR
TPEVTCVVVDVSHEDPEVKFNWYVDGVEVHNAKT-KPREEQYNSTYRVVSVLTVLHQDWLNG KEYKCK-VSNKALPAPIEKTSIKAKGQPREPQVYTLPPSREEMT-KNQVSLSCAVKGFYPSDIAVEW
ESNGQPENNYKTTPPVLDSDGSFFLVSKLTVDKSR-WQQGNVFSCSVMHEALHNHYTQKSLSLSP GK (SEQ ID NO: 11); (b) a second polypeptide comprising a light chain, the polypeptide comprising the sequence DIQMTQSPSSLSASVGDRVTITCKSSQSLLYTSSQK-NYLAWYQQKPGKAPKLLIYWASTRESGVP SRF-SGSGSGTDFTLTISSLQPEDFATYYCQQYYAYPWTF-GQGTKVEIKRTVAAPSVFIFPPSDEQL
KSGTASVVCLLNNFYPREAKVQWKVDNALQSGN-SQESVTEQDSKDSTYSLSSTLTLSKADYEK HKVY-ACEVTHQGLSSPVTKSFNRGEC (SEQ ID NO: 12); and a third polypeptide comprising a Fc sequence, the polypeptide comprising the sequence DKTHTCPPCPAPELLGGPS-VFLFPPKPKDTLMISRTPEVTCVVVDVSHEDPEVKF-NWYVDGVEV
HNAKTKPREEQYNSTYRVVSVLTVLHQDWLNG-KEYKCKVSNKALPAPIEKTISKAKGQPREPQ
VYTLPPSREEMTKNQVSLWCLVKGFYPSDIAVEW-ESNGQPENNYKTTPPVLDSGDSFFLYSKLT VDKSR-WQQGNVFSCSVMHEALHNHYTQKSSLSPGK (SEQ ID NO: 13).

The use of knobs into holes as a method of producing multispecific antibodies and/or one-armed antibodies and/or immunoadhesins is well known in the art. See U.S. Pat. No. 5,731,168, PCT Pub. No. WO2009089004, and US Pat. Pub. No. 20090182127. See also Marvin and Zhu. Acta Pharmacologica Sincia (2005) 26(6):649-658 and Kontermann (2005) Acta Pharmacol. Sin., 26:1-9. In one embodiment, the antibody comprises Fc mutations constituting "knobs" and "holes" as described in WO2005/063816. For example, a hole mutation can be one or more of T366A, L368A and/or Y407V in an Fc polypeptide, and a cavity mutation can be T366W in an Fc polypeptide.

Other anti-c-met antibodies suitable for use in the methods of the invention are described herein and known in the art. For example, anti-c-met antibodies disclosed in WO05/016382 (including but not limited to antibodies 13.3.2, 9.1.2, 8.70.2, 8.90.3); an anti-c-met antibodies produced by the hybridoma cell line deposited with ICLC number PD 03001 at the CBA in Genoa, or that recognizes an epitope on the extracellular domain of the β chain of the HGF receptor, and said epitope is the same as that recognized by the monoclonal antibody); anti-c-met antibodies disclosed in WO2007/1126799 (including but not limited to 04536, 05087, 05088, 05091, 05092, 04687, 05097, 05098, 05100, 05101, 04541, 05093, 05094, 04537, 05102, 05105, 04696, 04682); anti c-met antibodies disclosed in WO2009/007427 (including but not limited to an antibody deposited at CNCM, Institut Pasteur. Paris. France, on Mar. 14, 2007 under the number 1-3731, on Mar. 14, 2007 under the number 1-3732, on Jul. 6, 2007 under the number 1-3786, on Mar. 14, 2007 under the number 1-3724; an anti-c-met antibody disclosed in 20110129481; an anti-c-met antibody disclosed in US20110104176; an anti-c-met antibody disclosed in WO2009/134776; an anti-c-met antibody disclosed in WO2010/059654; an anti-c-met antibody disclosed in WO2011020925 (including but not limited to an antibody secreted from a hybridoma deposited at the CNCM, Institut Pasteur, Paris, France, on Mar. 12, 2008 under the number 1-3949 and the hybridoma deposited on Jan. 14, 2010 under the number 1-4273).

In some embodiments, the c-met antagonist is an anti-hepatocyte growth factor (HGF) antibody, including but not limited to, humanized anti-HGF antibody TAK701, rilotumumab, Ficlatuzumab, and/or humanized antibody 2B8 described in WO2007/143090. In some embodiments, the anti-HGF antibody is an anti-HGF antibody described in U.S. Pat. No. 7,718,174B2.

In some embodiments, the c-met antagonist is a c-met small molecule inhibitor. In some embodiments, the c-met small molecule inhibitor is a selective c-met small molecule inhibitor.

In one embodiment, the c-met antagonist binds c-met extracellular domain. In some embodiments, the c-met antagonist binds c-met kinase domain. In some embodiments, the c-met antagonist competes for c-met binding with HGF. In some embodiments, the c-met antagonist competes for HGF binding to c-met. In some embodiments, the c-met antagonist binds HGF.

In certain embodiments, the c-met antagonist is any one of: SGX-523, Crizotinib; JNJ-38877605 (CAS no. 943540-75-8), BMS-698769, PHA-665752 (Pfizer), SU5416, INC-280 (Incyte; SU11274 (Sugen; [(3Z)—N-(3-chlorophenyl)-3-({3,5-dimethyl-4-[(4-methylpiperazin-1-yl)carbonyl]-1H-pyrrol-2-yl}methylene)-N-methyl-2-oxoindoline-5-sulfonamide; CAS no. 658084-23-2]). Foretinib, MGCD-265 (MethylGene; MGCD-265 targets the c-MET, VEGFR1, VEGFR2, VEGFR3, Ron and Tie-2 receptors; CAS no. 875337-44-3), Tivantinib (ARQ 197), LY-2801653 (Lilly), LY2875358 (Lilly), MP-470, Rilotumumab (AMG 102, anti-HGF monoclonal antibody), antibody 223C4 or humanized antibody 223C4 (WO209/007427), humanized L2G7 (humanized TAK701; humanized anti-HGF monoclonal antibody); EMD 1214063 (Merck Sorono), EMD 1204831 (Merck Serono), NK4, Cabozantinib (carbozantinib is a dual inhibitor of met and VEGFR2), MP-470 (SuperGen; is an inhibitor of c-KIT, MET, PDGFR, Flt3, and AXL), Comp-1. Ficlatuzumab (AV-299; anti-HGF monoclonal antibody), E7050 (Cas no. 1196681-49-8; E7050 is a dual c-met and VEGFR2 inhibitor (Esai); MK-2461 (Merck; N-((2R)-1,4-Dioxan-2-ylmethyl)-N-methyl-N'-[3-(1-methyl-1H-pyrazol-4-yl)-5-oxo-5H-benzo[4,5]cyclohepta[1,2-b]pyridin-7-yl]sulfamide; CAS no. 917879-39-1); MK8066 (Merck). PF4217903 (Pfizer). AMG208 (Amgen), SGX-126, RP1040, LY2801653, AMG458. EMD637830, BAY-853474. DP-3590. In certain embodiments, the c-met antagonist is any one or more of crizotinib, tivantinib, carbozantinib, MGCD-265, ticlatuzumab, humanized TAK-701, rilotumumab, foretinib, h224G11, DN-30, MK-2461, E7050, MK-8033, PF-4217903, AMG208, JNJ-38877605, EMD1204831, INC-280, LY-2801653, SGX-126, RP1040, LY2801653, BAY-853474, and/or LA480. In certain embodiments, the c-met antagonist is any one or more of crizotinib, tivantinib, carbozantinib, MGCD-265, ficlatuzumab, humanized TAK-701, rilotumumab, and/or foretinib.

Anti-VEGF Antibodies and Antagonists

The VEGF antigen to be used for production of VEGF antibodies may be, e.g., the $VEGF_{165}$ molecule as well as other isoforms of VEGF or a fragment thereof containing the desired epitope. In one embodiment, the desired epitope is the one recognized by bevacizumab, which binds to the same epitope as the monoclonal anti-VEGF antibody A4.6.1 produced by hybridoma ATCC HB 10709 (known as "epitope A.4.6.1" defined herein). Other forms of VEGF useful for generating anti-VEGF antibodies of the invention will be apparent to those skilled in the art.

Human VEGF was obtained by first screening a cDNA library prepared from human cells, using bovine VEGF cDNA as a hybridization probe. Leung et al. (1989) Science, 246:1306. One cDNA identified thereby encodes a 165-amino acid protein having greater than 95% homology to bovine VEGF; this 165-amino acid protein is typically referred to as human VEGF (hVEGF) or $VEGF_{165}$. The mitogenic activity of human VEGF was confirmed by expressing the human VEGF cDNA in mammalian host cells. Media conditioned by cells transfected with the human VEGF cDNA promoted the proliferation of capillary endothelial cells, whereas control cells did not. Leung et al. (1989) Science, supra. Further efforts were undertaken to clone and express VEGF via recombinant DNA techniques. (See, e.g., Ferrara, Laboratory Investigation 72:615-618 (1995), and the references cited therein).

VEGF is expressed in a variety of tissues as multiple homodimeric forms (121, 145, 165, 189, and 206 amino acids per monomer) resulting from alternative RNA splicing. $VEGF_{121}$ is a soluble mitogen that does not bind heparin; the longer forms of VEGF bind heparin with progressively higher affinity. The heparin-binding forms of VEGF can be cleaved in the carboxy terminus by plasmin to release a diffusible form(s) of VEGF. Amino acid sequencing of the carboxy terminal peptide identified after plasmin cleavage is $Arg_{110}$-$Ala_{111}$. Amino terminal "core" protein, VEGF (1-110) isolated as a homodimer, binds neutralizing monoclonal antibodies (such as the antibodies referred to as 4.6.1 and 3.2E3.1.1) and soluble forms of VEGF receptors with similar affinity compared to the intact $VEGF_{165}$ homodimer.

Several molecules structurally related to VEGF have also been identified recently, including placenta growth factor (PlGF), VEGF-B, VEGF-C, VEGF-D and VEGF-E. Ferrara and Davis-Smyth (1987) Endocr. Rev., supra; Ogawa et al. J. Biological Chem. 273:31273-31281 (1998); Meyer et al. EMBO J., 18:363-374 (1999). A receptor tyrosine kinase, Flt-4 (VEGFR-3), has been identified as the receptor for VEGF-C and VEGF-D. Joukov et al. EMBO. J. 15:1751 (1996); Lee et al. PNAS USA 93:1988-1992 (1996); Achen et al. (1998) PNAS USA 95:548-553. VEGF-C has been shown to be involved in the regulation of lymphatic angiogenesis. Jeltsch et al. Science 276:1423-1425 (1997).

Two VEGF receptors have been identified, flt-1 (also called VEGFR-1) and KDR (also called VEGFR-2). Shibuya et al. (1990) Oncogene 8:519-527; de Vries et al. (1992) Science 255:989-991; Terman et al. (1992) Biochem. Biophys. Res. Commun. 187:1579-1586. Neuropilin-1 has been shown to be a selective VEGF receptor, able to bind the heparin-binding VEGF isoforms (Soker et al. (1998) Cell 92:735-45).

Anti-VEGF antibodies that are useful in the methods of the invention include any antibody, or antigen binding fragment thereof, that bind with sufficient affinity and specificity to VEGF and can reduce or inhibit the biological activity of VEGF. An anti-VEGF antibody will usually not bind to other VEGF homologues such as VEGF-B or VEGF-C, nor other growth factors such as PlGF, PDGF, or bFGF.

In certain embodiments of the invention, the anti-VEGF antibodies include, but are not limited to, a monoclonal antibody that binds to the same epitope as the monoclonal anti-VEGF antibody A4.6.1 produced by hybridoma ATCC HB 10709; a recombinant humanized anti-VEGF monoclonal antibody generated according to Presta et al. (1997) Cancer Res. 57:4593-4599. In one embodiment, the anti-VEGF antibody is "bevacizumab (BV)", also known as "rhuMAb VEGF" or "AVASTIN®". It comprises mutated human IgG1 framework regions and antigen-binding complementarity-determining regions from the murine anti-hVEGF monoclonal antibody A.4.6.1 that blocks binding of human VEGF to its receptors. Approximately 93% of the amino acid sequence of bevacizumab, including most of the framework regions, is derived from human IgG1, and about 7% of the sequence is derived from the murine antibody A4.6.1.

Bevacizumab (AVASTIN®) was the first anti-angiogenesis therapy approved by the FDA and is approved for the treatment glioblastoma (first- and second-line treatment in combination with intravenous 5-FU-based chemotherapy), advanced non-squamous, glioblastoma (glioblastoma) (first-line treatment of unresectable, locally advanced, recurrent or glioblastoma in combination with carboplatin and paclitaxel) and metastatic HER2-negative breast cancer (previously untreated, metastatic HER2-negative breast cancer in combination with paclitaxel).

Bevacizumab and other humanized anti-VEGF antibodies are further described in U.S. Pat. No. 6,884,879 issued Feb. 26, 2005. Additional antibodies include the G6 or B20 series antibodies (e.g., G6-31, B20-4.1), as described in PCT Publication No. WO2005/012359, PCT Publication No. WO2005/044853, and U.S. Patent Application 60/991,302, the content of these patent applications are expressly incorporated herein by reference. For additional antibodies see U.S. Pat. Nos. 7,060,269, 6,582,959, 6,703,020; 6,054,297; WO98/45332; WO 96/30046; WO94/10202; EP 0666868B1; U.S. Patent Application Publication Nos. 2006009360, 20050186208, 20030206899, 20030190317, 20030203409, and 20050112126; and Popkov et al., Journal of Immunological Methods 288:149-164 (2004). Other antibodies include those that bind to a functional epitope on human VEGF comprising of residues F17, M18, D19, Y21, Y25, Q89, I191, K101, E103, and C104 or, alternatively, comprising residues F17, Y21, Q22, Y25, D63, I83 and Q89.

In one embodiment of the invention, the anti-VEGF antibody has a light chain variable region comprising the following amino acid sequence: DIQMTQSPSS LSASVGDRVT ITCSASQDIS NYLNWYQQKP GKAPKVLIYF TSSLHSGVPS RFSGSGSGTD FTLTISSLQP EDFATYYCQQ YSTVPWTFGQ GTKVEIKR. (SEQ ID NO: 15) and a heavy chain variable region comprising the following amino acid sequence: EVQLVESGGG LVQPGGSLRL SCAASGYTFT NYGMNWVRQA PGKGLEWVGW INTYGEPTY AADFKRRFTF SLDTSKSTAY LQMNSLRAED TAVYYCAKYP HYYGSSHWYF DVWGQGTLVT VSS (SEQ ID NO: 14)

A "G6 series antibody" according to this invention, is an anti-VEGF antibody that is derived from a sequence of a G6 antibody or G6-derived antibody according to any one of FIGS. 7, 24-26, and 34-35 of PCT Publication No. WO2005/012359, the entire disclosure of which is expressly incorporated herein by reference. See also PCT Publication No. WO2005/1044853, the entire disclosure of which is expressly incorporated herein by reference. In one embodiment, the G6 series antibody binds to a functional epitope on human VEGF comprising residues F17, Y21, Q22, Y25, D63, I83 and Q89.

A "B20 series antibody" according to this invention is an anti-VEGF antibody that is derived from a sequence of the B20 antibody or a B20-derived antibody according to any one of FIGS. 27-29 of PCT Publication No. WO2005/012359, the entire disclosure of which is expressly incorporated herein by reference. See also PCT Publication No. WO2005/044853, and U.S. Patent Application 60/991,302, the content of these patent applications are expressly incorporated herein by reference. In one embodiment, the B20 series antibody binds to a functional epitope on human VEGF comprising residues F17, M18, D19, Y21, Y25, Q89, I91, K101, E103, and C104.

A "functional epitope" according to this invention refers to amino acid residues of an antigen that contribute energetically to the binding of an antibody. Mutation of any one of the energetically contributing residues of the antigen (for example, mutation of wild-type VEGF by alanine or homolog mutation) will disrupt the binding of the antibody such that the relative affinity ratio (IC50 mutant VEGF/IC50 wild-type VEGF) of the antibody will be greater than 5 (see Example 2 of WO2005/012359). In one embodiment, the relative affinity ratio is determined by a solution binding phage displaying ELISA. Briefly, 96-well Maxisorp immunoplates (NUNC) are coated overnight at 4° C. with an Fab form of the antibody to be tested at a concentration of 2 µg/ml in PBS, and blocked with PBS, 0.5% BSA, and 0.05% Tween20 (PBT) for 2 h at room temperature. Serial dilutions of phage displaying hVEGF alanine point mutants (residues 8-109 form) or wild type hVEGF (8-109) in PBT are first incubated on the Fab-coated plates for 15 min at room temperature, and the plates are washed with PBS, 0.05% Tween20 (PBST). The bound phage is detected with an anti-M13 monoclonal antibody horseradish peroxidase (Amersham Pharmacia) conjugate diluted 1:5000 in PBT, developed with 3,3',5,5'-tetramethylbenzidine (TMB, Kirkegaard & Perry Labs, Gaithersburg, Md.) substrate for approximately 5 min, quenched with 1.0 M $H_3PO_4$, and read spectrophotometrically at 450 nm. The ratio of IC50 values (IC50,ala/IC50,wt) represents the fold of reduction in binding affinity (the relative binding affinity).

VEGF Receptor Molecules

The two best characterized VEGF receptors are VEGFR1 (also known as Flt-1) and VEGFR2 (also known as KDR and FLK-1 for the murine homolog). The specificity of each receptor for each VEGF family member varies but VEGF-A binds to both Flt-1 and KDR. Both Flt-I and KDR belong to the family of receptor tyrosine kinases (RTKs). The RTKs comprise a large family of transmembrane receptors with diverse biological activities. At least nineteen (19) distinct RTK subfamilies have been identified. The receptor tyrosine kinase (RTK) family includes receptors that are crucial for the growth and differentiation of a variety of cell types (Yarden and Ullrich (1988) Ann. Rev. Biochem. 57:433-478; Ullrich and Schlessinger (1990) Cell 61:243-254). The intrinsic function of RTKs is activated upon ligand binding, which results in phosphorylation of the receptor and multiple cellular substrates, and subsequently in a variety of cellular responses (Ullrich & Schlessinger (1990) Cell 61:203-212). Thus, receptor tyrosine kinase mediated signal transduction is initiated by extracellular interaction with a specific growth factor (ligand), typically followed by receptor dimerization, stimulation of the intrinsic protein tyrosine kinase activity and receptor trans-phosphorylation. Binding sites are thereby created for intracellular signal transduction molecules and lead to the formation of complexes with a spectrum of cytoplasmic signaling molecules that facilitate the appropriate cellular response, (e.g., cell division, differentiation, metabolic effects, changes in the extracellular microenvironment) see. Schlessinger and Ullrich (1992) Neuron 9:1-20. Structurally, both Flt-1 and KDR have seven immunoglobulin-like domains in the extracellular domain, a single transmembrane region, and a consensus tyrosine kinase sequence which is interrupted by a kinase-insert domain. Matthews et al. (1991) PNAS USA 88:9026-9030; Terman et al. (1991) Oncogene 6:1677-1683. The extracellular domain is involved in the binding of VEGF and the intracellular domain is involved in signal transduction.

VEGF receptor molecules, or fragments thereof, that specifically bind to VEGF can be used in the methods of the invention to bind to and sequester the VEGF protein, thereby preventing it from signaling. In certain embodiments, the VEGF receptor molecule, or VEGF binding fragment thereof, is a soluble form, such as sFlt-1. A soluble form of the receptor exerts an inhibitory effect on the biological activity of the VEGF protein by binding to VEGF, thereby preventing it from binding to its natural receptors present on the surface of target cells. Also included are VEGF receptor fusion proteins, examples of which are described below.

A chimeric VEGF receptor protein is a receptor molecule having amino acid sequences derived from at least two different proteins, at least one of which is a VEGF receptor protein (e.g., the flt-1 or KDR receptor), that is capable of binding to and inhibiting the biological activity of VEGF. In certain embodiments, the chimeric VEGF receptor proteins of the invention consist of amino acid sequences derived from only two different VEGF receptor molecules; however, amino acid sequences comprising one, two, three, four, five, six, or all seven Ig-like domains from the extracellular ligand-binding region of the flt-1 and/or KDR receptor can be linked to amino acid sequences from other unrelated proteins, for example, immunoglobulin sequences. Other amino acid sequences to which Ig-like domains are combined will be readily apparent to those of ordinary skill in the art. Examples of chimeric VEGF receptor proteins include, e.g., soluble Flt-1/Fc, KDR/Fc, or FLt-1/KDR/Fc (also known as VEGF Trap). (See for example PCT Application Publication No. WO97/44453).

A soluble VEGF receptor protein or chimeric VEGF receptor proteins of the invention includes VEGF receptor proteins which are not fixed to the surface of cells via a transmembrane domain. As such, soluble forms of the VEGF receptor, including chimeric receptor proteins, while capable of binding to and inactivating VEGF, do not comprise a transmembrane domain and thus generally do not become associated with the cell membrane of cells in which the molecule is expressed.

In one embodiment, the antibody(ies), e.g. the antibody (ies) used in the methods herein may incorporate any of the features, singly or in combination, as described in Sections 1-6 below:

1. Antibody Fragments

In certain embodiments, an antibody provided herein is an antibody fragment. Antibody fragments include, but are not limited to, Fab, Fab', Fab'-SH, F(ab')2, Fv, and scFv fragments, a one-armed antibody, and other fragments described below. For a review of certain antibody fragments, see Hudson et al. Nat. Med. 9:129-134 (2003). For a review of scFv fragments, see, e.g., Pluckthün, in The Pharmacology of Monoclonal Antibodies, vol. 113, Rosenburg and Moore eds., (Springer-Verlag, New York), pp. 269-315 (1994); see also WO 93/16185; and U.S. Pat. Nos. 5,571,894 and 5,587,458. For discussion of Fab and F(ab')2 fragments comprising salvage receptor binding epitope residues and having increased in vivo half-life, see U.S. Pat. No. 5,869, 046.

Diabodies are antibody fragments with two antigen-binding sites that may be bivalent or bispecific. See, for example, EP 404,097; WO 1993/01161; Hudson et al., Nat. Med. 9:129-134 (2003); and Hollinger et al., Proc. Natl. Acad. Sci. USA 90: 6444-6448 (1993). Triabodies and tetrabodies are also described in Hudson et al., Nat. Med. 9:129-134 (2003).

Single-domain antibodies are antibody fragments comprising all or a portion of the heavy chain variable domain or all or a portion of the light chain variable domain of an antibody. In certain embodiments, a single-domain antibody is a human single-domain antibody (Domantis, Inc., Waltham, Mass.; see, e.g., U.S. Pat. No. 6,248,516 RB).

One-armed antibodies (i.e., the heavy chain variable domain and the light chain variable domain form a single antigen binding arm) are disclosed in, for example, WO2005/063816; Martens et al, Clin Cancer Res (2006), 12: 6144. For treatment of pathological conditions requiring an antagonistic function, and where bivalency of an antibody results in an undesirable agonistic effect, the monovalent trait of a one-armed antibody (i.e., an antibody comprising a single antigen binding arm) results in and/or ensures an antagonistic function upon binding of the antibody to a target molecule. Furthermore, the one-armed antibody comprising a Fc region is characterized by superior pharmacokinetic attributes (such as an enhanced half life and/or reduced clearance rate in vivo) compared to Fab forms having similar/substantially identical antigen binding characteristics, thus overcoming a major drawback in the use of conventional monovalent Fab antibodies. Techniques for making one-armed antibodies include, but are not limited to, "knob-in-hole" engineering (see, e.g., U.S. Pat. No. 5,731, 168). Onartuzumab is an example of a one-armed antibody.

Antibody fragments can be made by various techniques, including but not limited to proteolytic digestion of an intact antibody as well as production by recombinant host cells (e.g. *E. coli* or phage), as described herein.

2. Chimeric and Humanized Antibodies

In certain embodiments, an antibody provided herein is a chimeric antibody. Certain chimeric antibodies are described, e.g., in U.S. Pat. No. 4,816,567; and Morrison et al., Proc. Natl. Acad. Sci. USA, 81:6851-6855 (1984)). In one example, a chimeric antibody comprises a non-human variable region (e.g., a variable region derived from a mouse, rat, hamster, rabbit, or non-human primate, such as a monkey) and a human constant region. In a further example, a chimeric antibody is a "class switched" antibody in which the class or subclass has been changed from that of the parent antibody. Chimeric antibodies include antigen-binding fragments thereof.

In certain embodiments, a chimeric antibody is a humanized antibody. Typically, a non-human antibody is humanized to reduce immunogenicity to humans, while retaining the specificity and affinity of the parental non-human antibody. Generally, a humanized antibody comprises one or more variable domains in which HVRs, e.g., CDRs, (or portions thereof) are derived from a non-human antibody, and FRs (or portions thereof) are derived from human antibody sequences. A humanized antibody optionally will also comprise at least a portion of a human constant region. In some embodiments, some FR residues in a humanized antibody are substituted with corresponding residues from a non-human antibody (e.g., the antibody from which the HVR residues are derived), e.g., to restore or improve antibody specificity or affinity.

Humanized antibodies and methods of making them are reviewed, e.g., in Almagro and Fransson, Front. Biosci. 13:1619-1633 (2008), and are further described, e.g., in Riechmann et al., Nature 332:323-329 (1988); Queen et al., Proc. Nat'l Acad. Sci. USA 86:10029-10033 (1989); U.S. Pat. Nos. 5,821,337, 7,527,791, 6,982,321, and 7,087,409; Kashmiri et al., Methods 36:25-34 (2005) (describing SDR (a-CDR) grafting); Padlan, Mol. Immunol. 28:489-498 (1991) (describing "resurfacing"); Dall'Acqua et al., Methods 36:43-60 (2005) (describing "FR shuffling"); and Osbourn et al., Methods 36:61-68 (2005) and Klimka et al., Br. J. Cancer, 83:252-260 (2000) (describing the "guided selection" approach to FR shuffling).

Human framework regions that may be used for humanization include but are not limited to: framework regions selected using the "best-fit" method (see, e.g., Sims et al. J. Immunol. 151:2296 (1993)); framework regions derived from the consensus sequence of human antibodies of a particular subgroup of light or heavy chain variable regions (see, e.g., Carter et al. Proc. Natl. Acad. Sci. USA, 89:4285 (1992); and Presta et al. J. Immunol., 151:2623 (1993)); human mature (somatically mutated) framework regions or human germline framework regions (see, e.g., Almagro and Fransson, Front. Biosci. 13:1619-1633 (2008)); and framework regions derived from screening FR libraries (see, e.g., Baca et al., J. Biol. Chem. 272:10678-10684 (1997) and Rosok et al., J. Biol. Chem. 271:22611-22618 (1996)).

3. Human Antibodies

In certain embodiments, an antibody provided herein is a human antibody. Human antibodies can be produced using various techniques known in the art. Human antibodies are described generally in van Dijk and van de Winkel, Curr. Opin. Pharmacol. 5: 368-74 (2001) and Lonberg, Curr. Opin. Immunol. 20:450-459 (2008).

Human antibodies may be prepared by administering an immunogen to a transgenic animal that has been modified to produce intact human antibodies or intact antibodies with human variable regions in response to antigenic challenge. Such animals typically contain all or a portion of the human immunoglobulin loci, which replace the endogenous immunoglobulin loci, or which are present extrachromosomally or integrated randomly into the animal's chromosomes. In such transgenic mice, the endogenous immunoglobulin loci have generally been inactivated. For review of methods for obtaining human antibodies from transgenic animals, see Lonberg, Nat. Biotech. 23:1117-1125 (2005). See also, e.g., U.S. Pat. Nos. 6,075,181 and 6,150,584 describing XENO-MOUSE™ technology; U.S. Pat. No. 5,770,429 describing HuMab® technology; U.S. Pat. No. 7,041,870 describing K-M MOUSE® technology, and U.S. Patent Application Publication No. US 2007/0061900, describing Veloci-Mouse® technology). Human variable regions from intact antibodies generated by such animals may be further modified, e.g., by combining with a different human constant region.

Human antibodies can also be made by hybridoma-based methods. Human myeloma and mouse-human heteromyeloma cell lines for the production of human monoclonal antibodies have been described. (See, e.g., Kozbor J. Immunol., 133: 3001 (1984); Brodeur et al., Monoclonal Antibody Production Techniques and Applications, pp. 51-63 (Marcel Dekker, Inc., New York, 1987); and Boerner et al., J. Immunol., 147: 86 (1991).) Human antibodies generated via human B-cell hybridoma technology are also described in Li et al., Proc. Natl. Acad. Sci. USA, 103:3557-3562 (2006). Additional methods include those described, for example, in U.S. Pat. No. 7,189,826 (describing production of monoclonal human IgM antibodies from hybridoma cell lines) and Ni, Xiandai Mianyixue, 26(4):265-268 (2006) (describing human-human hybridomas). Human hybridoma technology (Trioma technology) is also described in Vollmers and Brandlein, Histology and Histopathology, 20(3):927-937 (2005) and Vollmers and Brandlein, Methods and Findings in Experimental and Clinical Pharmacology, 27(3):185-91 (2005).

Human antibodies may also be generated by isolating Fv clone variable domain sequences selected from human-derived phage display libraries. Such variable domain sequences may then be combined with a desired human constant domain. Techniques for selecting human antibodies from antibody libraries are described below.

4. Library-Derived Antibodies

Antibodies of the invention may be isolated by screening combinatorial libraries for antibodies with the desired activity or activities. For example, a variety of methods are known in the art for generating phage display libraries and screening such libraries for antibodies possessing the desired binding characteristics. Such methods are reviewed, e.g., in Hoogenboom et al. in Methods in Molecular Biology 178: 1-37 (O'Brien et al., ed., Human Press, Totowa, N.J., 2001) and further described, e.g., in the McCafferty et al., Nature 348:552-554; Clackson et al., Nature 352: 624-628 (1991); Marks et al., J. Mol. Biol. 222: 581-597 (1992); Marks and Bradbury, in Methods in Molecular Biology 248:161-175 (Lo, ed., Human Press, Totowa, N.J., 2003); Sidhu et al., J. Mol. Biol. 338(2): 299-310 (2004); Lee et al., J. Mol. Biol. 340(5): 1073-1093 (2004); Fellouse, Proc. Natl. Acad. Sci. USA 101(34): 12467-12472 (2004); and Lee et al., J. Immunol. Methods 284(1-2): 119-132 (2004).

In certain phage display methods, repertoires of VH and VL genes are separately cloned by polymerase chain reaction (PCR) and recombined randomly in phage libraries, which can then be screened for antigen-binding phage as described in Winter et al., Ann. Rev. Immunol., 12: 433-455 (1994). Phage typically display antibody fragments, either as single-chain Fv (scFv) fragments or as Fab fragments. Libraries from immunized sources provide high-affinity antibodies to the immunogen without the requirement of constructing hybridomas. Alternatively, the naive repertoire can be cloned (e.g., from human) to provide a single source of antibodies to a wide range of non-self and also self antigens without any immunization as described by Griffiths et al., EMBO J, 12: 725-734 (1993). Finally, naive libraries can also be made synthetically by cloning unrearranged V-gene segments from stem cells, and using PCR primers containing random sequence to encode the highly variable CDR3 regions and to accomplish rearrangement in vitro, as described by Hoogenboom and Winter, J. Mol. Biol., 227: 381-388 (1992). Patent publications describing human antibody phage libraries include, for example: U.S. Pat. No. 5,750,373, and US Patent Publication Nos. 2005/0079574, 2005/0119455, 2005/0266000, 2007/0117126, 2007/0160598, 2007/0237764, 2007/0292936, and 2009/0002360.

Antibodies or antibody fragments isolated from human antibody libraries are considered human antibodies or human antibody fragments herein.

5. Multispecific Antibodies

In certain embodiments, an antibody provided herein is a multispecific antibody, e.g. a bispecific antibody. Multispecific antibodies are monoclonal antibodies that have binding specificities for at least two different sites. In certain embodiments, one of the binding specificities is for c-met and the other is for any other antigen. In certain embodiments, bispecific antibodies may bind to two different epitopes of c-met. Bispecific antibodies may also be used to localize cytotoxic agents to cells which express c-met. Bispecific antibodies can be prepared as full length antibodies or antibody fragments.

Techniques for making multispecific antibodies include, but are not limited to, recombinant co-expression of two immunoglobulin heavy chain-light chain pairs having different specificities (see Milstein and Cuello, Nature 305: 537 (1983), WO 93/08829, and Traunecker et al., EMBO J. 10: 3655 (1991)), and "knob-in-hole" engineering (see, e.g., U.S. Pat. No. 5,731,168). Multi-specific antibodies may also be made by engineering electrostatic steering effects for making antibody Fc-heterodimeric molecules (WO 2009/089004A1); cross-linking two or more antibodies or fragments (see, e.g., U.S. Pat. No. 4,676,980, and Brennan et al., Science, 229: 81 (1985)); using leucine zippers to produce bispecific antibodies (see, e.g., Kostelny et al., J. Immunol., 148(5):1547-1553 (1992)); using "diabody" technology for making bispecific antibody fragments (sec, e.g., Hollinger et al., Proc. Natl. Acad. Sci. USA, 90:6444-6448 (1993)); and using single-chain Fv (sFv) dimers (see, e.g. Gruber et al., J. Immunol., 152:5368 (1994)); and preparing trispecific antibodies as described, e.g., in Tutt et al. J. Immunol. 147: 60 (1991).

Engineered antibodies with three or more functional antigen binding sites, including "Octopus antibodies." are also included herein (see, e.g. US 2006/0025576A1).

The antibody or fragment herein also includes a "Dual Acting FAb" or "DAF" comprising an antigen binding site that binds to c-met as well as another, different antigen, such as EGFR (see, US 2008/0069820, for example).

6. Antibody Variants

In certain embodiments, amino acid sequence variants of the antibodies provided herein are contemplated. For example, it may be desirable to improve the binding affinity and/or other biological properties of the antibody. Amino acid sequence variants of an antibody may be prepared by introducing appropriate modifications into the nucleotide sequence encoding the antibody, or by peptide synthesis. Such modifications include, for example, deletions from, and/or insertions into and/or substitutions of residues within the amino acid sequences of the antibody. Any combination of deletion, insertion, and substitution can be made to arrive at the final construct, provided that the final construct possesses the desired characteristics, e.g., antigen-binding.

In certain embodiments, antibody variants having one or more amino acid substitutions are provided. Sites of interest for substitutional mutagenesis include the HVRs and FRs. Amino acid substitutions may be introduced into an antibody of interest and the products screened for a desired activity, e.g., retained/improved antigen binding, decreased immunogenicity, or improved ADCC or CDC.

One type of substitutional variant involves substituting one or more hypervariable region residues of a parent antibody (e.g. a humanized or human antibody). Generally, the resulting variant(s) selected for further study will have modifications (e.g., improvements) in certain biological properties (e.g., increased affinity, reduced immunogenicity) relative to the parent antibody and/or will have substantially retained certain biological properties of the parent antibody. An exemplary substitutional variant is an affinity matured antibody, which may be conveniently generated, e.g., using phage display-based affinity maturation techniques such as those described herein. Briefly, one or more HVR residues are mutated and the variant antibodies displayed on phage and screened for a particular biological activity (e.g. binding affinity).

Amino acid sequence insertions include amino- and/or carboxyl-terminal fusions ranging in length from one residue to polypeptides containing a hundred or more residues, as well as intrasequence insertions of single or multiple amino acid residues. Examples of terminal insertions include an antibody with an N-terminal methionyl residue. Other insertional variants of the antibody molecule include the fusion to the N- or C-terminus of the antibody to an enzyme (e.g. for ADEPT) or a polypeptide which increases the serum half-life of the antibody.

In certain embodiments, an antibody provided herein is altered to increase or decrease the extent to which the antibody is glycosylated. Addition or deletion of glycosylation sites to an antibody may be conveniently accomplished by altering the amino acid sequence such that one or more glycosylation sites is created or removed.

Where the antibody comprises an Fc region, the carbohydrate attached thereto may be altered. Native antibodies produced by mammalian cells typically comprise a branched, biantennary oligosaccharide that is generally attached by an N-linkage to Asn297 of the CH2 domain of the Fc region. See, e.g., Wright et al. TIBTECH 15:26-32 (1997). The oligosaccharide may include various carbohydrates, e.g., mannose, N-acetyl glucosamine (GlcNAc), galactose, and sialic acid, as well as a fucose attached to a GlcNAc in the "stem" of the biantennary oligosaccharide structure. In some embodiments, modifications of the oligosaccharide in an antibody of the invention may be made in order to create antibody variants with certain improved properties.

In one embodiment, antibody variants are provided having a carbohydrate structure that lacks fucose attached (directly or indirectly) to an Fc region. For example, the amount of fucose in such antibody may be from 1% to 80%, from 1% to 65%, front 5% to 65% or from 20% to 40%. The amount of fucose is determined by calculating the average amount of fucose within the sugar chain at Asn297, relative to the sum of all glycostructures attached to Asn 297 (e.g. complex, hybrid and high mannose structures) as measured by MALDI-TOF mass spectrometry, as described in WO 2008/077546, for example. Asn297 refers to the asparagine residue located at about position 297 in the Fc region (Eu numbering of Fc region residues); however, Asn297 may also be located about ±3 amino acids upstream or downstream of position 297, i.e., between positions 294 and 300, due to minor sequence variations in antibodies. Such fucosylation variants may have improved ADCC function. See, e.g., US Patent Publication Nos. US 2003/0157108 (Presta, L.); US 2004/0093621 (Kyowa Hakko Kogyo Co., Ltd). Examples of publications related to "defucosylated" or "fucose-deficient" antibody variants include: US 2003/0157108; WO 2000/61739; WO 2001/29246; US 2003/0115614; US 2002/0164328; US 2004/0093621; US 2004/0132140; US 2004/0110704; US 2004/0110282; US 2004/0109865; WO 2003/085119; WO 2003/084570; WO 2005/035586; WO 2005/035778; WO2005/053742; WO2002/031140; Okazaki et al. J. Mol. Biol. 336:1239-1249 (2004); Yamane-Ohnuki et al. Biotech. Bioeng. 87: 614 (2004). Examples of cell lines capable of producing defucosylated antibodies include Lec13 CHO cells deficient in protein fucosylation (Ripka et al. Arch. Biochem. Biophys. 249: 533-545 (1986); US Pat Appl No US 2003/0157108 A1, Presta. L; and WO 2004/056312 A1, Adams et al., especially at Example 11), and knockout cell lines, such as alpha-1,6-fucosyltransferase gene, FUT8, knockout CHO cells (see, e.g., Yamane-Ohnuki et al. Biotech. Bioeng. 87: 614 (2004); Kanda, Y. et al., Biotechnol. Bioeng., 94(4):680-688 (2006); and WO2003/085107).

Antibodies variants are further provided with bisected oligosaccharides, e.g., in which a biantennary oligosaccharide attached to the Fc region of the antibody is bisected by GlcNAc. Such antibody variants may have reduced fucosylation and/or improved ADCC function. Examples of such antibody variants are described, e.g., in WO 2003/011878 (Jean-Mairet et al.); U.S. Pat. No. 6,602,684 (Umana et al.); and US 2005/0123546 (Umana et al.). Antibody variants with at least one galactose residue in the oligosaccharide attached to the Fc region are also provided. Such antibody variants may have improved CDC function. Such antibody variants are described, e.g., in WO 1997/30087 (Patel et al.); WO 1998/58964 (Raju, S.); and WO 1999/22764 (Raju, S.).

In certain embodiments, one or more amino acid modifications may be introduced into the Fc region of an antibody provided herein, thereby generating an Fc region variant. The Fc region variant may comprise a human Fc region sequence (e.g., a human IgG1, IgG2, IgG3 or IgG4 Fc region) comprising an amino acid modification (e.g. a substitution) at one or more amino acid positions.

In certain embodiments, the invention contemplates an antibody variant that possesses some but not all effector functions, which make it a desirable candidate for applications in which the half life of the antibody in vivo is important yet certain effector functions (such as complement and ADCC) are unnecessary or deleterious.

Antibodies with reduced effector function include those with substitution of one or more of Fc region residues 238, 265, 269, 270, 297, 327 and 329 (U.S. Pat. No. 6,737,056). Such Fc mutants include Fc mutants with substitutions at two or more of amino acid positions 265, 269, 270, 297 and 327, including the so-called "DANA" Fc mutant with substitution of residues 265 and 297 to alanine (U.S. Pat. No. 7,332,581).

Certain antibody variants with improved or diminished binding to FcRs are described. (See, e.g., U.S. Pat. No. 6,737,056; WO 2004/056312, and Shields et al., J. Biol. Chem. 9(2): 6591-6604 (2001).)

In certain embodiments, an antibody variant comprises an Fc region with one or more amino acid substitutions which improve ADCC, e.g., substitutions at positions 298, 333, and/or 334 of the Fc region (EU numbering of residues).

In some embodiments, alterations are made in the Fc region that result in altered (i.e., either improved or diminished) C1q binding and/or Complement Dependent Cytotoxicity (CDC), e.g., as described in U.S. Pat. No. 6,194,551, WO 99/51642, and Idusogie et al. J. Immunol. 164: 4178-4184 (2000).

Antibodies with increased half lives and improved binding to the neonatal Fc receptor (FcRn), which is responsible for the transfer of maternal IgGs to the fetus (Guyer et al., J. Immunol. 117:587 (1976) and Kim et al., J. Immunol. 24:249 (1994)), are described in US2005/0014934A1 (Hinton et al.). Those antibodies comprise an Fc region with one or more substitutions therein which improve binding of the Fc region to FcRn. Such Fc variants include those with substitutions at one or more of Fc region residues: 238, 256, 265, 272, 286, 303, 305, 307, 311, 312, 317, 340, 356, 360, 362, 376, 378, 380, 382, 413, 424 or 434, e.g., substitution of Fc region residue 434 (U.S. Pat. No. 7,371,826).

See also Duncan & Winter, Nature 322:738-40 (1988); U.S. Pat. No. 5,648,260; U.S. Pat. No. 5,624,821; and WO 94/29351 concerning other examples of Fc region variants.

In certain embodiments, it may be desirable to create cysteine engineered antibodies, e.g., "thioMAbs." in which one or more residues of an antibody are substituted with cysteine residues. In particular embodiments, the substituted residues occur at accessible sites of the antibody. By substituting those residues with cysteine, reactive thiol groups are thereby positioned at accessible sites of the antibody and may be used to conjugate the antibody to other moieties, such as drug moieties or linker-drug moieties, to create an immunoconjugate, as described further herein. In certain embodiments, any one or more of the following residues may be substituted with cysteine; V205 (Kabat numbering) of the light chain; A118 (EU numbering) of the heavy chain; and S400 (EU numbering) of the heavy chain Fc region. Cysteine engineered antibodies may be generated as described, e.g., in U.S. Pat. No. 7,521,541.

In certain embodiments, an antibody provided herein may be further modified to contain additional nonproteinaceous moieties that are known in the art and readily available. The moieties suitable for derivatization of the antibody include but are not limited to water soluble polymers. Non-limiting examples of water soluble polymers include, but are not limited to, polyethylene glycol (PEG), copolymers of ethylene glycol/propylene glycol, carboxymethylcellulose, dextran, polyvinyl alcohol, polyvinyl pyrrolidone, poly-1,3-dioxolane, poly-1,3,6-trioxane, ethylene/maleic anhydride copolymer, polyaminoacids (either homopolymers or random copolymers), and dextran or poly(n-vinyl pyrrolidone) polyethylene glycol, propropylene glycol homopolymers, prolypropylene oxide/ethylene oxide co-polymers, polyoxyethylated polyols (e.g., glycerol), polyvinyl alcohol, and mixtures thereof. Polyethylene glycol propionaldehyde may have advantages in manufacturing due to its stability in water. The polymer may be of any molecular weight, and may be branched or unbranched. The number of polymers attached to the antibody may vary, and if more than one polymer is attached, they can be the same or different molecules. In general, the number and/or type of polymers used for derivatization can be determined based on considerations including, but not limited to, the particular properties or functions of the antibody to be improved, whether the antibody derivative will be used in a therapy under defined conditions, etc.

In another embodiment, conjugates of an antibody and nonproteinaceous moiety that may be selectively heated by exposure to radiation are provided. In one embodiment, the nonproteinaceous moiety is a carbon nanotube (Kam et al., Proc. Natl. Acad. Sci. USA 102: 11600-11605 (2005)). The radiation may be of any wavelength, and includes, but is not limited to, wavelengths that do not harm ordinary cells, but which heat the nonproteinaceous moiety to a temperature at which cells proximal to the antibody-nonproteinaceous moiety are killed.

In one embodiment, the medicament is an immunoconjugate comprising an antibody (such as a c-met antibody) conjugated to one or more cytotoxic agents, such as chemotherapeutic agents or drugs, growth inhibitory agents, toxins (e.g., protein toxins, enzymatically active toxins of bacterial, fungal, plant, or animal origin, or fragments thereof), or radioactive isotopes.

In one embodiment, an immunoconjugate is an antibody-drug conjugate (ADC) in which an antibody is conjugated to one or more drugs, including but not limited to a maytansinoid (see U.S. Pat. Nos. 5,208,020, 5,416,064 and European Patent EP 0 425 235 B1); an auristatin such as monomethylauristatin drug moieties DE and DF (MMAE and MMAF) (sec U.S. Pat. Nos. 5,635,483 and 5,780,588, and 7,498,298); a dolastatin; a calicheamicin or derivative thereof (see U.S. Pat. Nos. 5,712,374, 5,714,586, 5,739,116, 5,767,285, 5,770,701, 5,770,710, 5,773,001, and 5,877,296; Hinman et al., Cancer Res. 53:3336-3342 (1993); and Lode et al., Cancer Res. 58:2925-2928 (1998)); an anthracycline such as daunomycin or doxorubicin (see Kratz et al., Current Med. Chem. 13:477-523 (2006); Jeffrey et al., Bioorganic & Med. Chem. Letters 16:358-362 (2006); Torgov et al., Bioconj. Chem. 16:717-721 (2005); Nagy et al., Proc. Natl. Acad. Sci. USA 97:829-834 (2000); Dubowchik et al., Bioorg. & Med. Chem. Letters 12:1529-1532 (2002); King et al., J. Med. Chem. 45:4336-4343 (2002); and U.S. Pat. No. 6,630,579); methotrexate; vindesine; a taxane such as docetaxel, paclitaxel, larotaxel, tesetaxel, and ortataxel; a trichothecene; and CC1065.

In another embodiment, an immunoconjugate comprises an antibody as described herein conjugated to an enzymatically active toxin or fragment thereof, including but not limited to diphtheria A chain, nonbinding active fragments of diphtheria toxin, exotoxin A chain (from *Pseudomonas aeruginosa*), ricin A chain, abrin A chain, modeccin A chain, alpha-sarcin. *Aleurites fordii* proteins, dianthin proteins, *Phytolaca americana* proteins (PAPI, PAPII, and PAP-S), *momordica charantia* inhibitor, curcin, crotin, *sapaonaria officinalis* inhibitor, gelonin, mitogellin, restrictocin, phenomycin, enomycin, and the tricothecenes.

In another embodiment, an immunoconjugate comprises an antibody as described herein conjugated to a radioactive atom to form a radioconjugate. A variety of radioactive isotopes are available for the production of radioconjugates. Examples include $At^{211}$, $I^{131}$, $I^{125}$, $Y^{90}$, $Re^{186}$, $Re^{188}$, $Sm^{153}$, $Bi^{212}$, $P^{32}$, $Ph^{212}$ and radioactive isotopes of Lu. When the radioconjugate is used for detection, it may comprise a radioactive atom for scintigraphic studies, for example $tc^{99}m$ or $I^{123}$, or a spin label for nuclear magnetic resonance (NMR) imaging (also known as magnetic resonance imaging, mri), such as iodine-123 again, iodine-131, indium-111, fluorine-19, carbon-13, nitrogen-15, oxygen-17, gadolinium, manganese or iron.

Conjugates of an antibody and cytotoxic agent may be made using a variety of bifunctional protein coupling agents such as N-succinimidyl-3-(2-pyridyldithio) propionate (SPDP), succinimidyl-4-(N-maleimidomethyl) cyclohexane-1-carboxylate (SMCC), iminothiolane (IT), bifunctional derivatives of imidoesters (such as dimethyl adipimidate HCl), active esters (such as disuccinimidyl suberate), aldehydes (such as glutaraldehyde), bis-azido compounds (such as bis (p-azidobenzoyl) hexanediamine), bis-diazonium derivatives (such as bis-(p-diazoniumbenzoyl)-ethylenediamine), diisocyanates (such as toluene 2,6-diisocyanate), and bis-active fluorine compounds (such as 1,5-difluoro-2,4-dinitrobenzene). For example, a ricin immunotoxin can be prepared as described in Vitetta et al., Science 238:1098 (1987). Carbon-14-labeled 1-isothiocyanatobenzyl-3-methyldiethylene triaminepentaacetic acid (MX-DTPA) is an exemplary chelating agent for conjugation of radionucleotide to the antibody. See WO94/11026. The linker may be a "cleavable linker" facilitating release of a cytotoxic drug in the cell. For example, an acid-labile linker, peptidase-sensitive linker, photolabile linker, dimethyl linker or disulfide-containing linker (Chari et al., Cancer Res. 52:127-131 (1992); U.S. Pat. No. 5,208,020) may be used.

The immunuoconjugates or ADCs herein expressly contemplate, but are not limited to such conjugates prepared with cross-linker reagents including, but not limited to, BMPS, EMCS, GMBS, HBVS, LC-SMCC, MBS, MPBH, SBAP, SIA, SIAB, SMCC, SMPB, SMPH, sulfo-EMCS, sulfo-GMBS, sulfo-KMUS, sulfo-MBS, sulfo-SIAB, sulfo-SMCC, and sulfo-SMPB, and SVSB (succinimidyl-(4-vinylsulfone)benzoate) which are commercially available (e.g., from Pierce Biotechnology, Inc., Rockford, Ill., U.S.A).

Binding Assays and Other Assays

In one aspect, an antibody is tested for its antigen binding activity, e.g., by known methods such as ELISA. Western blot, etc.

In another aspect, competition assays may be used to identify an antibody that competes with an anti-c-met antibody comprising an HVR-L1 comprising amino acid sequence SEQ ID NO: 1; an HVR-L2 comprising amino acid sequence SEQ ID NO: 2; an HVR-L3 comprising amino acid sequence SEQ ID NO: 3; an HVR-H1 comprising amino acid sequence SEQ ID NO: 4; an HVR-H2 comprising amino acid sequence SEQ ID NO: 5; and an HVR-H3 comprising amino acid sequence SEQ ID NO: 6, and/or an anti-c-met antibody comprising a VH sequence of SEQ ID NO:7 and a VT, sequence of SEQ ID NO:8, for binding to human c-met. In some embodiments, competition assays may be used to identify an antibody that competes with onartuzumab for binding to human c-met.

Exemplary methods for mapping an epitope to which an antagonist (e.g., antibody) binds are well-known in the art. See, e.g., Merchant, M. et al. PNAS (2013) 110(32): E2987-E2996, and Morris (1996) "Epitope Mapping Protocols," in Methods in Molecular Biology vol. 66 (Humana Press, Totowa, N.J.). For example, the agent can be screened for both the ability to bind to human c-met or a fragment thereof and to an altered form of c-met or a fragment thereof where the amino acid residue(s) on the binding site(s) is/are altered. A c-met antagonist is determined to bind to the human c-met or fragment thereof if its binding to the altered form of c-met is reduced (for example, significantly reduced) as compared to the human c-met or fragment thereof. The binding assay for the altered form of c-met or fragment thereof can be carried out simultaneously with the binding assay for the human c-met or fragment thereof, for example as a counter-screen in a high throughput screening context. Alternatively, the binding assay for the altered form of c-met can be carried out after the agent has already been identified/confirmed to bind to the human c-met or fragment thereof. In some embodiments, the method comprises: comparing a) binding of the c-met antagonist (e.g., c-met antibody) to human c-met or a fragment thereof with b) the binding of the c-met antagonist to an altered form of c-met or fragment thereof that comprises an alteration at least one amino acid residues (including, for example, at least 2, 3, or 4 amino acid residues) of Q328, R331, L337, and N338, wherein a c-met antagonist that exhibits greater binding affinity to human c-met or fragment thereof to the altered form is selected as a c-met antagonist that selectively binds to a binding site on human c-met comprising such amino acid residue which is altered in the altered form.

III. Diagnostic Methods

In one aspect, the invention provides diagnostic methods, e.g. for identifying a cancer patient who is likely to respond to treatment with a c-met antagonist. In some embodiments, the c-met antagonist is an anti-c-met antibody. In some embodiments, the anti-c-met antibody is onartuzumab.

Provided are methods of identifying a patient having glioblastoma (e.g., previously treated glioblastoma) as likely to respond to a therapy comprising c-met antagonist antibody (e.g., onartuzumab), the methods comprising: (i) measuring the level or presence or absence of or prevalence (e.g., percentage of cells expressing HGF mRNA) of HGF in a sample from the patient; (ii) identifying the patient as more likely to respond to the therapy comprising c-met antagonist antibody (e.g., onartuzumab) when the sample has high HGF biomarker expression. In some embodiments, the method further comprises (iii) selecting the therapy comprising c-met antagonist antibody (e.g., onartuzumab) or recommending a therapy comprising c-met antagonist antibody (e.g., onartuzumab) for the patient. In some embodiments, the therapy comprises c-met antagonist antibody (e.g., onartuzumab) optionally in combination with a second cancer medicament. In some embodiments, the method is an in vitro method. In some embodiments, the methods further comprise (iv) treating the patient with therapy comprising c-met antagonist antibody (e.g., onartuzumab).

Provided are methods of identifying a patient having mesothelioma (e.g., previously treated mesothelioma) as likely to respond to a therapy comprising c-met antagonist antibody (e.g., onartuzumab), the methods comprising: (i) measuring the level or presence or absence of or prevalence (e.g., percentage of cells expressing HGF mRNA) of HGF in a sample from the patient; (ii) identifying the patient as more likely to respond to the therapy comprising c-met antagonist antibody (e.g., onartuzumab) when the sample has high HGF biomarker expression. In some embodiments, the method further comprises (iii) selecting the therapy comprising c-met antagonist antibody (e.g., onartuzumab) or recommending a therapy comprising c-met antagonist antibody (e.g., onartuzumab) for the patient. In some embodiments, the therapy comprises c-met antagonist antibody (e.g., onartuzumab) optionally in combination with a second cancer medicament. In some embodiments, the method is an in vitro method. In some embodiments, the methods further comprise (iv) treating the patient with therapy comprising c-met antagonist antibody (e.g., onartuzumab).

Provided are methods of identifying a patient having gastric cancer (e.g., previously treated gastric cancer) as likely to respond to a therapy comprising c-met antagonist antibody (e.g., onartuzumab), the methods comprising: (i) measuring the level or presence or absence of or prevalence (e.g., percentage of cells expressing HGF mRNA) of HGF in a sample from the patient; (ii) identifying the patient as more likely to respond to the therapy comprising c-met antagonist antibody (e.g., onartuzumab) when the sample has high HGF biomarker expression. In some embodiments, the method further comprises (iii) selecting the therapy comprising c-met antagonist antibody (e.g., onartuzumab) or recommending a therapy comprising c-met antagonist antibody (e.g., onartuzumab) for the patient. In some embodiments, the therapy comprises c-met antagonist antibody (e.g., onartuzumab) optionally in combination with a second cancer medicament. In some embodiments, the method is an in vitro method. In some embodiments, the methods further comprise (iv) treating the patient with therapy comprising c-met antagonist antibody (e.g., onartuzumab).

Provided are methods of identifying a patient having renal cell carcinoma (e.g., previously treated renal cell carcinoma) as likely to respond to a therapy comprising c-met antagonist antibody (e.g., onartuzumab), the methods comprising: (i) measuring the level or presence or absence of or prevalence (e.g., percentage of cells expressing HGF mRNA) of HGF in a sample from the patient; (ii) identifying the patient as more likely to respond to the therapy comprising c-met antagonist antibody (e.g., onartuzumab) when the sample has high HGF biomarker expression. In some embodiments, the method further comprises (iii) selecting the therapy comprising c-met antagonist antibody (e.g., onartuzumab) or recommending a therapy comprising c-met antagonist antibody (e.g., onartuzumab) for the patient. In some embodiments, the therapy comprises c-met antagonist antibody (e.g., onartuzumab) optionally in combination with a second cancer medicament. In some embodiments, the method is an in vitro method. In some embodiments, the methods further comprise (iv) treating the patient with therapy comprising c-met antagonist antibody (e.g., onartuzumab).

Provided are methods of identifying a patient having hepatocellular carcinoma (e.g., previously treated hepatocellular carcinoma) as likely to respond to a therapy comprising c-met antagonist antibody (e.g., onartuzumab), the methods comprising: (i) measuring the level or presence or absence of or prevalence (e.g., percentage of cells expressing HGF mRNA) of HGF in a sample from the patient; (ii) identifying the patient as more likely to respond to the therapy comprising c-met antagonist antibody (e.g., onartuzumab) when the sample has high HGF biomarker expression. In some embodiments, the method further comprises (iii) selecting the therapy comprising c-met antagonist antibody (e.g., onartuzumab) or recommending a therapy comprising c-met antagonist antibody (e.g., onartuzumab) for the patient. In some embodiments, the therapy comprises c-met antagonist antibody (e.g., onartuzumab) optionally in combination with a second cancer medicament. In some embodiments, the method is an in vitro method. In some embodiments, the methods further comprise (iv) treating the patient with therapy comprising c-met antagonist antibody (e.g., onartuzumab).

In one aspect, the invention provides diagnostic methods, e.g. for identifying a cancer patient who is likely to respond to treatment with a c-met antagonist and VEGF antagonist (e.g., bevacizumab).

Provided are methods of identifying a patient having glioblastoma (e.g., previously treated glioblastoma) as likely to respond to a therapy comprising (a) c-met antagonist antibody (e.g., onartuzumab) and (b) VEGF antagonist (e.g., bevacizumab), the methods comprising: (i) measuring the level or presence or absence of or prevalence (e.g., percentage of cells expressing HGF mRNA) of HGF in a sample from the patient; (ii) identifying the patient as more likely to respond to the therapy comprising (a) c-met antagonist antibody (e.g., onartuzumab) and (b) VEGF antagonist (e.g., bevacizumab) when the sample has high HGF biomarker expression. In some embodiments, the method further comprises (iii) selecting the therapy comprising (a) c-met antagonist antibody (e.g., onartuzumab) and (b) VEGF antagonist (e.g., bevacizumab) or recommending a therapy comprising (a) c-met antagonist antibody (e.g., onartuzumab) and (b) VEGF antagonist (e.g., bevacizumab) for the patient. In some embodiments, the method is an in vitro method. In some embodiments, the methods further comprise (iv) treating the patient with therapy comprising (a) c-met antagonist antibody (e.g., onartuzumab) and (b) anti-VEGF antibody (e.g., bevacizumab).

Provided are methods of identifying a patient having mesothelioma (e.g., previously treated mesothelioma) as likely to respond to a therapy comprising (a) c-met antagonist antibody (e.g., onartuzumab) and (b) VEGF antagonist (e.g., bevacizumab), the methods comprising: (i) measuring the level or presence or absence of or prevalence (e.g., percentage of cells expressing HGF mRNA) of HGF in a sample from the patient; (ii) identifying the patient as more likely to respond to the therapy comprising (a) c-met antagonist antibody (e.g., onartuzumab) and (b) VEGF antagonist (e.g., bevacizumab) when the sample has high HGF biomarker expression. In some embodiments, the method further comprises (iii) selecting the therapy comprising (a) c-met antagonist antibody (e.g., onartuzumab) and (b) VEGF antagonist (e.g., bevacizumab) or recommending a therapy comprising (a) c-met antagonist antibody (e.g., onartuzumab) and (b) VEGF antagonist (e.g., bevacizumab) for the patient. In some embodiments, the method is an in vitro method. In some embodiments, the methods further comprise (iv) treating the patient with therapy comprising (a) c-met antagonist antibody (e.g., onartuzumab) and (b) anti-VEGF antibody (e.g., bevacizumab).

Provided are methods of identifying a patient having gastric cancer (e.g., previously treated gastric cancer) as likely to respond to a therapy comprising (a) c-met antagonist antibody (e.g., onartuzumab) and (b) VEGF antagonist (e.g., bevacizumab), the methods comprising: (i) measuring the level or presence or absence of or prevalence (e.g., percentage of cells expressing HGF mRNA) of HGF in a sample from the patient; (ii) identifying the patient as more likely to respond to the therapy comprising (a) c-met antagonist antibody (e.g., onartuzumab) and (b) VEGF antagonist (e.g., bevacizumab) when the sample has high HGF biomarker expression. In some embodiments, the method further comprises (iii) selecting the therapy comprising (a) c-met antagonist antibody (e.g., onartuzumab) and (b) VEGF antagonist (e.g., bevacizumab) or recommending a therapy comprising (a) c-met antagonist antibody (e.g., onartuzumab) and (b) VEGF antagonist (e.g., bevacizumab) for the patient. In some embodiments, the method is an in vitro method. In some embodiments, the methods further comprise (iv) treating the patient with therapy comprising (a) c-met antagonist antibody (e.g., onartuzumab) and (h) anti-VEGF antibody (e.g., bevacizumab).

Provided are methods of identifying a patient having renal cell carcinoma (e.g., previously treated renal cell carcinoma) as likely to respond to a therapy comprising (a) c-met antagonist antibody (e.g., onartuzumab) and (b) VEGF antagonist (e.g., bevacizumab), the methods comprising: (i) measuring the level or presence or absence of or prevalence (e.g., percentage of cells expressing HGF mRNA) of HGF in a sample from the patient; (ii) identifying the patient as more likely to respond to the therapy comprising (a) c-met antagonist antibody (e.g., onartuzumab) and (b) VEGF antagonist (e.g., bevacizumab) when the sample has high HGF biomarker expression. In some embodiments, the method further comprises (iii) selecting the therapy comprising (a) c-met antagonist antibody (e.g., onartuzumab) and (b) VEGF antagonist (e.g., bevacizumab) or recommending a therapy comprising (a) c-met antagonist antibody (e.g., onartuzumab) and (b) VEGF antagonist (e.g., bevacizumab) for the patient. In some embodiments, the method is an in vitro method. In some embodiments, the methods further comprise (iv) treating the patient with therapy comprising (a) c-met antagonist antibody (e.g., onartuzumab) and (b) anti-VEGF antibody (e.g., bevacizumab).

Provided are methods of identifying a patient having hepatocellular carcinoma (e.g., previously treated hepatocellular carcinoma) as likely to respond to a therapy comprising (a) c-met antagonist antibody (e.g., onartuzumab) and (b) VEGF antagonist (e.g., bevacizumab), the methods comprising: (i) measuring the level or presence or absence of or prevalence (e.g., percentage of cells expressing HGF mRNA) of HGF in a sample from the patient; (ii) identifying the patient as more likely to respond to the therapy comprising (a) c-met antagonist antibody (e.g., onartuzumab) and (b) VEGF antagonist (e.g., bevacizumab) when the sample has high HGF biomarker expression. In some embodiments, the method further comprises (iii) selecting the therapy comprising (a) c-met antagonist antibody (e.g., onartuzumab) and (b) VEGF antagonist (e.g., bevacizumab) or recommending a therapy comprising (a) c-met antagonist antibody (e.g., onartuzumab) and (b) VEGF antagonist (e.g., bevacizumab) for the patient. In some embodiments, the method is an in vitro method. In some embodiments, the methods further comprise (iv) treating the patient with therapy comprising (a) c-met antagonist antibody (e.g., onartuzumab) and (b) anti-VEGF antibody (e.g., bevacizumab).

Provided are methods of providing a cancer diagnosis comprising: (i) measuring HGF biomarker (e.g., the level or presence or absence of or prevalence (e.g., percentage of cells expressing HGF mRNA) of HGF) in a sample from the patient; (ii) diagnosing the patient as having cancer comprising high HGF biomarker when the sample has high HGF biomarker expression. In some embodiments, the method further comprises (iii) selecting the therapy comprising c-met antagonist antibody (e.g., onartuzumab) or recommending a therapy comprising c-met antagonist antibody (e.g., onartuzumab) for the patient. In some embodiments, the therapy comprises c-met antagonist antibody (e.g., onartuzumab) optionally in combination with a second cancer medicament. In some embodiments, the method is an in vitro method. In some embodiments, the methods further comprise (iv) treating the patient with therapy comprising c-met antagonist antibody (e.g., onartuzumab).

Provided are methods of providing a cancer diagnosis comprising: (i) measuring HGF biomarker (e.g., the level or presence or absence of or prevalence (e.g., percentage of cells expressing HGF mRNA) of HGF) in a sample from the patient; (ii) diagnosing the patient as having cancer comprising high HGF biomarker when the sample has high HGF biomarker expression. In some embodiments, the method further comprises (iii) selecting a therapy comprising (a) c-met antagonist antibody (e.g., onartuzumab) and (b) VEGF antagonist (e.g., bevacizumab) or recommending a therapy comprising (a) c-met antagonist antibody (e.g., onartuzumab) and (b) VEGF antagonist (e.g., bevacizumab) for the patient. In some embodiments, the method is an in vitro method. In some embodiments, the methods further comprise (iv) treating the patient with therapy comprising (a) c-met antagonist antibody (e.g., onartuzumab) and (b) anti-VEGF antibody (e.g., bevacizumab).

Provided are methods of providing a glioblastoma diagnosis comprising: (i) measuring HGF biomarker (e.g., the level or presence or absence of or prevalence (e.g., percentage of cells expressing HGF mRNA) of HGF) in a sample from the patient; (ii) diagnosing the patient as having glioblastoma comprising high HGF biomarker when the sample has high HGF biomarker expression. In some embodiments, the method further comprises (iii) selecting the therapy comprising c-met antagonist antibody (e.g., onartuzumab) or recommending a therapy comprising c-met antagonist antibody (e.g., onartuzumab) for the patient. In some embodiments, the therapy comprises c-met antagonist antibody (e.g., onartuzumab) optionally in combination with a second cancer medicament. In some embodiments, the method is an in vitro method. In some embodiments, the methods further comprise (iv) treating the patient with therapy comprising c-met antagonist antibody (e.g., onartuzumab).

Provided are methods of providing a glioblastoma diagnosis comprising: (i) measuring HGF biomarker (e.g., the level or presence or absence of or prevalence (e.g., percentage of cells expressing HGF mRNA) of HGF) in a sample from the patient; (ii) diagnosing the patient as having glioblastoma comprising high HGF biomarker when the sample has high HGF biomarker expression. In some embodiments, the method further comprises (iii) selecting a therapy comprising (a) c-met antagonist antibody (e.g., onartuzumab) and (b) VEGF antagonist (e.g., bevacizumab) or recommending a therapy comprising (a) c-met antagonist antibody (e.g., onartuzumab) and (b) VEGF antagonist (e.g., bevacizumab) for the patient. In some embodiments, the method is an in vitro method. In some embodiments, the methods further comprise (iv) treating the patient with therapy comprising (a) c-met antagonist antibody (e.g., onartuzumab) and (b) anti-VEGF antibody (e.g., bevacizumab).

Provided are methods of providing a mesothelioma diagnosis comprising: (i) measuring HGF biomarker (e.g., the level or presence or absence of or prevalence (e.g., percentage of cells expressing HGF mRNA) of HGF) in a sample from the patient; (ii) diagnosing the patient as having mesothelioma comprising high HGF biomarker when the sample has high HGF biomarker expression. In some embodiments, the method further comprises (iii) selecting the therapy comprising c-met antagonist antibody (e.g., onartuzumab) or recommending a therapy comprising c-met antagonist antibody (e.g., onartuzumab) for the patient. In some embodiments, the therapy comprises c-met antagonist antibody (e.g., onartuzumab) optionally in combination with a second cancer medicament. In some embodiments, the method is an in vitro method. In some embodiments, the methods further comprise (iv) treating the patient with therapy comprising c-met antagonist antibody (e.g., onartuzumab).

Provided are methods of providing a mesothelioma diagnosis comprising: (i) measuring HGF biomarker (e.g., the level or presence or absence of or prevalence (e.g., percentage of cells expressing HGF mRNA) of HGF) in a sample from the patient; (ii) diagnosing the patient as having mesothelioma comprising high HGF biomarker when the sample has high HGF biomarker expression. In some embodiments, the method further comprises (iii) selecting a therapy comprising (a) c-met antagonist antibody (e.g., onartuzumab) and (b) VEGF antagonist (e.g., bevacizumab) or recommending a therapy comprising (a) c-met antagonist antibody (e.g., onartuzumab) and (b) VEGF antagonist (e.g., bevacizumab) for the patient. In some embodiments, the method is an in vitro method. In some embodiments, the methods further comprise (iv) treating the patient with therapy comprising (a) c-met antagonist antibody (e.g., onartuzumab) and (b) anti-VEGF antibody (e.g., bevacizumab).

Provided are methods of providing a gastric cancer diagnosis comprising: (i) measuring HGF biomarker (e.g., the level or presence or absence of or prevalence (e.g., percentage of cells expressing HGF mRNA) of HGF) in a sample from the patient; (ii) diagnosing the patient as having gastric cancer comprising high HGF biomarker when the sample has high HGF biomarker expression. In some embodiments, the method further comprises (iii) selecting the therapy comprising c-met antagonist antibody (e.g., onartuzumab) or recommending a therapy comprising c-met antagonist antibody (e.g., onartuzumab) for the patient. In some embodiments, the therapy comprises c-met antagonist antibody (e.g., onartuzumab) optionally in combination with a second cancer medicament. In some embodiments, the method is an in vitro method. In some embodiments, the methods further comprise (iv) treating the patient with therapy comprising c-met antagonist antibody (e.g., onartuzumab).

Provided are methods of providing a gastric cancer diagnosis comprising: (i) measuring HGF biomarker (e.g., the level or presence or absence of or prevalence (e.g., percentage of cells expressing HGF mRNA) of HGF) in a sample from the patient; (ii) diagnosing the patient as having gastric cancer comprising high HGF biomarker when the sample has high HGF biomarker expression. In some embodiments, the method further comprises (iii) selecting a therapy comprising (a) c-met antagonist antibody (e.g., onartuzumab) and (b) VEGF antagonist (e.g., bevacizumab) or recommending a therapy comprising (a) c-met antagonist antibody (e.g., onartuzumab) and (b) VEGF antagonist (e.g., bevacizumab) for the patient. In some embodiments, the method is an in vitro method. In some embodiments, the methods further comprise (iv) treating the patient with therapy comprising (a) c-met antagonist antibody (e.g., onartuzumab) and (b) anti-VEGF antibody (e.g., bevacizumab).

Provided are methods of providing a renal cell carcinoma diagnosis comprising: (i) measuring HGF biomarker (e.g., the level or presence or absence of or prevalence (e.g., percentage of cells expressing HGF mRNA) of HGF) in a sample from the patient; (ii) diagnosing the patient as having renal cell carcinoma comprising high HGF biomarker when the sample has high HGF biomarker expression. In some embodiments, the method further comprises (iii) selecting the therapy comprising c-met antagonist antibody (e.g., onartuzumab) or recommending a therapy comprising c-met antagonist antibody (e.g., onartuzumab) for the patient. In some embodiments, the therapy comprises c-met antagonist antibody (e.g., onartuzumab) optionally in combination with a second cancer medicament. In some embodiments, the method is an in vitro method. In some embodiments, the methods further comprise (iv) treating the patient with therapy comprising c-met antagonist antibody (e.g., onartuzumab).

Provided are methods of providing a renal cell carcinoma diagnosis comprising: (i) measuring HGF biomarker (e.g., the level or presence or absence of or prevalence (e.g., percentage of cells expressing HGF mRNA) of HGF) in a sample from the patient; (ii) diagnosing the patient as having renal cell carcinoma comprising high HGF biomarker when the sample has high HGF biomarker expression. In some embodiments, the method further comprises (iii) selecting a therapy comprising (a) c-met antagonist antibody (e.g., onartuzumab) and (b) VEGF antagonist (e.g., bevacizumab) or recommending a therapy comprising (a) c-met antagonist antibody (e.g., onartuzumab) and (b) VEGF antagonist (e.g., bevacizumab) for the patient. In some embodiments, the method is an in vitro method. In some embodiments, the methods further comprise (iv) treating the patient with therapy comprising (a) c-met antagonist antibody (e.g., onartuzumab) and (b) anti-VEGF antibody (e.g., bevacizumab).

Provided are methods of providing a hepatocellular carcinoma diagnosis comprising: (i) measuring HGF biomarker (e.g., the level or presence or absence of or prevalence (e.g., percentage of cells expressing HGF mRNA) of HGF) in a sample from the patient; (ii) diagnosing the patient as having hepatocellular carcinoma comprising high HGF biomarker when the sample has high HGF biomarker expression. In some embodiments, the method further comprises (iii) selecting the therapy comprising c-met antagonist antibody (e.g., onartuzumab) or recommending a therapy comprising c-met antagonist antibody (e.g., onartuzumab) for the patient. In some embodiments, the therapy comprises c-met antagonist antibody (e.g., onartuzumab) optionally in combination with a second cancer medicament. In some embodiments, the method is an in vitro method. In some embodiments, the methods further comprise (iv) treating the patient with therapy comprising c-met antagonist antibody (e.g., onartuzumab).

Provided are methods of providing a hepatocellular carcinoma diagnosis comprising: (i) measuring HGF biomarker (e.g., the level or presence or absence of or prevalence (e.g., percentage of cells expressing HGF mRNA) of HGF) in a sample from the patient; (ii) diagnosing the patient as having hepatocellular carcinoma comprising high HGF biomarker when the sample has high HGF biomarker expression. In some embodiments, the method further comprises (iii) selecting a therapy comprising (a) c-met antagonist antibody (e.g., onartuzumab) and (b) VEGF antagonist (e.g., bevacizumab) or recommending a therapy comprising (a) c-met antagonist antibody (e.g., onartuzumab) and (b) VEGF antagonist (e.g., bevacizumab) for the patient. In some embodiments, the method is an in vitro method. In some embodiments, the methods further comprise (iv) treating the patient with therapy comprising (a) c-met antagonist antibody (e.g., onartuzumab) and (b) anti-VEGF antibody (e.g., bevacizumab).

Provided are methods of recommending a treatment to a patient comprising: (i) measuring HGF biomarker (e.g., the level or presence or absence of or prevalence (e.g., percentage of cells expressing HGF mRNA) of HGF) in a sample from the patient; (ii) recommending treatment with c-met antagonist (optionally with a combination of c-met antagonist and VEGF antagonist) when the sample has high HGF biomarker expression. In some embodiments, the method further comprises (iii) selecting a therapy comprising c-met antagonist antibody (e.g., onartuzumab). In some embodiments, the methods further comprise (iv) treating the patient with therapy comprising c-met antagonist antibody (e.g., onartuzumab). In some embodiments, the therapy comprises c-met antagonist antibody (e.g., onartuzumab) optionally in combination with a second cancer medicament. In some embodiments, the therapy comprises c-met antagonist antibody (e.g., onartuzumab) in combination with a VEGF antagonist. In some embodiments, the method is an in vitro method.

Provided are methods of recommending a treatment to a glioblastoma patient comprising: (i) measuring HGF biomarker (e.g., the level or presence or absence of or prevalence (e.g., percentage of cells expressing HGF mRNA) of HGF) in a sample from the patient; (ii) recommending treatment with c-met antagonist (optionally with a combination of c-met antagonist and VEGF antagonist) when the sample has high HGF biomarker expression. In some embodiments, the method further comprises (iii) selecting a therapy comprising c-met antagonist antibody (e.g., onartuzumab). In some embodiments, the methods further comprise (iv) treating the patient with therapy comprising c-met antagonist antibody (e.g., onartuzumab). In some embodiments, the therapy comprises c-met antagonist antibody (e.g., onartuzumab) optionally in combination with a second cancer medicament. In some embodiments, the therapy comprises c-met antagonist antibody (e.g., onartuzumab) in combination with a VEGF antagonist. In some embodiments, the method is an in vitro method.

Provided are methods of recommending a treatment to a mesothelioma patient comprising: (i) measuring HGF biomarker (e.g., the level or presence or absence of or prevalence (e.g., percentage of cells expressing HGF mRNA) of HGF) in a sample from the patient; (ii) recommending treatment with c-met antagonist (optionally with a combination of c-met antagonist and VEGF antagonist) when the sample has high HGF biomarker expression. In some embodiments, the method further comprises (iii) selecting a therapy comprising c-met antagonist antibody (e.g., onartuzumab). In some embodiments, the methods further comprise (iv) treating the patient with therapy comprising c-met antagonist antibody (e.g., onartuzumab). In some embodiments, the therapy comprises c-met antagonist antibody (e.g., onartuzumab) optionally in combination with a second cancer medicament. In some embodiments, the therapy comprises c-met antagonist antibody (e.g., onartuzumab) in combination with a VEGF antagonist. In some embodiments, the method is an in vitro method.

Provided are methods of recommending a treatment to a gastric cancer patient comprising: (i) measuring HGF biomarker (e.g., the level or presence or absence of or prevalence (e.g., percentage of cells expressing HGF mRNA) of HGF) in a sample from the patient; (ii) recommending treatment with c-met antagonist (optionally with a combination of c-met antagonist and VEGF antagonist) when the sample has high HGF biomarker expression. In some embodiments, the method further comprises (iii) selecting a therapy comprising c-met antagonist antibody (e.g., onartuzumab). In some embodiments, the method is an in vitro method. In some embodiments, the methods further comprise (iv) treating the patient with therapy comprising c-met antagonist antibody (e.g., onartuzumab). In some embodiments, the therapy comprises c-met antagonist antibody (e.g., onartuzumab) optionally in combination with a second cancer medicament. In some embodiments, the therapy comprises c-met antagonist antibody (e.g., onartuzumab) in combination with a VEGF antagonist.

Provided are methods of recommending a treatment to a renal cell carcinoma patient comprising: (i) measuring HGF biomarker (e.g., the level or presence or absence of or prevalence (e.g., percentage of cells expressing HGF mRNA) of HGF) in a sample from the patient; (ii) recommending treatment with c-met antagonist (optionally with a combination of c-met antagonist and VEGF antagonist) when the sample has high HGF biomarker expression. In some embodiments, the method further comprises (iii) selecting a therapy comprising c-met antagonist antibody (e.g., onartuzumab). In some embodiments, the method is an in vitro method. In some embodiments, the methods further comprise (iv) treating the patient with therapy comprising c-met antagonist antibody (e.g., onartuzumab). In some embodiments, the therapy comprises c-met antagonist antibody (e.g., onartuzumab) optionally in combination with a second cancer medicament. In some embodiments, the therapy comprises c-met antagonist antibody (e.g., onartuzumab) in combination with a VEGF antagonist.

Provided are methods of recommending a treatment to a hepatocellular carcinoma patient comprising: (i) measuring HGF biomarker (e.g., the level or presence or absence of or prevalence (e.g., percentage of cells expressing HGF mRNA) of HGF) in a sample from the patient; (ii) recommending treatment with c-met antagonist (optionally with a combination of c-met antagonist and VEGF antagonist) when the sample has high HGF biomarker expression. In some embodiments, the method further comprises (iii) selecting a therapy comprising c-met antagonist antibody (e.g., onartuzumab). In some embodiments, the methods further comprise (iv) treating the patient with therapy comprising c-met antagonist antibody (e.g., onartuzumab). In some embodiments, the therapy comprises c-met antagonist antibody (e.g., onartuzumab) optionally in combination with a second cancer medicament. In some embodiments, the therapy comprises c-met antagonist antibody (e.g., onartuzumab) in combination with a VEGF antagonist. In some embodiments, the method is an in vitro method.

In some embodiments of any of the inventions provided herein, the sample is obtained prior to treatment with c-met antagonist. In some embodiments of any of the inventions provided herein, the sample is obtained prior to treatment with VEGF antagonist. In some embodiments of any of the inventions provided herein, the sample is obtained prior to treatment with c-met antagonist and VEGF antagonist. In some embodiments, the sample is obtained prior to treatment with a cancer medicament. In some embodiments, the sample is obtained after the cancer has metastasized. In some embodiments, the sample is formalin fixed and paraffin embedded (FFPE). In some embodiments, a first sample is tested for HGF expression (e.g., using ISH or PCR). In some embodiments, the sample is of a biopsy (e.g., a core biopsy), a surgical specimen (e.g., a specimen from a surgical resection), or a fine needle aspirate.

A sample from the patient is tested for expression of one or more of the biomarkers herein. The source of the tissue or cell sample may be solid tissue as from a fresh, frozen and/or preserved organ or tissue sample or biopsy or aspirate (including but not limited to a fine needle aspirate); blood or any blood constituents; bodily fluids such as cerebrospinal fluid, amniotic fluid, peritoneal fluid, bronchiolar lavage, pleural fluid, sputum, or interstitial fluid; cells from any time in gestation or development of the subject. The tissue sample may contain compounds which are not naturally intermixed with the tissue in nature such as preservatives, anticoagulants, buffers, fixatives, nutrients, antibiotics, or the like. Examples of tumor samples herein include, but are not limited to, tumor biopsies, tumor cells, serum, plasma, circulating plasma proteins, ascitic fluid, primary cell cultures or cell lines derived from tumors or exhibiting tumor-like properties, bronchiolar lavage, pleural fluid, sputum, cerebrospinal fluid, urine, as well as preserved tumor samples, such as formalin-fixed, paraffin-embedded tumor samples (including, but not limited to formalin-fixed paraffin-embedded fine needle aspirate samples) or frozen tumor samples. In one embodiment, the patient sample is a formalin-fixed paraffin-embedded (FFPE) tumor sample (e.g., a glioblastoma tumor sample, a mesothelioma tumor sample, or a gastric cancer tumor sample). In one embodiment, the patient sample is a biopsy (e.g., a needle biopsy). In one embodiment, the patient sample is a formalin-fixed paraffin-embedded sample from a fine needle aspirate. In one embodiment, the sample is a FFPE tumor sample from a core biopsy (e.g., a glioblastoma core biopsy, a mesothelioma core biopsy, a gastric cancer core biopsy, or a renal cell carcinoma core biopsy). In one embodiment, the patient sample is a surgical resection sample. The sample may be obtained prior to or during the patient's treatment with a cancer medicament (such as an anti-c-met antagonist). The sample may be obtained prior to or during the patient's prior treatment with a cancer medicament. The sample may be obtained from the primary tumor or from a metastatic tumor. The sample may be obtained when the cancer is first diagnosed or, for example, after the tumor has metastasized. A tumor sample may include cancer cells, lymphocytes, leukocytes, stroma, blood vessels, connective tissue, basal lamina, and any other cell type in association with the tumor. In some embodiments, the tumor sample is of lung, lymph node, stomach, liver, brain, or kidney. In some embodiments, the tumor is macro-dissected, e.g., to remove morphologically normal brain tissue from a glioblastoma tumor sample. In some embodiments, the macro-dissected glioblastoma tumor sample comprises benign stromal cells (e.g., reactive astrocytes, glial cells, pericytes and/or endothelial cells). In some embodiments, the tumor is macro-dissected, e.g., to remove morphologically normal mesothelium tissue from a mesothelioma tumor sample. In some embodiments, the macro-dissected mesothelioma tumor sample comprises benign stromal cells. In some embodiments, the tumor is macro-dissected, e.g., to remove morphologically normal gastric tissue from a gastric cancer tumor sample. In some embodiments, the macro-dissected gastric cancer tumor sample comprises benign stromal cells (e.g., fibroblasts, macrophages and/or endothelial cells). In some embodiments, the tumor is macro-dissected, e.g., to remove morphologically normal renal tissue from a renal cell carcinoma tumor sample. In some embodiments, the macro-dissected renal cell carcinoma tumor sample comprises benign stromal cells. In some embodiments, the tumor is macro-dissected, e.g., to remove morphologically normal hepatic tissue from a hepatocellular carcinoma tumor sample. In some embodiments, the macro-dissected hepatocellular carcinoma tumor sample comprises benign stromal cells.

A cancer or biological sample which displays HGF mRNA expression is one which, in a diagnostic test, expresses (including overexpresses) HGF mRNA. A glioblastoma sample which displays HGF mRNA expression is one which, in a diagnostic test, expresses (including overexpresses) HGF mRNA. In some embodiments, a glioblastoma sample includes tumor cells and benign stromal cells. A mesothelioma sample which displays HGF mRNA expression is one which, in a diagnostic test, expresses (including overexpresses) HGF mRNA. In some embodiments, a mesothelioma sample includes tumor cells and benign stromal cells. A gastric cancer sample which displays HGF mRNA expression is one which, in a diagnostic test, expresses (including overexpresses) HGF mRNA. In some embodiments, a gastric cancer sample includes tumor cells and benign stromal cells. A renal cell carcinoma sample which displays HGF mRNA expression is one which, in a diagnostic test, expresses (including overexpresses) HGF mRNA. In some embodiments, a renal cell carcinoma sample includes tumor cells and benign stromal cells. A hepatocellular carcinoma sample which displays HGF mRNA expression is one which, in a diagnostic test, expresses (including overexpresses) HGF mRNA. In some embodiments, a hepatocellular carcinoma sample includes tumor cells and benign stromal cells. A sarcoma sample which displays HGF mRNA expression is one which, in a diagnostic test, expresses (including overexpresses) HGF mRNA. In some embodiments, a sarcoma sample includes tumor cells and benign stromal cells.

A cancer or biological sample which displays c-met amplification is one which, in a diagnostic test, has amplified c-met gene. In some embodiments, amplified c-met gene is an average (in a population of cell) of greater than or equal to 4 or more copies of the c-met gene, 5 or more copies of the c-met gene, or an average of eight or more copies of a c-met gene, or more, such as 10 or more, 12 or more, 15 or more or 20 or more copies of a c-met gene.

Various methods for determining expression of mRNA, protein, or gene amplification include, but are not limited to, gene expression profiling, polymerase chain reaction (PCR) including quantitative real time PCR (qRT-PCR), reverse transcriptase quantitative PCR (rt-qPCR), RNA-Seq, FISH, CISH, microarray analysis, serial analysis of gene expression (SAGE), MassARRAY, proteomics, immunohistochemistry (IHC), Northern and Southern blot analyses, in situ hybridization (e.g., single or multiplex nucleic acid in situ hybridization technology such as Advanced Cell Diagnostic's RNAscope technology), RNAse protection assays, and microarrays (e.g., Illumina BeadArray™ technology; Beads Array for Detection of Gene Expression (BADG E)). Biomarkers may also be measured by polymerase chain reaction (PCR)-based assays, e.g., quantitative PCR, real-time PCR, quantitative real-time PCR (qRT-PCR), reverse transcriptase PCR (RT-PCR), and reverse transcriptase quantitative PCR (rt-qPCR). Other amplification-based methods include, for example, transcript-mediated amplification (TMA), strand displacement amplification (SDA), nucleic acid sequence based amplification (NASBA), and signal amplification methods such as bDNA. Nucleic acid biomarkers also may be measured by, for example, NanoString nCounter, and high coverage expression profiling (Hi-CEP). Analysis of amplified nucleic acid sequences can be performed using various technologies such as microchips, fluorescence polarization assays, sequencing, and matrix-assisted laser desorption ionization (MALDI) mass spectrometry. In some embodiments, amplified nucleic acids are analyzed by sequencing. In some embodiments, nucleic acid expression is measured and/or quantified. In some embodiments, protein expression is measured and/or quantified.

Various exemplary methods for determining biomarker expression will now be described in more detail.

PCR assays are well known in the art, including but not limited to real-time PCR (RT-PCR) assays such as quantitative PCR assays, including reverse transcriptase quantitative PCR (rt-qPCR). Platforms for performing quantitative PCR assays include: Fluidigm (e.g., BioMark™ HD System), Roche Molecular System (e.g., cobas 4800 system).

In one embodiment, HGF nucleic acid (e.g., HGF mRNA) is detected using a method comprising (a) producing cDNA from the sample by reverse transcription using at least one primer; (b) amplifying the cDNA; and (c) detecting the presence of the amplified cDNA. In addition, such methods can include one or more steps that allow one to determine the levels of mRNA in a sample (e.g., by simultaneously or separately examining the levels of a comparative control mRNA sequence of a gene, e.g., a housekeeping gene such as an actin family member). Optionally, the sequence of the amplified cDNA can be determined.

In some embodiments, HGF nucleic acid (e.g., HGF mRNA) is detected using a method comprising (a) performing PCR on nucleic acid (e.g., mRNA) extracted from a patient cancer sample (such as a FFPE fixed patient cancer sample); and (b) determining expression of nucleic acid in the sample.

At the nucleic acid level, biomarkers may be measured by electrophoresis, Northern and Southern blot analyses, in situ hybridization (e.g., single or multiplex nucleic acid in situ hybridization), RNAse protection assays, and microarrays (e.g., Illumina BeadArray™ technology; Beads Array for Detection of Gene Expression (BADG E)). Biomarkers may also be measured by polymerase chain reaction (PCR)-based assays, e.g., quantitative PCR, real-time PCR, quantitative real-time PCR (qRT-PCR), reverse transcriptase PCR (rt-PCR), and reverse transcriptase quantitative PCR (rt-qPCR). Other amplification-based methods include, for example, transcript-mediated amplification (TMA), strand displacement amplification (SDA), nucleic acid sequence based amplification (NASBA), and signal amplification methods such as bDNA. Nucleic acid biomarkers also may be measured by sequencing-based techniques such as, for example, serial analysis of gene expression (SAGE), RNA-Seq, and high-throughput sequencing technologies (e.g., massively parallel sequencing), and Sequenom MassARRAY® technology. Nucleic acid biomarkers also may be measured by, for example, NanoString nCounter, and high coverage expression profiling (HiCEP).

Of the techniques listed above, a sensitive and flexible quantitative method is rt-qPCR, which can be used to compare mRNA levels in different sample populations, in normal and tumor tissues, with or without drug treatment, to characterize patterns of gene expression, to discriminate between closely related mRNAs, and to analyze RNA structure.

The first step is the isolation of mRNA from a target sample. The starting material is typically total RNA isolated from human tumors or tumor cell lines, and corresponding normal tissues or cell lines, respectively. Thus RNA can be isolated from a variety of primary tumors, including breast, lung, colon, prostate, brain, liver, kidney, pancreas, stomach, gall bladder, spleen, thymus, testis, ovary, uterus, etc., the corresponding normal tissues, or tumor cell lines. If the source of mRNA is a primary tumor, mRNA can be extracted, for example, from frozen or archived paraffin-embedded and fixed (e.g. formalin-fixed) tissue samples. General methods for mRNA extraction are well known in the art and are disclosed in standard textbooks of molecular biology, including Ausubel et al., *Current Protocols of Molecular Biology*, John Wiley and Sons (1997). Methods for RNA extraction from paraffin embedded tissues are disclosed, for example, in Rupp and Locker, *Lab Invest.* 56:A67 (1987), and De Andres et al., *Bio Techniques* 18:42044 (1995). In particular, RNA isolation can be performed using purification kit, buffer set and protease from commercial manufacturers, such as Qiagen, according to the manufacturer's instructions. For example, total RNA from cells in culture can be isolated using Qiagen RNeasy mini-columns. Other commercially available RNA isolation kits include MASTERPURE® Complete DNA and RNA Purification Kit (EPICENTRE®, Madison. Wis.), and Paraffin Block RNA Isolation Kit (Ambion, Inc.). Total RNA from tissue samples can be isolated using RNA Stat-60 (TelTest). RNA prepared from tumor can be isolated, for example, by cesium chloride density gradient centrifugation.

As RNA cannot serve as a template for PCR, the first step in gene expression profiling by PCR is the reverse transcription of the RNA template into cDNA, followed by its exponential amplification in a PCR reaction. The two most commonly used reverse transcriptases are avilo myeloblastosis virus reverse transcriptase (AMY-RT) and Moloney murine leukemia virus reverse transcriptase (MMLV-RT). The reverse transcription step is typically primed using specific primers, random hexamers, or oligo-dT primers, depending on the circumstances and the goal of expression profiling. For example, extracted RNA can be reverse-transcribed using a GENEAMP™ RNA PCR kit (Perkin Elmer, Calif., USA), following the manufacturer's instructions. The derived cDNA can then be used as a template in the subsequent PCR reaction. Although the PCR step can use a variety of thermostable DNA-dependent DNA polymerases, it typically employs the Taq DNA polymerase, which has a 5'-3' nuclease activity but lacks a 3'-5' proof-reading endonuclease activity. Thus, TAQMAN® PCR typically utilizes the 5'-nuclease activity of Taq or Tth polymerase to hydrolyze a hybridization probe bound to its target amplicon, but any enzyme with equivalent 5' nuclease activity can be used. Two oligonucleotide primers are used to generate an amplicon typical of a PCR reaction. A third oligonucleotide, or probe, is designed to detect nucleotide sequence located between the two PCR primers. The probe is non-extendible by Taq DNA polymerase enzyme, and is labeled with a reporter fluorescent dye and a quencher fluorescent dye. Any laser-induced emission from the reporter dye is quenched by the quenching dye when the two dyes are located close together as they are on the probe. During the amplification reaction, the Taq DNA polymerase enzyme cleaves the probe in a template-dependent manner. The resultant probe fragments disassociate in solution, and signal from the released reporter dye is free from the quenching effect of the second fluorophore. One molecule of reporter dye is liberated for each new molecule synthesized, and detection of the unquenched reporter dye provides the basis for quantitative interpretation of the data.

TAQMAN® PCR can be performed using commercially available equipment, such as, for example, ABI PRISM 7700® Sequence Detection System® (Perkin-Elmer-Applied Biosystems, Foster City, Calif., USA), or Lightcycler (Roche Molecular Biochemicals, Mannheim. Germany). In a one embodiment, the 5' nuclease procedure is run on a real-time quantitative PCR device such as the ABI PRISM 7700® Sequence Detection System. The system consists of a thermocycler, laser, charge-coupled device (CCD), camera and computer. The system amplifies samples in a 96-well format on a thermocycler. During amplification, laser-induced fluorescent signal is collected in real-time through fiber optics cables for all 96 wells, and detected at the CCD. The system includes software for running the instrument and for analyzing the data.

5'-Nuclease assay data are initially expressed as Ct, or the threshold cycle. Fluorescence values are recorded during every cycle and represent the amount of product amplified to that point in the amplification reaction. The point when the fluorescent signal is first recorded as statistically significant is the threshold cycle (Ct).

To minimize errors and the effect of sample-to sample variation. PCR is usually performed using an internal standard that is expressed at a constant level among different tissues, and is unaffected by the experimental treatment. RNAs most frequently used to normalize patterns of gene expression are mRNAs for the housekeeping genes glyceraldehyde-3-phosphate-dehydrogenase (GAPDH) and β-actin.

A more recent variation of the PCR technique is quantitative real time PCR (qRT-PCR), which measures PCR product accumulation through a dual-labeled fluorigenic probe (i.e., TAQMAN® probe). The technique of quantitative real time polymerase chain reaction refers to a form of PCR wherein the amount of PCR product is measured at each step in a PCR reaction. This technique has been described in various publications including Cronin et al., *Am. J. Pathol.* 164(1):35-42 (2004); and Ma et al., *Cancer Cell* 5:607-616 (2004). Real time PCR is compatible both with quantitative competitive PCR, where internal competitor for each target sequence is used for normalization, and with quantitative comparative PCR using a normalization gene contained within the sample, or a housekeeping gene for PCR. For further details see, e.g. Held et al., *Genome Research* 6:986-994 (1996). The technique of "reverse transcription quantitative polymerase chain reaction (rt-qPCR) is a form of PCR wherein the nucleic acid to be amplified is RNA that is first reverse transcribed into cDNA and the amount of PCR product is measured at each step in a PCR reaction.

The steps of a representative protocol for profiling gene expression using fixed, paraffin-embedded tissues as the RNA source, including mRNA isolation, purification, primer extension and amplification are given in various published journal articles (for example: Godfrey et al., *J. Malec. Diagnostics* 2: 84-91 (2000); Specht et al., *Am. J. Pathol.* 158: 419-29 (2001)). Briefly, a representative process starts with cutting about 10 microgram thick sections of paraffin-embedded tumor tissue samples. The RNA is then extracted, and protein and DNA are removed. After analysis of the RNA concentration, RNA repair and/or amplification steps may be included, if necessary, and RNA is reverse transcribed using gene specific promoters followed by PCR.

According to one aspect of the present invention, PCR primers and probes are designed based upon intron sequences present in the gene to be amplified. In this embodiment, the first step in the primer/probe design is the delineation of intron sequences within the genes. This can be done by publicly available software, such as the DNA BLAT software developed by Kent, W., *Genome Res.* 12(4):656-64 (2002), or by the BLAST software including its variations. Subsequent steps follow well established methods of PCR primer and probe design.

Accordingly, in one embodiment, the HGF biomarker may be determined using a method comprising: (a) providing a sample comprising or suspected of comprising a target nucleic acid; (b) isolating mRNA from said sample; (c) purifying mRNA from said sample; (d) performing reverse transcription of the RNA into cDNA; (e) providing at least one set of two PCR probes capable of hybridizing to the cDNA of said target nucleic acid (f) providing a third probe designed to hybridize to said target nucleic acid between the two PCR probes, wherein the third probe is non-extendable by Taq-DNA polymerase and is labeled with a reporter fluorescent dye and a quencher fluorescent dye; (g) amplifying the cDNA of said target nucleic acid using PCR; (h) quantifying the amount of said target nucleic acid in said sample by detecting the amount of unquenched reporter dye; (i) comparing the amount of said target nucleic acid in said sample to the expression level of an internal standard.

In one embodiment, the HGF biomarker may be determined using a method comprising: (a) providing a sample comprising or suspected of comprising HGF nucleic acid, wherein the sample comprises a paraffin-embedded, formalin-fixed tissue sample (e.g., a paraffin-embedded, formalin-fixed glioblastoma, mesothelioma, gastric cancer, renal cell carcinoma, hepatocellular carcinoma, or sarcoma tissue sample); (b) isolating HGF mRNA from said sample; (c) purifying HGF mRNA from said sample; (d) performing reverse transcription of the RNA into cDNA; (e) providing at least one set of two PCR probes capable of hybridizing to the cDNA of HGF (f) providing a third probe designed to hybridize to said target nucleic acid between the two PCR probes, wherein the third probe is non-extendable by Taq-DNA polymerase and is labeled with a reporter fluorescent dye and a quencher fluorescent dye; (g) amplifying the cDNA of HGF using PCR; (h) quantifying the amount of HGF nucleic acid in said sample by detecting the amount of unquenched reporter dye; (i) comparing the amount of HGF nucleic acid in said sample to the expression level of one or more internal standards (e.g., the expression level of GAPDH, β-actin, AL-1377271, and/or VPS-33B) based on the difference of the Ct value of HGF and the mean Ct value of the internal standard.

In some embodiments, a high amount of the HGF biomarker (high HGF biomarker) is high HGF mRNA (e.g., in a sample, e.g., in a tumor section of a patient's cancer, e.g., glioblastoma, mesothelioma, gastric cancer, renal cell carcinoma, hepatocellular carcinoma, or sarcoma). In some embodiments. HGF mRNA expression is determined using an amplification based assay. In some embodiments, the amplification based assay is a PCR based assay. In some embodiments, the PCR based assay is quantitative PCR, real-time PCR, quantitative real-time PCR (qRT-PCR), reverse transcriptase PCR (rt-PCR) or reverse transcription quantitative PCR (rt-qPCR). In some embodiments, HGF mRNA expression is determined using rt-qPCR. In some embodiments. HGF mRNA expression is determined using Fluidigm Gene Expression Analysis. In some embodiments, high HGF mRNA is determined based on the relative expression level compared to a standard established by measuring the HGF mRNA levels in tumor samples obtained from a reference population of patients comprising a representative number of patients comprising patients with a particular cancer (e.g., glioblastoma, mesothelioma, gastric cancer, renal cell carcinoma, hepatocellular carcinoma, or sarcoma). In some embodiments, the representative number of patients is 10 or more patients. In some embodiments, the representative number of patients is 25 or more patients. In some embodiments, the representative number of patients is 50 or more patients. In some embodiments, the representative number of patients is 100 or more patients. In some embodiments, the reference population of patients described herein comprises a representative number of glioblastoma patients (e.g., recurrent glioblastoma). In some embodiments, the reference population of patients described herein comprises a representative number of mesothelioma patients (e.g., recurrent mesothelioma). In some embodiments, the reference population of patients described herein comprises a representative number of gastric cancer patients (e.g., recurrent gastric cancer). In some embodiments, the reference population of patients described herein comprises a representative number of renal cell carcinoma patients (e.g., recurrent renal cell carcinoma). In some embodiments, the reference population of patients described herein comprises a representative number of hepatocellular carcinoma patients (e.g., recurrent hepatocellular carcinoma). In some embodiments, the reference population of patients described herein comprises a representative number of sarcoma patients (e.g., recurrent sarcoma). In some embodiments, high HGF mRNA expression level of a patient tumor sample is an HGF mRNA expression level greater than the HGF mRNA expression level of 50% of the tumor samples obtained from a reference patient population comprising patients with a particular cancer (e.g., glioblastoma, mesothelioma, gastric cancer, renal cell carcinoma, hepatocellular carcinoma, or sarcoma). In some embodiments, high HGF mRNA expression level of a patient tumor sample is an HGF mRNA expression level greater than the HGF mRNA expression level of 60% of the tumor samples obtained from a reference patient population comprising patients with a particular cancer (e.g., glioblastoma, mesothelioma, gastric cancer, renal cell carcinoma, hepatocellular carcinoma, or sarcoma). In some embodiments, high HGF mRNA expression level of a patient tumor sample is an HGF mRNA expression level greater than the HGF mRNA expression level of 65% of the rumor samples obtained from a reference patient population comprising patients with a particular cancer (e.g., glioblastoma, mesothelioma, gastric cancer, renal cell carcinoma, hepatocellular carcinoma, or sarcoma). In some embodiments, high HGF mRNA expression level of a patient tumor sample is an HGF mRNA expression level greater than the HGF mRNA expression level of 70% of the tumor samples obtained from a reference patient population comprising patients with a particular cancer (e.g., glioblastoma, mesothelioma, gastric cancer, renal cell carcinoma hepatocellular carcinoma, or sarcoma). In some embodiments, high HGF mRNA expression level of a patient tumor sample is an HGF mRNA expression level greater than the HGF mRNA expression level of 75% of the tumor samples obtained from a reference patient population comprising patients with a particular cancer (e.g., glioblastoma, mesothelioma, gastric cancer, renal cell carcinoma, hepatocellular carcinoma, or sarcoma). In some embodiments, high HGF mRNA expression level of a patient tumor sample is an HGF mRNA expression level greater than the HGF mRNA expression level of 80% of the tumor samples obtained from a reference patient population comprising patients with a particular cancer (e.g., glioblastoma, mesothelioma, gastric cancer, renal cell carcinoma hepatocellular carcinoma, or sarcoma). In some embodiments, the tumor sample comprises glioblastoma tumor cells and benign stroma cells. In some embodiments, the tumor sample comprises mesothelioma tumor cells and benign stroma cells. In some embodiments, the tumor sample comprises gastric cancer tumor cells and benign stroma cells. In some embodiments, the tumor sample comprises renal cell carcinoma tumor cells and benign stroma cells. In some embodiments, the tumor sample comprises hepatocellular carcinoma tumor cells and benign stroma cells. In some embodiments, the tumor sample comprises sarcoma tumor cells and benign stroma cells.

In some embodiments, high HGF mRNA biomarker is determined using an amplification based assay. In some embodiments, the amplification based assay is a PCR based assay. In some embodiments, the PCR based assay is quantitative PCR, real-time PCR, quantitative real-time PCR (qRT-PCR), reverse transcriptase PCR (rt-PCR) or reverse transcription quantitative PCR (rt-qPCR). In some embodiments, the PCR based assay is rt-qPCR. In some embodiments, high HGF mRNA biomarker is determined using Fluidigm Gene Expression Analysis. In some embodiments, high HGF mRNA biomarker is determined by determining the Ct of HGF mRNA compared to the Ct of mRNA from reference genes. In some embodiments, the reference genes are genes that are stably expressed at equal levels across multiple cell lines, in fresh-frozen tissue samples, and in formalin-fixed paraffin-embedded tissue samples. In some embodiments, the Ct of several reference genes is determined and the mean Ct is compared to the Ct of HGF mRNA. In some embodiments, high HGF mRNA biomarker is determined by determining the delta Ct of HGF expression, wherein delta Ct equals the mean Ct of HGF minus the mean Ct of the target genes.

In some embodiments, a low amount of the HGF biomarker (low HGF biomarker) is low HGF mRNA biomarker (e.g., in a sample, e.g., in a tumor section of a patient's cancer, e.g., glioblastoma, mesothelioma, gastric cancer, renal cell carcinoma, hepatocellular carcinoma, or sarcoma). In some embodiments, low mRNA expression is determined using an amplification based assay. In some embodiments, the amplification based assay is a PCR based assay. In some embodiments, the PCR based assay is quantitative PCR, real-time PCR, quantitative real-time PCR (qRT-PCR), reverse transcriptase PCR (rt-PCR) or reverse transcription quantitative PCR (rt-qPCR). In some embodiments, HGF mRNA expression is determined using rt-qPCR. In some embodiments, HGF mRNA expression is determined using Fluidigm Gene Expression Analysis. In some embodiments, low HGF mRNA is determined based on the relative expression level compared to a standard established by measuring the HGF mRNA levels in tumor samples obtained from a reference population of patients comprising a representative number of patients comprising patients with a particular cancer (e.g., glioblastoma, mesothelioma, gastric cancer, renal cell carcinoma, hepatocellular carcinoma, or sarcoma). In some embodiments, the representative number of patients is 10 or more patients. In some embodiments, the representative number of patients is 25 or more patients. In some embodiments, the representative number of patients is 50 or more patients. In some embodiments, the representative number of patients is 100 or more patients. In some embodiments, the reference population of patients described herein comprises a representative number of glioblastoma patients (e.g., recurrent glioblastoma). In some embodiments, the reference population of patients described herein comprises a representative number of mesothelioma patients (e.g., recurrent mesothelioma). In some embodiments, the reference population of patients described herein comprises a representative number of gastric cancer patients (e.g., recurrent gastric cancer). In some embodiments, the reference population of patients described herein comprises a representative number of renal cell carcinoma patients (e.g., recurrent renal cell carcinoma). In some embodiments, the reference population of patients described herein comprises a representative number of hepatocellular carcinoma patients (e.g., recurrent hepatocellular carcinoma). In some embodiments, the reference population of patients described herein comprises a representative number of sarcoma patients (e.g., recurrent sarcoma). In some embodiments, low HGF mRNA expression level of a patient tumor sample is an HGF mRNA expression level less than the HGF mRNA expression level of 50% of the tumor samples obtained from a reference patient population comprising patients with a particular cancer (e.g., glioblastoma, mesothelioma, gastric cancer, renal cell carcinoma, hepatocellular carcinoma, or sarcoma). In some embodiments, low HGF mRNA expression level of a patient tumor sample is an HGF mRNA expression level less than the HGF mRNA expression level of 60% of the tumor samples obtained from a reference patient population comprising patients with a particular cancer (e.g., glioblastoma, mesothelioma, gastric cancer, renal cell carcinoma, hepatocellular carcinoma, or sarcoma). In some embodiments, low HGF mRNA expression level of a patient tumor sample is an HGF mRNA expression level less than the HGF mRNA expression level of 65% of the tumor samples obtained from a reference patient population comprising patients with a particular cancer (e.g., glioblastoma, mesothelioma, gastric cancer, renal cell carcinoma, hepatocellular carcinoma, or sarcoma). In some embodiments, low HGF mRNA expression level of a patient tumor sample is an HGF mRNA expression level less than the HGF mRNA expression level of 70% of the tumor samples obtained from a reference patient population comprising patients with a particular cancer (e.g., glioblastoma, mesothelioma, gastric cancer, renal cell carcinoma, hepatocellular carcinoma, or sarcoma). In some embodiments, low HGF mRNA expression level of a patient tumor sample is an HGF mRNA expression level less than the HGF mRNA expression level of 75% of the tumor samples obtained from a reference patient population comprising patients with a particular cancer (e.g., glioblastoma, mesothelioma, gastric cancer, renal cell carcinoma, hepatocellular carcinoma, or sarcoma). In some embodiments, low HGF mRNA expression level of a patient tumor sample is an HGF mRNA expression level less than the HGF mRNA expression level of 80% of the tumor samples obtained from a reference patient population comprising patients with a particular cancer (e.g., glioblastoma, mesothelioma, gastric cancer, renal cell carcinoma, hepatocellular carcinoma, or sarcoma). In some embodiments, the tumor sample comprises glioblastoma tumor cells and benign stroma cells. In some embodiments, the tumor sample comprises mesothelioma tumor cells and benign stroma cells. In some embodiments, the tumor sample comprises gastric cancer tumor cells and benign stroma cells. In some embodiments, the tumor sample comprises renal cell carcinoma tumor cells and benign stroma cells. In some embodiments, the tumor sample comprises hepatocellular carcinoma tumor cells and benign stroma cells. In some embodiments, the tumor sample comprises sarcoma tumor cells and benign stroma cells.

In some embodiments, low HGF mRNA biomarker is determined using an amplification based assay. In some embodiments, the amplification based assay is a PCR based assay. In some embodiments, the PCR based assay is quantitative PCR, real-time PCR, quantitative real-time PCR (qRT-PCR), reverse transcriptase PCR (rt-PCR) or reverse transcription quantitative PCR (rt-qPCR). In some embodiments, the PCR based assay is rt-qPCR. In some embodiments, low HGF mRNA biomarker is determined using Fluidigm Gene Expression Analysis. In some embodiments, low HGF mRNA biomarker is determined by determining the Ct of HGF mRNA compared to the Ct of mRNA from reference genes. In some embodiments, the reference genes are genes that are stably expressed at equal levels across multiple cell lines, in fresh-frozen tissue samples, and/or in formalin-fixed paraffin-embedded tissue samples. In some embodiments, the Ct of several reference genes is determined and the mean Ct is compared to the Ct of HGF mRNA. In some embodiments, low HGF mRNA biomarker is determined by determining the delta Ct of HGF expression, wherein delta Ct equals the mean Ct of HGF minus the mean Ct of the target genes.

ISH refers to a type of hybridization that uses a complementary DNA or RNA strand (i.e., probe) to localize a specific DNA or RNA sequence in a portion or section of tissue (in situ). The primer and probe types include but are not limited to double stranded DNA (dsDNA), single stranded DNA (ssDNA), single stranded complimentary RNA (sscRNA), messenger RNA (mRNA), micro RNA (miRNA), and synthetic oligonucleotides. In some embodiment, the probe is labeled, e.g., with a fluorescent label (e.g., FISH, or fluorescent in situ hybridization). In some embodiment, the probe is labeled, e.g., with a chromogenic label (e.g., CISH, or chromogenic in situ hybridization). In some embodiments, ISH is performed (e.g., using a DNA primer, then ISH signal is amplified using hybridization-based signal amplification, e.g., using amplification probes and label probes. Examples of hybridization-based signal amplification include use of branched DNA molecules to amplify ISH signal. Exemplary platforms utilizing hybridization-based signal amplification include: QuantiGene (Affymetrix); RNAScope® (Advanced Cell Technology). ISH may be performed in singleplex (single target) or multiplex (multiple targets). For example, for the QuantiGene assay, probe sets are used to hybridize to target mRNA. A typical probe set uses up to 20 or more oligonucleotide probe pairs. Following hybridization of the probe sets, preamplifier, amplifier and label probes are added to generate signal for visualization. The preamplifier probe binds to the target specific probe, then the amplifier probes hind to the preamplifier probes, followed by binding of label probes to the amplifier probes. For example, for the RNAscope® assay technology (Advanced Cell Technology), two or more capture probes hybridize contiguously onto a target mRNA. The capture probes may contain, e.g., an 18-25 base region complementary to the target RNA, a spacer sequence, and a 15-base tail. A pair of target probes are used, each possessing a different type of tail sequence, and hybridizing contiguously to a target region (for about 50 bp). The two "tail" sequences on the probes form a 28-base hybridization site for the preamplifier probe, which contains many (e.g., 20) binding sites for the amplifier probe, which, in turn contains many (e.g., 20) binding sites for the label probes. The preamplifier, amplifier and label probes are hybridized sequentially to each capture probe pair, resulting in the accumulation of as many as 8,000 label molecules per 1 kb of target RNA. The label probe can be conjugated to either a fluorophore or a chromogenic enzyme (e.g., horse radish peroxidase or alkaline phosphatase), enabling viewing of hybridization signals under a standard bright-field or epifluorescent microscope, respectively. Accordingly, in one embodiment, the HGF biomarker may be determined using methods comprising: (a) providing a sample comprising or suspected of comprising said target nucleic acid; (b) providing at least one set of two or more capture probes capable of hybridizing to said target nucleic acid; (c) providing: (i) an amplifier capable of hybridizing to a label probe; (ii) a preamplifier capable of hybridizing to the amplifier and capable of hybridizing to said set of two or more capture probes; (iii) a label probe; (d) hybridizing said set of two or more capture probes to said target nucleic acid; (e) capturing the preamplifier, amplifier and label probe to said set of two or more capture probes, thereby capturing the label probe to said target nucleic acid; and (f) detecting the presence, absence, or amount of the label associated with the captured label probe.

In some embodiments, high amount of the HGF biomarker (high HGF biomarker) is high HGF mRNA biomarker (e.g., in a sample, e.g., in a tumor section of a patient's cancer, e.g., glioblastoma, mesothelioma, gastric cancer, renal cell carcinoma, hepatocellular carcinoma, or sarcoma). In some embodiments, HGF mRNA expression is determined using ISH. In some embodiments, high HGF mRNA biomarker is 1% or more HGF ISH signal positive cells in the sample. In some embodiments, high HGF mRNA biomarker is 2% or more of HGF ISH signal positive cells in the sample. In some embodiments, a high HGF mRNA biomarker is 3% or more HGF ISH signal positive cells in the sample. In some embodiments, high HGF mRNA biomarker is 4% or more HGF ISH signal positive cells in the sample. In some embodiments, high HGF mRNA biomarker is 5% or more HGF ISH signal positive cells in the sample. In some embodiments, high HGF mRNA biomarker is 6% or more HGF ISH signal positive cells in the sample. In some embodiments, high HGF mRNA biomarker is 7% or more HGF ISH signal positive cells in the sample. In some embodiments, high HGF mRNA biomarker is 8% or more HGF ISH signal positive cells in the sample. In some embodiments, high HGF mRNA biomarker is 9% or more HGF ISH signal positive cells in the sample. In some embodiments, high HGF mRNA biomarker is 10% or more HGF ISH signal positive cells in the sample. In some embodiments, high HGF mRNA biomarker is 12% or more HGF ISH signal positive cells in the sample. In some embodiments, high HGF mRNA biomarker is 15% or more HGF ISH signal positive cells. In some embodiments, high HGF mRNA biomarker is 20% or more HGF ISH signal positive cells. In some embodiments, high HGF mRNA biomarker is 25% or more HGF ISH signal positive cells in the sample. In some embodiments, high HGF mRNA biomarker is 30% or more HGF ISH signal positive cells in the sample. In some embodiments, high HGF mRNA biomarker is 35% or more HGF ISH signal positive cells in the sample. In some embodiments, high HGF mRNA biomarker is 40% or more HGF ISH signal positive cells in the sample. In some embodiments, high HGF mRNA biomarker is 50% or more HGF ISH signal positive cells in the sample. In some embodiments, high HGF mRNA biomarker is 55% or more HGF ISH signal positive cells in the sample. In some embodiments, high HGF mRNA biomarker is 60% or more HGF ISH signal positive cells in the sample. In some embodiments, high HGF mRNA biomarker is 65% or more HGF ISH signal positive cells in the sample. In some embodiments, high HGF mRNA biomarker is 70% or more HGF ISH signal positive cells in the sample. In some embodiments, high HGF mRNA biomarker is 75% or more HGF ISH signal positive cells in the sample. In some embodiments, the cells are glioblastoma tumor cells and benign stroma cells. In some embodiments, the cells are mesothelioma tumor cells and benign stroma cells. In some embodiments, the cells are gastric cancer tumor cells and benign stroma cells. In some embodiments, the cells are renal cell carcinoma tumor cells and benign stroma cells. In some embodiments, the cells are hepatocellular carcinoma tumor cells and benign stroma cells. In some embodiments, the cells are sarcoma tumor cells and benign stroma cells.

In some embodiments, high HGF mRNA biomarker is presence (e.g., in a sample, e.g., in a tumor section of a patient's cancer, e.g., glioblastoma, mesothelioma, gastric cancer, renal cell carcinoma, hepatocellular carcinoma, or sarcoma) of about 10 or more HGF ISH signal positive cells. In some embodiments, high HGF mRNA biomarker is presence of about 11 or more ISH signal positive cells. In some embodiments, high HGF mRNA biomarker is presence of about 12 or more HGF ISH signal positive cells. In some embodiments, high HGF mRNA biomarker is presence of about 13 or more HGF ISH signal positive cells. In some embodiments, high HGF mRNA biomarker is presence of about 14 or more HGF ISH signal positive cells. In some embodiments, high HGF mRNA biomarker is presence of about 15 or more HGF ISH signal positive cells. In some embodiments, high HGF mRNA biomarker is presence of about 16 or more HGF ISH signal positive cells. In some embodiments, high HGF mRNA biomarker is presence of about 20 or more HGF ISH signal positive cells. In some embodiments, high HGF mRNA biomarker is presence of about 25 or more HGF ISH signal positive cells. In some embodiments, high HGF mRNA biomarker is presence of about 30 or more HGF ISH signal positive cells. In some embodiments, high HGF mRNA biomarker is presence of about 35 or more HGF ISH signal positive cells. In some embodiments, high HGF mRNA biomarker is presence of about 40 or more HGF ISH signal positive cells. In some embodiments, high HGF mRNA biomarker is presence of about 45 or more HGF ISH signal positive cells. In some embodiments, high HGF mRNA biomarker is presence of about 50 or more of HGF ISH signal positive cells. In some embodiments, high HGF mRNA biomarker is presence of about 55 or more HGF ISH signal positive cells. In some embodiments, high HGF mRNA biomarker is presence of about 60 or more HGF ISH signal positive cells. In some embodiments, high HGF mRNA biomarker is presence of about 70 or more HGF ISH signal positive cells. In some embodiments, high HGF mRNA biomarker is presence of about 75 or more HGF ISH signal positive cells. In some embodiments, high HGF mRNA biomarker is presence of about 80 or more HGF ISH signal positive cells. In some embodiments, the cells are glioblastoma tumor cells and benign stroma cells. In some embodiments, the cells are mesothelioma tumor cells and benign stroma cells. In some embodiments, the cells are gastric cancer tumor cells and benign stroma cells. In some embodiments, the cells are renal cell carcinoma tumor cells and benign stroma cells. In some embodiments, the cells are hepatocellular carcinoma tumor cells and benign stroma cells. In some embodiments, the cells are sarcoma tumor cells and benign stroma cells.

In some embodiments, high HGF mRNA biomarker is an ISH score of greater than 2+. In some embodiments, high HGF mRNA biomarker is an ISH score of greater than 3+. In some embodiments, high HGF mRNA biomarker is an ISH score of 2+ or 3+. In some embodiments, high HGF mRNA biomarker is an ISH score of greater than 1+.

In some embodiments, high HGF mRNA biomarker is presence of HGF ISH positive signal in numerous cells (e.g., as observed using a light microscope equipped with a low power objective). In some embodiments, high HGF mRNA biomarker is presence of HGF ISH positive signal in frequent cells (e.g., as observed using a light microscope using a moderate or high power objective).

In some embodiments, high HGF mRNA biomarker is presence of HGF ISH positive signal that is easily observed viewing the sample with a light microscope equipped with a low power objective (e.g., 10× objective). In some embodiments, high HGF mRNA biomarker is presence of HGF ISH positive signal that is observed viewing the sample with a light microscope equipped with a moderate power objective (e.g., 20× objective) or a high power objective (e.g., 40× objective).

In some embodiments, high HGF mRNA biomarker is presence of more than 2 foci comprising HGF ISH signal positive cells (e.g., in a sample, e.g., in a tumor section of a patient's cancer, e.g., glioblastoma, mesothelioma, gastric cancer, renal cell carcinoma, hepatocellular carcinoma, or sarcoma). As used herein, "foci" (or a "focus") refers to one or more HGF ISH signal positive cell(s) surrounded by HGF mRNA ISH signal negative cells. In some embodiments, high HGF mRNA biomarker is presence or more than 3 foci comprising HGF ISH signal positive cells. In some embodiments, high HGF mRNA biomarker is presence of more than 4 foci comprising HGF ISH signal positive cells. In some embodiments, high HGF mRNA biomarker is presence of more than 5 foci comprising HGF ISH signal positive cells. In some embodiments, high HGF mRNA biomarker is presence of more than 6 foci comprising HGF ISH signal positive cells. In some embodiments, high HGF mRNA biomarker is presence of more than 7 foci comprising HGF ISH signal positive cells. In some embodiments, high HGF mRNA biomarker is presence of more than 8 foci comprising HGF ISH signal positive cells. In some embodiments, high HGF mRNA biomarker is presence of more than 9 foci comprising HGF ISH signal positive cells. In some embodiments, high HGF mRNA biomarker is presence of more than 10 foci comprising HGF ISH signal positive cells. In some embodiments, high HGF mRNA biomarker is presence of more than 11 foci comprising HGF ISH signal positive cells. In some embodiments, high HGF mRNA biomarker is presence of more than 12 foci comprising HGF ISH signal positive cells. In some embodiments, high HGF mRNA biomarker is presence of more than 13 foci comprising HGF ISH signal positive cells. In some embodiments, high HGF mRNA biomarker is presence of more than 14 foci comprising HGF ISH signal positive cells. In some embodiments, high HGF mRNA biomarker is presence of more than 15 foci comprising HGF ISH signal positive cells. In some embodiments, high HGF mRNA biomarker is presence of more than 16 foci comprising HGF ISH signal positive cells. In some embodiments, high HGF mRNA biomarker is presence of more than 17 foci comprising HGF ISH signal positive cells. In some embodiments, high HGF mRNA biomarker is presence of more than 18 foci comprising HGF ISH signal positive cells. In some embodiments, high HGF mRNA biomarker is presence of more than 19 foci comprising HGF ISH signal positive cells (or more, such as more than 20, 25, 30, 35, 40, 45, 50 or more foci comprising HGF ISH signal positive cells). In some embodiments, the cells are glioblastoma tumor cells and benign stroma cells. In some embodiments, the cells are mesothelioma tumor cells and benign stroma cells. In some embodiments, the cells are gastric cancer tumor cells and benign stroma cells. In some embodiments, the cells are renal cell carcinoma tumor cells and benign stroma cells. In some embodiments, the cells are hepatocellular carcinoma tumor cells and benign stroma cells. In some embodiments, the cells are sarcoma tumor cells and benign stroma cells.

In some embodiments, foci are visible when a slide is viewed using a light microscope with low magnification (e.g., roughly equivalent to a 10× objective). In some embodiments, foci are visible when a slide is viewed using a light microscope with moderate magnification (e.g., roughly equivalent to a 20× objective). In some embodiments, foci are visible when a slide is viewed using a light microscope with high magnification (e.g., roughly equivalent to a 40× objective).

In some embodiments, low HGF mRNA biomarker is an ISH score of less than 2+. In some embodiments, low HGF mRNA biomarker is an ISH score of less than 1+. In some embodiments, low HGF mRNA biomarker is an ISH score of 0 or 1+. In some embodiments, low HGF mRNA biomarker is an ISH score of 0.

In some embodiments, low HG mRNA biomarker is presence of HGF ISH positive signal in few cells, e.g., ten or fewer, such as 9, 8, 7, 6, or fewer (e.g., as observed using a light microscope equipped with a moderate or high power objective), e.g., in a section of a patient's cancer (e.g., glioblastoma, mesothelioma, gastric cancer, renal cell carcinoma, hepatocellular carcinoma, or sarcoma). In some embodiments, low HGF mRNA biomarker is presence of HGF ISH positive signal in no cells (e.g., as observed using a light microscope equipped with a moderate or high power objective).

In some embodiments, HGF mRNA ISH positive signal is compared with a positive control, e.g., HGF ISH performed on KP4 pancreatic tumor cells (Riken BioResource Center, order no. RCB1005) which are known to express and secrete HGF. In some embodiments. HGF mRNA ISH positive signal is compared with a negative control, e.g., KP4 cells probed with DapB ISH probe.

In some embodiments, IHC (discussed further below) and ISH assay formats comprise a series of treatment steps conducted on a tissue section mounted on a suitable solid support for microscopic inspection, e.g., a glass slide or other planar support, to highlight by selective staining certain morphological indicators of disease states or detection of biological markers.

In some embodiments, before performing detection of a target in the ISH or IHC (further discussed below) assay format, a pre-detection procedure is to be performed. It may involve, e.g., the steps of: cutting and trimming tissue, fixation, dehydration, paraffin infiltration, cutting in thin sections, mounting onto glass slides, baking, deparaffination, rehydration, antigen retrieval, blocking steps, applying primary antibody, washing, applying secondary antibody-enzyme conjugate and washing.

Many methods of fixing and embedding tissue specimens are known, for example, alcohol fixation and formalin-fixation and subsequent paraffin embedding (FFPE). Methods of fixing and embedding tissue specimens are further discussed below regarding IHC.

In some embodiments, target antigens are retrieved or unmasked, through pre-treatment of the specimens to increase reactivity of the majority of targets. An extensive review of antigen retrieval (antigen unmasking) may be found in Shi et al. 1997, J Histochem Cytochem, 45(3):327. Antigen retrieval includes a variety of methods by which the availability of the target for interaction with a specific detection reagent is maximized. The most common techniques are enzymatic digestion with a proteolytic enzyme (for example proteinase, pronase, pepsin, papain, trypsin or neuraminidase) in an appropriate buffer or heat induced epitope retrieval (HIER) using microwave irradiation, heating in a water bath, a steamer, a regular oven, an autoclave or a pressure cooker in an appropriately pH stabilized buffer, usually containing EDTA, EGTA, Tris-HCl, citrate, urea, glycin-HCl or boric acid. The antigen retrieval buffer may be aqueous, but may also contain other solvents, including solvents with a boiling point above that of water. Additionally, in some embodiments, the signal-to-noise ratio may be increased by different physical methods, including application of vacuum and ultrasound, or freezing and thawing of the sections before or during incubation of the reagents. Endogenous biotin binding sites or endogenous enzyme activity (for example phosphatase, catalase or peroxidase) may be removed as a step in the detection procedure, e.g., endogenous biotin and peroxidase activity may be removed by treatment with peroxides. Endogenous phosphatase activity may be removed by treatment with levamisole. Endogenous phosphatases and esterases may be destroyed by heating. Blocking of non-specific binding sites with inert proteins like, horse serum albumin (HSA), casein, bovine serum albumin (BSA), and ovalbumin, fetal calf serum or other sera, or detergents like Tween20, Triton X-100. Saponin, Brij or Pluronics may be used. Blocking non-specific binding sites in the tissue or cells with unlabeled and target non-specific versions of the specific reagents may also be used.

In some embodiments, hybridization is performed at temperatures that are about 15 to about 25° C. below melting point $T_m$ for the probe. The hybridization is performed by using a hybridization buffer that contains components (e.g., organic solvents, ionic solutions) in addition to the probe. Post-hybridization wash may be performed in order to remove unbound probe and probe that is only partly bound. Washing may be performed, e.g., at a temperature that is about 10 to about 15 degrees Celsius below the $T_m$ and/or by using solutions with decreasing salt concentrations.

In some embodiments, the tissue section may be mounted on slides following the critical incubation with the immuno-specific reagents following the procedure (a) of the method. The rest of the process of detection is then conducted on the slide mounted tissue sections. In some embodiments, samples may also be prepared and target molecules detected using the free floating technique. In this method a tissue section is brought into contact with different reagents and wash buffers in suspension or freely floating in appropriate containers, for example micro centrifuge tubes.

RNA-Seq, also called Whole Transcriptome Shotgun Sequencing (WTSS) refers to the use of high-throughput sequencing technologies to sequence cDNA in order to get information about a sample's RNA content. Publications describing RNA-Seq include: Wang et al. "RNA-Seq: a revolutionary tool for transcriptomics" *Nature Reviews Genetics* 10 (1): 57-63 (January 2009); Ryan et al. *BioTechniques* 45 (1): 81-94 (2008); and Maher et al. "Transcriptome sequencing to detect gene fusions in cancer". *Nature* 458 (7234): 97-101 (January 2009).

Differential gene expression can also be identified, or confirmed using the microarray technique. Thus, the expression profile of glioblastoma-associated genes, mesothelioma-associated genes, gastric cancer-associated genes, renal cell carcinoma-associated genes, hepatocellular carcinoma-associated genes, or sarcoma-associated genes can be measured in either fresh or paraffin-embedded tumor tissue, using microarray technology. In this method, polynucleotide sequences of interest (including cDNAs and oligonucleotides) are plated, or arrayed, on a microchip substrate. The arrayed sequences are then hybridized with specific DNA probes from cells or tissues of interest. Just as in the PCR method, the source of mRNA typically is total RNA isolated from human tumors or tumor cell lines, and corresponding normal tissues or cell lines. Thus RNA can be isolated from a variety of primary tumors or tumor cell lines. If the source of mRNA is a primary tumor, mRNA can be extracted, for example, from frozen or archived paraffin-embedded and fixed (e.g. formalin-fixed) tissue samples, which are routinely prepared and preserved in everyday clinical practice.

In a specific embodiment of the microarray technique. PCR amplified inserts of cDNA clones are applied to a substrate in a dense array. Preferably at least 10.000 nucleotide sequences are applied to the substrate. The microarrayed genes, immobilized on the microchip at 10,000 elements each, are suitable for hybridization under stringent conditions. Fluorescently labeled cDNA probes may be generated through incorporation of fluorescent nucleotides by reverse transcription of RNA extracted from tissues of interest. Labeled cDNA probes applied to the chip hybridize with specificity to each spot of DNA on the array. After stringent washing to remove non-specifically bound probes, the chip is scanned by confocal laser microscopy or by another detection method, such as a CCD camera. Quantitation of hybridization of each arrayed element allows for assessment of corresponding mRNA abundance. With dual color fluorescence, separately labeled cDNA probes generated front two sources of RNA are hybridized pairwise to the array. The relative abundance of the transcripts from the two sources corresponding to each specified gene is thus determined simultaneously. The miniaturized scale of the hybridization affords a convenient and rapid evaluation of the expression pattern for large numbers of genes. Such methods have been shown to have the sensitivity required to detect rare transcripts, which are expressed at a few copies per cell, and to reproducibly detect at least approximately two-fold differences in the expression levels (Schena et al., *Proc. Natl. Acad. Sci. USA* 93(2):106-149 (1996)). Microarray analysis can be performed by commercially available equipment, following manufacturer's protocols, such as by using the Affymetrix GENCHIP™ technology, or Incyte's microarray technology.

The development of microarray methods for large-scale analysis of gene expression makes it possible to search systematically for molecular markers of cancer classification and outcome prediction in a variety of tumor types.

Serial analysis of gene expression (SAGE) is a method that allows the simultaneous and quantitative analysis of a large number of gene transcripts, without the need of providing an individual hybridization probe for each transcript. First, a short sequence tag (about 10-14 bp) is generated that contains sufficient information to uniquely identify a transcript, provided that the tag is obtained from a unique position within each transcript. Then, many transcripts are linked together to form long serial molecules, that can be sequenced, revealing the identity of the multiple tags simultaneously. The expression pattern of any population of transcripts can be quantitatively evaluated by determining the abundance of individual tags, and identifying the gene corresponding to each tag. For more details see, e.g. Velculescu et al., *Science* 270:484-487 (1995); and Velculescu et al., *Cell* 88:243-51 (1997).

The MASSARAY® (Sequenom, San Diego, Calif.) technology is an automated, high-throughput method of gene expression analysis using mass spectrometry (MS) for detection. According to this method, following the isolation of RNA, reverse transcription and PCR amplification, the cDNAs are subjected to primer extension. The cDNA-derived primer extension products are purified, and dispensed on a chip array that is pre-loaded with the components needed for MALTI-TOF MS sample preparation. The various cDNAs present in the reaction are quantitated by analyzing the peak areas in the mass spectrum obtained.

In general, methods of gene expression profiling can be divided into two large groups: methods based on hybridization analysis of polynucleotides, and methods based on sequencing of polynucleotides. The most commonly used methods known in the art for the quantification of mRNA expression in a sample include northern blotting and in situ hybridization (Parker & Barnes, *Methods in Molecular Biology* 106:247-283 (1999)); RNAse protection assays (Hod. Biotechniques 13:852-854 (1992)); and polymerase chain reaction (PCR) (Weis et al., *Trends in Genetics* 8:263-264 (1992)). Alternatively, antibodies may be employed that can recognize specific duplexes, including DNA duplexes, RNA duplexes, and DNA-RNA hybrid duplexes or DNA-protein duplexes. Representative methods for sequencing-based gene expression analysis include Serial Analysis of Gene Expression (SAGE), and gene expression analysis by massively parallel signature sequencing (MPSS).

HGF protein may be assayed from a patient sample (e.g., plasma, serum, urine, cerebrospinal, sputum, feces, breath condensate, tumor, other tissue. Methods for assaying HGF protein are known in the art and include ELISA, mass spectrometry, surface plasmon resonance, western blot. IHC, and other well-known methods. See, e.g., Mai et al. Molec Cancer Ther (2013)13(2):540-52. Kits for detecting HGF are available commercially.

Immunohistochemical (IHC) staining of tissue sections has been shown to be a reliable method of assessing or detecting presence of proteins in a sample. Immunohistochemistry techniques utilize an antibody to probe and visualize cellular antigens in situ, generally by chromogenic or fluorescent methods. Thus, antibodies or antisera, in some embodiments, polyclonal antisera, and in some embodiments, monoclonal antibodies specific for each marker are used to detect expression. As discussed in greater detail below, the antibodies can be detected by direct labeling of the antibodies themselves, for example, with radioactive labels, fluorescent labels, hapten labels such as, biotin, or an enzyme such as horse radish peroxidase or alkaline phosphatase. Alternatively, unlabeled primary antibody is used in conjunction with a labeled secondary antibody, comprising antisera, polyclonal antisera or a monoclonal antibody specific for the primary antibody. Immunohistochemistry protocols and kits are well known in the art and are commercially available.

In some embodiments, the IHC assay is a direct assay, wherein binding of antibody to the target antigen is determined directly. This direct assay uses a labeled reagent, such as a fluorescent tag or an enzyme-labeled primary antibody, which can be visualized without further antibody interaction. In some embodiments, the IHC assay is an indirect assay. In a typical indirect assay, unconjugated primary antibody binds to the antigen and then a labeled secondary antibody binds to the primary antibody. Where the secondary antibody is conjugated to an enzymatic label, a chromagenic or fluorogenic substrate is added to provide visualization of the antigen. Signal amplification occurs because several secondary antibodies may react with different epitopes on the primary antibody.

The primary and/or secondary antibody used for immunohistochemistry typically will be labeled with a detectable moiety. Numerous labels are available which can be generally grouped into the following categories:

(a) Radioisotopes, such as $^{35}S$, $^{14}C$, $^{125}I$, $^{3}H$, and $^{131}I$. The antibody can be labeled with the radioisotope using the techniques described in Current Protocols in Immunology, Volumes 1 and 2, Coligen et al., Ed. Wiley-Interscience, New York, N.Y., Pubs. (1991) for example and radioactivity can be measured using scintillation counting.

(b) Colloidal gold particles.

(c) Fluorescent labels including, but are not limited to, rare earth chelates (europium chelates), Texas Red, rhodamine, fluorescein, dansyl, Lissamine, umbelliferone, phycoerytherin, phycocyanin, or commercially available fluorophores such SPECTRUM ORANGE® and SPECTRUM GREEN® and/or derivatives of any one or more of the above. The fluorescent labels can be conjugated to the antibody using the techniques disclosed in Current Protocols in Immunology, supra, for example. Fluorescence can be quantified using a fluorimeter.

(d) Various enzyme-substrate labels are available and U.S. Pat. No. 4,275,149 provides a review of some of these. The enzyme generally catalyzes a chemical alteration of the chromogenic substrate that can be measured using various techniques. For example, the enzyme may catalyze a color change in a substrate, which can be measured spectrophotometrically. Alternatively, the enzyme may alter the fluorescence or chemiluminescence of the substrate. Techniques for quantifying a change in fluorescence are described above. The chemiluminescent substrate becomes electronically excited by a chemical reaction and may then emit light which can be measured (using a chemiluminometer, for example) or donates energy to a fluorescent acceptor. Examples of enzymatic labels include luciferases (e.g., firefly luciferase and bacterial luciferase; U.S. Pat. No. 4,737,456), luciferin, 2,3-dihydrophthalazinediones, malate dehydrogenase, urease, peroxidase such as horseradish peroxidase (HRPO), alkaline phosphatase, β-galactosidase, glucoamylase, lysozyme, saccharide oxidases (e.g., glucose oxidase, galactose oxidase, and glucose-6-phosphate dehydrogenase), heterocyclic oxidases (such as uricase and xanthine oxidase), lactoperoxidase, microperoxidase, and the like. Techniques for conjugating enzymes to antibodies are described in O'Sullivan et al. Methods for the Preparation of Enzyme-Antibody Conjugates for use in Enzyme Immunoassay, in Methods in Enzym. (ed J. Langone & H. Van Vunakis), Academic press, New York, 73:147-166 (1981).

Examples of enzyme-substrate combinations include, for example:

(i) Horseradish peroxidase (HRPO) with hydrogen peroxidase as a substrate, wherein the hydrogen peroxidase oxidizes a dye precursor [e.g., orthophenylene diamine (OPD) or 3,3',5,5'-tetramethyl benzidine hydrochloride (TMB)], 3,3-Diaminobenzidine (DAB) may also be used to visualize the HRP-labeled antibody;

(ii) alkaline phosphatase (AP) with para-Nitrophenyl phosphate as chromogenic substrate; and (iii) β-D-galactosidase (β-D-Gal) with a chromogenic substrate (e.g., p-nitrophenyl-β-D-galactosidase) or fluorogenic substrate (e.g., 4-methylumbelliferyl-β-D-galactosidase).

Numerous other enzyme-substrate combinations are available to those skilled in the art. For a general review of these, see U.S. Pat. Nos. 4,275,149 and 4,318,980.

Sometimes, the label is indirectly conjugated with the antibody. The skilled artisan will be aware of various techniques for achieving this. For example, the antibody can be conjugated with biotin and any of the four broad categories of labels mentioned above can be conjugated with avidin, or vice versa. Biotin binds selectively to avidin and thus, the label can be conjugated with the antibody in this indirect manner. Alternatively, to achieve indirect conjugation of the label with the antibody, the antibody is conjugated with a small hapten and one of the different types of labels mentioned above is conjugated with an anti-hapten antibody. Thus, indirect conjugation of the label with the antibody can be achieved.

Aside from the sample preparation procedures discussed above, further treatment of the tissue section prior to, during or following IHC may be desired. For example, epitope retrieval methods, such as heating the tissue sample in citrate buffer may be carried out [see, e.g., Leong et al. Appl. Immunohistochem. 4(3):201 (1996)].

Following an optional blocking step, the tissue section is exposed to primary antibody for a sufficient period of time and under suitable conditions such that the primary antibody binds to the target protein antigen in the tissue sample. Appropriate conditions for achieving this can be determined by routine experimentation.

The extent of binding of antibody to the sample is determined by using any one of the detectable labels discussed above. Preferably, the label is an enzymatic label (e.g. HRPO) which catalyzes a chemical alteration of the chromogenic substrate such as 3,3'-diaminobenzidine chromogen. Preferably the enzymatic label is conjugated to antibody which binds specifically to the primary antibody (e.g. the primary antibody is rabbit polyclonal antibody and secondary antibody is goat anti-rabbit antibody).

Specimens thus prepared may be mounted and coverslipped. Slide evaluation is then determined, e.g. using a microscope.

IHC may be combined with morphological staining, either prior to or thereafter. After deparaffinization, the sections mounted on slides may be stained with a morphological stain for evaluation. The morphological stain to be used provides for accurate morphological evaluation of a tissue section. The section may be stained with one or more dyes each of which distinctly stains different cellular components. In one embodiment, hematoxylin is use for staining cellular nucleic of the slides. Hematoxylin is widely available. An example of a suitable hematoxylin is hematoxylin II (Ventana). When lighter blue nuclei are desired, a bluing reagent may be used following hematoxylin staining. One of skill in the art will appreciate that staining may be optimized for a given tissue by increasing or decreasing the length of time the slides remain in the dye.

Automated systems for slide preparation and IHC processing are available commercially. The VENTANA® BenchMark XT system is an example of such an automated system. The Dako Autostainer Plus, and the Leica Bond III are also examples of such an automated system.

After staining, the tissue section may be analyzed by standard techniques of microscopy. Generally, a pathologist or the like assesses the tissue for the presence of abnormal or normal cells or a specific cell type and provides the loci of the cell types of interest. Thus, for example, a pathologist or the like would review the slides and identify normal cells (such as normal lung cells) and abnormal cells (such as abnormal or neoplastic lung cells). Any means of defining the loci of the cells of interest may be used (e.g., coordinates on an X-Y axis).

In some embodiments, IHC is performed using an anti-HGF antibody.

In some embodiments, c-met biomarker is examined, e.g., using IHC. Anti-c-met antibodies suitable for use in IHC are well known in the art, and include SP-44 (Ventana), DL-21 (Upstate), D1C2 (Cell Signaling Technologies), ab27492 (Abcam), PA1-37483 (Pierce Antibodies), Met4 (a monoclonal antibody produced by hybridoma cell line Accession Number PTA-7680 deposited in the American Type Culture Collection; see, e.g., U.S. Pat. No. 6,548,640). In some embodiments, the anti-c-met antibody is SP44. In some embodiments, the anti-c-met antibody is DL-21. In some embodiments, the anti-c-met antibody is D1C2. In some embodiments, the anti-c-met antibody is Met4. One of ordinary skill understands that additional suitable anti-c-met antibodies may be identified and characterized by comparing with c-met antibodies using the IHC protocol and examples disclosed herein, for example.

Control cell lines (e.g., centrifuged into a pellet and formalin fixed and paraffin embedded, e.g., and prepared as a tissue microarray, and e.g., stained with SP44) with various staining intensities (e.g., when stained with c-met antibody SP44) may be utilized as controls for IHC analysis. For example, H441 (strong c-met staining intensity); EBC1 (strong c-met staining intensity), A549 (moderate c-met staining intensity); SKMES1 (moderate c-met staining intensity) H1703 (weak c-met staining intensity). HEK-293 (weak c-met staining intensity); H460 (weak c-met staining intensity), and TOV-1121) (negative c-met staining intensity), LXFL529 (negative c-met staining intensity), H522 (negative c-met staining intensity), H23 (negative c-met staining intensity) or H1155 (negative c-met staining intensity). One of ordinary skill understands that other control cell pellets with negative, weak, moderate and high c-met staining intensity may readily be identified using the teachings of the present application and methods well known in the art and disclosed herein. Accordingly, in some embodiments, strong c-met staining intensity is c-met staining intensity of a control cell having c-met staining intensity of H441 and/or EBC1. In some embodiments, moderate c-met staining intensity is c-met staining intensity of a control cell having c-met staining intensity of A549 and/or SKMES1. In some embodiments, weak c-met staining intensity is c-met staining intensity of a control cell having c-met staining intensity of HEK-293 and/or H460. In some embodiments, negative c-met staining intensity is c-met staining intensity of a control cell having c-met staining intensity of LXFL529, H522, H23, and/or H1155. Use of control cell pellets with different staining intensity for IHC analysis, e.g., while scoring and analyzing c-met IHC of cancer samples, is well known in the art. A c-met immunohistochemistry protocol and scoring scheme is exemplified herein. In some embodiments, c-met IHC is analyzed using the following scheme:

TABLE X

| Diagnostic | Clinical Score | Scoring Criteria |
|---|---|---|
| Positive | 3+ | ≥50% tumor cells with membrane and/or cytoplasmic staining with strong intensity |
|  | 2+ | ≥50% tumor cells with membrane and/or cytoplasmic staining with moderate or higher intensity but <50% tumor cells with strong intensity |
| Negative | 1+ | ≥50% tumor cells with membrane and/or cytoplasmic staining with weak or higher intensity but <50% tumor cells with moderate or higher intensity |
|  | 0 | Samples with no staining, or with <50% tumor cells with membrane and/or cytoplasmic staining (could be combination of any staining intensities) |

In some embodiments, c-Met IHC is analyzed using the following scheme:

TABLE B

| Diagnostic | Clinical Score | Scoring Criteria |
|---|---|---|
| Positive | 3+ | ≥50% tumor cells with membrane and/or cytoplasmic staining with strong intensity |
|  | 2+ | ≥50% tumor cells with membrane and/or cytoplasmic staining with moderate or higher intensity but <50% tumor cells with strong intensity |
|  | 1+ | ≥50% tumor cells with membrane and/or cytoplasmic staining with weak or higher intensity but <50% tumor cells with moderate or higher intensity |
| Negative | 0 | Samples with no staining, or with <50% tumor cells with membrane and/or cytoplasmic staining (could be combination of any staining intensities) |

In some embodiments, c-met IHC is analyzed according to Table X or Table B, and the cancer is glioblastoma, mesothelioma, hepatocellular carcinoma, renal cell carcinoma, gastric cancer, sarcoma (e.g., osteosarcoma), non-small cell lung cancer, small cell lung cancer, breast cancer, gall bladder cancer, or pancreatic cancer. In some embodiments, c-met is analyzed according to Table B, and the cancer is glioblastoma. In some embodiments, c-met is analyzed according to Table B, and the cancer is mesothelioma. In some embodiments, c-met is analyzed according to Table B, and the cancer is gastric cancer. In some embodiments, c-met is analyzed according to Table B, and the cancer is renal cell carcinoma. In some embodiments, c-met is analyzed according to Table B, and the cancer is hepatocellular carcinoma. In some embodiments, c-met is analyzed according to Table B, and the cancer is sarcoma.

In some embodiments, a patient's tumor is c-met positive when 1% or more of the tumor cells in the sample express c-met protein (e.g., express c-met protein at any intensity). In some embodiments, a patient's tumor is c-met positive when more than 1% of the tumor cells in the sample express c-met protein (e.g., express c-met protein at any intensity). In some embodiments, a patient's tumor is c-met positive when 5% or more of the tumor cells in the sample express c-met protein (e.g., express c-met protein at any intensity). In some embodiments, a patient's tumor is c-met positive when 10% or more of the tumor cells in the sample express c-met protein (e.g., express c-met protein at any intensity).

In some embodiments, a patient's tumor is c-met positive when 15% or more of the tumor cells in the sample express c-met protein. In some embodiments, a patient's tumor is c-met positive when 20% or more of the tumor cells in the sample express c-met protein (e.g., express c-met protein at any intensity). In some embodiments, a patient's tumor is c-met positive when 25% or more of the tumor cells in the sample express c-met protein (e.g., express c-met protein at any intensity). In some embodiments, a patient's tumor is c-met positive when 30% or more of the tumor cells in the sample express c-met protein (e.g., express c-met protein at any intensity). In some embodiments, a patient's tumor is c-met positive when 35% or more of the tumor cells in the sample express c-met protein (e.g., express c-met protein at any intensity). In some embodiments, a patient's tumor is c-met positive when 40% or more of the tumor cells in the sample express c-met protein (e.g., express c-met protein at any intensity). In some embodiments, a patient's tumor is c-met positive when 45% or more of the tumor cells in the sample express c-met protein (e.g., express c-met protein at any intensity). In some embodiments, a patient's tumor is c-met positive when 50% or more of the tumor cells in the sample express c-met protein (e.g., express c-met protein at any intensity). In some embodiments, a patient's tumor is c-met positive when 55% or more of the tumor cells in the sample express c-met protein (e.g., express c-met protein at any intensity). In some embodiments, a patient's tumor is c-met positive when 60% or more of the tumor cells in the sample express c-met protein (e.g., express c-met protein at any intensity). In some embodiments, a patient's tumor is c-met positive when 65% or more of the tumor cells in the sample express c-met protein (e.g., express c-met protein at any intensity). In some embodiments, a patient's tumor is c-met positive when 70% or more of the tumor cells in the sample express c-met protein (e.g., express c-met protein at any intensity). In some embodiments, a patient's tumor is c-met positive when 75% or more of the tumor cells in the sample express c-met protein (e.g., express c-met protein at any intensity). In some embodiments, a patient's tumor is c-met positive when 80% or more of the tumor cells in the sample express c-met protein (e.g., express c-met protein at any intensity). In some embodiments, a patient's tumor is c-met positive when 85% or more of the tumor cells in the sample express c-met protein (e.g., express c-met protein at any intensity). In some embodiments, a patient's tumor is c-met positive when 90% or more of the tumor cells in the sample express c-met protein (e.g., express c-met protein at any intensity). In some embodiments, a patient's tumor is c-met positive when 95% or more of the tumor cells in the sample express c-met protein (e.g., express c-met protein at any intensity). In some embodiments, c-met expression is membranous. In some embodiments, c-met expression is cytoplasmic. In some embodiments, c-met-expression is membranous and cytoplasmic. In some embodiments, the cancer is glioblastoma, mesothelioma, hepatocellular carcinoma, renal cell carcinoma, gastric cancer, sarcoma (e.g., osteosarcoma), non-small cell lung cancer, small cell lung cancer, breast cancer, gall bladder cancer, or pancreatic cancer. In some embodiments, the cancer is glioblastoma (e.g., recurrent glioblastoma). In some embodiments, the cancer is mesothelioma. In some embodiments, the cancer is gastric cancer. In some embodiments, the cancer is renal cell carcinoma. In some embodiments, the cancer is hepatocellular carcinoma cancer. In some embodiments, the cancer is sarcoma.

In some embodiments, a patient's tumor is c-met positive when 1% or more of the tumor cells in the sample express c-met protein with a moderate and/or strong staining intensity. In some embodiments, a patient's tumor is c-met positive when more than 1% of the tumor cells in the sample express c-met protein with a moderate and/or strong staining intensity. In some embodiments, a patient's tumor is c-met positive when 5% or more of the tumor cells in the sample express c-met protein with a moderate and/or strong staining intensity. In some embodiments, a patient's tumor is c-met positive when 10% or more of the tumor cells in the sample express c-met protein with a moderate and/or strong staining intensity. In some embodiments, a patient's tumor is c-met positive when 15% or more of the tumor cells in the sample express c-met protein. In some embodiments, a patient's tumor is c-met positive when 20% or more of the tumor cells in the sample express c-met protein with a moderate and/or strong staining intensity. In some embodiments, a patient's tumor is c-met positive when 25% or more of the tumor cells in the sample express c-met protein with a moderate and/or strong staining intensity. In some embodiments, a patient's tumor is c-met positive when 30% or more of the tumor cells in the sample express c-met protein with a moderate and/or strong staining intensity. In some embodiments, a patient's tumor is c-met positive when 35% or more of the tumor cells in the sample express c-met protein with a moderate and/or strong staining intensity. In some embodiments, a patient's tumor is c-met positive when 40% or more of the tumor cells in the sample express c-met protein with a moderate and/or strong staining intensity. In some embodiments, a patient's tumor is c-met positive when 45% or more of the tumor cells in the sample express c-met protein with a moderate and/or strong staining intensity. In some embodiments, a patient's tumor is c-met positive when 50% or more of the tumor cells in the sample express c-met protein with a moderate and/or strong staining intensity. In some embodiments, a patient's tumor is c-met positive when 55% or more of the tumor cells in the sample express c-met protein with a moderate and/or strong staining intensity. In some embodiments, a patient's tumor is c-met positive when 60% or more of the tumor cells in the sample express c-met protein with a moderate and/or strong staining intensity. In some embodiments, a patient's tumor is c-met positive when 65% or more of the tumor cells in the sample express c-met protein with a moderate and/or strong staining intensity. In some embodiments, a patient's tumor is c-met positive when 70% or more of the tumor cells in the sample express c-met protein with a moderate and/or strong staining intensity. In some embodiments, a patient's tumor is c-met positive when 75% or more of the tumor cells in the sample express c-met protein with a moderate and/or strong staining intensity. In some embodiments, a patient's tumor is c-met positive when 80% or more of the tumor cells in the sample express c-met protein with a moderate and/or strong staining intensity. In some embodiments, a patient's tumor is c-met positive when 85% or more of the tumor cells in the sample express c-met protein with a moderate and/or strong staining intensity. In some embodiments, a patient's tumor is c-met positive when 90% or more of the tumor cells in the sample express c-met protein with a moderate and/or strong staining intensity. In some embodiments, a patient's tumor is c-met positive when 95% or more of the tumor cells in the sample express c-met protein with a moderate and/or strong staining intensity. In some embodiments, c-met expression is membranous. In some embodiments, c-met expression is cytoplasmic. In some embodiments, c-met-expression is membranous and cytoplasmic. In some embodiments, the cancer is glioblastoma, mesothelioma, hepatocellular carcinoma, renal cell carcinoma, gastric cancer, sarcoma (e.g., osteosarcoma), non-small cell lung cancer, small cell lung cancer, breast cancer, gall bladder cancer, or pancreatic cancer. In some embodiments, the cancer is glioblastoma (e.g., recurrent glioblastoma). In some embodiments, the cancer is mesothelioma. In some embodiments, the cancer is gastric cancer. In some embodiments, the cancer is renal cell carcinoma. In some embodiments, the cancer is hepatocellular carcinoma cancer. In some embodiments, the cancer is sarcoma.

In some embodiments, a patient's tumor is c-met positive when a maximum staining intensity of the tumor is 1. In some embodiments, a patient's tumor is c-met positive when a maximum staining intensity of the tumor is 2. In some embodiments, a patient's tumor is c-met positive when a maximum staining intensity of the tumor is 3. In some embodiments, c-met expression is membranous. In some embodiments, c-met expression is cytoplasmic. In some embodiments, c-met-expression is membranous and cytoplasmic. In some embodiments, the cancer is glioblastoma, mesothelioma, hepatocellular carcinoma, renal cell carcinoma, gastric cancer, sarcoma (e.g., osteosarcoma), non-small cell lung cancer, small cell lung cancer, breast cancer, gall bladder cancer, or pancreatic cancer. In some embodiments, the cancer is glioblastoma (e.g., recurrent glioblastoma). In some embodiments, the cancer is mesothelioma. In some embodiments, the cancer is gastric cancer. In some embodiments, the cancer is renal cell carcinoma. In some embodiments, the cancer is hepatocellular carcinoma cancer. In some embodiments, the cancer is sarcoma. In some embodiments, c-met polypeptide or HGF is measured using IHC. In some embodiments, c-met polypeptide is measured using IHC and the patient sample is formalin-fixed and paraffin embedded. In some embodiments, c-met polypeptide is measured by contacting the sample with an agent that binds (in some embodiments, specifically binds) to c-met polypeptide, thereby forming a complex between the agent and c-met biomarker, whereby the tumor is c-met positive when 50% or more of the tumor cells in the sample have moderate or high c-met staining intensity. In some embodiments, the tumor is c-met positive when 50% or more of the tumor cells in the sample have high c-met staining intensity. In some embodiments, the tumor is c-met positive when 50% or more of the tumor cells in the sample have moderate c-met staining intensity. In some embodiments, the tumor is c-met positive when 50% or more of the tumor cells in the sample have low, moderate or high c-met staining intensity. In some embodiments, the agent that binds c-met is anti-c-met antibody SP44. In some embodiments, the agent that binds c-met is anti-c-met antibody D1C1. In some embodiments, the agent that binds c-met is anti-c-met antibody Met4. In some embodiments, the agent that binds c-met is anti-c-met antibody DL21. In some embodiments, c-met intensity is determined by comparing c-met staining in the sample to a reference level. In some embodiments, the reference level is c-met staining of control cell pellets (e.g., control cell line A549, SKMES1, EBC-1, H441, or cells or cell lines having comparable intensity to any one of A549, SKMES1, EBC-1, H441). In some embodiments, moderate c-met staining intensity means c-met staining intensity of control cell line A549. In some embodiments, moderate c-met staining intensity means c-met staining intensity of control cell line SKMES1. In some embodiments, strong c-met staining intensity means c-met staining intensity of control cell line EBC-1. In some embodiments, strong c-met staining intensity means c-met staining intensity of control cell line H441. In some embodiments, the patient sample(s) is/are obtained prior to treatment with c-met antagonist and/or VEGF antagonist. In some embodiments, the sample is obtained after the cancer has metastasized. In some embodiments, the sample is obtained prior to treatment with a cancer medicament. In some embodiments, the sample is of a biopsy, a surgical specimen, or a fine needle aspirate. In some embodiments, the sample is formalin fixed and paraffin embedded. In some embodiments, wherein control cell pellets are formalin fixed and paraffin embedded. In some embodiments, the control cell pellets are prepared as a tissue microarray. In some embodiments, c-met expression is membranous. In some embodiments, c-met expression is cytoplasmic. In some embodiments, c-met-expression is membranous and cytoplasmic. In some embodiments, the cancer is glioblastoma, mesothelioma, hepatocellular carcinoma, renal cell carcinoma, gastric cancer, sarcoma (e.g., osteosarcoma), non-small cell lung cancer, small cell lung cancer, breast cancer, gall bladder cancer, or pancreatic cancer. In some embodiments, the cancer is glioblastoma (e.g., recurrent glioblastoma). In some embodiments, the cancer is mesothelioma. In some embodiments, the cancer is gastric cancer. In some embodiments, the cancer is renal cell carcinoma. In some embodiments, the cancer is hepatocellular carcinoma cancer. In some embodiments, the cancer is sarcoma. In some embodiments, c-met IHC is scored (e.g., as c-met positive) using an H-score. In some embodiments, HGF IHC is scored (e.g., as HGF positive) using an H-score. Methods for calculating an H-score are disclosed in the art. Briefly, the proportion of tumor cells showing staining at weak, moderate, and strong intensity (e.g., using cell line controls as discussed herein) may be counted or estimated as percentage of the total number of tumor cells in a given glioblastoma sample. The composite H score is calculated based on the formula: (% tumor cells staining at weak intensity x1)+(% tumor cells staining at moderate intensity x2)+(% tumor cells staining at strong intensity x3). Following this formula, a given tumor can be associated with a value between "0" (none of the tumor cells show any staining) and "300" (100% of the tumor cells show strong staining). In some embodiments of any of the methods herein, the high c-Met or HGF expression corresponds to an H-score of about 160 or higher (about 161, 162, 163, 164, 165, 166, 167, 168, 169, or higher), 160 or higher, about 160 to about 230, about 160 to 230, about 160 (any of about 161, 162, 163, 164, 165, 166, 167, 168, 169, or higher to any of about 220, 221, 223, 224, 225, 226, 227, 228, 229, 230 or higher), 230 or higher, any of about 220, 221, 223, 224, 225, 226, 227, 228, 229, 230 or higher), about 170 or higher, or 170 or higher (e.g., any of about 171, 172, 173, 175, 175, 176, 177, 178, 179, 180 or higher). In one embodiment, the H-score is about 180 or higher. In some embodiments, the H score is greater than about 10. In some embodiments, the H score is greater than about 25. In some embodiments, the H score is greater than about 50. In some embodiments, the H score is greater than about 75. In some embodiments, the H score is greater than about 100. In some embodiments, the H score is greater than about 125. In some embodiments, the H score is greater than about 150. In some embodiments, the H score is greater than about 175. In some embodiments, the H score is greater than about 200. In some embodiments, c-met expression is membranous. In some embodiments, c-met expression is cytoplasmic. In some embodiments, c-met-expression is membranous and cytoplasmic. In some embodiments, the cancer is glioblastoma, mesothelioma, hepatocellular carcinoma, renal cell carcinoma, gastric cancer, sarcoma (e.g., osteosarcoma), non-small cell lung cancer, small cell lung cancer, breast cancer, gall bladder cancer, or pancreatic cancer. In some embodiments, the cancer is glioblastoma (e.g., recurrent glioblastoma). In some embodiments, the cancer is mesothelioma. In some embodiments, the cancer is gastric cancer. In some embodiments, the cancer is renal cell carcinoma. In some embodiments, the cancer is hepatocellular carcinoma cancer. In some embodiments, the cancer is sarcoma.

In some embodiments, analysis (e.g., IHC analysis) further comprises morphological staining, either prior to or thereafter. In one embodiment, hematoxylin is use for staining cellular nucleic of the slides. Hematoxylin is widely available. An example of a suitable hematoxylin is Hematoxylin II (Ventana). When lighter blue nuclei are desired, a bluing reagent may be used following hematoxylin staining.

IV. Therapeutic Methods

Uses of a c-met antagonist for effectively treating cancer patients are provided. Uses of a c-met antagonist and VEGF antagonist for effectively treating cancer patients are provided. In particular, an HGF biomarker is used to identify a patient population in which onartuzumab, onartuzumab plus a second cancer medicament, onartuzumab plus a chemotherapeutic agent, or onartuzumab plus VEGF antagonist, treatment provides clinically meaningful benefit.

Cancer medicaments can be used in combination with other cancer medicaments. For example, a c-met antibody may be co-administered with an additional c-met antagonist. Such combination therapies noted above encompass combined administration (where two or more therapeutic agents are included in the same or separate formulations), and separate administration, in which case, administration of a first medicament can occur prior to, simultaneously, and/or following, administration of a second medicament. Examples of cancer medicaments include, without limitation, surgery, radiation therapy (radiotherapy), biotherapy, immunotherapy, chemotherapy (e.g., temozolomide), or a combination of these therapies. In addition, cytotoxic agents, anti-angiogenic and anti-proliferative agents can be used in combination with the anti-VEGF antagonist and/or the c-met antagonist.

An exemplary and non-limiting list of chemotherapeutic agents contemplated is provided herein under "Definition", or described herein. In one embodiment, the chemotherapeutic agent is temozolomide. In another embodiment, the chemotherapeutic agent is administered concomitantly with radiotherapy.

The medicament(s) herein can be administered by any suitable means, including parenteral, intrapulmonary, and intranasal, and, if desired for local treatment, intralesional administration. Parenteral infusions include intramuscular, intravenous, intraarterial, intraperitoneal, or subcutaneous administration. Dosing can be by any suitable route, e.g. by injections, such as intravenous or subcutaneous injections, depending in part on whether the administration is brief or chronic. Various dosing schedules including but not limited to single or multiple administrations over various timepoints, bolus administration, and pulse infusion are contemplated herein.

For the prevention or treatment of disease, the appropriate dosage of an antibody of the invention (when used alone or in combination with one or more other additional therapeutic agents) will depend on the type of disease to be treated, the type of antibody, the severity and course of the disease, whether the antibody is administered for preventive or therapeutic purposes, previous therapy, the patient's clinical history and response to the antibody, and the discretion of the attending physician. The antibody is suitably administered to the patient at one time or over a series of treatments. For repeated administrations over several days or longer, depending on the condition, the treatment would generally be sustained until a desired suppression of disease symptoms occurs. However, other dosage regimens may be useful. The progress of this therapy is easily monitored by conventional techniques and assays.

Depending on the type and severity of the disease, about 1 ug/kg to 100 mg/kg (e.g., 0.1-20 mg/kg) of the anti-c-met antibody as an initial candidate dosage for administration to the subject, whether, for example, by one or more separate administrations, or by continuous infusion. In one embodiment, desirable dosages include, for example, 6 mg/kg, 8 mg/kg, 10 mg/kg, and 15 mg/kg. For repeated administrations or cycles over several days or longer, depending on the condition, the treatment is sustained until the cancer is treated, as measured by the methods described above or known in the art. However, other dosage regimens may be useful. In one example, the anti-c-met antibody is administered once every week, every two weeks, or every three weeks, at a dose range from about 6 mg/kg to about 15 mg/kg, including but not limited to 6 mg/kg, 8 mg/kg, 10 mg/kg or 15 mg/kg. The progress of the therapy of the invention is easily monitored by conventional techniques and assays. In other embodiments, such dosing regimen is used in combination with a chemotherapy regimen in glioblastoma. Further information about suitable dosages is provided in the Example below. In other embodiments, such dosing regimen is used in combination with a chemotherapy regimen in mesothelioma. In other embodiments, such dosing regimen is used in combination with a chemotherapy regimen in gastric cancer. In other embodiments, such dosing regimen is used in combination with a chemotherapy regimen in renal cell carcinoma. In other embodiments, such dosing regimen is used in combination with a chemotherapy regimen in hepatocellular carcinoma. In other embodiments, such dosing regimen is used in combination with a chemotherapy regimen in sarcoma. In some embodiments, the effective amount of the anti-c-met antibody is 15 mg/kg every three weeks, administered, for example, intravenously. In some embodiments, the effective amount of the anti-c-met antibody is 10 mg/kg every two weeks, administered, for example, intravenously.

Depending on the type and severity of the disease, about 1 ug/kg to 100 mg/kg (e.g., 0.1-20 mg/kg) of the anti-VEGF antibody as an initial candidate dosage for administration to the subject, whether, for example, by one or more separate administrations, or by continuous infusion. In one embodiment, desirable dosages include, for example, 6 mg/kg, 8 mg/kg, 10 mg/kg, and 15 mg/kg. For repeated administrations or cycles over several days or longer, depending on the condition, the treatment is sustained until the cancer is treated, as measured by the methods described above or known in the art. However, other dosage regimens may be useful. In one example, the anti-VEGF antibody is administered once every week, every two weeks, or every three weeks, at a dose range from about 6 mg/kg to about 15 mg/kg, including but not limited to 6 mg/kg, 8 mg/kg, 10 mg/kg or 15 mg/kg. The progress of the therapy of the invention is easily monitored by conventional techniques and assays. In other embodiments, such dosing regimen is used in combination with a chemotherapy regimen in glioblastoma. Further information about suitable dosages is provided in the Example below. In other embodiments, such dosing regimen is used in combination with a chemotherapy regimen in mesothelioma. In other embodiments, such dosing regimen is used in combination with a chemotherapy regimen in gastric cancer. In other embodiments, such dosing regimen is used in combination with a chemotherapy regimen in renal cell carcinoma. In other embodiments, such dosing regimen is used in combination with a chemotherapy regimen in hepatocellular carcinoma. In other embodiments, such dosing regimen is used in combination with a chemotherapy regimen in sarcoma. In some embodiments, the effective amount of said anti-VEGF antibody is 10 mg/kg intravenously every two weeks, administered, for example, initially intravenously over 90 minutes, with subsequent infusions over 60 minutes and then 30 minutes. In some embodiments, the effective amount of said anti-VEGF antibody is 15 mg/kg intravenously every three weeks administered, for example, initially intravenously over 90 minutes, with subsequent infusions over 60 minutes and then 30 minutes. In the methods described above, the anti-VEGF antibody is administered second to said patient at the first cycle and then subsequent administrations of said anti-VEGF antibody are either prior to or after said chemotherapeutic. In another embodiment, the anti-VEGF antibody is administered concurrently with said chemotherapeutic and radiotherapy. In some embodiments, administration of steroid to the patient is discontinued.

In some embodiments, the effective amount of onartuzumab is 15 mg/kg intravenously every three weeks, and the effective amount of bevacizumab is 15 mg/kg intravenously every three weeks.

In some other aspects of any of the methods and uses, treatment further comprises administration of an additional cancer medicament. Exemplary cancer medicaments include antagonist of other factors that are involved in tumor growth, such as EGFR, ErbB3, ErbB4, or TNF. Sometimes, it may be beneficial to also administer one or more cytokines to the subject. In one embodiment, the VEGF antibody is co-administered with a growth inhibitory agent. For example, the growth inhibitory agent may be administered first, followed by the VEGF antibody. However, simultaneous administration or administration of the VEGF antibody first is also contemplated. Suitable dosages for the growth inhibitory agent are those presently used and may be lowered due to the combined action (synergy) of the growth inhibitory agent and anti-VEGF antibody.

The formulation herein may also contain more than one active compound as necessary for the particular indication being treated, preferably those with complementary activities that do not adversely affect each other. For example, it may be desirable to further provide antibodies which bind to EGFR, VEGF (e.g. an antibody which binds a different epitope or same epitope on VEGF), VEGFR, or ErbB2 (e.g., Herceptin®) in the one formulation. Alternatively, or in addition, the composition may comprise a chemotherapeutic agent, or a cytotoxic agent. Such molecules are suitably present in combination in amounts that are effective for the purpose intended.

In certain aspects of any of the methods and uses, other therapeutic agents useful for combination cancer therapy with the antibody of the invention include other anti-angiogenic agents. Many anti-angiogenic agents have been identified and are known in the arts, including those listed by Carmeliet and Jain (2000). In one embodiment, the anti-VEGF antibody is used in combination with another VEGF antagonist or a VEGF receptor antagonist such as VEGF variants, soluble VEGF receptor fragments, aptamers capable of blocking VEGF or VEGFR, neutralizing anti-VEGFR antibodies, low molecule weight inhibitors of VEGFR tyrosine kinases and any combinations thereof. Alternatively, or in addition, two or more anti-VEGF antibodies may be co-administered to the subject.

As will be understood by those of ordinary skill in the art, the appropriate doses of chemotherapeutic agents or other anti-cancer agents will be generally around those already employed in clinical therapies, e.g., where the chemotherapeutics are administered alone or in combination with other chemotherapeutics. Variation in dosage will likely occur depending on the condition being treated. The physician administering treatment will be able to determine the appropriate dose for the individual subject.

In some embodiments, treatment results in a clinical or therapeutic benefit imparted to a patient at risk for, or suffering from, cancer (e.g., glioblastoma, mesothelioma, gastric cancer, renal cell carcinoma, hepatocellular carcinoma, or sarcoma) upon administration of the cancer medicament. Such benefit includes any one or more of: extending survival (e.g., increasing overall and/or progression-free survival); resulting in an objective response (including a complete response or a partial response); or improving signs or symptoms of cancer, etc., including extending time to deterioration of clinically relevant disease-related symptoms experienced by patients with glioblastoma (e.g., previously treated glioblastoma), extending time to deterioration of clinically relevant disease-related symptoms experienced by patients with mesothelioma (e.g., previously treated mesothelioma), extending time to deterioration of clinically relevant disease-related symptoms experienced by patients with gastric cancer (e.g., previously treated gastric cancer), extending time to deterioration of clinically relevant disease-related symptoms experienced by patients with renal cell carcinoma (e.g., previously treated renal cell carcinoma), extending time to deterioration of clinically relevant disease-related symptoms experienced by patients with hepatocellular carcinoma (e.g., previously treated hepatocellular carcinoma), or extending time to deterioration of clinically relevant disease-related symptoms experienced by patients with sarcoma (e.g., previously treated sarcoma). In some embodiments, the symptom is any one or more (in any combination) of seizure, neurocognitive functions (including but not limited to: orientation to person, time and/or place), reading, writing, and comprehension. In some embodiments, the symptom is any one or more (in any combination) of chest wall pain, pleural effusion, shortness of breath, fatigue, anemia, wheezing, hoarseness, cough, blood in the sputum, abdominal pain, ascites, abdominal masses, problems with bowel function, weight loss, blood clots, disseminated intravascular coagulation, jaundice, low blood sugar levels, and pulmonary emboli. In some embodiments, the symptom is any one or more (in any combination) of indigestion, heartburn, weakness, fatigue, bloating, abdominal pain, nausea, vomiting, diarrhea, constipation, weight loss, bleeding, anemia, and dysphagia. In some embodiments, the symptom is any one or more (in any combination) of hematuria (or blood in the urine), flank pain, a mass in the abdomen or flank, weight loss, loss of appetite, fever, high blood pressure, malaise, night sweats, anemia, erythrocytosis, varicocele, hypertension, and hypercalcemia. In some embodiments, the symptom is any one or more (in any combination) of yellow skin, bloating from fluid in the abdomen, easy bruising from blood clotting abnormalities, loss of appetite, unintentional weight loss, abdominal pain, nausea, vomiting, and malaise. In one embodiment, the biomarker(s) (e.g., HGF mRNA expression, for example, as determined using ISH and/or rt-qPCR) is used to identify the patient who is expected to have extended survival (e.g., increased overall and/or progression-free survival) when treated with c-met antagonist. In some embodiments, the biomarker(s) (e.g., HGF mRNA expression, for example, as determined using ISH and/or rt-qPCR) is used to identify the patient who is expected to have extended survival (e.g., increased overall and/or progression-free survival) when treated with c-met antagonist and VEGF antagonist, relative to a patient who is treated with VEGF antagonist alone. The incidence of biomarker(s) herein (e.g. as determined by HGF mRNA ISH and/or rt-qPCR analysis) effectively predicts, or predicts with high sensitivity, such effective response.

In some embodiments, extending survival means increasing overall or progression free survival in a patient treated in accordance with the present invention relative to an untreated patient and/or relative to a patient treated with one or more approved anti-tumor agents, but not receiving treatment in accordance with the present invention. In a particular example, extending survival means extending progression-free survival (PFS) and/or overall survival (OS) of cancer patients receiving a therapy of the present invention (e.g. treatment with a c-met antagonist (e.g., onartuzumab) relative to untreated patients and/or relative to patients treated with one or more approved anti-tumor agents, but not receiving treatment with a c-met antagonist. In another particular example, extending survival means extending progression-free survival (PFS) and/or overall survival (OS) of cancer patients (e.g., a population of cancer patients) receiving a therapy of the present invention (e.g. treatment with a c-met antagonist (e.g., onartuzumab) relative to untreated patients (e.g. a population of cancer patients) and/or relative to patients (e.g., a population of cancer patients) treated with one or more approved anti-tumor agents, but not receiving treatment with a c-met antagonist. In another particular example, extending survival means extending progression-free survival (PFS) and/or overall survival (OS) of cancer patients receiving a combination therapy of the present invention (e.g. treatment with a combination of c-met antagonist (e.g., onartuzumab) and VEGF antagonist (e.g., bevacizumab) relative to patients treated with bevacizumab only. In another particular example, extending survival means extending progression-free survival (PFS) and/or overall survival (OS) of cancer patients (e.g., a population of cancer patients) receiving a combination therapy of the present invention (e.g. treatment with a combination of onartuzumab and bevacizumab) relative to patients (e.g. a population of cancer patients) treated with bevacizumab only.

In some embodiments, treatment results in improvement of signs or symptoms of cancer, etc., including extending time to deterioration of clinically relevant disease-related symptoms experienced by patients with glioblastoma (e.g., previously treated glioblastoma). In some embodiments, the symptom is any one or more (in any combination) of seizure, neurocognitive functions (including but not limited to: orientation to person, time and/or place), reading, writing, and comprehension. In some embodiments, methods are provided for preventing increase in such cancer signs or symptoms.

In some embodiments, treatment results in improvement of signs or symptoms of cancer, etc., including extending time to deterioration of clinically relevant disease-related symptoms experience by patients with mesothelioma (e.g., previously treated mesothelioma). In some embodiments, the symptom is any one or more (in any combination) of chest wall pain, pleural effusion, shortness of breath, fatigue, anemia, wheezing, hoarseness, cough, blood in the sputum, abdominal pain, ascites, abdominal masses, problems with bowel function, weight loss, blood clots, disseminated intravascular coagulation, jaundice, low blood sugar levels, and pulmonary emboli. In some embodiments, methods are provided for preventing increase in such cancer signs or symptoms.

In some embodiments, treatment results in improvement of signs or symptoms of cancer, etc., including extending time to deterioration of clinically relevant disease-related symptoms experience by patients with gastric cancer (e.g., previously treated gastric cancer). In some embodiments, the symptom is any one or more (in any combination) of indigestion, heartburn, weakness, fatigue, bloating, abdominal pain, nausea, vomiting, diarrhea, constipation, weight loss, bleeding, anemia, and dysphagia. In some embodiments, methods are provided for preventing increase in such cancer signs or symptoms.

In some embodiments, treatment results in improvement of signs or symptoms of cancer, etc., including extending time to deterioration of clinically relevant disease-related symptoms experience by patients with hepatocellular carcinoma (e.g., previously treated hepatocellular carcinoma). In some embodiments, the symptom is any one or more (in any combination of yellow skin, bloating from fluid in the abdomen, easy bruising from blood clotting abnormalities, loss of appetite, unintentional weight loss, abdominal pain, nausea, vomiting, and malaise. In some embodiments, methods are provided for preventing increase in such cancer signs or symptoms.

In some embodiments, treatment results in improvement of signs or symptoms of cancer, etc., including extending time to deterioration of clinically relevant disease-related symptoms experience by patients with renal cell carcinoma (e.g., previously treated renal cell carcinoma). In some embodiments, the symptom is any one or more (in any combination) of hematuria (or blood in the urine), flank pain, a mass in the abdomen or flank, weight loss, loss of appetite, fever, high blood pressure, malaise, night sweats, anemia, erythrocytosis, varicocele, hypertension, and hypercalcemia. In some embodiments, methods are provided for preventing increase in such cancer signs or symptoms.

In some embodiments, the patient is a glioblastoma patient. In some embodiments, the patient did not receive prior treatment with a c-met antagonist. In some embodiments, the patient did not receive prior treatment with an intracerebral agent. In some embodiments, the patient did not have urine proteinuria of greater than 1.0 g of protein in 24 hours, as assayed using a urine dipstick test for proteinuria. In some embodiments, the patient did not have inadequately controlled hypertension (e.g., systolic blood pressure greater than 150 mmHg and/or diastolic blood pressure greater than 100 mmHg while on antihypertensive medication). In some embodiments, the patient did not have a prior history of hypertensive crisis or hypertensive encephalopathy. In some embodiments, the patient did not have a prior history of myocardial infarction (e.g., within 12 months) or unstable angina (e.g., within 6 months). In some embodiments, the patient did not have a history of stroke or transient ischemic attacks (e.g., within 6 months). In some embodiments, the patient did not have significant vascular disease (e.g., aortic aneurysm requiring surgical repair or recent peripheral arterial thrombosis, e.g., within 6 months). In some embodiments, the patient did not have a history of abdominal fistula or gastrointestinal perforation (e.g., within 6 months). In some embodiments, the patient did not have Evidence of bleeding diathesis or coagulopathy (e.g., in the absence of therapeutic anticoagulation). In some embodiments, the patient did not have history of intracranial abscess (e.g., within 6 months).

In some embodiments, the patient received prior treatment with temozolomide. In some embodiments, the patient received no more than one prior line of chemotherapy (e.g., one prior line of temozolomide, e.g., concurrent or adjuvant temozolomide). In some embodiments, the patient had a Karnofsky performance status of greater than or equal to 70%.

In another aspect, provided are methods for evaluating adverse events in a patient associated with treatment of a previously treated glioblastoma, mesothelioma, gastric cancer, renal cell carcinoma, hepatocellular carcinoma, or sarcoma using any of the methods disclosed herein, wherein treatment is with a c-met antagonist (e.g., onartuzumab), the methods comprising the steps of monitoring a patient for one or more adverse event. In some embodiments, the patient is monitored for the number and/or severity of one or more adverse events. Exemplary adverse events are disclosed herein, and include but are not limited to: peripheral edema.

In another aspect, provided are methods for evaluating adverse events in a patient associated with treatment of a previously treated glioblastoma, mesothelioma, gastric cancer, renal cell carcinoma, hepatocellular carcinoma, or sarcoma using any of the methods disclosed herein, wherein treatment is with a c-met antagonist (e.g., onartuzumab) and a chemotherapeutic, the methods comprising the steps of monitoring a patient for one or more adverse event. In some embodiments, the patient is monitored for the number and/or severity of one or more adverse events. Exemplary adverse events are disclosed herein, and include but are not limited to: peripheral edema.

In another aspect, provided are methods for evaluating adverse events in a patient associated with treatment of a previously treated glioblastoma or renal cell carcinoma using any of the methods disclosed herein, wherein treatment is with a c-met antagonist (e.g., onartuzumab) and VEGF antagonist (e.g., bevacizumab), the methods comprising the steps of monitoring a patient for one or more adverse event. In some embodiments, the patient is monitored for the number and/or severity of one or more adverse events. Exemplary adverse events are disclosed herein, and include but are not limited to: peripheral edema.

It is understand that any of the formulations or therapeutic methods described herein may be carried out using an immunoconjugate of an antibody in place of or in addition to the antibody as the medicament.

V. Articles of Manufacture

In another embodiment of the invention, an article of manufacture for use in treating cancer (such as glioblastoma, mesothelioma, gastric cancer, renal cell carcinoma, hepatocellular carcinoma, or sarcoma) is provided. In some embodiments, the cancer is a previously treated cancer (such as previously treated (e.g., second line) glioblastoma, mesothelioma, gastric cancer, renal cell carcinoma, hepatocellular carcinoma, or sarcoma). The article of manufacture comprises a container and a label or package insert on or associated with the container. Suitable containers include, for example, bottles, vials, syringes, etc. The containers may be formed from a variety of materials such as glass or plastic. The container holds or contains a composition comprising the cancer medicament as the active agent and may have a sterile access port (for example the container may be an intravenous solution hag or a vial having a stopper pierceable by a hypodermic injection needle).

The article of manufacture may further comprise a second container comprising a pharmaceutically-acceptable diluent buffer, such as bacteriostatic water for injection (BWFI), phosphate-buffered saline, Ringer's solution and dextrose solution. The article of manufacture may further include other materials desirable from a commercial and user standpoint, including other buffers, diluents, filters, needles, and syringes.

The article of manufacture of the present invention also includes information, for example in the form of a package insert, indicating that the composition is used for treating cancer based on expression of biomarker(s) as disclosed herein. The insert or label may take any form, such as paper or on electronic media such as a magnetically recorded medium (e.g., floppy disk) or a CD-ROM. The label or insert may also include other information concerning the pharmaceutical compositions and dosage forms in the kit or article of manufacture.

The invention also concerns a method for manufacturing an article of manufacture comprising combining in a package a pharmaceutical composition comprising a c-met antagonist (e.g., an anti-c-met antibody, e.g. onartuzumab) and a package insert indicating that the pharmaceutical composition is for treating a patient with cancer (e.g., glioblastoma, mesothelioma, gastric cancer, renal cell carcinoma, hepatocellular carcinoma, or sarcoma) based on expression of an HGF biomarker as disclosed herein. In some embodiments, the cancer is a previously treated cancer (e.g., second line glioblastoma, mesothelioma, gastric cancer, renal cell carcinoma, hepatocellular carcinoma, or sarcoma).

The invention also concerns a method for manufacturing an article of manufacture comprising combining in a package a pharmaceutical composition comprising a VEGF antagonist (e.g., bevacizumab) and a package insert indicating that the pharmaceutical composition is for treating a patient with cancer (e.g., glioblastoma, mesothelioma, gastric cancer, renal cell carcinoma, hepatocellular carcinoma, or sarcoma) based on expression of an HGF biomarker as disclosed herein. In some embodiments, the cancer is a previously treated cancer (e.g., second line glioblastoma, mesothelioma, gastric cancer, renal cell carcinoma, hepatocellular carcinoma, or sarcoma).

The article of manufacture may further comprise an additional container comprising a pharmaceutically acceptable diluent buffer, such as bacteriostatic water for injection (BWFI), phosphate-buffered saline, Ringer's solution, and/ or dextrose solution. The article of manufacture may further include other materials desirable from a commercial and user standpoint, including other buffers, diluents, filters, needles, and syringes.

VI. Diagnostic Kits

The invention also concerns diagnostic kits useful for detecting any one or more of the biomarker(s) identified herein. Accordingly, a diagnostic kit is provided which comprises one or more reagents for determining expression of one or more HGF biomarkers in a sample from a cancer patient (e.g., a glioblastoma, mesothelioma, gastric cancer, renal cell carcinoma, hepatocellular carcinoma, or sarcoma patient). Optionally, the kit further comprises instructions to use the kit to select a cancer medicament (e.g. a c-met antagonist, such as an anti-c-met antibody, e.g., onartuzumab) for treating the glioblastoma, mesothelioma, gastric cancer, renal cell carcinoma, hepatocellular carcinoma, or sarcoma patient if the patient's cancer has been determined to have a high amount of an HGF biomarker (e.g., by ISH, or PCR). In some embodiments, the cancer patient is a previously treated cancer patient (e.g., a previously treated glioblastoma, mesothelioma, gastric cancer, renal cell carcinoma, hepatocellular carcinoma, or sarcoma patient). Optionally, the kit further comprises instructions to use the kit to select a cancer medicament (e.g. a c-met antagonist, such as an anti-c-met antibody, e.g., onartuzumab) for treating the previously treated glioblastoma, mesothelioma, gastric cancer, renal cell carcinoma, hepatocellular carcinoma, or sarcoma patient if the patient's cancer has been determined to have a high amount of an HGF biomarker (e.g., by ISH, or PCR). In another embodiment, the kit further comprises instructions to use the kit to select treatment with c-met antagonist antibody (e.g., onartuzumab) and VF F antagonist (e.g., bevacizumab) if the patient's cancer (e.g., glioblastoma, mesothelioma, gastric cancer, renal cell carcinoma, hepatocellular carcinoma, or sarcoma) has been determined to have a high amount of an HGF biomarker. In some embodiments, the kit comprises primers and/or probes (e.g., 1, 2, 3, 4, or more) that are complementary to HGF mRNA.

VII. Methods of Advertising

The invention herein also concerns a method for advertising a cancer medicament comprising promoting, to a target audience, the use of the cancer medicament (e.g. anti-c-met antibody, optionally in combination with anti-VEGF antibody) for treating a patient with cancer based on expression of an HGF biomarker as disclosed herein.

Advertising is generally paid communication through a non-personal medium in which the sponsor is identified and the message is controlled. Advertising for purposes herein includes publicity, public relations, product placement, sponsorship, underwriting, and sales promotion. This term also includes sponsored informational public notices appearing in any of the print communications media designed to appeal to a mass audience to persuade, inform, promote, motivate, or otherwise modify behavior toward a favorable pattern of purchasing, supporting, or approving the invention herein.

The advertising and promotion of the diagnostic method herein may be accomplished by any means. Examples of advertising media used to deliver these messages include television, radio, movies, magazines, newspapers, the internet, and billboards, including commercials, which are messages appearing in the broadcast media. Advertisements also include those on the seats of grocery carts, on the walls of an airport walkway, and on the sides of buses, or heard in telephone hold messages or in-store PA systems, or anywhere a visual or audible communication can be placed.

More specific examples of promotion or advertising means include television, radio, movies, the internet such as webcasts and webinars, interactive computer networks intended to reach simultaneous users, fixed or electronic billboards and other public signs, posters, traditional or electronic literature such as magazines and newspapers, other media outlets, presentations or individual contacts by, e.g., e-mail, phone, instant message, postal, courier, mass, or carrier mail, in-person visits, etc.

The type of advertising used will depend on many factors, for example, on the nature of the target audience to be reached, e.g., hospitals, insurance companies, clinics, doctors, nurses, and patients, as well as cost considerations and the relevant jurisdictional laws and regulations governing advertising of medicaments and diagnostics. The advertising may be individualized or customized based on user characterizations defined by service interaction and/or other data such as user demographics and geographical location.

In some embodiments, promoting refers to promotion of therapeutic agent(s), such as an anti-c-met antagonist (e.g., onartuzumab) and/or VEGF antagonist (e.g., bevacizumab), for an indication, such as glioblastoma (e.g., recurrent glioblastoma), mesothelioma (e.g., recurrent mesothelioma), gastric cancer (e.g., recurrent gastric cancer), renal cell carcinoma (e.g., recurrent renal cell carcinoma), hepatocellular carcinoma (e.g., recurrent hepatocellular carcinoma), or sarcoma (e.g., recurrent sarcoma) treatment, where such promoting is authorized by the Food and Drug Administration (FDA) as having been demonstrated to be associated with statistically significant therapeutic efficacy and acceptable safety in a population of subjects.

Sequence

SEQ ID NO: 16
MKAPAVLAPGILVLLFTLVQRSNGECKEALAKSEMNVNMKYQLPNFTAET

PIQNVILHEHHIFLGATNYIYVLNEEDLQKVAEYKTGPVLEHPDCFPCQD

CSSKANLSGGVWKDNINMALVVDTYYDDQLISCGSVNRGTCQRHVFPHNH

TADIQSEVHCIFSPQIEEPSQCPDCVVSAEGAKVLSSVKDRFINEFVGNT

INSSYFPDHPLHSISVRRLKETKDGFMFLTDQSYIDVLPEFRDSYPIKYV

HAFESNNFIYFLTVQRETLDAQTFHTRIIRFCSINSGLHSYMEMPLECIL

TEKRKKRSTKKEVFNILQAAYVSKPGAQLARQIGASLNDDILFGVFAQSK

PDSAEPMDRSAMCAFPIKYVNDFFNKIVNKNNVRCLQHFYGPNHEHCFNR

TLLRNSSGCEARRDEYRTEFTTALQRVDLFMGQFSEVLLTSISTFIKGDL

TIANLGTSEGRFMQVVVSRSGPSTPHVNFLLDSHPVSPEVIVEHTLNQNG

YTLVITGKKITKIPLNGLGCRHFQSCSQCLSAPPFVQCGWCHDKCVRSEE

CLSGTWTQQICLPAIYKVFPNSAPLEGGTRLTICGWDFGFRRNNKFDLKK

TRVLLGNESCTLTLSESTMNTLKCTVGPAMNKHFNMSIIISNGHGTTQYS

TFSYVDPVITSISPKYGPMAGGTLLTLTGNYLNSGNSRHISIGGKTCTLK

SVSNSILECYTPAQTISTEFAVKLKIDLANRETSIFSYREDPIVYEIHPT

KSFISGGSTITGVGKNLNSVSVPRMVINVHEAGRNFTVACQHRSNSEIIC

CTTPSILQQLNLQLPLKTKAFFMLDGILSKYFDLIYVHNPVFKPFEKPVM

ISMGNENVLEIKGNDIDPEAVKGEVLKVGNKSCENIHLHSEAVLCTVPND

LLKLNSELNIEWKQAISSTVLGKVIVQPDQNFTGLIAGVVSISTALLLLL

GFFLWLKKRKQIKDLGSELVRYDARVHTPHLDRLVSARSVSPTTEMVSNE

SVDYRATFPEDQFPNSSQNGSCRQVQYPLTDMSPILTSGDSDISSPLLQN

TVHIDLSALNPELVQAVQHVVIGPSSLIVHFNEVIGRGHFGCVYHGTLLD

NDGKKIHCAVKSLNRITDIGEVSQFLTEGIIMKDFSHPNVLSLLGICLRS

EGSPLVVLPYMKHGDLRNFIRNETHNPTVKDLIGFGLQVAKGMKYLASKK

FVHRDLAARNCMLDEKFTVKVADEGLARDMYDKEYYSVGNKTGAKLPVKW

MALESLQTQKFTTKSDVWSFGVLLWELMTRGAPPYPDVNTFDITVYLLQG

RRLLQPEYCPDPLYEVMLKCWHPKAEMRPSFSELVSRISAIFSTFIGEHY

VHVNATYVNVKCVAPYPSLLSSEDNADDEVDTRPASFWETS

EXAMPLES

Example 1: In-Situ Hybridization Analysis of HGF mRNA Expression in Glioblastoma Samples Samples:

Pre-treatment patient glioblastoma samples were analyzed from a blind, Phase II, randomized, multicenter trial (further described below) designed to evaluate preliminary activity and safety of treatment with onartuzumab plus bevacizumab versus bevacizumab plus placebo in patients with recurrent glioblastoma. Submission of a formalin-fixed paraffin-embedded tumor specimen of representative glioblastoma was required for all patients enrolled into the study.

In-Situ Hybridization (ISH): The ISH assay was performed using a set of target DNA probes which were hybridized to the target RNA of interest, followed by hybridization-based signal amplification. The target probes were oligonucleotides that were designed to hybridize as pairs, with each pair creating a binding site for a preamplifier. The preamplifier was hybridized to the target probes at a temperature that favored hybridization to the target probe pairs, but not individual target probes. This ensured that if unpaired target probes hybridized non-specifically to a non-specific RNA, no signal amplification occurred. Then, the amplifier was hybridized to the preamplifier. Finally, the label probe, which is conjugated to a chromogenic molecule, was hybridized to the amplifier.

The assay was performed according to the manufacturer's directions (RNAScope 2.0 Manual Assay) except that pretreatment steps were altered relative to the manufacturer's directions. Alteration of the pretreatment steps was important, e.g., for optimizing signal.

Protocol:
1. Slides were baked at 60° C. for 60 minutes
2. Deparaffinization/Rehydration: slides were treated with 3× Xylene (EMD Millipore Chemicals; catalog number XX0060-4) for 5 minutes, followed by 2×100% Reagent Alcohol (Thermo Scientific; catalog number 9111) for 2 minutes.

All reagents that are stored at 4 C were brought to room temperature. The probes were preheated to 40 C approximately 10 minutes prior to use.

3. Slides were air dried, and a hydrophobic barrier was drawn around the tissue
4. Pretreatment (PT) 1 solution (Endogenous peroxidase. Advanced Cell Diagnostics, catalog number 310020) was added by dropper to each slide so that the specimens were covered, then the samples were incubated at room temperature for 10 minutes, then slides were transferred to $H_2O$ 2×2 minutes
5. 1.5 liters of Pretreatment (PT) 2 solution (Advanced Cell Diagnostics; catalog number 320043; solution came as 10× stock solution and was diluted to 1× in $dH_2O$ prior to use) were prepared and transferred into the PT module, slides were then placed in the PT module containing the PT2 solution and boiled in this for 20 minutes at 92 C, then slides were placed in the PT module (Lab Vision™ PT Module, Thermo Scientific, part. No. A80400112) and kept at 92 C for 20 minutes, then slides were transferred to $H_2O$ to cool down slides 2×2 minutes.
6. Pretreatment (PT) 3 (Advanced Cell Diagnostics; Catalog number 310020) was added to each slide by dropper so that the specimens were covered, the slides were placed at 40° C. for 20 minutes, then transferred to Phosphate Buffered Saline 2×2 minutes
7. Slides were fixed in 4% paraformaldehyde in PBS pH7.4 (Genentech Media Prep) for 5 minutes at room temperature, then washed in PBS for 2×1-5 minutes to rinse out the paraformaldehyde
8. Probe Hybridization was performed according to the manufacturer's directions (see, RNAScope 2.0 Manual Assay protocol. Probes (HGF probes or control probes) were hybridized 2 hours at 40° C., then washed 2× in wash buffer (RNAscope 50×FFPE Wash Buffer; Advanced Cell Diagnostics catalog number 310091; diluted to 1× in dH2O) for 2 min each
8. Amplification step 1: slide were incubated for 30 min at 40° C., then washed 2× in wash buffer for 2 min each
9. Amplification step 2: slides were incubated for 15 minutes at 40° C., then washed 2× in wash buffer for 2 min each
10. Amplification step 3: slides were incubated for 30 minutes at 40° C., then washed 2× in wash buffer for 2 min each
11. Amplification step 4: slides were incubated for 15 minutes at 40° C., then washed 2× in wash buffer for 2 min each
12. Amplification step 5: slides were incubate for 30 minutes at room temperature, then washed 2× in wash buffer for 2 min each
13. Amplification step 6: slides were incubated for 15 minutes at room temperature, then washed 2× in wash buffer for 2 min each
14. Detection: DAB A and DAB B (both from the RNAscope® 2.0 Detection Kit-Brown; Advanced Cell Diagnostics; order number 310033) were mixed 1:1, added to slides, then slides were incubated for 10 minutes at room temperature, then rinsed in dH2O
15. Counterstain: Gill's Hematoxylin (Gill's Hematoxylin #2; Polysciences, Inc.; order no. 24243-500) diluted 1:1 in water was added to slides for 2 min, then slides were rinsed in dH2O. Slides were dipped 5× in ammonium water (Ammonium hydroxide; Sigma Aldrich; 221228-25ML-A—diluted to 0.01% in dH2O), then slides were dipped 5× in dH2O
16. Dehydration: slides were dipped 1×70% Reagent Alcohol (70% REAGENTS ALCOHOL, American MasterTech Scientific, Inc.; #ALREA70GAL) for 2 minutes, then in 2×100% Reagent Alcohol for 2 minutes each, then 1× Xylene for 5 minutes.
17. Slides were coverslipped in Permount mounting medium (Tissue Tek® Glas™ Mounting Media; Sakura; order no. 6419).

Steps 6-11 were performed in a humidity control tray (HybEZ™ Humidity Control Tray; Advanced Cell Diagnostics; order no. 310012, used with dH2O-soaked humidifying paper. HybEZ™ Humidifying Paper; ACD; order no. 310015) and incubated in a HybEZ™ Oven (Advanced Cell Diagnostics; order no. 241000ACD).

The probes used in the HGF ISH were: HGF probe: Hs-HGF probes (Advanced Cell Diagnostics; order no. 310761); Positive control probes IIs-UBC probes (ubiquitin C) (Advanced Cell Diagnostics; order no. 310041); and Negative control probes DapB probes (dihydrodipicolinate reductase) (Advanced Cell Diagnostics; order no. 310043).

Scoring Glioblastoma Samples with ISH of HGF mRNA:

Samples displaying positive HGF ISH signal displayed punctate brown dots in the nucleus and/or cytoplasm of cells. Positive HGF ISH signal was observed in tumor cells and benign stromal cells (e.g., reactive astrocytes, glial cells, pericytes and endothelial cells), and positive HGF ISH signal was never observed in morphologically normal brain tissue (for example, in cases where extensive portions of normal brain was present on the section away from the tumor). HGF ISH signal was focal in the vast majority of (if not all) samples, such that positive HGF ISH signal in tumor and/or benign stroma could be observed in some portions of a section and was not observed in other portions of the section. Indeed, it was not unusual for sections to have positive HGF ISH signal in some fields and to lack HGF ISH signal in other fields (sometimes several fields lacked HGF ISH signal). Accordingly, the entire section was scored for presence or absence and prevalence of positive ISH signal in tumor and benign stromal cells, except that morphologically normal brain tissue present on a section away from the tumor was not scored. In some cases, normal brain tissue may have been present within the area included in the tissue field that was subjected to scoring analysis (for example, when normal brain tissue was contained within a tumor area).

Sections from the same tumors were also hybridized with positive (UBC) and negative (DapB) control probes as a control. Any case without UBC positive control ISH positive signal was excluded from the analysis.

The ISH assay had extremely low levels of non-specific (or background) signal, which facilitated detection of low level and prevalence of positive HGF ISH signal. Level of background signal in the assay was evaluated by inclusion of a positive and negative control for HGF expression and background staining in every experiment: The KP4 cell line is known to express and secrete HGF. Slides were prepared with sections of FFPE-fixed KP4 cell pellet and analyzed using the HGF probes (positive control) and DapB probes (negative control). DapB is a bacterial gene that is not expressed in mammalian cells, and thus, positive DapB ISH signal is not expected to be observed in KP4 cells.

Figure 8:
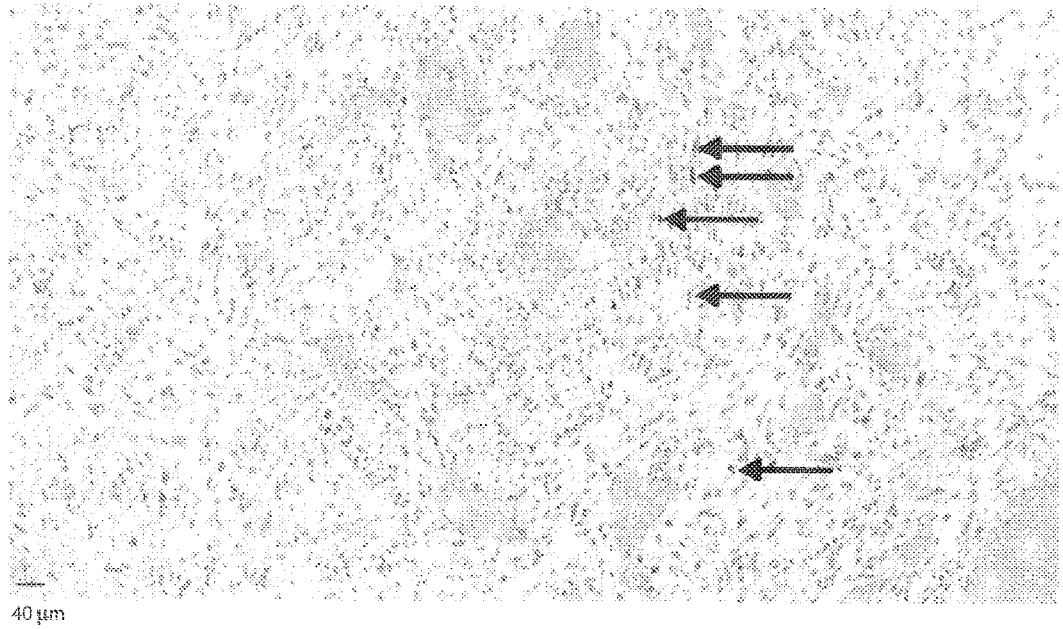
FIG. 8: Exemplary photomicrograph of a glioblastoma section that displayed 3+ HGF ISH signal. The section was viewed using the 10× objective and positive cells were readily identified. Arrows point to exemplary HGF ISH signal positive cells.
Figure 9:
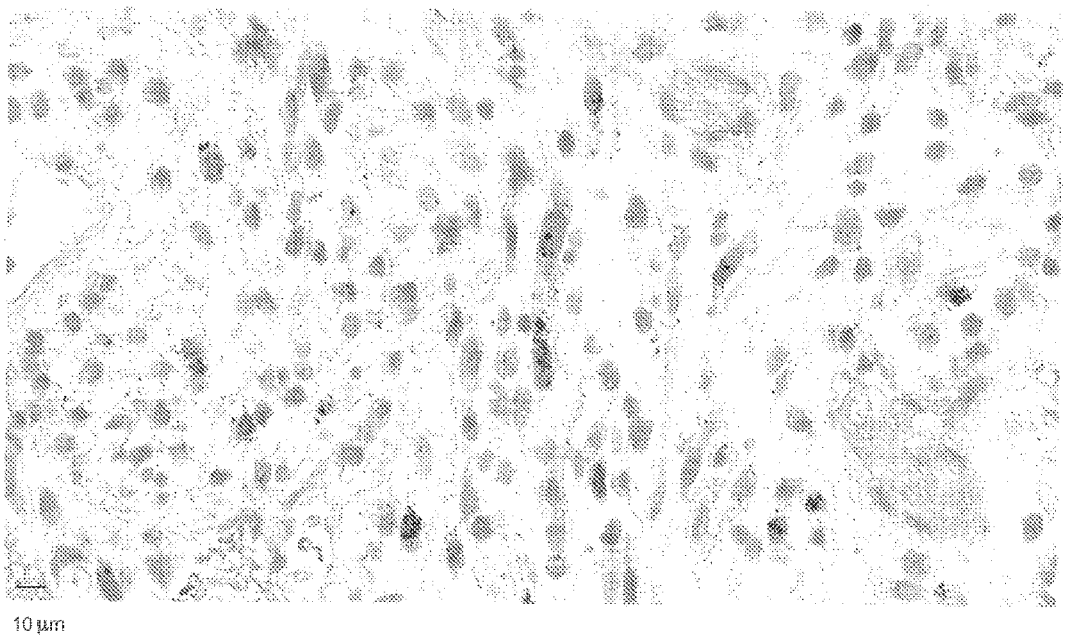
FIG. 9: Exemplary photomicrograph of the glioblastoma section shown in FIG. 10 viewed at high magnification (roughly equivalent to 40× objective). HGF ISH signal was observed in multiple cells scattered throughout the field.

Scoring was performed by scanning the entire section using the 10× objective on a light microscope, then scanning the entire section using the 20× or 40× objective as described below. Samples were scored according to the prevalence of cells with positive HGF ISH signal on a scale from 0 to 3+ as described below. To determine whether signal was present in rare, occasional or numerous cells, the following approach was taken: The entire tumor section was scanned (focusing on tumor and adjacent benign stroma in the sample and excluding extensive portions of morphologically normal brain tissue away from the tumor, as described above) using the 10× objective. If positive HGF ISH signal was easily observed using the 10× objective, the sample was characterized as showing HGF ISH signal in numerous cells, and scored as HGF ISH 3+. FIG. 8 shows a photomicrograph of a glioblastoma section that displayed 3+ HGF ISH signal, viewed under low magnification. FIG. 9 shows a photomicrograph of the same section, viewed at high magnification.

Figure 10:
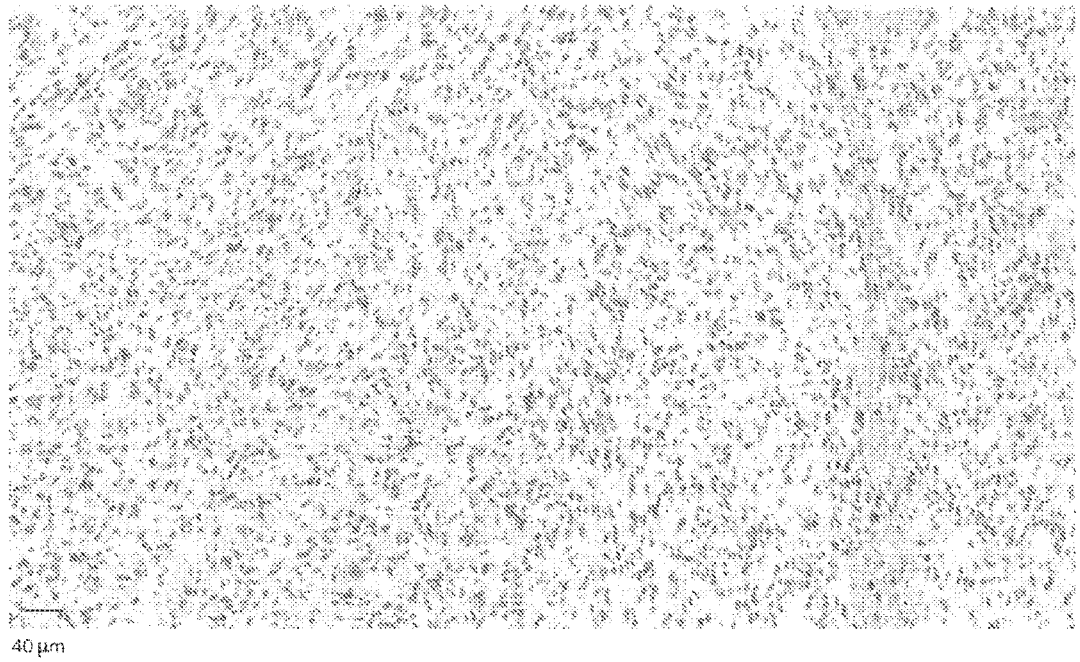
FIG. 10: Exemplary photomicrograph of a glioblastoma section that displayed 1+ HGF ISH signal. The section was viewed using low magnification (roughly equivalent to a 10× objective) and it was difficult to identify HGF ISH signal positive cells.
Figure 11:
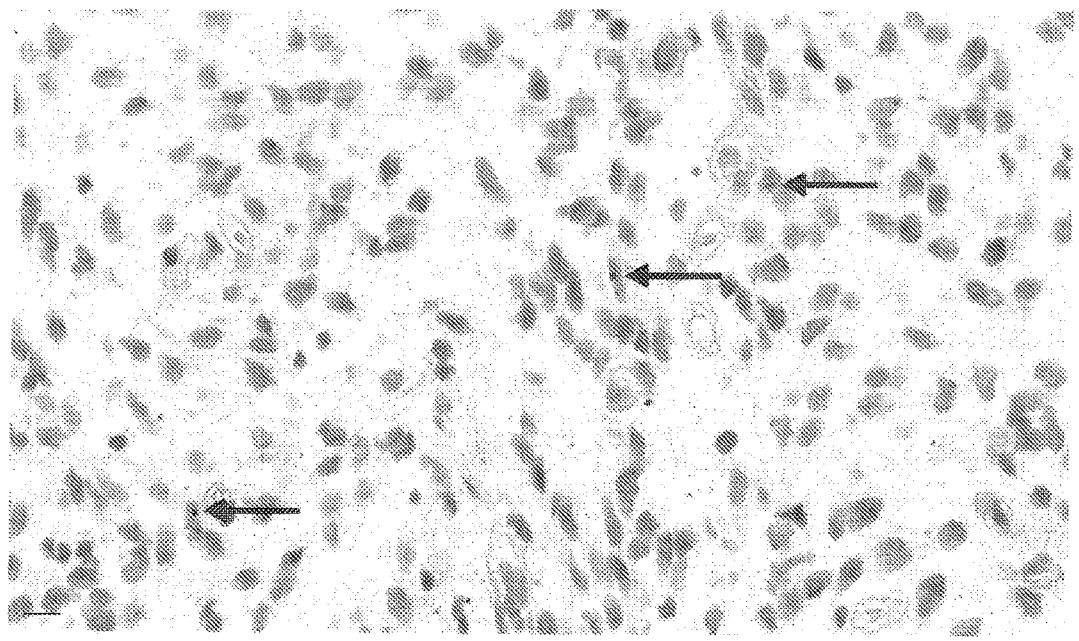
FIG. 11: Exemplary photomicrograph of the glioblastoma section shown in FIG. 10 viewed at high magnification (roughly equivalent to a 40× objective). Weak HGF ISH signal was observed in cells scattered throughout the field. Arrows point to exemplary HGF ISH signal positive cells.
Figure 12:
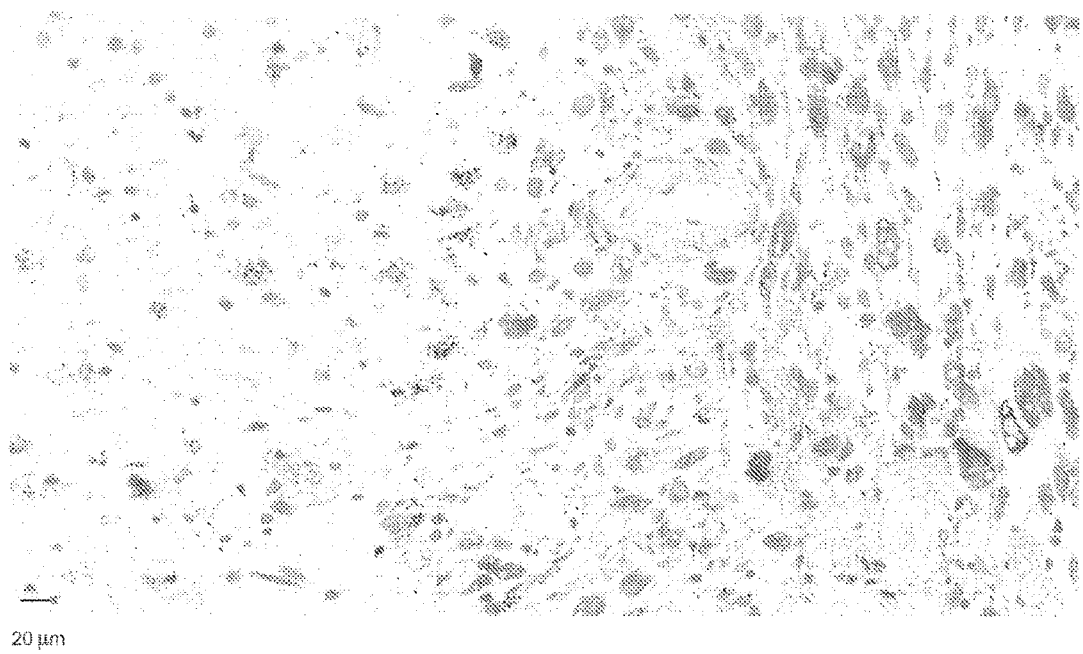
FIG. 12: Exemplary photomicrograph of a glioblastoma section that displayed 3+ HGF ISH signal, viewed at moderate magnification (roughly equivalent to a 20× objective). HGF ISH positive signal was observed in multiple cells at the invasive edge of the tumor.

If positive HGF ISH signal was not easily observed using the 10× objective, the entire tumor section was scanned using the 20× and/or 40× objective. If positive HGF ISH signal was observed in multiple cells as viewed under 20 or 40× (typically in several fields of the slide; sometimes several fields of the section had to be scanned before locating a field with positive signal), the sample was characterized as showing HGF ISH signal in occasional cells and scored as HGF ISH 2+. If very few cells (typically about 10 or fewer in an entire section) with positive HGF ISH signal were observed, e.g., usually requiring the search of multiple fields of the slide before observing positive HGF ISH signal, the samples was characterized as showing HGF ISH signal in rare cells, and scored as HGF ISH 1+. FIG. 10 shows an exemplary photomicrograph of a glioblastoma section that displayed 1+ HGF ISH signal. The section was viewed using low magnification (roughly equivalent to a 10× objective) and it was difficult to identify HGF ISH signal positive cells. FIG. 11 shows an exemplary photomicrograph of the same glioblastoma section viewed at high magnification (roughly equivalent to a 40× objective). Weak HGF ISH signal is observed in cells scattered throughout the field. Arrows point to exemplary HGF ISH signal positive cells. FIG. 12 shows an exemplary photomicrograph of a glioblastoma section that displayed 3+ HGF ISH signal, viewed at moderate magnification (roughly equivalent to a 20× objective). HGF ISH positive signal was observed in multiple cells at the invasive edge of the tumor.

If no HGF ISH signal was observed in a section, the sample was scored as HGF ISH 0.

128 samples were evaluated, 4 samples had inadequate tissue to evaluate, 8 samples were excluded based on inadequate RNA quality (staining was negative for positive control UBC gene ISH). 27 samples were negative for HGF (23%), 49 samples were 1+ for HGF (42%), 34 samples were 2+ for HGF (29%) and 6 samples were 3+ for HGF (5%), 34% were scored as HGF diagnostic positive (HGF ISH 2+ and 3+). 22 samples showed positive HGF ISH signal in tumor cells that were obviously malignant based on cytological criteria (cellular/nuclear atypia).

Figure 13:
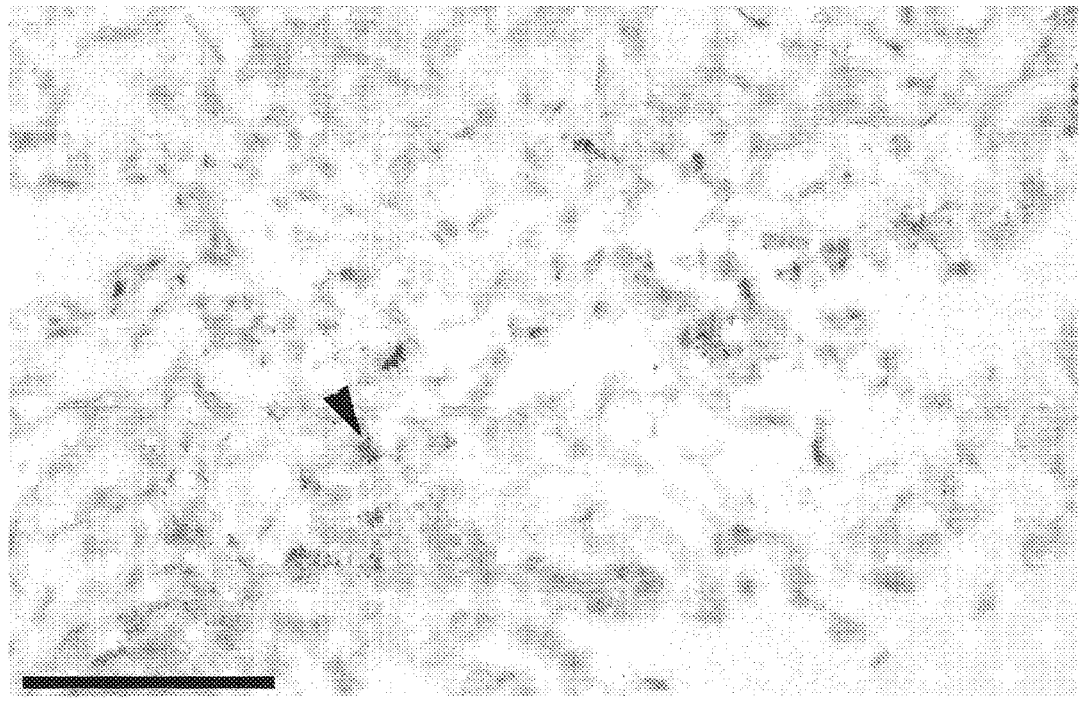
FIG. 13: shows representative in situ hybridization for HGF RNA in a gastric cancer with focal (arrowhead) high expression (3+) in stromal cells. Probe hybridization is shown by the brown chromogen dots against a blue haematoxylin counterstain. Bar=100 um.

Example 2: In-Situ Hybridization Analysis of HGF mRNA Expression in Gastric Cancer and Mesothelioma Samples Formalin-fixed paraffin-embedded gastric cancer samples were subjected to ISH analysis for HGF RNA as described above for glioblastoma samples, and samples were scored essentially as described above for glioblastoma samples, except that the stromal cells found in the gastric cancer samples included fibroblasts, macrophages, endothelial cells. In some cases, a tumor sample may include cancer cells, lymphocytes, leukocytes, stroma, blood vessels, connective tissue, basal lamina, and any other cell type in association with the tumor. FIG. 13: shows representative in situ hybridization of HGF in a gastric cancer with focal (arrowhead) high expression (3+) in stromal cells. Probe hybridization is shown by the brown chromogen against a blue haematoxylin counterstain. Bar=100 um.

Figure 14:
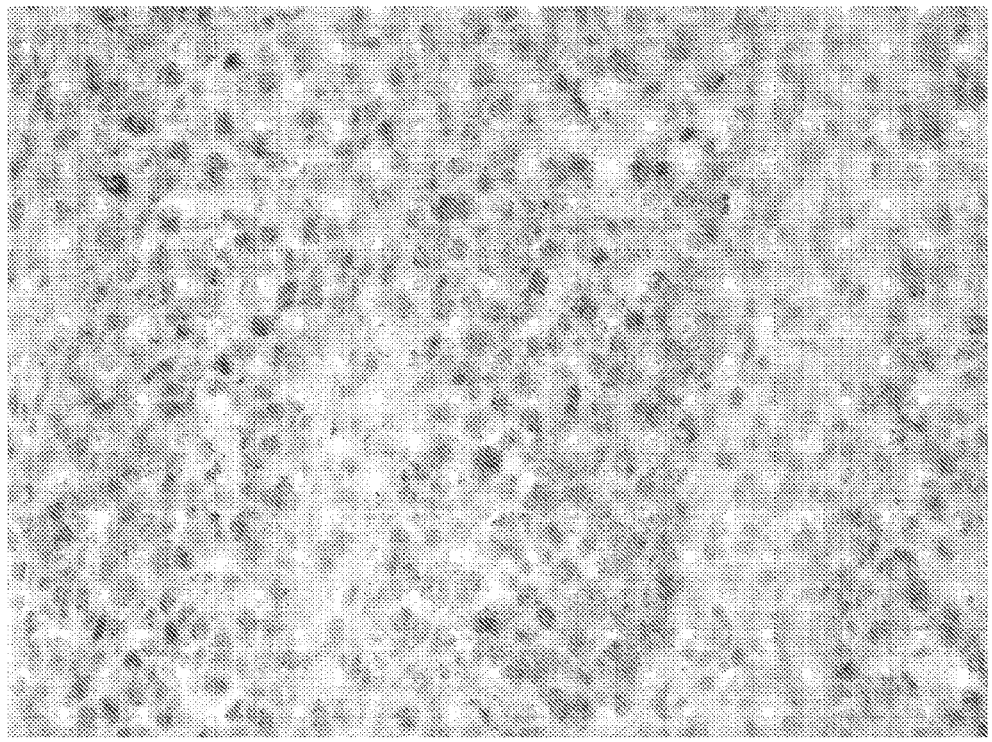
FIG. 14: shows representative in situ hybridization for HGF RNA in a mesothelioma cancer. Probe hybridization is shown by the red chromogen against a blue haematoxylin counterstain.
Figure 16:
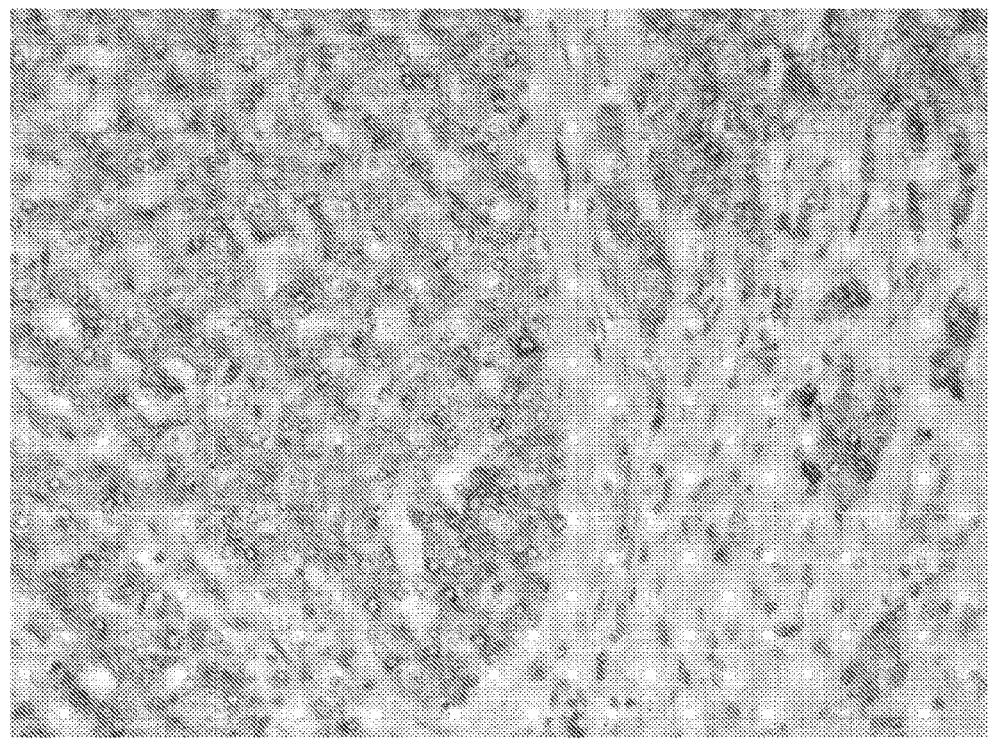
FIG. 16: shows representative in situ hybridization for HGF in mesothelioma cancer displaying autocrine HGF expression. Probe hybridization is shown by the red chromogen against a blue haematoxylin counterstain.
Figure 15:
FIG. 15: shows representative in situ hybridization for HGF RNA in mesothelioma cancer with intratumoral heterogeneity in HGF expression. Probe hybridization is shown by the red chromogen against a blue haematoxylin counterstain.
Figure 15:
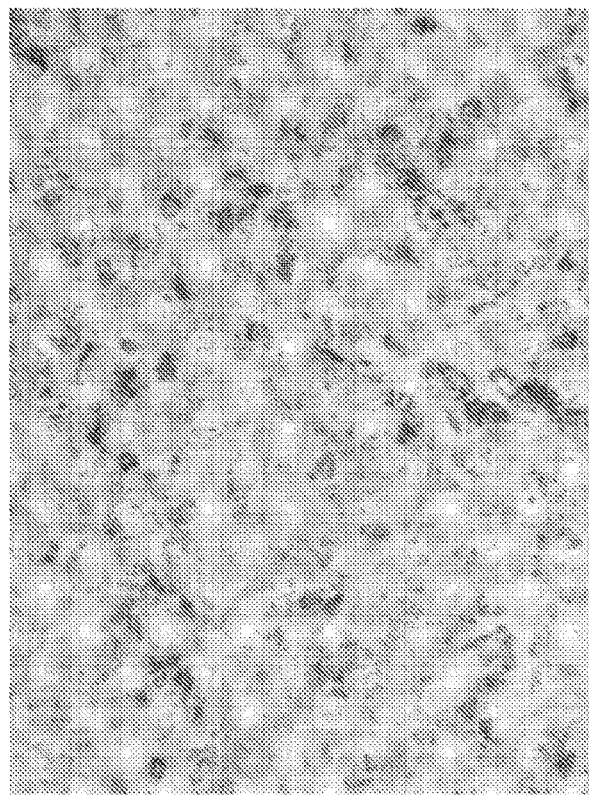

Formalin-fixed paraffin-embedded mesothelioma samples were subjected to ISH analysis for HGF RNA as described above for glioblastoma samples, and samples were scored essentially as described above for glioblastoma samples. FIG. 14: shows representative in situ hybridization for HGF RNA in a mesothelioma cancer with focal high expression (3+) in stromal cells. Probe hybridization is shown by the red chromogen against a blue haematoxylin counterstain. FIG. 15: shows representative in situ hybridization for HGF RNA in mesothelioma cancer with intratumoral heterogeneity in HGF expression. Probe hybridization is shown by the red chromogen against a blue haematoxylin counterstain. FIG. 16: shows representative in situ hybridization for HGF RNA in mesothelioma cancer displaying autocrine HGF expression. Probe hybridization is shown by the red chromogen against a blue haematoxylin counterstain.

Example 3: A Randomized, Double-Blind, Placebo-Controlled, Multicenter Phase II Study Evaluating the Efficacy and Safety of Onartuzumab in Combination with Bevacizumab in Patients with Recurrent Glioblastoma This was a randomized, double-blind, placebo-controlled, multicenter Phase II trial to evaluate the efficacy and safety of onartuzumab+bevacizumab relative to placebo+bevacizumab in patients with glioblastoma at first recurrence.

Background:

Standard treatment for newly diagnosed glioblastoma is surgical debulking followed by radiotherapy and temozolomide (TMZ) with additional maintenance TMZ. Despite the survival benefit associated with such treatment, almost all patients relapse following initial therapy. Patients with recurrent glioblastoma have a median progression-free survival (PFS) of about 4 months and OS of less than 10 months. The optimal management for patients with recurrent glioblastoma remains unclear, as there have been no randomized trials directly comparing active intervention with supportive care. The most important prognostic factors for benefit from re-intervention are pre-treatment performance status and patient age. Active interventions include repeated surgery, re-irradiation, or systemic therapy with an aim to improving or preserving neurological function and prolong progression-free survival (PFS) and overall survival (OS). Chemotherapy with TMZ demonstrated an increase in survival as second-line therapy in initial trials. However, TMZ is now generally used as a component of first-line treatment and hence there is no established chemotherapy regimen available for recurrent glioblastoma.

Study Design:

Patients were randomly assigned (1:1) to one of the two treatment arms: placebo+bevacizumab (Arm A) or onartuzumab+bevacizumab (Arm B). Patients were stratified based on Karnofsky performance status (70%-80% vs. 90%-100%) and age (<50 vs. ≥50 years), as these characteristics have been identified as prognostic factors in patients with recurrent glioblastoma who receive active treatment using a Cox proportional hazards model. The availability of paraffin-embedded tumor sample representative of the glioblastoma diagnosis was mandatory for randomization into the study. Tissue from recurrent surgery was preferred, but tissue from initial surgery was sufficient for study entry. Study treatment continued until disease progression, unacceptable toxicity, patient or physician decision to discontinue, or death. Crossover from placebo+bevacizumab (Arm A) to onartuzumab treatment was not allowed. Upon treatment discontinuation, patients were followed every 6 weeks for survival. FIG. 1 shows an overview of study design.

To characterize the safety and tolerability profile of placebo+bevacizumab and onartuzumab+bevacizumab patients were monitored throughout the study for adverse events (all grades), serious adverse events, any adverse events requiring drug interruption or discontinuation, changes in laboratory values, and physical examination findings.

Efficacy Outcome Measures:

The efficacy outcome measures for this study were as follows.

The primary efficacy outcome measure for this study was:
Progression-free survival (PFS), defined as the time from date of randomization to the date of first documented disease progression or death, whichever occurs first. Disease progression will be determined on the basis of investigator assessment using the RANO criteria. Because glioblastoma does not typically exhibit prolonged disease inactivity (in contrast to low-grade glioma), the duration of time without tumor progression is usually clinically meaningful.

The secondary efficacy outcome measures for this study were:
Overall survival (OS), defined as the time from randomization until death from any cause Overall survival-9 (OS-9), defined as the percentage of patients who are alive at 9 months after randomization Progression-free survival-6 (PFS-6), defined as the percentage of patients who are alive and progression free at 6 months after randomization Overall response rate (ORR), defined as the percentage of patients enrolled in each treatment arm who are judged by the investigators to have an objective response as determined using the RANO criteria Duration of response (DOR), defined as the time from the first occurrence of a documented objective response to disease progression (as determined by the investigator using the RANO criteria) or death from any cause during the study The safety outcome measures for this study were as follows:
Incidence, nature, and severity of adverse events, including serious adverse events (SAEs), according to NCI CTCAE version 4.0

Changes in clinical laboratory results during and following administration of the study drugs Incidence and serum levels of ATAs against onartuzumab The PK outcome measures for this study were as follows:
Minimum concentration of onartuzumab and bevacizumab ($C_{min}$) in serum prior to the first infusion on Day 1 of Cycles 1, 2, 3 and 4 and at the study drug discontinuation visit (SDDV)

Maximum concentration of onartuzumab and bevacizumab ($C_{max}$) in serum 30 minutes after the last infusion on Day 1 of Cycles 1, 2, 3, and 4

The exploratory outcome measures for this study were as follows:
Corticosteroid use Changes in biomarkers, and correlation of biomarkers with PFS, ORR, and OS Neurocognitive function as determined using the MMSE Patient-reported outcomes of glioblastoma and treatment-related symptom severity and interference as determined using the MDASI-BT Materials and Methods Patients:

Patients were potentially eligible for this study if they had glioblastoma at first recurrence after concurrent or adjuvant chemoradiotherapy. Patients in the study met the following criteria for study entry:

Disease Characteristics included the following:
Histologically confirmed glioblastoma at first recurrence after concurrent or adjuvant chemoradiotherapy Imaging confirmation of first tumor progression or regrowth as defined by the RANO criteria Prior treatment with temozolomide (TMZ).

No more than one prior line of chemotherapy. Concurrent and adjuvant TMZ-based chemotherapy, including the combination of TMZ with an investigational agent, is considered one line of chemotherapy.

No prior treatment with bevacizumab or other VEGF- or VEGF-receptor-targeted agent No prior exposure to experimental treatment targeting either the HGF or Met pathway Prior therapy with gamma knife or other focal high-dose radiotherapy is allowed, but the patient must have subsequent histologic documentation of recurrence, unless the recurrence is a new lesion outside the irradiated field No prior treatment with prolifeprospan 20 with carmustine wafer No prior intracerebral agent Recovery from the toxic effects of prior therapy
No evidence of recent hemorrhage on baseline MRI of the brain
No need for urgent palliative intervention for primary disease (e.g., impending herniation)
Availability of formalin-fixed paraffin-embedded tumor tissue representative of glioblastoma
Patient Characteristics included the following:
Willingness and ability to provide written informed consent and to comply with the study protocol as judged by the investigator
Age ≥18 years
Karnofsky performance status ≥70%
Stable or decreasing dose of corticosteroids within 5 days prior to randomization
Patients who meet any one of certain criteria were excluded from study entry, including the following:
Patients unable to undergo brain MRI scans with IV gadolinium
Absolute neutrophil count (ANC) <1.5×10$^9$/L; platelet count <100×10$^9$/L; or hemoglobin (Hb) <9.0 g/dL within 7 days prior to enrollment. Note: The use of transfusion or other intervention to achieve Hb ≥9 g/dL is acceptable.
Total bilirubin ≥1.5×ULN (except in patients diagnosed with Gilbert's disease) AST (SGOT), ALT (SGPT), or alkaline phosphatase (ALP) ≥2.5×ULN
Serum creatinine ≥1.5×ULN or calculated creatinine clearance (CrCl)<60 mL/min (Cockcroft and Gault)
Urine dipstick test for proteinuria ≥2+; Patients found to have ≥2+ proteinuria should undergo a 24-hour urine collection and must demonstrate ≤1.0 g of protein in 24 hours).
International normalized ratio (INR), protothrombin time (PT), or activated partial thromboplastin time (ATT) as follows:
  In the absence of therapeutic intent to anticoagulate the patient: INR>1.5 or PT>1.5×ULN or aPTT>1.5× ULN
  OR
  In the presence of therapeutic intent to anticoagulate the patient: INR or PT and aPTT not within therapeutic limits (according to the medical standard in the institution) or patient has not been on a stable dose of anticoagulants for at least 2 weeks before randomization. (Note: Per ASCO guidelines, low-molecular-weight heparin [LMWH] should be the preferred approach.)
Inadequately controlled hypertension (defined as systolic blood pressure >150 mmHg and/or diastolic blood pressure >100 mmHg while on antihypertensive medication)
Uncontrolled diabetes, as evidenced by fasting serum glucose level >200 mg/dL
Prior history of hypertensive crisis or hypertensive encephalopathy
New York Heart Association (NYHA) Grade II or greater congestive cardiac failure
History of myocardial infarction (within 12 months) or unstable angina (within 6 months) prior to randomization
History of stroke or transient ischemic attacks within 6 months prior to randomization
Significant vascular disease (e.g., aortic aneurysm requiring surgical repair or recent peripheral arterial thrombosis) within 6 months prior to randomization
Evidence of bleeding diathesis or coagulopathy (in the absence of therapeutic anticoagulation)
History of abdominal fistula or gastrointestinal perforation within 6 months prior to randomization
History of intracranial abscess within 6 months prior to randomization
Major surgical procedure, open biopsy, or significant traumatic injury within 28 days prior to randomization
Anticipation of need for major surgical procedure during the course of the trial
Serious non-healing wound, active ulcer, or untreated bone fracture
History of another malignancy in the previous 3 years, with a disease-free interval of <3 years. Patients with prior history of in situ cancer or basal or squamous cell skin cancer are eligible.
Evidence of any active infection requiring hospitalization or IV antibiotics within 2 weeks prior to randomization
Known hypersensitivity to any excipients of onartuzumab or bevacizumab
Hypersensitivity to Chinese hamster ovary cell products or other recombinant human or humanized antibody
Study Treatment
Onartuzumab/Onartuzumab Placebo.
Onartuzumab was provided as a sterile liquid in a single-use 15-cc vial containing 600 mg of onartuzumab. Onartuzumab Drug Product was formulated as 60 mg/ml, onartuzumab in 10 mM histidine acetate, 120 mM sucrose, 0.4 mg/mL polysorbate 20, pH 5.4. Onartuzumab placebo consisted of 250 cc 0.9% normal saline solution (NSS) IV bags and will be provided by the investigative site. Once onartuzumab was diluted, the solution must be administered within 8 hours.
Bevacizumab.
Bevacizumab was supplied as a clear to slightly opalescent, colorless to pale brown, sterile liquid for IV infusion in single-use vials that are preservative-free. It was supplied in 20-mL (400-mg, 25 mg/mL) glass vials with a 16-mL fill. The formulation contained sodium phosphate, trehalose, polysorbate 20, and Sterile Water for Injection (SWFI), USP.
Dosage, Administration
Dosing of onartuzumab/bevacizumab/placebo depended on the assigned treatment arm. In this study, onartuzumab/onartuzumab placebo was administered first followed by bevacizumab. After a recommended observation period of 60 minutes following at the end of onartuzumab/onartuzumab placebo infusion, bevacizumab was administered.
Patients in Arm A received onartuzumab placebo throughout the study. Patients in arm B received 15 mg/kg onartuzumab every three weeks throughout the study. The dose of onartuzunmb/onartuzumab placebo was based on the patient's weight at screening. This dose was administered throughout the study and will not change according to weight. Liquid onartuzumab was diluted with 0.9% NSS into a total volume of 250 mL. Once onartuzumab was diluted into NSS, the solution was recommended to be used within 8 hours. Dextrose should not be used for dilution of onartuzumab. Any remaining solution was recommended to be discarded. Onartuzumab/onartuzumab placebo was administered as IV infusions. The first dose was infused over 60 minutes (±10 minutes). The onartuzumab/onartuzumab placebo infusion may be slowed or interrupted for patients who experience infusion-associated symptoms. Patients were observed for at least 60 minutes after onartuzumab/onartuzumab placebo dosing for fever, chills, or other infusion-associated symptoms. Subsequently, doses of onartuzumab/onartuzumab placebo were administered over 30 (±10) minutes, provided the patient tolerated the previous infusions.

Patients in Arm A and Arm B received 15 mg/kg bevacizumab every three weeks (after onartuzumab infusion) throughout the study. The dose of bevacizumab was based on the patient's weight at screening and will remain the same throughout the study unless the patient's weight changes by >10%. Bevacizumab was diluted in 0.9% sodium chloride injection, USP, to a total volume of 100 mL. The initial dose was delivered over 90±15 minutes. If the first infusion was tolerated without any infusion-associated adverse events (fever and/or chills), the second infusion was delivered over 60±10 minutes. If the 60-minute infusion was well tolerated, all subsequent infusions were delivered over 30±10 minutes.

Statistical Analysis.

The treatment comparison of PFS was based on a stratified log-rank test at the 0.05 level of significance (two-sided). The stratification factors were Karnofsky performance status (70%-80% vs. 90%-100%) and age (<50 vs. ≥50 years). Kaplan-Meier methodology was used to estimate median PFS for each treatment arm, and the Kaplan-Meier curve was constructed to provide a visual description of the difference between onartuzumab+bevacizumab and placebo+bevacizumab. Estimates of the treatment effect were expressed as hazard ratios (HRs) through use of a stratified Cox model, including 95% confidence intervals (CIs). OS was defined as the time from randomization until death due to any cause. Data for patients who are not reported as having died at the time of analysis were censored at the date when they were last known to be alive; if no post-baseline data were available, OS was censored at the date of randomization. The analysis methods were the same as those for PFS. OS-9 was defined as the percentage of patients who are alive at 9 months. Kaplan-Meier methods are used to estimate OS-9, along with the standard error and the corresponding 95% CIs using Greenwood's formula. The 95% CI and p-value for the difference between the OS-9 from Arms A and B are determined by the z-test using the standard errors estimated from Greenwood's formula. PFS-6 is defined as the percentage of patients who are alive and progression free at 6 months (24 weeks). The analysis methods are the same as those for OS-9. Objective response was defined as a CR or PR. Patients without a post-baseline disease assessment are considered as nonresponders. The analysis population for ORR is all randomized patients with measurable disease at baseline. An estimate of ORR and its 95% CI is calculated using the Blyth-Still-Casella method for each treatment arm. CIs for the difference in ORRs between the two arms are determined using the normal approximation to the binomial distribution. DOR is defined as the time from the initial response to disease progression or death among patients who have experienced a CR or PR during study. Patients who had not progressed or died at the time of analysis are censored at the last disease assessment date. DOR is estimated using Kaplan-Meier methodology. Comparisons between treatment arms through use of the unstratified log-rank test were made for descriptive purposes only.

Exploratory Analyses include the following:

Mini-Mental State Examination (MMSE).

Changes from baseline of neurocognitive function using the MMSE are summarized by treatment arm and timepoint.

Corticosteroids.

The use of corticosteroids at baseline and changes in dexamethasone-equivalent dose from baseline is summarized by treatment arm and timepoint.

Biomarkers.

Exploratory biomarker analyses was performed in an effort to understand the association of these markers with study drug response, including efficacy and/or adverse events.

Patient-Reported Outcomes (PROs).

PROs of disease- and treatment-related symptom severity and symptom interference are assessed using the MD Anderson Symptom Inventory-Brain Tumor questionnaire (MDASI-BT). For all patients, the MDASI-BT symptom severity and symptom interference subscales are summarized by the mean (and 95% CI) and plotted by time. The mean (and 95% CI) changes from baseline (Cycle 1 Day 1 pre-dose) as well as the absolute scores at each timepoint are reported. Scoring is based on the MDASI and MDASI-BT validation papers (Cleeland et al., Cancer (2000) 89:1634-46; Armstrong et al., Neurooncol (2006) 80:27-35). The mean (and 95% CI) change from baseline (Cycle 1 Day 1) is compared between the two primary treatment arms (onartuzumab+bevacizumab and bevacizumab+placebo).

Results.

129 patients were randomized into the two arms. The median survival follow-up in months was 9.9 (Pbo+Bev), 9.8 (Ona+Bev). The clinical data cutoff date for this analysis was Nov. 7, 2013.

Figure 2:
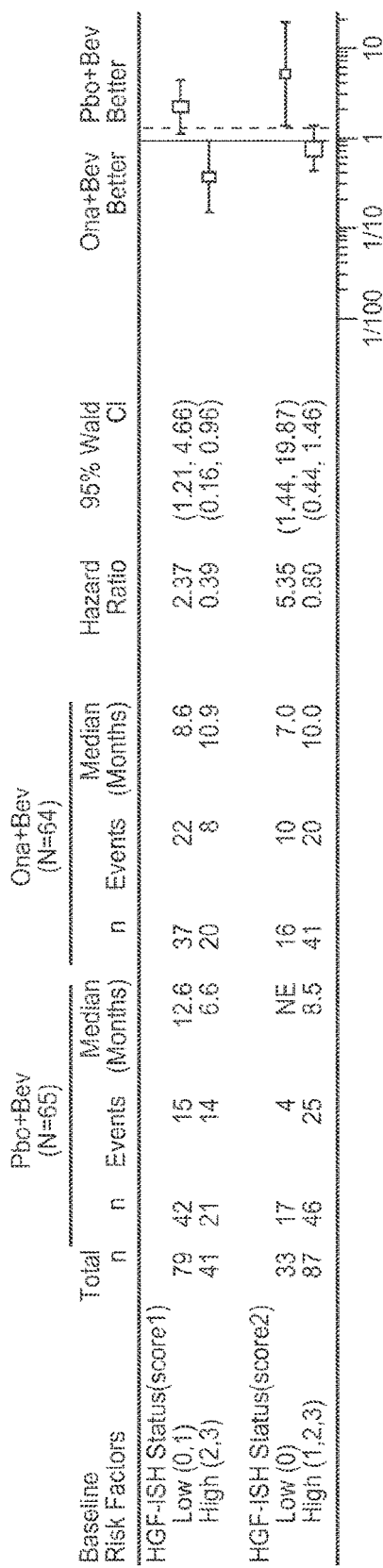
FIG. 2: shows sub-group analysis of overall survival according to HGF ISH status. 41 patients (approximately 32% of total patients) had HGF 2+ or 3+ samples. HRs were unstratified.

In recurrent glioblastoma patients, treatment with the combination of c-met antagonist onartuzumab and VEGF antagonist bevacizumab demonstrated:

(i) a markedly longer PFS and OS in HGF ISH 2+/3+ relative to the control arm; and (ii) a markedly shorter PFS and OS in HGF ISH 0/1+ relative to the control arm FIG. 2: shows sub-group analysis of overall survival according to HGF ISH status. Patients with high HGF ISH (2+/3+) had a median overall survival of 6.6 months when treated with placebo+bevacizumab versus a median overall survival of 10.9 months when treated with onartuzumab+bevacizumab (HR=0.39 (95% CI 0.16, 0.96)). Patients with low HGF ISH (0/1+) had a median overall survival of 12.6 months when treated with placebo+bevacizumab versus a median overall survival of 8.6 months when treated with onartuzumab+bevacizumab (HR=2.37 (95% CI 1.21, 4.66)).

Figure 3:
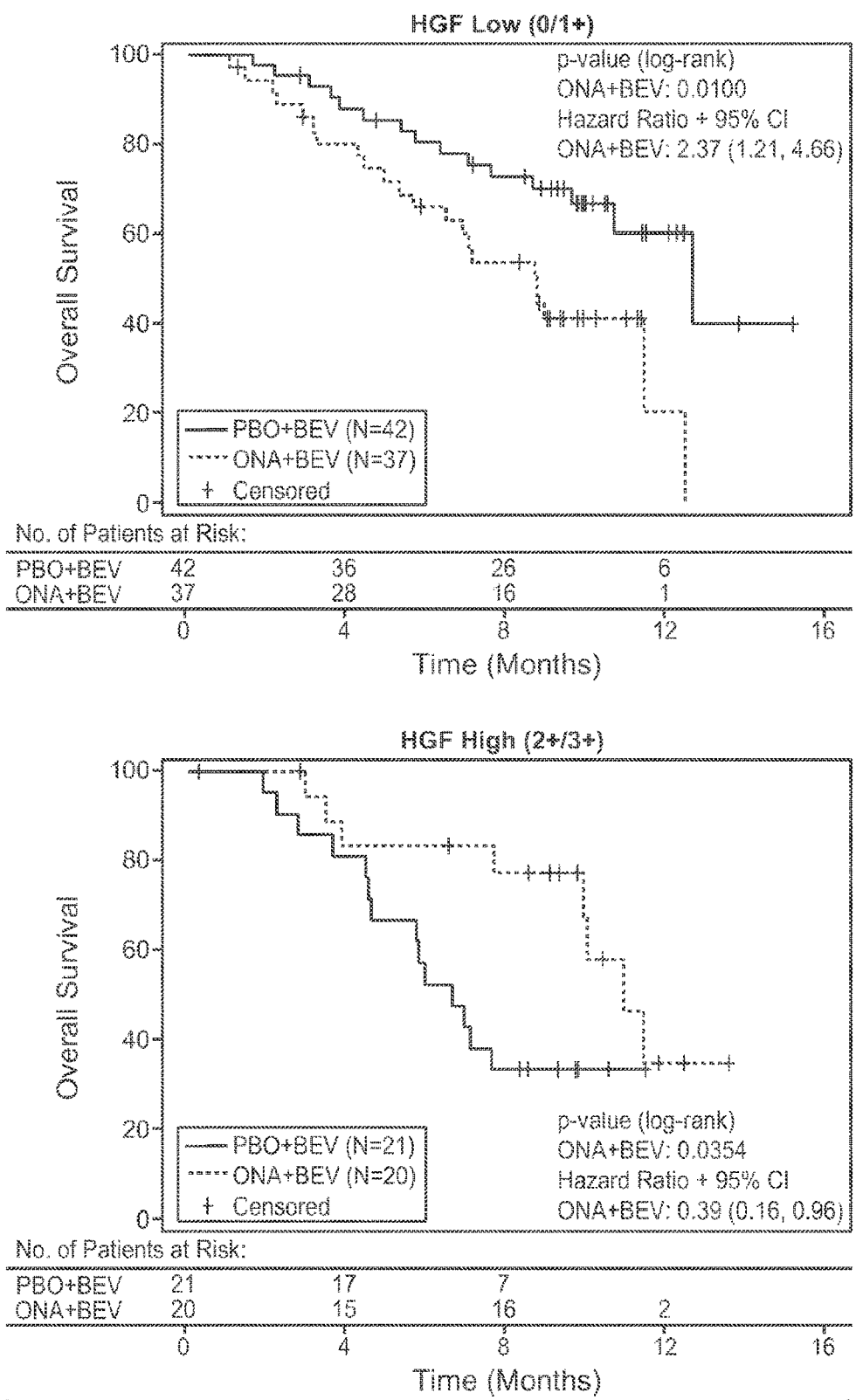
FIG. 3: shows Kaplan-Meier analysis for overall survival in HGF ISH low (0/1+) patients and HGF ISH high (2+/3+) patients. Bevacizumab+placebo arm=solid line. Bevacizumab+onartuzumab arm=dashed line.

FIG. 3: shows Kaplan-Meier analysis for overall survival in HGF ISH low (0/1+) patients and HGF ISH high (2+/3+) patients.

Figure 4:
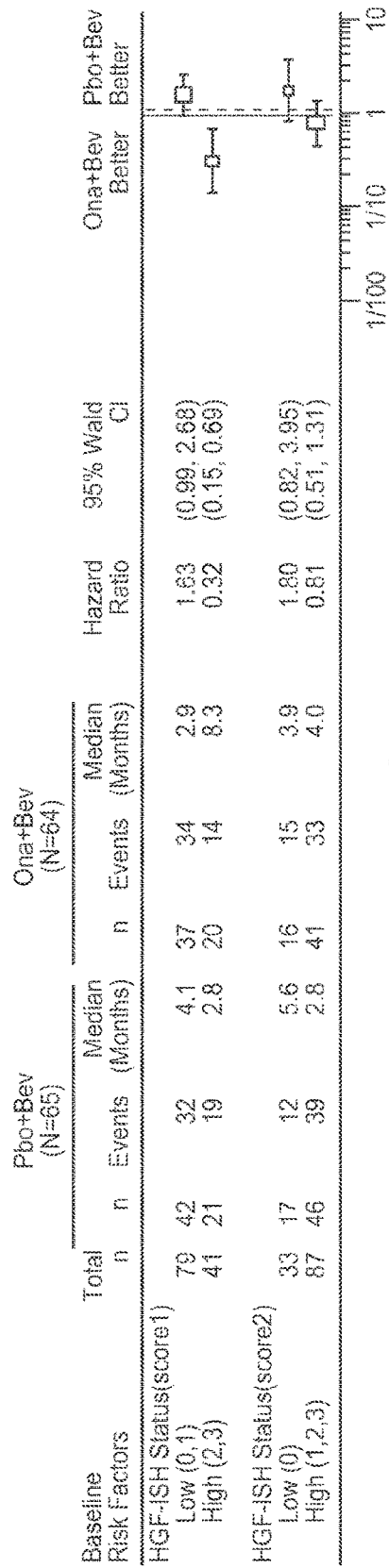
FIG. 4: shows sub-group analysis of progression-free survival according to HGF ISH status. HRs were unstratified.

FIG. 4: shows sub-group analysis of progression-free survival according to HGF ISH status. Patients with high HGF ISH (2+/3+) had a median progression-free survival of 2.8 months when treated with placebo+bevacizumab versus a median overall survival of 8.3 months when treated with onartuzumab+bevacizumab (HR=0.32 (95% CI 0.15, 0.6)). Patients with low HGF ISH (0/1+) had a median progression-free survival of 4.1 months when treated with placebo+bevacizumab versus a median overall survival of 2.9 months when treated with onartuzumab+bevacizumab (HR=1.63 (95% CI 0.99, 2.68)).

Figure 5:
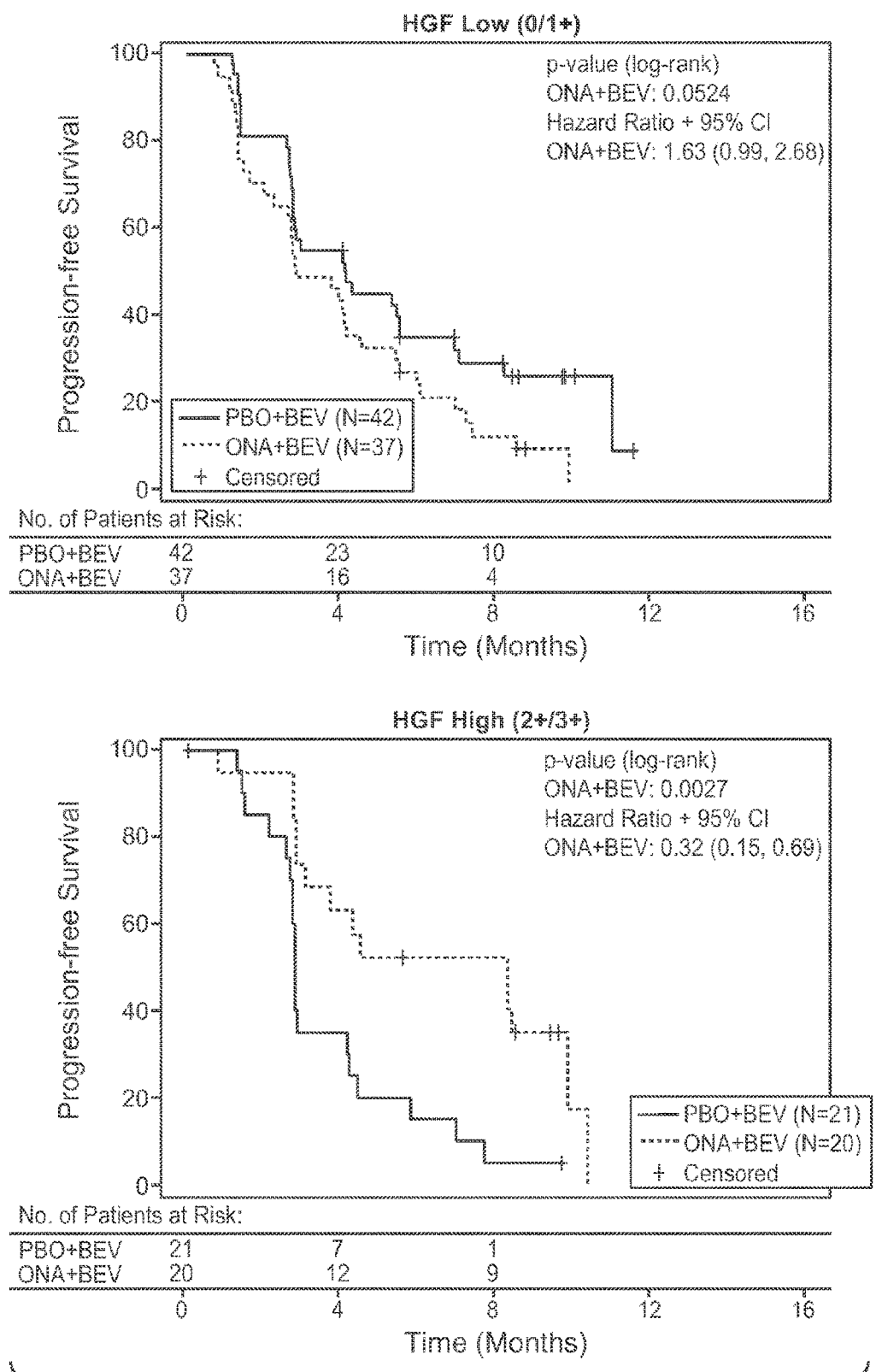
FIG. 5: shows Kaplan-Meier analysis for progression-free survival in HGF ISH low (0/1+) patients and HGF ISH high (2+/3+) patients. Bevacizumab+placebo arm=solid line. Bevacizumab+onartuzumab arm=dashed line.

FIG. 5: shows Kaplan-Meier analysis for progression-free survival in HGF ISH low (0/1+) patients and HGF ISH high (2+/3+) patients.

Figure 6:
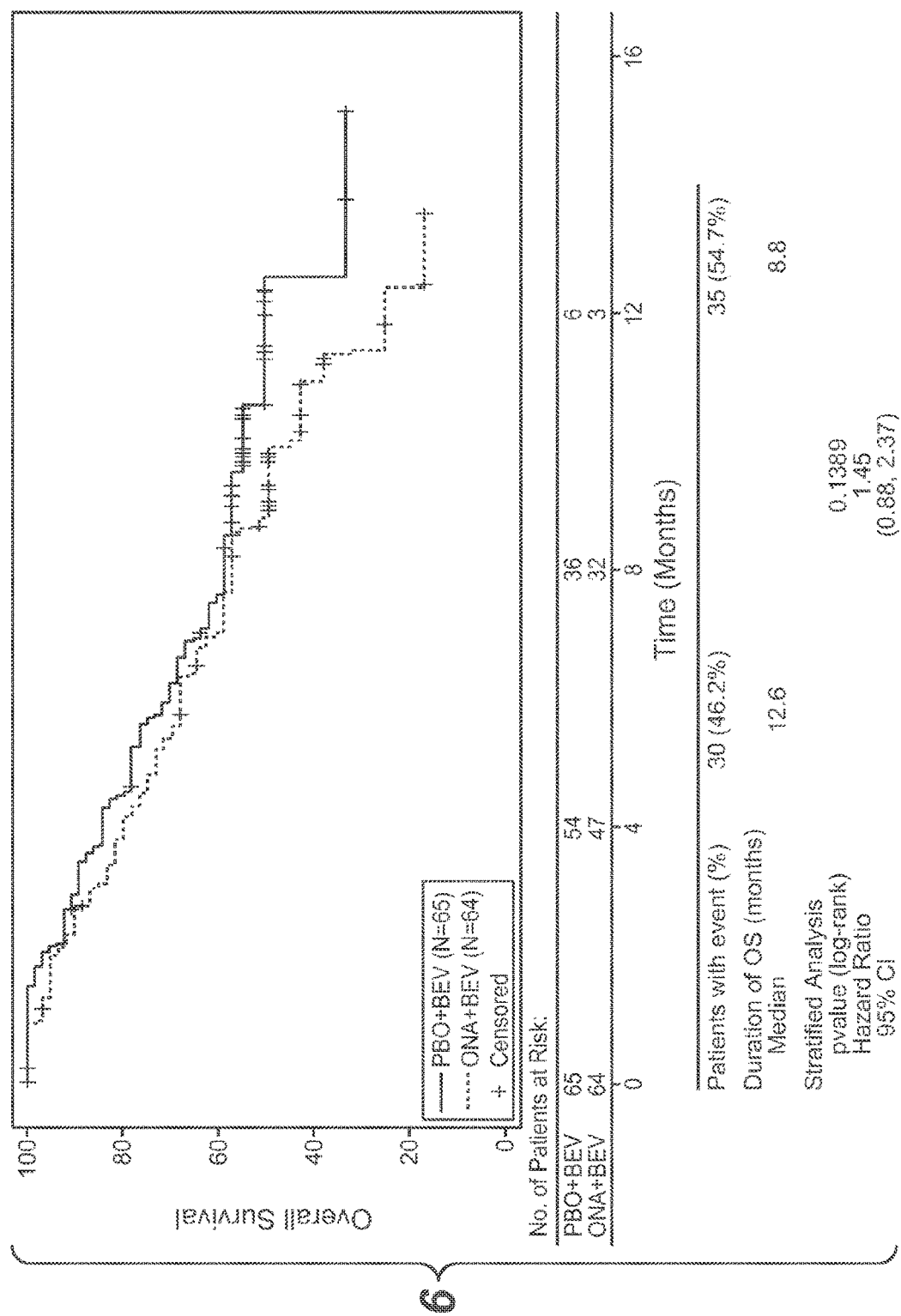
FIG. 6 shows analysis of overall survival in patients randomized to bevacizumab+placebo (solid line) verses patients randomized to bevacizumab+onartuzumab (dashed line). HR was from stratified analysis.

FIG. 6 shows analysis of overall survival in all patients randomized to bevacizumab+placebo (solid line) versus patients randomized to bevacizumab+onartuzumab (dashed line).

Figure 7:
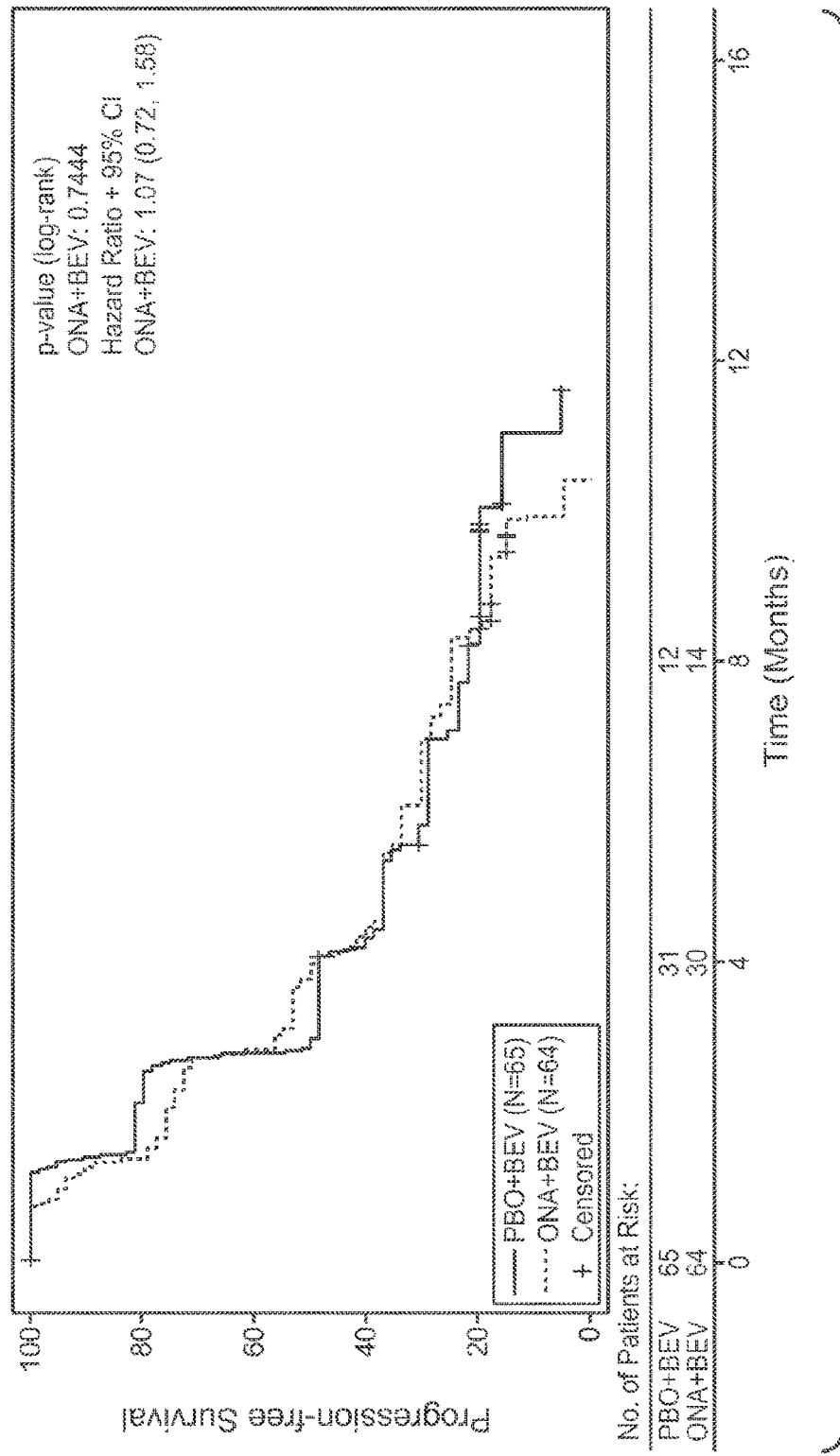
FIG. 7: shows analysis of progression-free survival in patients randomized to bevacizumab+placebo (solid line) verses patients randomized to bevacizumab+onartuzumab (dashed line). HR was from stratified analysis.

FIG. 7: shows analysis of progression-free survival in all patients randomized to bevacizumab+placebo (solid line) versus patients randomized to bevacizumab+onartuzumab (dashed line).

Although the foregoing invention has been described in some detail by way of illustration and example for purposes of clarity of understanding, the descriptions and examples should not be construed as limiting the scope of the invention.

Example 3a: Analysis of the Randomized, Double-Blind, Placebo-Controlled, Multicenter Phase II Study Evaluating the Efficacy and Safety of Onartuzumab in Combination with Bevacizumab in Patients with Recurrent Glioblastoma Using PCR The randomized, double-blind, placebo-controlled, multicenter Phase II trial to evaluate the efficacy and safety of onartuzumab+bevacizumab relative to placebo+bevacizumab in patients with glioblastoma at first recurrence described above was evaluated using PCR. For this analysis. HGF mRNA expression levels were evaluated using Fluidigm Gene Expression Analysis.

Protocol:

10 microgram thick sections of paraffin-embedded, formalin-fixed glioblastoma tumor tissue samples were cut. The RNA was then extracted, and protein and DNA were removed. 2 µl of total RNA was reverse-transcribed to cDNA and pre-amplified in a single reaction using Superscript III/Platinum Taq (Invitrogen) and Pre-amplification reaction mix (Invitrogen). Primer/probe sets selected to detect the expression of HGF were included in a pre-amplification reaction (which included an additional 95 probe primer pairs) at a final dilution of 0.05× original Taqman assay concentration (Applied Biosystems). The thermocycling conditions were as follows: 1 cycle of 50° C. for 15 min, 1 cycle of 70° C. for 2 min, then 14 cycles of 95° C. for 15 sec and 60° C. for 4 min.

Pre-amplified cDNA was diluted 1.94-fold and then amplified using Taqman Universal PCR MasterMix (Applied Biosystems) on the BioMark BMK-M-96.96 platform (Fluidigm) according to the manufacturer's instructions. All samples were assayed in triplicate. Two custom-designed reference genes that were previously evaluated for their expression stability across multiple cell lines, fresh-frozen tissue samples, and FFPE tissue samples, AL-1377271 and VPS-33B, were included in the expression panel. A mean of the Ct values for the two reference genes was calculated for each sample, and expression levels of HGF was determined using the delta Ct (dCt) method as follows: Mean Ct (Target Gene)−Mean Ct (Reference Genes).

Results.

129 patients were randomized into the two arms. The median survival follow-up in months was 9.9 (Pbo+Bev), 9.8 (Ona+Bev). The clinical data cutoff date for this analysis was Nov. 7, 2013.

In recurrent glioblastoma patients, treatment with the combination of c-met antagonist onartuzumab and VEGF antagonist bevacizumab demonstrated:

(i) A markedly longer PFS and OS in patients with upper 25% HGF-PCR expression relative to the control arm; and (ii) A markedly shorter PFS and OS in patients with lower 75% HGF-PCR expression relative to the control arm.

Figure 17:
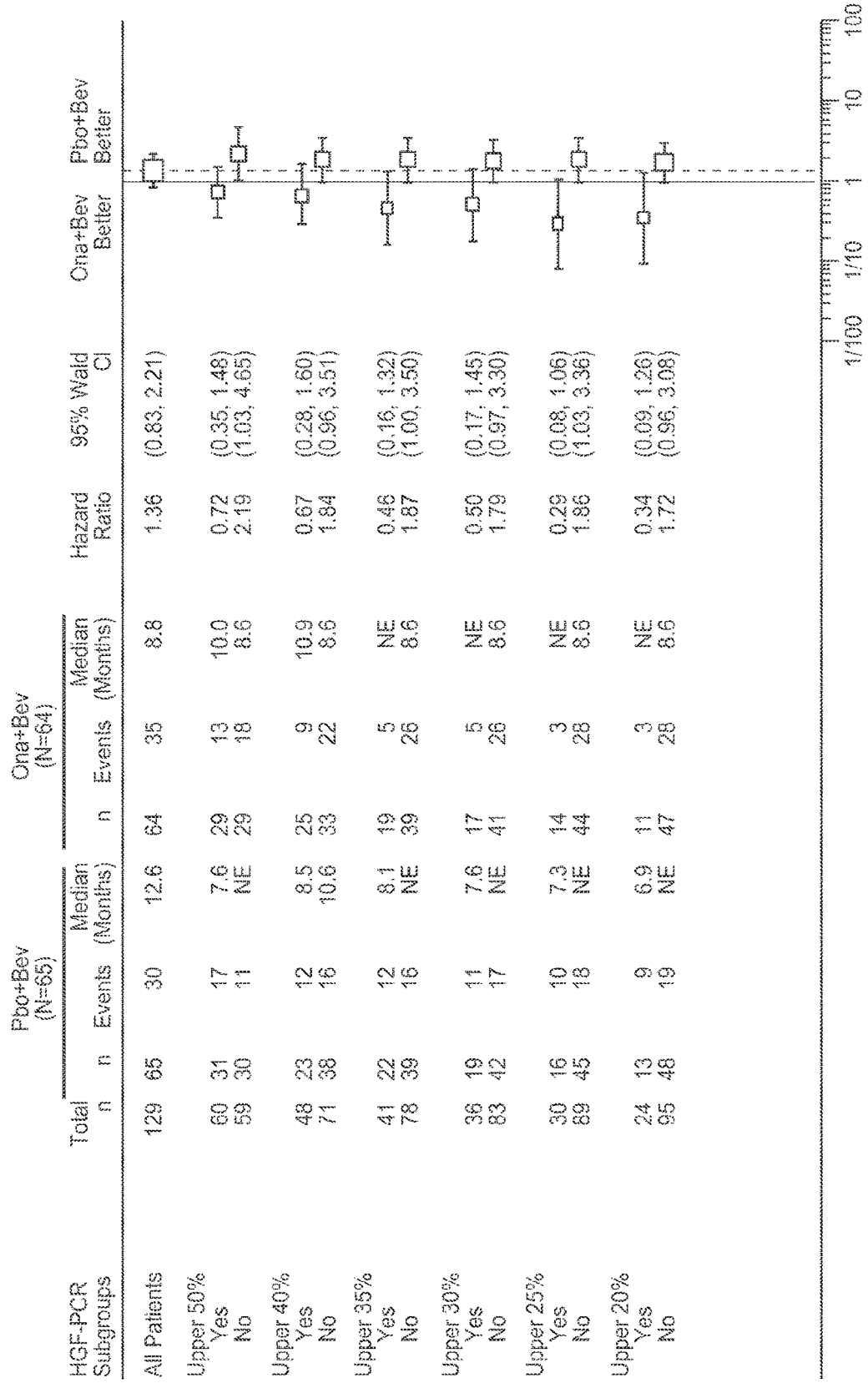
FIG. 17: shows sub-group analysis of overall survival according to HGF-PCR status. HRs were unstratified.

FIG. 17: shows sub-group analysis of overall survival according to HGF-PCR expression. Patients with high HGF-PCR (upper 25%) had a median overall survival of 7.3 months in placebo+bevacizumab arm versus an unreached median overall survival in onartuzumab+bevacizumab arm (HR=0.29 (95% CI 0.08, 1.06)). Patients with low HGF-PCR (lower 75%) had an unreached median overall survival in placebo+bevacizumab arm versus a median overall survival of 8.6 months in onartuzumab+bevacizumab arm (HR=1.86 (95% CI 1.03, 3.36)).

Figure 18:
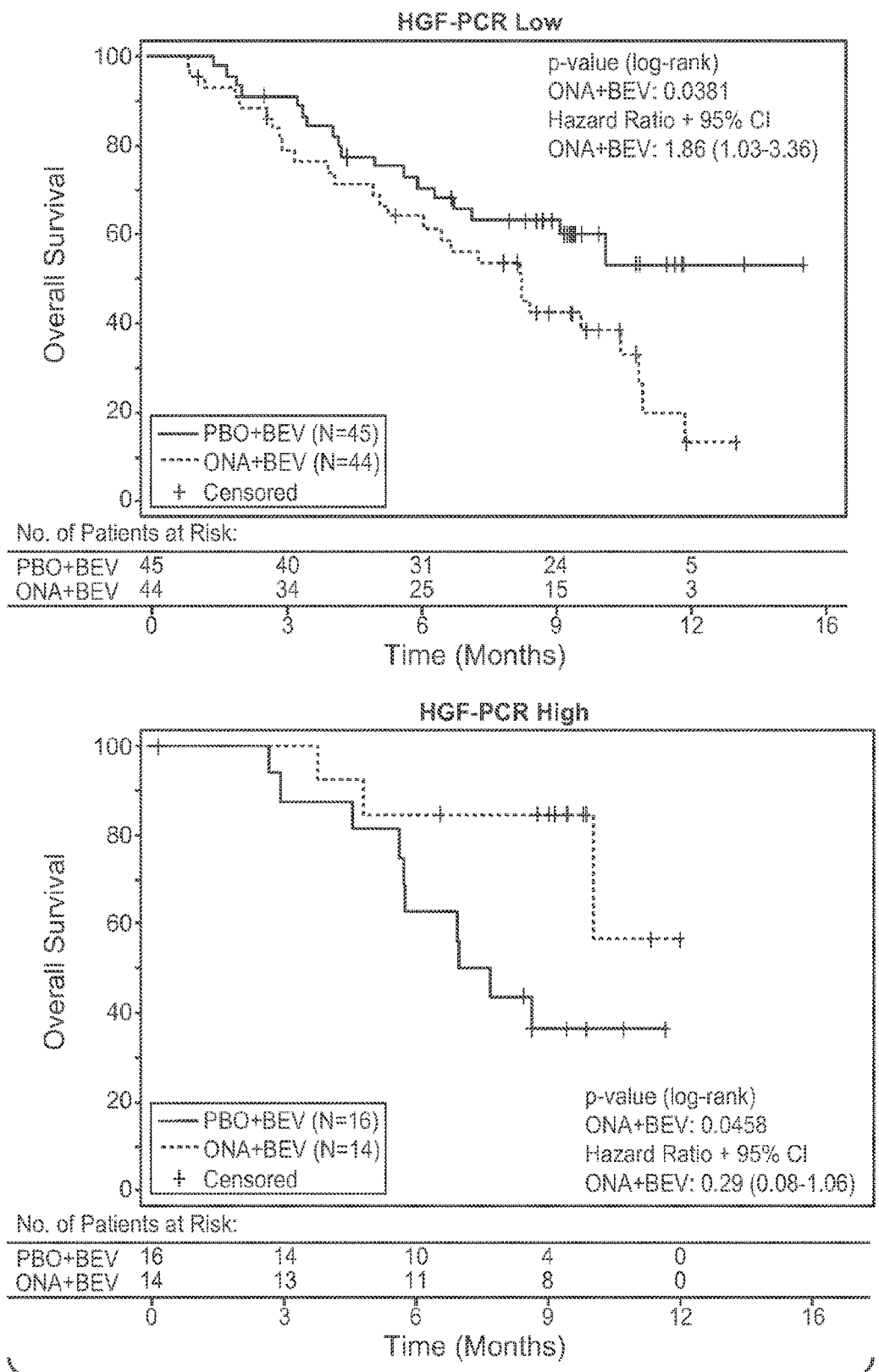
FIG. 18: shows Kaplan-Meier analysis for overall survival in HGF-PCR low (lower 75%) patients and HGF-PCR high (upper 25%) patients. Bevacizumab+placebo arm=solid line. Bevacizumab+onartuzumab arm=dashed line.

FIG. 18: shows Kaplan-Meier analysis for overall survival in low HGF-PCR (lower 75%) patients and high HGF-PCR (upper 25%) patients.

Figure 19:
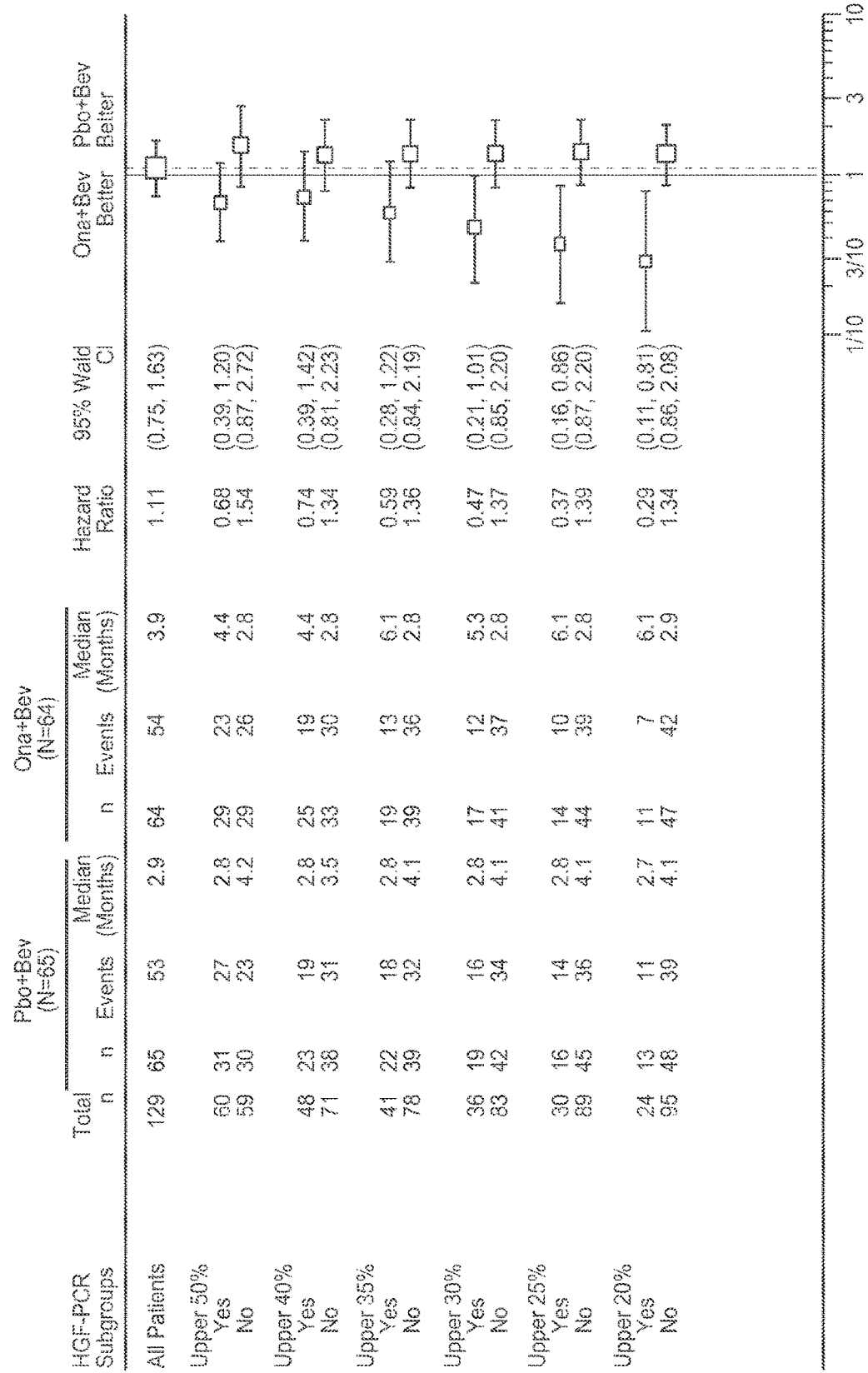
FIG. 19: shows sub-group analysis of progression-free survival according to HGF-PCR status. HRs were unstratified.

FIG. 19: shows sub-group analysis of progression free survival according to HGF-PCR expression. Patients with high HGF-PCR (upper 25%) had a median progression free survival of 2.8 months in placebo+bevacizumab arm versus a median progression free survival of 6.1 months in onartuzumab+bevacizumab arm (HR=0.37 (95% CI 0.16, 0.86)). Patients with low HGF-PCR (lower 75%) had a median progression free survival of 4.1 months in placebo+bevacizumab arm versus a median progression free survival of 2.9 months in onartuzumab+bevacizumab arm (HR=1.39 (95% CI 0.87, 2.20)).

Figure 20:
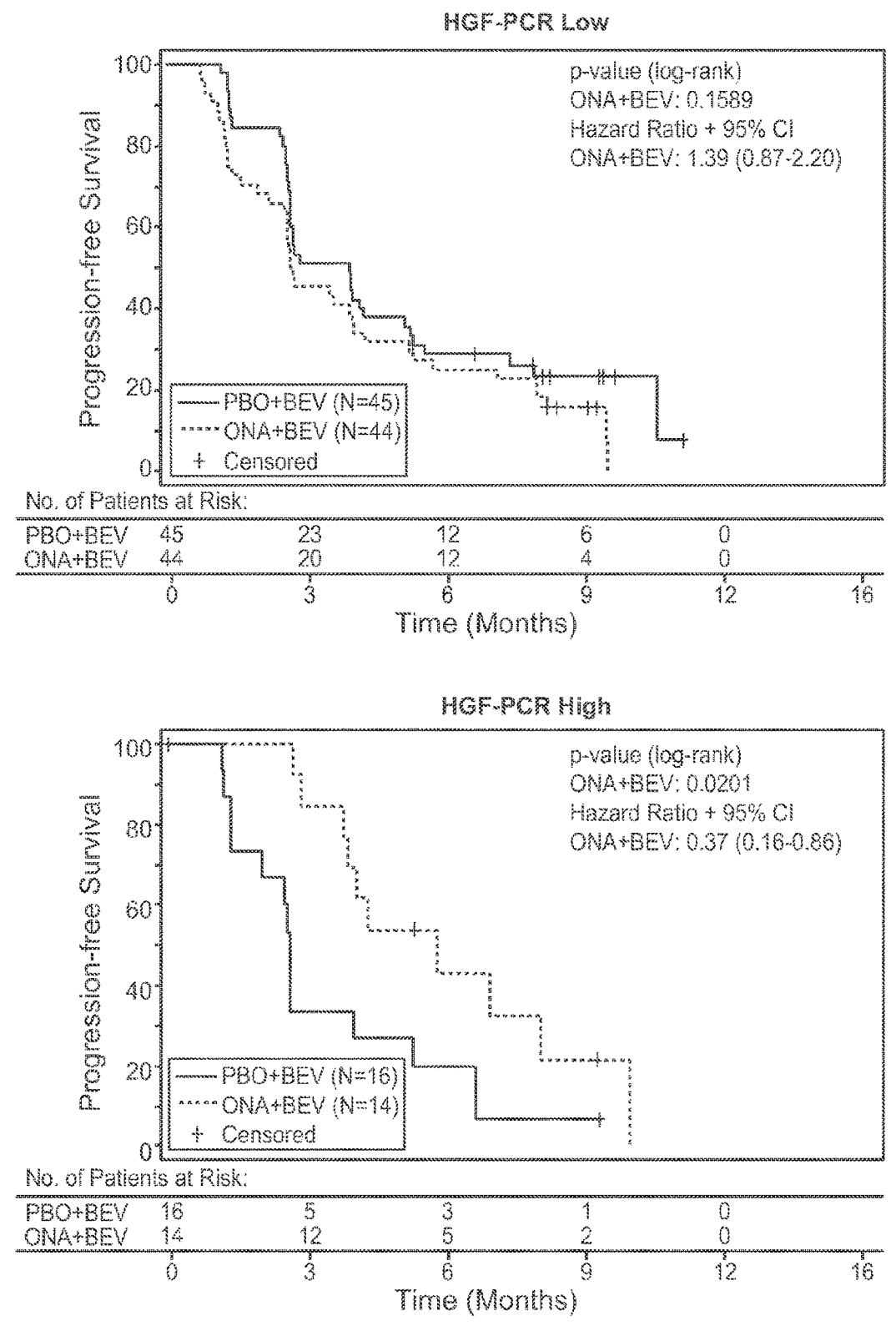
FIG. 20: shows Kaplan-Meier analysis for progression-free survival in HGF-PCR low (lower 75%) patients and HGF-PCR high (upper 25%) patients. Bevacizumab+placebo arm=solid line. Bevacizumab+onartuzumab arm=dashed line.

FIG. 20: shows Kaplan-Meier analysis for progression free survival in low HGF-PCR (lower 75%) patients and high HGF-PCR (upper 25%) patients.

FIG. 21: shows overall response rate (ORR) in HGF-PCR high (upper 25%) patients in bevacizumab+onartuzumab arm compared to patients in bevacizumab+placebo arm.

Figure 22:
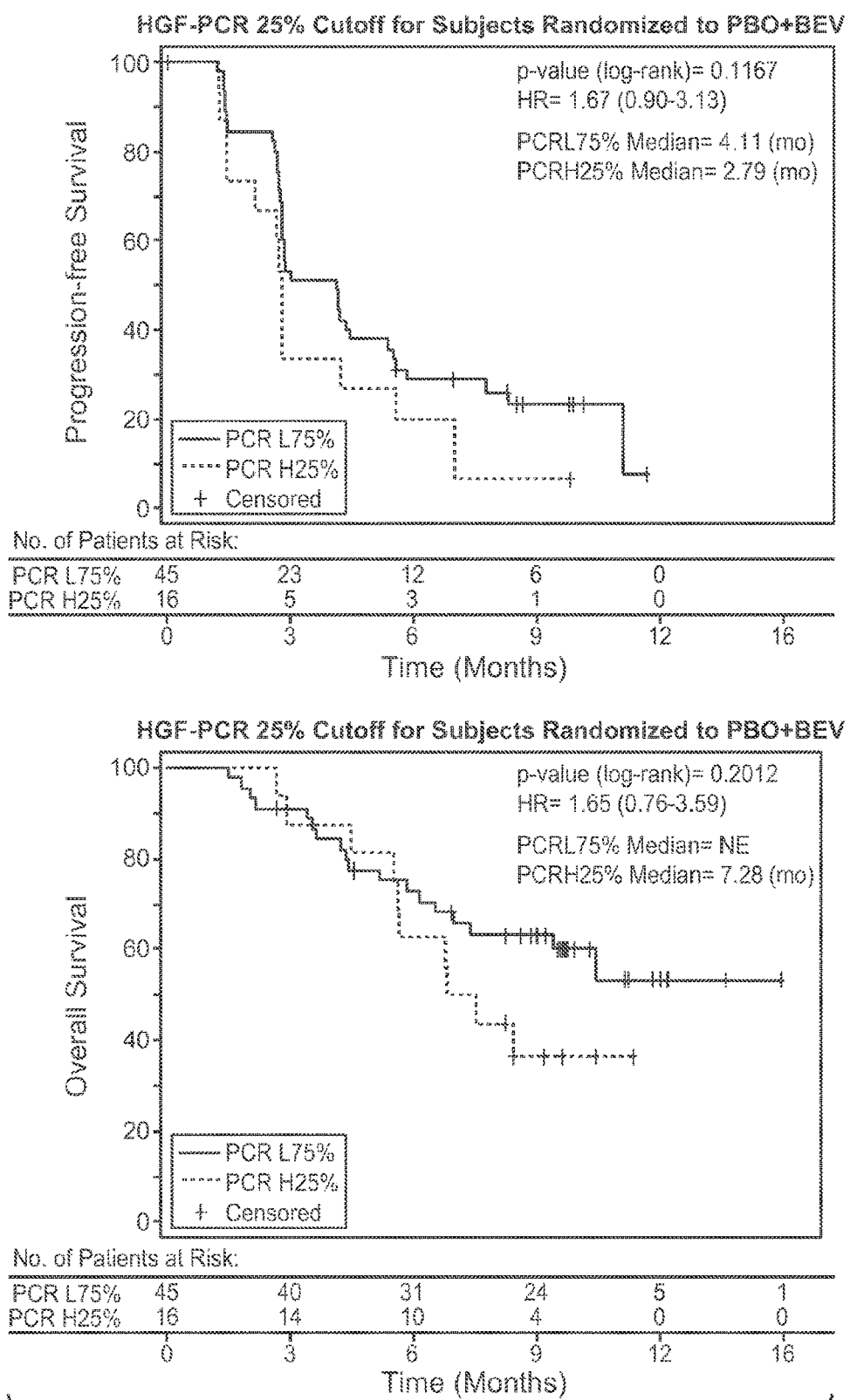
FIG. 22: shows prognostic effect for progression free survival (top) and overall survival (bottom) in HGF-PCR low (lower 75%) patients and HGF-PCR high (upper 25%) patients in bevacizumab+placebo arm.

FIG. 22: shows prognostic effect in progression free survival and overall survival in HGF-PCR low (lower 75%) patients and HGF-PCR high (upper 25%) patients in bevacizumab+placebo arm.

What is claimed is:

1. A method for treating a patient with cancer comprising administering an effective amount of a c-met antagonist to the patient if the patient's cancer is known to have a high amount of the HGF biomarker, wherein the patient's cancer is previously treated glioblastoma, wherein HGF biomarker is HGF mRNA, and HGF biomarker mRNA expression is assayable in a sample from the patient using in situ hybridization (ISH), wherein high HGF biomarker is:

(a) an ISH score of 2+ and/or 3+;

(b) presence of about 12 or more HGF ISH signal positive cells in the sample; or (c) 1% or more HGF ISH signal positive cells in the sample.

2. The method of claim 1, wherein the c-met antagonist is an antagonist anti-c-met antibody.

3. The method of claim 2, wherein the anti-c-met antibody comprises a (a) HVR1 comprising sequence GYTFTSYWLH (SEQ ID NO: 1); (b) HVR2 comprising sequence GMIDPSNSDTRFNPNFKD (SEQ ID NO: 2); (c) HVR3-HC comprising sequence ATYRSYVTPLDY (SEQ ID NO: 3); (d) HVR1-LC comprising sequence KSSQSLLYTSSQKNYLA (SEQ ID NO: 4); (e) HVR2-LC comprising sequence WASTRES (SEQ ID NO: 5); and (f) HVR3-LC comprising sequence QQYYAYPWT (SEQ ID NO: 6).

4. The method of claim 2, wherein the anti-c-met antibody binds an onartuzumab epitope.

5. The method of claim 2, wherein the anti-c-met antibody is onartuzumab.

6. The method of claim 2, wherein an effective amount of the anti-c-met antibody is 15 mg/kg every three weeks.

7. The method of claim 2, wherein an effective amount of the anti-c-met antibody is 10 mg/kg every two weeks.

8. The method of claim 1, wherein the c-met antagonist is one or more of crizotinib, tivantinib, carbozantinib, MGCD-265, ficlatuzumab, humanized TAK-701, rilotumumab, foretinib, h224G11, DN-30, MK-2461, E7050, MK-8033, PF-4217903, AMG208, JNJ-38877605, EMD1204831, INC-280, LY-2801653, SGX-126, RP1040, LY2801653, BAY-853474, and/or LA480.

9. The method of claim 1, wherein treatment is with an effective amount of a combination of a c-met antagonist and VEGF antagonist.

10. The method of claim 9, wherein the VEGF antagonist is an anti-VEGF antibody.

11. The method of claim 10, wherein said anti-VEGF antibody is bevacizumab.

12. The method of claim 10, wherein the anti-VEGF antibody binds the A4.6.1 epitope.

13. The method of claim 10, wherein the anti-VEGF antibody comprises a variable heavy chain (VH) and a variable light chain (VL), wherein the VH has an amino acid sequence of EVQLVESGGG LVQPGGSLRL SCAASGYTFT NYGMNWVRQA PGKGLEWVGW INTYTGEPTY AADFKRRFTF SLDTSKSTAY LQMNSLRAED TAVYYCAKYP HYYGSSHWYF DVWGQGTLVT VSS (SEQ ID NO: 14) and the VL has an amino acid sequence of DIQMTQSPSS LSASVGDRVT ITCSASQDIS NYLNWYQQKP GKAPKVLIYF TSSLHSGVPS RFSGSGSGTD FTLTISSLQP EDFATYYCQQ YSTVPWTFGQ GTKVEIKR (SEQ ID NO: 15).

14. The method of claim 10, wherein said effective amount of said anti-VEGF antibody is 10 mg/kg intravenously every two weeks.

15. The method of claim 10, wherein said effective amount of said anti-VEGF antibody is 15 mg/kg intravenously every three weeks.

16. The method of claim 10, wherein said effective amount of said anti-VEGF antibody is administered initially intravenously over 90 minutes, with subsequent infusions over 60 minutes and then 30 minutes.

17. The method of claim 10, wherein said anti-VEGF antibody is administered second to said patient at the first cycle.

18. The method of claim 10, wherein subsequent administrations of said anti-VEGF antibody are either prior to or after said c-met antagonist.

19. The method of claim 10, wherein said VEGF antagonist is administered concurrently with said c-met antagonist.

20. The method of claim 1, wherein the patient has greater PFS and/or OS relative to a patient who does not have high HGF biomarker.

21. The method of claim 1, wherein the patient is less than 50 years old.

22. The method of claim 1, wherein the patient is equal to or greater than 50 years old.

23. The method of claim 1, wherein the patient has a Karnofsky performance status of 70% to 80%.

24. The method of claim 1, wherein the patient has a Karnofsky performance status of 90% to 100%.

25. The method of claim 1, wherein the patient has greater PFS and/or OS relative to a patient who is treated with VEGF antagonist alone.

* * * * *

SEQUENCE LISTING

<160> NUMBER OF SEQ ID NOS: 16

<210> SEQ ID NO 1
<211> LENGTH: 10
<212> TYPE: PRT
<213> ORGANISM: Artificial Sequence
<220> FEATURE:
<223> OTHER INFORMATION: Synthetic peptide

<400> SEQUENCE: 1

Gly Tyr Thr Phe Thr Ser Tyr Trp Leu His
1               5                   10

<210> SEQ ID NO 2
<211> LENGTH: 18

```
<212> TYPE: PRT
<213> ORGANISM: Artificial Sequence
<220> FEATURE:
<223> OTHER INFORMATION: Synthetic peptide

<400> SEQUENCE: 2

Gly Met Ile Asp Pro Ser Asn Ser Asp Thr Arg Phe Asn Pro Asn Phe
1               5                   10                  15

Lys Asp

<210> SEQ ID NO 3
<211> LENGTH: 12
<212> TYPE: PRT
<213> ORGANISM: Artificial Sequence
<220> FEATURE:
<223> OTHER INFORMATION: Synthetic peptide

<400> SEQUENCE: 3

Ala Thr Tyr Arg Ser Tyr Val Thr Pro Leu Asp Tyr
1               5                   10

<210> SEQ ID NO 4
<211> LENGTH: 17
<212> TYPE: PRT
<213> ORGANISM: Artificial Sequence
<220> FEATURE:
<223> OTHER INFORMATION: Synthetic peptide

<400> SEQUENCE: 4

Lys Ser Ser Gln Ser Leu Leu Tyr Thr Ser Ser Gln Lys Asn Tyr Leu
1               5                   10                  15

Ala

<210> SEQ ID NO 5
<211> LENGTH: 7
<212> TYPE: PRT
<213> ORGANISM: Artificial Sequence
<220> FEATURE:
<223> OTHER INFORMATION: Synthetic peptide

<400> SEQUENCE: 5

Trp Ala Ser Thr Arg Glu Ser
1               5

<210> SEQ ID NO 6
<211> LENGTH: 9
<212> TYPE: PRT
<213> ORGANISM: Artificial Sequence
<220> FEATURE:
<223> OTHER INFORMATION: Synthetic peptide

<400> SEQUENCE: 6

Gln Gln Tyr Tyr Ala Tyr Pro Trp Thr
1               5

<210> SEQ ID NO 7
<211> LENGTH: 119
<212> TYPE: PRT
<213> ORGANISM: Artificial Sequence
<220> FEATURE:
<223> OTHER INFORMATION: Synthetic polypeptide

<400> SEQUENCE: 7

Glu Val Gln Leu Val Glu Ser Gly Gly Gly Leu Val Gln Pro Gly Gly
1               5                   10                  15
```

```
Ser Leu Arg Leu Ser Cys Ala Ala Ser Gly Tyr Thr Phe Thr Ser Tyr
         20                  25                  30

Trp Leu His Trp Val Arg Gln Ala Pro Gly Lys Gly Leu Glu Trp Val
             35                  40                  45

Gly Met Ile Asp Pro Ser Asn Ser Asp Thr Arg Phe Asn Pro Asn Phe
     50                  55                  60

Lys Asp Arg Phe Thr Ile Ser Ala Asp Thr Ser Lys Asn Thr Ala Tyr
 65                  70                  75                  80

Leu Gln Met Asn Ser Leu Arg Ala Glu Asp Thr Ala Val Tyr Tyr Cys
                 85                  90                  95

Ala Thr Tyr Arg Ser Tyr Val Thr Pro Leu Asp Tyr Trp Gly Gln Gly
            100                 105                 110

Thr Leu Val Thr Val Ser Ser
            115

<210> SEQ ID NO 8
<211> LENGTH: 114
<212> TYPE: PRT
<213> ORGANISM: Artificial Sequence
<220> FEATURE:
<223> OTHER INFORMATION: Synthetic polypeptide

<400> SEQUENCE: 8

Asp Ile Gln Met Thr Gln Ser Pro Ser Ser Leu Ser Ala Ser Val Gly
 1               5                  10                  15

Asp Arg Val Thr Ile Thr Cys Lys Ser Ser Gln Ser Leu Leu Tyr Thr
             20                  25                  30

Ser Ser Gln Lys Asn Tyr Leu Ala Trp Tyr Gln Gln Lys Pro Gly Lys
         35                  40                  45

Ala Pro Lys Leu Leu Ile Tyr Trp Ala Ser Thr Arg Glu Ser Gly Val
     50                  55                  60

Pro Ser Arg Phe Ser Gly Ser Gly Ser Gly Thr Asp Phe Thr Leu Thr
 65                  70                  75                  80

Ile Ser Ser Leu Gln Pro Glu Asp Phe Ala Thr Tyr Tyr Cys Gln Gln
                 85                  90                  95

Tyr Tyr Ala Tyr Pro Trp Thr Phe Gly Gln Gly Thr Lys Val Glu Ile
            100                 105                 110

Lys Arg

<210> SEQ ID NO 9
<211> LENGTH: 222
<212> TYPE: PRT
<213> ORGANISM: Artificial Sequence
<220> FEATURE:
<223> OTHER INFORMATION: Synthetic polypeptide

<400> SEQUENCE: 9

Cys Pro Pro Cys Pro Ala Pro Glu Leu Leu Gly Gly Pro Ser Val Phe
 1               5                  10                  15

Leu Phe Pro Pro Lys Pro Lys Asp Thr Leu Met Ile Ser Arg Thr Pro
             20                  25                  30

Glu Val Thr Cys Val Val Val Asp Val Ser His Glu Asp Pro Glu Val
         35                  40                  45

Lys Phe Asn Trp Tyr Val Asp Gly Val Glu Val His Asn Ala Lys Thr
     50                  55                  60

Lys Pro Arg Glu Glu Gln Tyr Asn Ser Thr Tyr Arg Val Val Ser Val
 65                  70                  75                  80
```

```
Leu Thr Val Leu His Gln Asp Trp Leu Asn Gly Lys Glu Tyr Lys Cys
                85                  90                  95

Lys Val Ser Asn Lys Ala Leu Pro Ala Pro Ile Glu Lys Thr Ile Ser
            100                 105                 110

Lys Ala Lys Gly Gln Pro Arg Glu Pro Gln Val Tyr Thr Leu Pro Pro
        115                 120                 125

Ser Arg Glu Glu Met Thr Lys Asn Gln Val Ser Leu Ser Cys Ala Val
    130                 135                 140

Lys Gly Phe Tyr Pro Ser Asp Ile Ala Val Glu Trp Glu Ser Asn Gly
145                 150                 155                 160

Gln Pro Glu Asn Asn Tyr Lys Thr Thr Pro Pro Val Leu Asp Ser Asp
                165                 170                 175

Gly Ser Phe Phe Leu Val Ser Lys Leu Thr Val Asp Lys Ser Arg Trp
            180                 185                 190

Gln Gln Gly Asn Val Phe Ser Cys Ser Val Met His Glu Ala Leu His
        195                 200                 205

Asn His Tyr Thr Gln Lys Ser Leu Ser Leu Ser Pro Gly Lys
    210                 215                 220

<210> SEQ ID NO 10
<211> LENGTH: 222
<212> TYPE: PRT
<213> ORGANISM: Artificial Sequence
<220> FEATURE:
<223> OTHER INFORMATION: Synthetic polypeptide

<400> SEQUENCE: 10

Cys Pro Pro Cys Pro Ala Pro Glu Leu Leu Gly Gly Pro Ser Val Phe
1               5                   10                  15

Leu Phe Pro Pro Lys Pro Lys Asp Thr Leu Met Ile Ser Arg Thr Pro
            20                  25                  30

Glu Val Thr Cys Val Val Val Asp Val Ser His Glu Asp Pro Glu Val
        35                  40                  45

Lys Phe Asn Trp Tyr Val Asp Gly Val Glu Val His Asn Ala Lys Thr
    50                  55                  60

Lys Pro Arg Glu Glu Gln Tyr Asn Ser Thr Tyr Arg Val Val Ser Val
65                  70                  75                  80

Leu Thr Val Leu His Gln Asp Trp Leu Asn Gly Lys Glu Tyr Lys Cys
                85                  90                  95

Lys Val Ser Asn Lys Ala Leu Pro Ala Pro Ile Glu Lys Thr Ile Ser
            100                 105                 110

Lys Ala Lys Gly Gln Pro Arg Glu Pro Gln Val Tyr Thr Leu Pro Pro
        115                 120                 125

Ser Arg Glu Glu Met Thr Lys Asn Gln Val Ser Leu Trp Cys Leu Val
    130                 135                 140

Lys Gly Phe Tyr Pro Ser Asp Ile Ala Val Glu Trp Glu Ser Asn Gly
145                 150                 155                 160

Gln Pro Glu Asn Asn Tyr Lys Thr Thr Pro Pro Val Leu Asp Ser Asp
                165                 170                 175

Gly Ser Phe Phe Leu Tyr Ser Lys Leu Thr Val Asp Lys Ser Arg Trp
            180                 185                 190

Gln Gln Gly Asn Val Phe Ser Cys Ser Val Met His Glu Ala Leu His
        195                 200                 205

Asn His Tyr Thr Gln Lys Ser Leu Ser Leu Ser Pro Gly Lys
    210                 215                 220
```

```
<210> SEQ ID NO 11
<211> LENGTH: 449
<212> TYPE: PRT
<213> ORGANISM: Artificial Sequence
<220> FEATURE:
<223> OTHER INFORMATION: Synthetic polypeptide

<400> SEQUENCE: 11

Glu Val Gln Leu Val Glu Ser Gly Gly Gly Leu Val Gln Pro Gly Gly
1               5                   10                  15

Ser Leu Arg Leu Ser Cys Ala Ala Ser Gly Tyr Thr Phe Thr Ser Tyr
            20                  25                  30

Trp Leu His Trp Val Arg Gln Ala Pro Gly Lys Gly Leu Glu Trp Val
        35                  40                  45

Gly Met Ile Asp Pro Ser Asn Ser Asp Thr Arg Phe Asn Pro Asn Phe
    50                  55                  60

Lys Asp Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ala Thr Tyr Arg Ser Tyr Val Thr Pro Leu Asp Tyr Trp Gly Gln Gly
            100                 105                 110

Thr Leu Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys Asp Lys
    210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Asn Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Glu Glu Met Thr Lys Asn Gln Val Ser Leu Ser
        355                 360                 365
```

Cys Ala Val Lys Gly Phe Tyr Pro Ser Asp Ile Ala Val Glu Trp Glu
            370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Val Ser Lys Leu Thr Val Asp Lys
                405                 410                 415

Ser Arg Trp Gln Gln Gly Asn Val Phe Ser Cys Ser Val Met His Glu
                420                 425                 430

Ala Leu His Asn His Tyr Thr Gln Lys Ser Leu Ser Leu Ser Pro Gly
            435                 440                 445

Lys

<210> SEQ ID NO 12
<211> LENGTH: 220
<212> TYPE: PRT
<213> ORGANISM: Artificial Sequence
<220> FEATURE:
<223> OTHER INFORMATION: Synthetic polypeptide

<400> SEQUENCE: 12

Asp Ile Gln Met Thr Gln Ser Pro Ser Ser Leu Ser Ala Ser Val Gly
1               5                   10                  15

Asp Arg Val Thr Ile Thr Cys Lys Ser Ser Gln Ser Leu Leu Tyr Thr
            20                  25                  30

Ser Ser Gln Lys Asn Tyr Leu Ala Trp Tyr Gln Gln Lys Pro Gly Lys
        35                  40                  45

Ala Pro Lys Leu Leu Ile Tyr Trp Ala Ser Thr Arg Glu Ser Gly Val
50                  55                  60

Pro Ser Arg Phe Ser Gly Ser Gly Ser Gly Thr Asp Phe Thr Leu Thr
65                  70                  75                  80

Ile Ser Ser Leu Gln Pro Glu Asp Phe Ala Thr Tyr Tyr Cys Gln Gln
                85                  90                  95

Tyr Tyr Ala Tyr Pro Trp Thr Phe Gly Gln Gly Thr Lys Val Glu Ile
            100                 105                 110

Lys Arg Thr Val Ala Ala Pro Ser Val Phe Ile Phe Pro Pro Ser Asp
        115                 120                 125

Glu Gln Leu Lys Ser Gly Thr Ala Ser Val Val Cys Leu Leu Asn Asn
    130                 135                 140

Phe Tyr Pro Arg Glu Ala Lys Val Gln Trp Lys Val Asp Asn Ala Leu
145                 150                 155                 160

Gln Ser Gly Asn Ser Gln Glu Ser Val Thr Glu Gln Asp Ser Lys Asp
                165                 170                 175

Ser Thr Tyr Ser Leu Ser Ser Thr Leu Thr Leu Ser Lys Ala Asp Tyr
            180                 185                 190

Glu Lys His Lys Val Tyr Ala Cys Glu Val Thr His Gln Gly Leu Ser
        195                 200                 205

Ser Pro Val Thr Lys Ser Phe Asn Arg Gly Glu Cys
    210                 215                 220

<210> SEQ ID NO 13
<211> LENGTH: 227
<212> TYPE: PRT
<213> ORGANISM: Artificial Sequence
<220> FEATURE:
<223> OTHER INFORMATION: Synthetic polypeptide

<400> SEQUENCE: 13

```
Asp Lys Thr His Thr Cys Pro Pro Cys Pro Ala Pro Glu Leu Leu Gly
1               5                   10                  15
Gly Pro Ser Val Phe Leu Phe Pro Pro Lys Pro Lys Asp Thr Leu Met
            20                  25                  30
Ile Ser Arg Thr Pro Glu Val Thr Cys Val Val Val Asp Val Ser His
        35                  40                  45
Glu Asp Pro Glu Val Lys Phe Asn Trp Tyr Val Asp Gly Val Glu Val
    50                  55                  60
His Asn Ala Lys Thr Lys Pro Arg Glu Glu Gln Tyr Asn Ser Thr Tyr
65                  70                  75                  80
Arg Val Val Ser Val Leu Thr Val Leu His Gln Asp Trp Leu Asn Gly
                85                  90                  95
Lys Glu Tyr Lys Cys Lys Val Ser Asn Lys Ala Leu Pro Ala Pro Ile
            100                 105                 110
Glu Lys Thr Ile Ser Lys Ala Lys Gly Gln Pro Arg Glu Pro Gln Val
        115                 120                 125
Tyr Thr Leu Pro Pro Ser Arg Glu Glu Met Thr Lys Asn Gln Val Ser
    130                 135                 140
Leu Trp Cys Leu Val Lys Gly Phe Tyr Pro Ser Asp Ile Ala Val Glu
145                 150                 155                 160
Trp Glu Ser Asn Gly Gln Pro Glu Asn Asn Tyr Lys Thr Thr Pro Pro
                165                 170                 175
Val Leu Asp Ser Asp Gly Ser Phe Phe Leu Tyr Ser Lys Leu Thr Val
            180                 185                 190
Asp Lys Ser Arg Trp Gln Gln Gly Asn Val Phe Ser Cys Ser Val Met
        195                 200                 205
His Glu Ala Leu His Asn His Tyr Thr Gln Lys Ser Leu Ser Leu Ser
    210                 215                 220
Pro Gly Lys
225

<210> SEQ ID NO 14
<211> LENGTH: 123
<212> TYPE: PRT
<213> ORGANISM: Artificial Sequence
<220> FEATURE:
<223> OTHER INFORMATION: Synthetic polypeptide

<400> SEQUENCE: 14

Glu Val Gln Leu Val Glu Ser Gly Gly Gly Leu Val Gln Pro Gly Gly
1               5                   10                  15
Ser Leu Arg Leu Ser Cys Ala Ala Ser Gly Tyr Thr Phe Thr Asn Tyr
            20                  25                  30
Gly Met Asn Trp Val Arg Gln Ala Pro Gly Lys Gly Leu Glu Trp Val
        35                  40                  45
Gly Trp Ile Asn Thr Tyr Thr Gly Glu Pro Thr Tyr Ala Ala Asp Phe
    50                  55                  60
Lys Arg Arg Phe Thr Phe Ser Leu Asp Thr Ser Lys Ser Thr Ala Tyr
65                  70                  75                  80
Leu Gln Met Asn Ser Leu Arg Ala Glu Asp Thr Ala Val Tyr Tyr Cys
                85                  90                  95
Ala Lys Tyr Pro His Tyr Tyr Gly Ser Ser His Trp Tyr Phe Asp Val
            100                 105                 110
Trp Gly Gln Gly Thr Leu Val Thr Val Ser Ser
        115                 120
```

```
<210> SEQ ID NO 15
<211> LENGTH: 108
<212> TYPE: PRT
<213> ORGANISM: Artificial Sequence
<220> FEATURE:
<223> OTHER INFORMATION: Synthetic polypeptide

<400> SEQUENCE: 15

Asp Ile Gln Met Thr Gln Ser Pro Ser Ser Leu Ser Ala Ser Val Gly
1               5                   10                  15

Asp Arg Val Thr Ile Thr Cys Ser Ala Ser Gln Asp Ile Ser Asn Tyr
            20                  25                  30

Leu Asn Trp Tyr Gln Gln Lys Pro Gly Lys Ala Pro Lys Val Leu Ile
        35                  40                  45

Tyr Phe Thr Ser Ser Leu His Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Ser Thr Val Pro Trp
                85                  90                  95

Thr Phe Gly Gln Gly Thr Lys Val Glu Ile Lys Arg
            100                 105

<210> SEQ ID NO 16
<211> LENGTH: 1390
<212> TYPE: PRT
<213> ORGANISM: Artificial Sequence
<220> FEATURE:
<223> OTHER INFORMATION: Synthetic polypeptide

<400> SEQUENCE: 16

Met Lys Ala Pro Ala Val Leu Ala Pro Gly Ile Leu Val Leu Leu Phe
1               5                   10                  15

Thr Leu Val Gln Arg Ser Asn Gly Glu Cys Lys Glu Ala Leu Ala Lys
            20                  25                  30

Ser Glu Met Asn Val Asn Met Lys Tyr Gln Leu Pro Asn Phe Thr Ala
        35                  40                  45

Glu Thr Pro Ile Gln Asn Val Ile Leu His Glu His His Ile Phe Leu
    50                  55                  60

Gly Ala Thr Asn Tyr Ile Tyr Val Leu Asn Glu Glu Asp Leu Gln Lys
65                  70                  75                  80

Val Ala Glu Tyr Lys Thr Gly Pro Val Leu Glu His Pro Asp Cys Phe
                85                  90                  95

Pro Cys Gln Asp Cys Ser Ser Lys Ala Asn Leu Ser Gly Gly Val Trp
            100                 105                 110

Lys Asp Asn Ile Asn Met Ala Leu Val Val Asp Thr Tyr Tyr Asp Asp
        115                 120                 125

Gln Leu Ile Ser Cys Gly Ser Val Asn Arg Gly Thr Cys Gln Arg His
    130                 135                 140

Val Phe Pro His Asn His Thr Ala Asp Ile Gln Ser Glu Val His Cys
145                 150                 155                 160

Ile Phe Ser Pro Gln Ile Glu Glu Pro Ser Gln Cys Pro Asp Cys Val
                165                 170                 175

Val Ser Ala Leu Gly Ala Lys Val Leu Ser Ser Val Lys Asp Arg Phe
            180                 185                 190

Ile Asn Phe Phe Val Gly Asn Thr Ile Asn Ser Ser Tyr Phe Pro Asp
        195                 200                 205
```

```
His Pro Leu His Ser Ile Ser Val Arg Arg Leu Lys Glu Thr Lys Asp
    210                 215                 220

Gly Phe Met Phe Leu Thr Asp Gln Ser Tyr Ile Asp Val Leu Pro Glu
225                 230                 235                 240

Phe Arg Asp Ser Tyr Pro Ile Lys Tyr Val His Ala Phe Glu Ser Asn
                245                 250                 255

Asn Phe Ile Tyr Phe Leu Thr Val Gln Arg Glu Thr Leu Asp Ala Gln
                260                 265                 270

Thr Phe His Thr Arg Ile Ile Arg Phe Cys Ser Ile Asn Ser Gly Leu
            275                 280                 285

His Ser Tyr Met Glu Met Pro Leu Glu Cys Ile Leu Thr Glu Lys Arg
        290                 295                 300

Lys Lys Arg Ser Thr Lys Lys Glu Val Phe Asn Ile Leu Gln Ala Ala
305                 310                 315                 320

Tyr Val Ser Lys Pro Gly Ala Gln Leu Ala Arg Gln Ile Gly Ala Ser
                325                 330                 335

Leu Asn Asp Asp Ile Leu Phe Gly Val Phe Ala Gln Ser Lys Pro Asp
                340                 345                 350

Ser Ala Glu Pro Met Asp Arg Ser Ala Met Cys Ala Phe Pro Ile Lys
            355                 360                 365

Tyr Val Asn Asp Phe Phe Asn Lys Ile Val Asn Lys Asn Asn Val Arg
        370                 375                 380

Cys Leu Gln His Phe Tyr Gly Pro Asn His Glu His Cys Phe Asn Arg
385                 390                 395                 400

Thr Leu Leu Arg Asn Ser Ser Gly Cys Glu Ala Arg Arg Asp Glu Tyr
                405                 410                 415

Arg Thr Glu Phe Thr Thr Ala Leu Gln Arg Val Asp Leu Phe Met Gly
            420                 425                 430

Gln Phe Ser Glu Val Leu Leu Thr Ser Ile Ser Thr Phe Ile Lys Gly
        435                 440                 445

Asp Leu Thr Ile Ala Asn Leu Gly Thr Ser Glu Gly Arg Phe Met Gln
            450                 455                 460

Val Val Val Ser Arg Ser Gly Pro Ser Thr Pro His Val Asn Phe Leu
465                 470                 475                 480

Leu Asp Ser His Pro Val Ser Pro Glu Val Ile Val Glu His Thr Leu
                485                 490                 495

Asn Gln Asn Gly Tyr Thr Leu Val Ile Thr Gly Lys Lys Ile Thr Lys
                500                 505                 510

Ile Pro Leu Asn Gly Leu Gly Cys Arg His Phe Gln Ser Cys Ser Gln
            515                 520                 525

Cys Leu Ser Ala Pro Pro Phe Val Gln Cys Gly Trp Cys His Asp Lys
530                 535                 540

Cys Val Arg Ser Glu Glu Cys Leu Ser Gly Thr Trp Thr Gln Gln Ile
545                 550                 555                 560

Cys Leu Pro Ala Ile Tyr Lys Val Phe Pro Asn Ser Ala Pro Leu Glu
                565                 570                 575

Gly Gly Thr Arg Leu Thr Ile Cys Gly Trp Asp Phe Gly Phe Arg Arg
                580                 585                 590

Asn Asn Lys Phe Asp Leu Lys Lys Thr Arg Val Leu Leu Gly Asn Glu
            595                 600                 605

Ser Cys Thr Leu Thr Leu Ser Glu Ser Thr Met Asn Thr Leu Lys Cys
        610                 615                 620
```

```
Thr Val Gly Pro Ala Met Asn Lys His Phe Asn Met Ser Ile Ile Ile
625                 630                 635                 640

Ser Asn Gly His Gly Thr Thr Gln Tyr Ser Thr Phe Ser Tyr Val Asp
                645                 650                 655

Pro Val Ile Thr Ser Ile Ser Pro Lys Tyr Gly Pro Met Ala Gly Gly
                660                 665                 670

Thr Leu Leu Thr Leu Thr Gly Asn Tyr Leu Asn Ser Gly Asn Ser Arg
            675                 680                 685

His Ile Ser Ile Gly Gly Lys Thr Cys Thr Leu Lys Ser Val Ser Asn
690                 695                 700

Ser Ile Leu Glu Cys Tyr Thr Pro Ala Gln Thr Ile Ser Thr Glu Phe
705                 710                 715                 720

Ala Val Lys Leu Lys Ile Asp Leu Ala Asn Arg Glu Thr Ser Ile Phe
                725                 730                 735

Ser Tyr Arg Glu Asp Pro Ile Val Tyr Glu Ile His Pro Thr Lys Ser
                740                 745                 750

Phe Ile Ser Gly Gly Ser Thr Ile Thr Gly Val Gly Lys Asn Leu Asn
            755                 760                 765

Ser Val Ser Val Pro Arg Met Val Ile Asn Val His Glu Ala Gly Arg
770                 775                 780

Asn Phe Thr Val Ala Cys Gln His Arg Ser Asn Ser Glu Ile Ile Cys
785                 790                 795                 800

Cys Thr Thr Pro Ser Leu Gln Gln Leu Asn Leu Gln Leu Pro Leu Lys
                805                 810                 815

Thr Lys Ala Phe Phe Met Leu Asp Gly Ile Leu Ser Lys Tyr Phe Asp
                820                 825                 830

Leu Ile Tyr Val His Asn Pro Val Phe Lys Pro Phe Glu Lys Pro Val
            835                 840                 845

Met Ile Ser Met Gly Asn Glu Asn Val Leu Glu Ile Lys Gly Asn Asp
850                 855                 860

Ile Asp Pro Glu Ala Val Lys Gly Glu Val Leu Lys Val Gly Asn Lys
865                 870                 875                 880

Ser Cys Glu Asn Ile His Leu His Ser Glu Ala Val Leu Cys Thr Val
                885                 890                 895

Pro Asn Asp Leu Leu Lys Leu Asn Ser Glu Leu Asn Ile Glu Trp Lys
                900                 905                 910

Gln Ala Ile Ser Ser Thr Val Leu Gly Lys Val Ile Val Gln Pro Asp
            915                 920                 925

Gln Asn Phe Thr Gly Leu Ile Ala Gly Val Val Ser Ile Ser Thr Ala
            930                 935                 940

Leu Leu Leu Leu Leu Gly Phe Phe Leu Trp Leu Lys Lys Arg Lys Gln
945                 950                 955                 960

Ile Lys Asp Leu Gly Ser Glu Leu Val Arg Tyr Asp Ala Arg Val His
                965                 970                 975

Thr Pro His Leu Asp Arg Leu Val Ser Ala Arg Ser Val Ser Pro Thr
                980                 985                 990

Thr Glu Met Val Ser Asn Glu Ser Val Asp Tyr Arg Ala Thr Phe Pro
            995                 1000                1005

Glu Asp Gln Phe Pro Asn Ser Ser Gln Asn Gly Ser Cys Arg Gln
            1010                1015                1020

Val Gln Tyr Pro Leu Thr Asp Met Ser Pro Ile Leu Thr Ser Gly
            1025                1030                1035

Asp Ser Asp Ile Ser Ser Pro Leu Leu Gln Asn Thr Val His Ile
```

|      |     |     |     |     |     |     |     |     |     |     |     |
|------|-----|-----|-----|-----|-----|-----|-----|-----|-----|-----|-----|
|      | 1040 |     |     |     | 1045 |     |     |     | 1050 |     |     |
| Asp  | Leu | Ser | Ala | Leu | Asn | Pro | Glu | Leu | Val | Gln | Ala | Val | Gln | His |
|      | 1055 |     |     |     | 1060 |     |     |     | 1065 |     |     |
| Val  | Val | Ile | Gly | Pro | Ser | Ser | Leu | Ile | Val | His | Phe | Asn | Glu | Val |
|      | 1070 |     |     |     | 1075 |     |     |     | 1080 |     |     |
| Ile  | Gly | Arg | Gly | His | Phe | Gly | Cys | Val | Tyr | His | Gly | Thr | Leu | Leu |
|      | 1085 |     |     |     | 1090 |     |     |     | 1095 |     |     |
| Asp  | Asn | Asp | Gly | Lys | Lys | Ile | His | Cys | Ala | Val | Lys | Ser | Leu | Asn |
|      | 1100 |     |     |     | 1105 |     |     |     | 1110 |     |     |
| Arg  | Ile | Thr | Asp | Ile | Gly | Glu | Val | Ser | Gln | Phe | Leu | Thr | Glu | Gly |
|      | 1115 |     |     |     | 1120 |     |     |     | 1125 |     |     |
| Ile  | Ile | Met | Lys | Asp | Phe | Ser | His | Pro | Asn | Val | Leu | Ser | Leu | Leu |
|      | 1130 |     |     |     | 1135 |     |     |     | 1140 |     |     |
| Gly  | Ile | Cys | Leu | Arg | Ser | Glu | Gly | Ser | Pro | Leu | Val | Val | Leu | Pro |
|      | 1145 |     |     |     | 1150 |     |     |     | 1155 |     |     |
| Tyr  | Met | Lys | His | Gly | Asp | Leu | Arg | Asn | Phe | Ile | Arg | Asn | Glu | Thr |
|      | 1160 |     |     |     | 1165 |     |     |     | 1170 |     |     |
| His  | Asn | Pro | Thr | Val | Lys | Asp | Leu | Ile | Gly | Phe | Gly | Leu | Gln | Val |
|      | 1175 |     |     |     | 1180 |     |     |     | 1185 |     |     |
| Ala  | Lys | Gly | Met | Lys | Tyr | Leu | Ala | Ser | Lys | Lys | Phe | Val | His | Arg |
|      | 1190 |     |     |     | 1195 |     |     |     | 1200 |     |     |
| Asp  | Leu | Ala | Ala | Arg | Asn | Cys | Met | Leu | Asp | Glu | Lys | Phe | Thr | Val |
|      | 1205 |     |     |     | 1210 |     |     |     | 1215 |     |     |
| Lys  | Val | Ala | Asp | Phe | Gly | Leu | Ala | Arg | Asp | Met | Tyr | Asp | Lys | Glu |
|      | 1220 |     |     |     | 1225 |     |     |     | 1230 |     |     |
| Tyr  | Tyr | Ser | Val | His | Asn | Lys | Thr | Gly | Ala | Lys | Leu | Pro | Val | Lys |
|      | 1235 |     |     |     | 1240 |     |     |     | 1245 |     |     |
| Trp  | Met | Ala | Leu | Glu | Ser | Leu | Gln | Thr | Gln | Lys | Phe | Thr | Thr | Lys |
|      | 1250 |     |     |     | 1255 |     |     |     | 1260 |     |     |
| Ser  | Asp | Val | Trp | Ser | Phe | Gly | Val | Leu | Leu | Trp | Glu | Leu | Met | Thr |
|      | 1265 |     |     |     | 1270 |     |     |     | 1275 |     |     |
| Arg  | Gly | Ala | Pro | Pro | Tyr | Pro | Asp | Val | Asn | Thr | Phe | Asp | Ile | Thr |
|      | 1280 |     |     |     | 1285 |     |     |     | 1290 |     |     |
| Val  | Tyr | Leu | Leu | Gln | Gly | Arg | Arg | Leu | Leu | Gln | Pro | Glu | Tyr | Cys |
|      | 1295 |     |     |     | 1300 |     |     |     | 1305 |     |     |
| Pro  | Asp | Pro | Leu | Tyr | Glu | Val | Met | Leu | Lys | Cys | Trp | His | Pro | Lys |
|      | 1310 |     |     |     | 1315 |     |     |     | 1320 |     |     |
| Ala  | Glu | Met | Arg | Pro | Ser | Phe | Ser | Glu | Leu | Val | Ser | Arg | Ile | Ser |
|      | 1325 |     |     |     | 1330 |     |     |     | 1335 |     |     |
| Ala  | Ile | Phe | Ser | Thr | Phe | Ile | Gly | Glu | His | Tyr | Val | His | Val | Asn |
|      | 1340 |     |     |     | 1345 |     |     |     | 1350 |     |     |
| Ala  | Thr | Tyr | Val | Asn | Val | Lys | Cys | Val | Ala | Pro | Tyr | Pro | Ser | Leu |
|      | 1355 |     |     |     | 1360 |     |     |     | 1365 |     |     |
| Leu  | Ser | Ser | Glu | Asp | Asn | Ala | Asp | Asp | Glu | Val | Asp | Thr | Arg | Pro |
|      | 1370 |     |     |     | 1375 |     |     |     | 1380 |     |     |
| Ala  | Ser | Phe | Trp | Glu | Thr | Ser |
|      | 1385 |     |     |     | 1390 |     |